US012760016B2

(12) United States Patent
Zhang et al.

(10) Patent No.: US 12,760,016 B2
(45) Date of Patent: Oct. 13, 2026

(54) CLASS OF POLYCYCLIC COMPOUNDS INHIBITING RNA HELICASE DHX33 AND THE APPLICATION THEREOF

(71) Applicant: Shenzhen KeYe Life Technologies, Co., Ltd, Shenzhen (CN)

(72) Inventors: Yandong Zhang, Shenzhen (CN); Xianglu Li, Shenzhen (CN)

(73) Assignee: Shenzhen KeYe Life Technologies, Co., Ltd, Shenzhen (CN)

( * ) Notice: Subject to any disclaimer, the term of this patent is extended or adjusted under 35 U.S.C. 154(b) by 925 days.

(21) Appl. No.: 17/907,952

(22) PCT Filed: Sep. 1, 2021

(86) PCT No.: PCT/CN2021/115973

§ 371 (c)(1),
(2) Date: Aug. 29, 2022

(87) PCT Pub. No.: WO2022/127199

PCT Pub. Date: Jun. 23, 2022

(65) Prior Publication Data

US 2023/0146233 A1 May 11, 2023

(30) Foreign Application Priority Data

| | | |
|---|---|---|
| Dec. 16, 2020 | (CN) | 202011487589.4 |
| Dec. 23, 2020 | (CN) | 202011532460.0 |
| Dec. 30, 2020 | (CN) | 202011609191.3 |
| Mar. 1, 2021 | (CN) | 202110225711.9 |
| Jun. 29, 2021 | (CN) | 202110724793.1 |
| Jun. 29, 2021 | (CN) | 202110724794.6 |

(51) Int. Cl.

| | |
|---|---|
| ***C07D 471/04*** | (2006.01) |
| ***C07D 403/06*** | (2006.01) |
| ***C07D 405/14*** | (2006.01) |
| ***C07D 409/14*** | (2006.01) |
| ***C07D 417/14*** | (2006.01) |
| ***C07D 491/056*** | (2006.01) |

(52) U.S. Cl.

CPC ......... *C07D 471/04* (2013.01); *C07D 403/06* (2013.01); *C07D 405/14* (2013.01); *C07D 409/14* (2013.01); *C07D 417/14* (2013.01); *C07D 491/056* (2013.01)

(58) Field of Classification Search

CPC .. C07D 471/04; C07D 403/06; C07D 405/14; C07D 409/14; C07D 417/14; C07D 491/056

See application file for complete search history.

(56) References Cited

U.S. PATENT DOCUMENTS

| | | | |
|---|---|---|---|
| 2004/0122046 A1 | 6/2004 | Elliott |
| 2011/0269753 A1 | 11/2011 | Balasubramanian et al. |
| 2017/0313711 A1 | 11/2017 | Vlaar et al. |

FOREIGN PATENT DOCUMENTS

| | | |
|---|---|---|
| CN | 108342365 A | 7/2018 |
| CN | 110295233 A | 10/2019 |
| CN | 112266385 A | 1/2021 |
| CN | 112538078 A | 3/2021 |
| CN | 112661754 A | 4/2021 |
| CN | 112898284 A | 6/2021 |
| WO | 2011/097607 A1 | 8/2011 |
| WO | 2013/123071 A1 | 8/2013 |

OTHER PUBLICATIONS

CAS Registry No. 591225-42-2 (which entered STN on Sep. 23, 2003) (Year: 2003).*
CAS Registry No. 831189-36-7 (which entered STN Feb. 15, 2005) (Year: 2005).*
CAS Registry No. 1287413-34-6 (which entered STN Apr. 29, 2011) (Year: 2011).*
Brodsky, "RNA Helicase DHX33 Puts a New Twist on NLRP3 Inflammasome Activation," Immunity, 39: 94-96 (2013).
McMillan et al., "Chemistry—First Approach for Nomination of Personalized Treatment in Lung Cancer," Cell, 173: 864-878 (2018).
International Search Report issued in corresponding International Patent Application No. PCT/CN2021/115973 dated Nov. 25, 2021.
Ciapetti et al., "Molecular Variations Based on Isosteric Replacements", Chapter 8, The Practice of Medicinal Chemistry, Elsevier Science & Technology, 2015, pp. 181-241.

* cited by examiner

*Primary Examiner* — Matthew P Coughlin
*Assistant Examiner* — Quincy McKoy
(74) *Attorney, Agent, or Firm* — Morgan, Lewis & Bockius LLP

(57) ABSTRACT

The present disclosure relates to a class of polycyclic compound inhibiting RNA helicase DHX33 and the application thereof. In particular, the present disclosure relates to a compound as represented by formula VII or a pharmaceutically acceptable form thereof, a pharmaceutical composition comprising the same, a preparation method thereof, and a medical use thereof for preventing and/or treating DHX33-related diseases.

VII

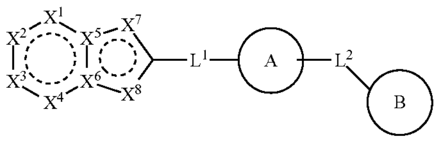

8 Claims, 1 Drawing Sheet

CLASS OF POLYCYCLIC COMPOUNDS INHIBITING RNA HELICASE DHX33 AND THE APPLICATION THEREOF

TECHNICAL FIELD

The present disclosure belongs to the field of medicinal chemistry, and relates to a small molecule inhibitor of DHX33, a pharmaceutical composition comprising the same, a preparation method thereof and a medical use thereof for preventing and/or treating DHX33-related diseases.

BACKGROUND

The present disclosure relates to compounds that inhibit the RNA helicase activity of DHX33. DHX33 belongs to the DEAD/H-box protein family of RNA helicases, wherein DEAD/H represents the abbreviation of the amino acid sequence, i.e., Asp-Glu-Ala-Asp/His. This sequence, together with many other conservative amino acid sequences, appears in the protein sequences of the members of the RNA helicase family and is highly involved in the binding with nucleic acid substrates and ATP hydrolysis. Although these family members have these same sequences in common, each RNA helicase has particular specificity and unique biological function. Human DHX33 protein has a molecular weight of approximately 72 kDa and has the function of unwinding nucleic acids. It utilizes the biological energy released by ATP hydrolysis to drive changes in the conformation of the complex of RNA and protein, thus participating in a variety of metabolic activities of RNA, specifically, a series of biological processes such as the transcription, splicing, editing, translation and degradation of RNA. The function of DHX33 is not merely limited to the modification of RNA molecules. Studies have demonstrated that, in addition to unwinding the two strands of RNA, DHX33 protein is also involved in the metabolism of DNA. Specifically, DHX33 protein is capable of unwinding the double-stranded structure of DNA and playing an important role in the process of gene expression.

Studies have demonstrated that, by binding to a variety of cancer-related gene promoters, DHX33 affects the methylation status of DNA and thus regulates the expression of a variety of cancer genes and the signaling pathways related to the development of tumor at genome level, which plays a crucial role in a variety of cellular activities such as the growth, proliferation, migration, apoptosis and glycometabolism of cells. In addition, it has been found that DHX33 is capable of sensing the invasion of foreign double-stranded RNA molecules and playing an important role in the innate immunity of cells. As a very important cell growth regulatory gene, DHX33 is highly expressed in a variety of cancers such as lung cancer, lymphoma, glioblastoma, breast cancer, colon cancer, liver cancer. The occurrence and development of a variety of cancers depend on the high expression of DHX33 protein. Genetic knockout of DHX33 is capable of significantly inhibiting the occurrence and development of the lung cancer driven by RAS oncogene. It has been confirmed by in-vivo and in-vitro experiments that, upon the inhibition of DHX33 protein, the occurrence and development of a variety of cancers such as breast cancer, colon cancer, brain glioma and lymphoma are inhibited significantly.

Studies have demonstrated that the function of DHX33 protein depends on its helicase activity. A DHX33 mutant lacking the helicase activity does not have the function of DHX33 protein, and the function of the wild-type DHX33 gene cannot be replaced. The present disclosure provides the structures and the synthetic methods of a variety of compounds capable of inhibiting the enzymatic activity of DHX33, and these compounds possess uses in the preparation of a drug for treating a disease or a disorder at least partially mediated by DHX33.

SUMMARY

In the present disclosure, a series of small molecule compounds that inhibit the RNA helicase activity of DHX33 have been found through extensive studies, and these compounds have potential value in preventing and/or treating DHX33-related diseases.

In a first aspect, the present disclosure provides a compound having the structure of formula VII or a pharmaceutically acceptable form thereof:

VII

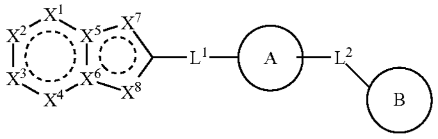

wherein

- $X^1$ is N or $CR^1$, $X^2$ is N or $CR^2$, $X^3$ is N or $CR^3$, $X^4$ is N or $CR^4$, $X^1$ and $X^6$ are N or C;
- $R^1$, $R^2$, $R^3$ and $R^4$ are each independently hydrogen, halogen, amino, nitro, hydroxyl, cyano, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, —NH($C_{1-6}$ alkyl), —N($C_{1-6}$ alkyl)$_2$, $C_{1-6}$ hydroxyalkyl, —O—($C_{1-6}$ alkylene)-O—($C_{1-6}$ alkyl), —S—($C_{1-6}$ alkylene)-O—($C_{1-6}$ alkyl), —C(═O)—NH—($C_{1-6}$ alkyl), —C(═O)—NH—($C_{1-6}$ alkylene)-N($C_{1-6}$ alkyl)$_2$, or —C(═O)—O—($C_{1-6}$ alkyl);
- alternatively, $R^2$ and $R^3$ together with the atoms to which they are attached form a 5-7 membered heterocyclyl;
- $X^7$ and $X^8$ are N, $NR^5$, $CR^5$, or $CR^5R^{11}$, at least one of $X^7$ and $X^8$ is N or $NR^5$, $R^5$ and $R^{11}$ are each independently hydrogen, halogen, $C_{1-6}$ alkyl, $C_{2-4}$ alkenyl, $C_{2-4}$ alkynyl, —($C_{1-4}$ alkylene)-O—($C_{1-4}$ alkyl), or —($C_{1-4}$ alkylene)-S—($C_{1-4}$ alkyl);
- $L^1$ is —$CR^6$═$CR^6$, —$NR^6$C(═O)—, —$NR^6$S(═O)$_2$—, —$NR^6$(═O)—, —C(═O)$NR^6$—, —S(═O)$_2NR^6$—, or —S(═O)$NR^6$—;
- each $R^6$ is independently hydrogen, cyano, halogen, $C_{1-6}$ alkyl, $C_{1-6}$ haloalkyl, $C_{1-6}$ alkoxy, $C_{2-4}$ alkenyl, $C_{2-4}$ alkynyl, $C_{3-8}$ cycloalkyl, $C_{6-10}$ aryl, or a 6-10 membered heteroaryl;
- alternatively, $R^1$ and $R^6$ together with the atoms to which they are attached form a 5-7 membered heterocyclyl or a 5-7 membered heteroaryl;
- ring A is a 5-10 membered heteroaryl or a 3-8 membered heterocyclyl, ring A is optionally substituted with one or more $R^7$;
- each $R^7$ is independently halogen, $C_{1-6}$ alkyl, or $C_{1-6}$ haloalkyl;
- $L^2$ is a single bond, O, S, or $CR^8R^9$;
- $R^8$ and $R^9$ are each independently hydrogen, halogen, or $C_{1-6}$ alkyl;
- ring B is $C_{6-10}$ aryl, a 5-12 membered heteroaryl, or a 3-8 membered heterocyclyl, ring B is optionally substituted with one or more $R^{10}$; when ring B is a furan ring, $R^1$, $R^2$, $R^3$ and $R^4$ are not hydrogen at the same time;

each $R^{10}$ is independently halogen, cyano, amino, nitro, hydroxyl, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{3-4}$ cycloalkyl, —C(═O)—O—($C_{1-6}$ alkyl), —C(═O)—$NH_2$, —C(═O)—NH($C_{1-6}$ alkyl), —C(═O)—NH($C_{1-6}$ alkylene-$NH_2$), —C(═O)—N($C_{1-6}$ alkylene-$NH_2$)—C(═O)—$NH_2$, —C(═O)—N($C_{1-6}$ alkylene-$NH_2$)—C(═O)—NH($C_{1-6}$ alkyl), —NH($C_{1-6}$ alkyl), —N($C_{1-6}$ akyl)$_2$, —NH—C(═O)—($C_{1-6}$ alkyl), —$C_{1-6}$ alkylene-NH—C(═O)—$C_{1-6}$ alkyl, benzyl, $C_{6-10}$ aryl, a 5-7 membered heterocyclyl, or a 5-7 membered heteroaryl, said 5-7 membered heterocyclyl or 5-7 membered heteroaryl is optionally substituted with one or more substituents selected from hydrogen, halogen, cyano, amino, hydroxyl, $C_{1-6}$ alkyl and $C_{1-6}$ alkoxy;

said pharmaceutically acceptable form is selected from a pharmaceutically acceptable salt, an ester, a stereoisomer, a tautomer, a solvate, a N-oxide, an isotopically labeled form, a metabolite and a prodrug.

In some embodiments, $R^1$, $R^2$, $R^3$ and $R^4$ in the above-mentioned compound of formula VII or the pharmaceutically acceptable form thereof are each independently hydrogen, halogen, amino, nitro, hydroxyl, cyano, $C_{1-6}$ alkyl, $C_{1-6}$ haloalkyl, $C_{1-6}$ alkoxy, $C_{1-6}$ haloalkoxy, —NH($C_{1-6}$ alkyl), —N($C_{1-6}$ alkyl)$_2$, $C_{1-4}$ hydroxyalkyl, —O—($C_{1-6}$ alkylene)-O—($C_{1-6}$ alkyl), —C(═O)—NH—($C_{1-6}$ alkyl), —C(═O)—NH—($C_{1-6}$ alkylene)-N($C_{1-6}$ alkyl)$_2$, or —C(═O)—($C_{1-6}$ alkyl).

In some preferred embodiments, $R^1$, $R^2$, $R^3$ and $R^4$ in the above-mentioned compound of formula VII or the pharmaceutically acceptable form thereof are each independently hydrogen, halogen, amino, nitro, hydroxyl, cyano, $C_{1-4}$ alkyl, $C_{1-4}$ haloalkyl, $C_{1-4}$ alkoxy, $C_{1-4}$ haloalkoxy, —NH($C_{1-4}$ alkyl), —N($C_{1-4}$ alkyl)$_2$, $C_{1-4}$ hydroxyalkyl, —O—($C_{1-4}$ alkylene)-O—($C_{1-4}$ alkyl), —C(═O)—NH—($C_{1-4}$ alkyl), —C(═O)—NH—($C_{1-4}$ alkylene)-N($C_{1-4}$ alkyl)$_2$, or —C(═O)—O—($C_{1-4}$ alkyl).

In some more preferred embodiments, $R^1$, $R^2$, $R^3$ and R in the above-mentioned compound of formula VII or the pharmaceutically acceptable form thereof are each independently hydrogen, halogen, amino, nitro, hydroxyl, $C_{1-4}$ alkyl, $C_{1-4}$ haloalkyl, $C_{1-4}$ alkoxy, or $C_{1-4}$ haloalkoxy.

In some particularly preferred embodiments, $R^1$, $R^2$, $R^3$ and $R^4$ in the above-mentioned compound of formula VII or the pharmaceutically acceptable form thereof are each independently hydrogen, halogen, amino, nitro, hydroxyl, methyl, methoxy, or trifluoromethyl, and at least two of $R^1$, $R^2$, $R^3$ and $R^4$ are hydrogen at the same time.

In some embodiments, $R^2$ and $R^3$ in the above-mentioned compound of formula VII or the pharmaceutically acceptable form thereof, together with the atoms to which they are attached, form a 5-7 membered heterocyclyl.

In some embodiments, $R^1$, $R^2$. $R^3$ and $R^4$ in the above-mentioned compound of formula VII or the pharmaceutically acceptable form thereof are not hydrogen at the same time.

In some embodiments, $R^{10}$ and $R^{11}$ in the above-mentioned compound of formula VII or the pharmaceutically acceptable form thereof are each independently hydrogen, halogen, $C_{1-6}$ alkyl, $C_{2-4}$ alkenyl, —($C_{1-4}$ alkylene)-O—($C_{1-4}$ alkyl), or —($C_{1-4}$ alkylene)-S—($C_{1-4}$ alkyl).

In some preferred embodiments, $R^5$ and $R^{11}$ in the above-mentioned compound of formula VII or the pharmaceutically acceptable form thereof are each independently hydrogen, halogen, or methyl.

In some embodiments, $L^1$ in the above-mentioned compound of formula VII or the pharmaceutically acceptable form thereof is —$CR^6$ ═CR, —$NR^6$C(═O)—, —$NR^6$S(═O)$_2$—, —C(═O)$NR^6$—, or —S(═O)$_2$$NR^6$—, and each $R^6$ is independently hydrogen, cyano, halogen, $C_{1-6}$ alkyl, $C_{1-6}$ haloalkyl, $C_{1-6}$ alkoxy, $C_{2-4}$ alkenyl, $C_{2-4}$ alkynyl, $C_{3-8}$ cycloalkyl or $C_{6-10}$ aryl.

In some preferred embodiments, $L^1$ in the above-mentioned compound of formula VII or the pharmaceutically acceptable form thereof is —$CR^6$ ═$CR^6$, —NHC(═O)—, —N($CH_3$)—C(═O)—, —NH—S(═O)$_2$—, —C(═O)NH—, or —S(═O)$_2$NH—, and each $R^6$ is independently hydrogen, cyano, or methyl.

In some embodiments, $R^5$ and $R^6$ in the above-mentioned compound of formula VII or the pharmaceutically acceptable form thereof, together with the atoms to which they are attached, form a 5-7 membered heterocyclyl or a 5-7 membered heteroaryl.

In some embodiments, ring A in the above-mentioned compound of formula VII or the pharmaceutically acceptable form thereof is a 5-10 membered heteroaryl, ring A is optionally substituted with one or more $R^7$; and each $R^7$ is independently halogen, $C_{1-4}$ alkyl, or $C_{1-4}$ haloalkyl.

In some preferred embodiments, ring A in the above-mentioned compound of formula VII or the pharmaceutically acceptable form thereof is pyrrolyl, pyrazolyl, imidazolyl, thiazolyl, thiadiazolyl, or oxazolyl, ring A is optionally substituted with one or more $R^7$, and each $R^7$ is independently halogen, methyl, ethyl, or trifluoromethyl.

In some more preferred embodiments, ring A in the above-mentioned compound of formula VII or the pharmaceutically acceptable form thereof is pyrrolyl or imidazolyl, ring A is optionally substituted with one or more R, and each $R^7$ is independently halogen or methyl.

In some particularly preferred embodiments, ring A in the above-mentioned compound of formula VII or the pharmaceutically acceptable form thereof is

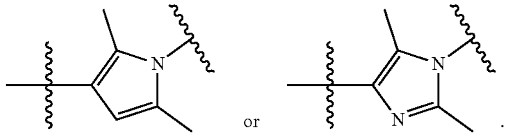

In some embodiments, $L^2$ in the above-mentioned compound of formula VII or the pharmaceutically acceptable form thereof is a single bond, O, S, or $CR^8R^9$; and $R^8$ and $R^9$ are each independently hydrogen, halogen, or $C_{1-4}$ alkyl.

In some preferred embodiments, $L^2$ in the above-mentioned compound of formula VII or the pharmaceutically acceptable form thereof is a single bond or $CR^8R^9$; and $R^8$ and $R^9$ are each independently hydrogen, halogen, or methyl.

In some embodiments, ring B in the above-mentioned compound of formula VII or the pharmaceutically acceptable form thereof is $C_{6-10}$ aryl or a 5-12 membered heteroaryl, ring B is optionally substituted with one or more $R^{10}$, when ring B is a furan ring, $R^1$, $R^2$, $R^3$ and R are not hydrogen at the same time, and each $R^{10}$ is independently halogen, cyano, amino, nitro, hydroxyl, $C_{1-6}$ alkyl, $C_{1-6}$ haloalkyl, $C_{1-6}$ alkoxy, $C_{1-6}$ haloalkoxy, $C_{3-4}$ cycloalkyl, —C(═O)—O—($C_{1-6}$ alkyl), —C(═O)—$NH_2$, —C(═O)—NH($C_{1-6}$ alky), —NH($C_{1-6}$ alkyl), —N($C_{1-6}$ alkyl)$_2$, —NH—C(═O)—($C_{1-6}$ alkyl), —$C_{1-6}$ alkylene-NH—C(═O)—$C_{1-6}$ alkyl, benzyl, $C_{1-6}$ aryl, a 5-7 membered heterocyclyl, or a 5-7 membered heteroaryl, said 5-7 membered heterocyclyl or 5-7 membered heteroaryl is optionally substituted with one or more substituents selected from hydrogen, halogen, cyano, amino, hydroxyl, $C_{1-4}$ alkyl and $C_{1-6}$ alkoxy.

In some preferred embodiments, ring B in the above-mentioned compound of formula VII or the pharmaceutically acceptable form thereof is $C_{6-10}$ aryl or a 5-10 membered heteroaryl, ring B is optionally substituted with one or more $R^{10}$, and each $R^{10}$ is independently halogen, cyano, amino, nitro, hydroxyl, $C_{1-4}$ alkyl, $C_{1-4}$ haloalkyl, $C_{1-4}$ alkoxy, $C_{1-4}$ haloalkoxy, $C_{3-4}$ cycloalkyl, —C(═O)—O—($C_{1-4}$ alkyl), —C(═O)—$NH_2$, —$C_{1-4}$ alkylene-NH—C(═O)—$C_{1-4}$ alkyl, benzyl, $C_{6-10}$ aryl, or a 5-7 membered heteroaryl.

In some more preferred embodiments, ring B in the above-mentioned compound of formula VII or the pharmaceutically acceptable form thereof is phenyl, pyrazinyl, pyridyl, pyrimidinyl, furanyl, oxazolyl, thienyl, thiazolyl, pyrazolyl, or imidazolyl, ring B is optionally substituted with one or more $R^{10}$, and each $R^{10}$ is independently halogen, cyano, amino, nitro, hydroxyl, methyl, ethyl, isopropyl, cyclopropyl, trifluoromethyl, methoxy, trifluoromethoxy, —C(═O)—$OCH_3$, —C(═O)—$OCH_2CH_3$, phenyl, benzyl, pyridyl, —C(═O)—$NH_2$, or —$CH_2$—NH—C(═O)—$CH_3$.

In some particularly preferred embodiments, ring B in the above-mentioned compound of formula VII or the pharmaceutically acceptable form thereof is

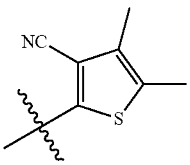 , 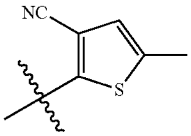 , 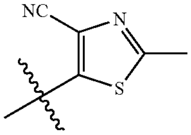 , 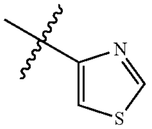 , 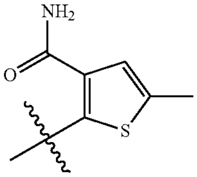 , 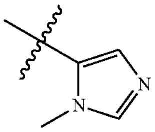 , 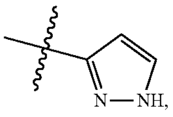 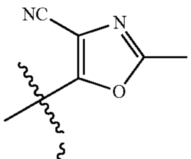 , 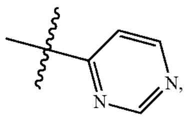 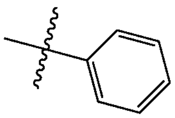 , 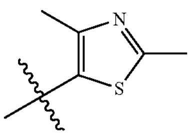 , 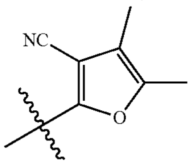 , -continued

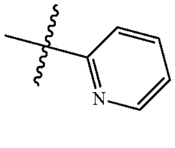 , 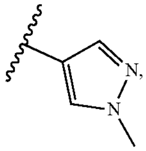 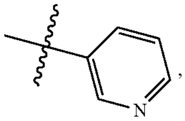 , 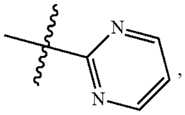 , 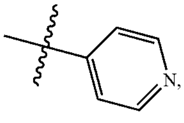 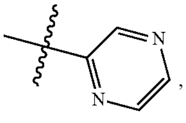 , 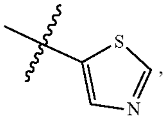 , 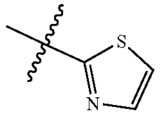 , or 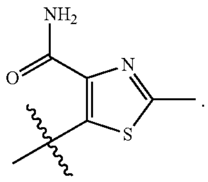 .

In some embodiments, the above-mentioned compound of formula VII or the pharmaceutically acceptable form thereof is a compound having the structure of any one of formula VII to formula VII-9 or a pharmaceutically acceptable form thereof:

VII-1

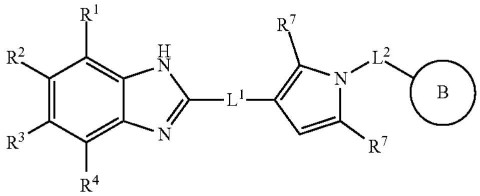

VII-2

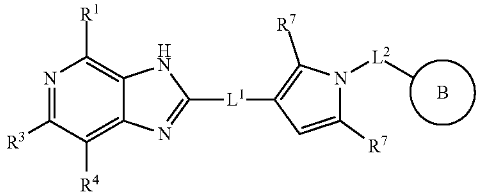

VII-3

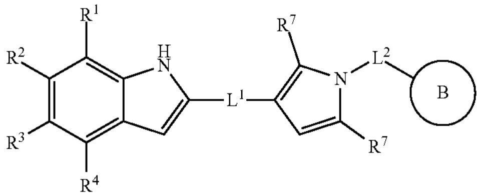

-continued

VII-4

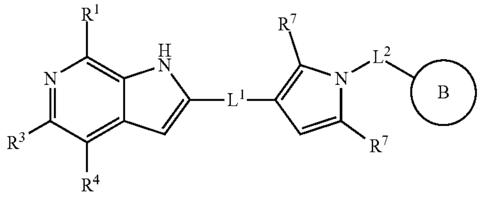

VII-5

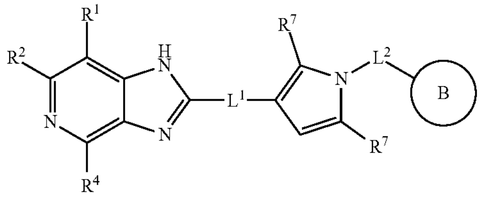

VII-6

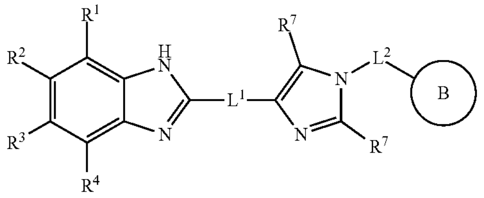

VII-7

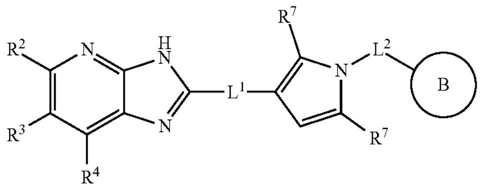

VII-8

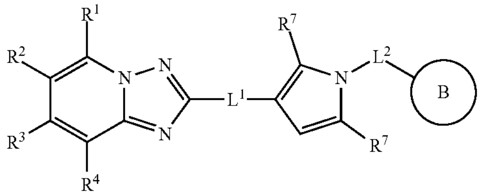

VII-9

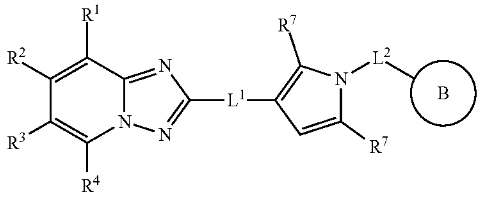

wherein $R^1$, $R^2$, $R^3$, $R^4$, $R^7$, $L^1$, $L^2$ and ring B are as defined in formula VII.

In some embodiments, the present disclosure provides a compound having the structure of formula I or a pharmaceutically acceptable form thereof:

I

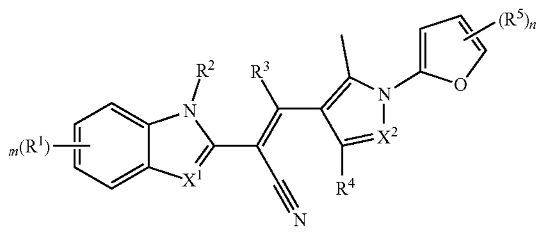

wherein each $R^1$ is independently halogen, amino, —NH($C_{1-4}$ alkyl), —N($C_{1-4}$ alkyl)$_2$, nitro, $C_{1-4}$ alkyl, $C_{1-4}$haloalkyl, $C_{1-4}$ alkoxy, $C_{1-4}$ haloalkoxy. $C_{1-4}$ hydroxyalkyl, —O—($C_{1-4}$ alkylene)-O—($C_{1-4}$ alkyl), —C(═O)—NH—($C_{1-4}$ alkylene)-N($C_{1-4}$ alkyl)$_2$, or —C(═O)—O—($C_{1-4}$ alkyl), alternatively, a plurality of $R^1$ and the atoms to which they are attached form a 5-7 membered ring;

$R^2$ is hydrogen, $C_{1-4}$ alkyl, or —($C_{1-4}$ alkylene)-O—($C_{1-4}$ alkyl);

$X^1$ is N or —$CR^6$;

$R^6$ is hydrogen or $C_{1-4}$ alkyl;

$R^3$ is hydrogen or $C_{1-4}$ alkyl;

$R^4$ is hydrogen or $C_{1-4}$ alkyl;

$X^2$ is N or —$CR^7$;

$R^7$ is hydrogen or $C_{1-4}$ alkyl;

each $R^5$ is independently halogen, cyano, $C_{1-4}$ alkyl, $C_{1-4}$ haloalkyl, $C_{1-4}$ alkoxy, $C_{1-4}$ haloalkoxy, $C_{3-6}$ cycloalkyl, —C(═O)—O—($C_{1-4}$ alkyl), phenyl, benzyl, pyridyl, —C(═O)—$NH_2$, or —NH—C(═O)—($C_{1-4}$ alkyl), said phenyl, benzyl and pyridyl are optionally substituted with one or more substituents selected from halogen, cyano, amino, hydroxyl, $C_{1-4}$ alkyl and $C_{1-4}$ alkoxy;

m is 0, 1, 2, 3 or 4;

n is 0, 1, 2, 3 or 4;

provided that m is not 0 when

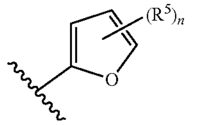

is

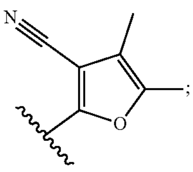

;

and said pharmaceutically acceptable form is selected from a pharmaceutically acceptable salt, an ester, a stereoisomer, a tautomer, a solvate, a N-oxide, an isotopically labeled form, a metabolite and a prodrug.

In some embodiments, each $R^1$ in the above-mentioned compound of formula I or the pharmaceutically acceptable form thereof is independently fluorine, chlorine, bromine, methyl, ethyl, isopropyl, trifluoromethyl, methoxy, ethoxy, isopropoxy, trifluoromethoxy, nitro, amino, —$NH(CH_3)$, —$NH(CH_2CH_3)$, —$N(CH_3)_2$, —$N(CH_2CH_3)_2$, —$CH_2OH$, —$CH_2CH_2OH$, —O—$(CH_2)_2$—$OCH_3$, —C(═O)—NH—$(CH_2)_2$—$N(CH_3)_2$, —C(═O)—NH—$(CH_2)_3$—$N(CH_3)_2$, —C(═O)—$OCH_3$, or —C(═O)—$OCH_2CH_3$, alternatively, two $R^1$ and the atoms to which they are attached form a 6 membered ring;

In some preferred embodiments, each $R^1$ in the above-mentioned compound of formula I or the pharmaceutically acceptable form thereof is independently fluorine, chlorine, bromine, methyl, trifluoromethyl, methoxy, ethoxy, isopropoxy, trifluoromethoxy, nitro, amino, —$NH(CH_3)$, —$N(CH_3)_2$, —$CH_2OH$, —O—$(CH_2)_2$—$OCH_3$, —C(═O)—NH—$(CH_2)_2$—$N(CH_3)_2$, or —C(═O)—$OCH_2CH_3$, alternatively, two $R^1$ and the atoms to which they are attached form

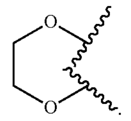

In some embodiments, $R^2$ in the above-mentioned compound of formula I or the pharmaceutically acceptable form thereof is hydrogen, methyl, ethyl, isopropyl, —$(CH_2)_2$—$OCH_3$, or —$CH_2OCH_3$.

In some preferred embodiments, $R^2$ in the above-mentioned compound of formula I or the pharmaceutically acceptable form thereof is hydrogen, methyl, ethyl, or —$CH_2OCH_3$.

In some embodiments, $R^4$ in the above-mentioned compound of formula I or the pharmaceutically acceptable form thereof is hydrogen, methyl, ethyl, or isopropyl.

In some preferred embodiments, $R^6$ in the above-mentioned compound of formula I or the pharmaceutically acceptable form thereof is hydrogen or methyl.

In some embodiments, $R^3$ in the above-mentioned compound of formula I or the pharmaceutically acceptable form thereof is hydrogen, methyl, ethyl, or isopropyl.

In some preferred embodiments, $R^3$ in the above-mentioned compound of formula I or the pharmaceutically acceptable form thereof is hydrogen or methyl.

In some embodiments, $R^4$ in the above-mentioned compound of formula I or the pharmaceutically acceptable form thereof is hydrogen, methyl, ethyl, or isopropyl.

In some preferred embodiments, $R^4$ in the above-mentioned compound of formula I or the pharmaceutically acceptable form thereof is hydrogen or methyl.

In some embodiments, $R^7$ in the above-mentioned compound of formula I or the pharmaceutically acceptable form thereof is hydrogen, methyl, ethyl, or isopropyl.

In some preferred embodiments, $R^7$ in the above-mentioned compound of formula I or the pharmaceutically acceptable form thereof is hydrogen or methyl.

In some embodiments, each $R^5$ in the above-mentioned compound of formula I or the pharmaceutically acceptable form thereof is independently fluorine, chlorine, bromine, cyano, methyl, ethyl, isopropyl, tert-butyl, cyclopropyl, cyclopentyl, cyclohexyl, methoxy, ethoxy, isopropoxy, trifluoromethoxy, —C(═O)—$OCH_3$, —C(═O)—$OCH_2CH_3$, phenyl, benzyl, pyridyl, —C(═O)—$NH_2$, —NH—C(═O)—$CH_3$, or —NH—C(═O)—$CH_2CH_3$.

In some preferred embodiments, each $R^5$ in the above-mentioned compound of formula I or the pharmaceutically acceptable form thereof is independently fluorine, chlorine, bromine, cyano, methyl, ethyl, isopropyl, tert-butyl, cyclopropyl, methoxy, trifluoromethoxy, —C(═O)—$OCH_3$, —C(═O)—$OCH_2CH_3$, phenyl, benzyl, pyridyl, —C(═O)—$NH_2$, or —NH—C(═O)—$CH_3$.

In some more preferred embodiments, each $R^5$ in the above-mentioned compound of formula I or the pharmaceutically acceptable form thereof is independently cyano, methyl, or phenyl.

In some embodiments, the above-mentioned compound of formula I or the pharmaceutically acceptable form thereof is a compound of formula Ia-1 or a pharmaceutically acceptable form thereof, Ia-1

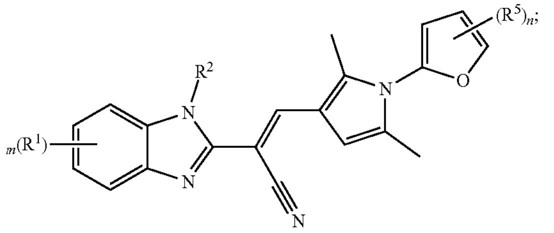

wherein $R^1$, $R^2$, $R^5$ m and n are as defined in formula I.

In some preferred embodiments, the above-mentioned compound of formula I or the pharmaceutically acceptable form thereof is a compound of formula Ib-1 or formula Ib-2 or a pharmaceutically acceptable form thereof, Ib-1

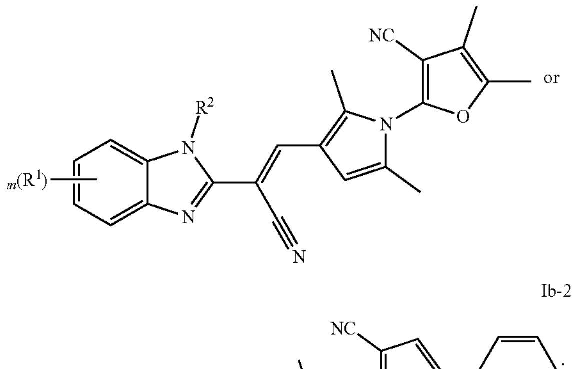

or

Ib-2

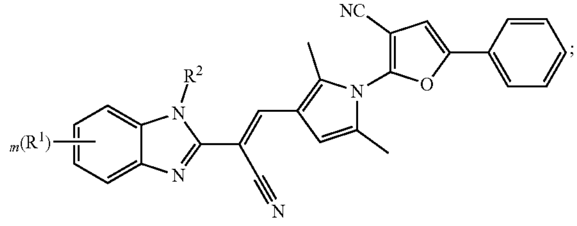

wherein $R^1$, $R^2$ and m are as defined in formula I.

In some embodiments, the present disclosure provides a compound having the structure of formula II or a pharmaceutically acceptable form thereof,

II

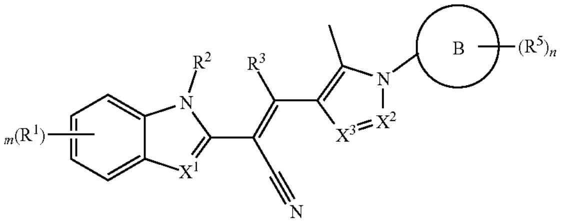

wherein each $R^1$ is independently halogen, amino, —NH($C_{1-4}$ alkyl), —N($C_{1-6}$ alkyl)$_2$, nitro, $C_{1-4}$ alkyl, $C_{1-4}$ haloalkyl, $C_{1-4}$ alkoxy, $C_{1-4}$ haloalkoxy, $C_{1-4}$ hydroxyalkyl, —O—($C_{1-4}$ alkylene)-O—($C_{1-4}$ alkyl), —C(═O)—NH—($C_{1-4}$ alkylene)-N($C_{1-4}$ alkyl)$_2$, or —C(═O)—O—($C_{1-4}$ alkyl), alternatively, a plurality of $R^1$ and the atoms to which they are attached form a 5-7 membered ring;

$R^2$ is hydrogen, $C_{1-4}$ alkyl, or —($C_{1-4}$ alkylene)-O—($C_{1-4}$ alkyl);

$X^1$ is N or —$CR^6$;

$R^6$ is hydrogen, halogen, or $C_{1-4}$ alkyl;

$R^3$ is hydrogen or $C_{1-6}$ alkyl, alternatively, $R^3$ and $R^2$ together with the atoms to which they are attached form a 5-6 membered ring;

$X^1$ is N or —$CR^7$;

$R^7$ is hydrogen, halogen, $C_{1-4}$ alkyl, or $C_{1-4}$ haloalkyl;

$X^3$ is N or —$CR^4$;

$R^4$ is hydrogen, halogen, or $C_{1-4}$ alkyl;

B is oxazolyl, isoxazolyl, oxadiazolyl, thienyl, thiazolyl, isothiazolyl, thiadiazolyl, phenyl, or pyridyl;

each $R^5$ is independently halogen, cyano, $C_{1-4}$ alkyl, $C_{1-4}$ haloalkyl, CIA alkoxy, $C_{1-4}$ haloalkoxy, $C_{3-6}$ cycloalkyl, —C(═O)—O—($C_{1-4}$ alkyl), phenyl, benzyl, pyridyl, —C(═O)—$NH_2$, or —NH—C(═O)—($C_{1-4}$ alkyl), said phenyl, benzyl and pyridyl are optionally substituted with one or more substituents selected from halogen, cyano, amino, hydroxyl, $C_{1-4}$ alkyl and $C_{1-6}$ alkoxy;

m is 0, 1, 2, 3 or 4;

n is 0, 1, 2, 3 or 4; and said pharmaceutically acceptable form is selected from a pharmaceutically acceptable salt, an ester, a stereoisomer, a tautomer, a solvate, a N-oxide, an isotopically labeled form, a metabolite and a prodrug.

In some embodiments, each $R^1$ in the above-mentioned compound of formula II or the pharmaceutically acceptable form thereof is independently fluorine, chlorine, bromine, methyl, ethyl, isopropyl, trifluoromethyl, methoxy, ethoxy, isopropoxy, trifluoromethoxy, nitro, amino, —NH($CH_3$), —NH($CH_2CH_3$), —N($CH_3$)$_2$, —N($CH_2CH_3$)$_2$, —$CH_2OH$, —$CH_2CH_2OH$, —O—($CH_2$)$_2$—$OCH_3$, —C(═O)—NH—($CH_2$)$_2$—N($CH_3$)$_2$, —C(═O)—NH—($CH_2$)$_3$—N($CH_3$)$_2$, —C(═O)—$OCH_3$, or —C(═O)—$OCH_2CH_3$.

In some preferred embodiments, each $R^1$ in the above-mentioned compound of formula II or the pharmaceutically acceptable form thereof is independently fluorine, chlorine, bromine, methyl, trifluoromethyl, methoxy, ethoxy, isopropoxy, trifluoromethoxy, nitro, amino, —NH($CH_3$), —N($CH_3$)$_2$, —$CH_2OH$, —O—($CH_2$)$_2$—$OCH_3$, —C(═O)—NH—($CH_2$)$_2$—N($CH_3$)$_2$, or —C(═O)—$OCH_2CH_3$.

In some more preferred embodiments, each $R^1$ in the above-mentioned compound of formula II or the pharmaceutically acceptable form thereof is independently fluorine, trifluoromethyl, methoxy, or trifluoromethoxy.

In some embodiments, m in the above-mentioned compound of formula II or the pharmaceutically acceptable form thereof is 0, 1, 2 or 3.

In some embodiments, $R^2$ in the above-mentioned compound of formula II or the pharmaceutically acceptable form thereof is hydrogen, methyl, ethyl, isopropyl, —($CH_2$)—$OCH_3$, or —$CH_2OCH_3$, alternatively, $R^2$ and $R^3$ together with the atoms to which they are attached form a 5-6 membered ring.

In some preferred embodiments, $R^2$ in the above-mentioned compound of formula II or the pharmaceutically acceptable form thereof is hydrogen, methyl, ethyl, or —$CH_2OCH_3$.

In some embodiments, $R^6$ in the above-mentioned compound of formula II or the pharmaceutically acceptable form thereof is hydrogen, fluorine, chlorine, bromine, methyl, ethyl, or isopropyl.

In some preferred embodiments, $R^6$ in the above-mentioned compound of formula II or the pharmaceutically acceptable form thereof is hydrogen or methyl.

In some embodiments, $R^3$ in the above-mentioned compound of formula II or the pharmaceutically acceptable form thereof is hydrogen, methyl, ethyl, or isopropyl, alternatively, $R^3$ and $R^2$ together with the atoms to which they are attached form a 5-6 membered ring.

In some preferred embodiments, $R^3$ in the above-mentioned compound of formula II or the pharmaceutically acceptable form thereof is hydrogen or methyl.

In some embodiments, $R^7$ in the above-mentioned compound of formula II or the pharmaceutically acceptable form thereof is hydrogen, fluorine, chlorine, bromine, methyl, ethyl, isopropyl, or trifluoromethyl.

In some preferred embodiments, $R^7$ in the above-mentioned compound of formula II or the pharmaceutically acceptable form thereof is hydrogen or methyl.

In some embodiments, $R^4$ in the above-mentioned compound of formula II or the pharmaceutically acceptable form thereof is hydrogen, fluorine, chlorine, bromine, methyl, ethyl, or isopropyl.

In some preferred embodiments, $R^4$ in the above-mentioned compound of formula II or the pharmaceutically acceptable form thereof is hydrogen or methyl.

In some embodiments, B in the above-mentioned compound of formula II or the pharmaceutically acceptable form thereof is

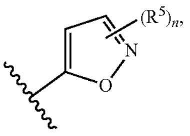

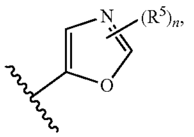

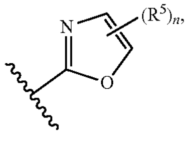

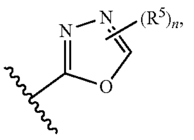

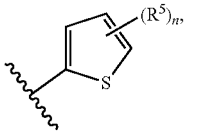

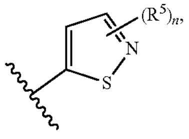

-continued

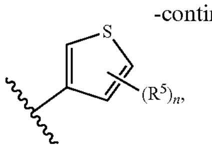

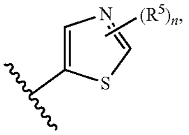

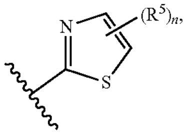

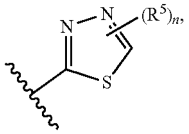

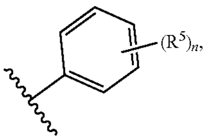

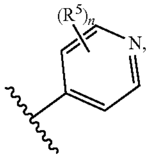

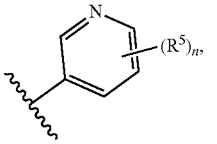

or

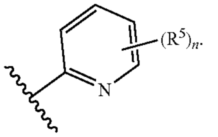

In some embodiments, each $R^5$ in the above-mentioned compound of formula II or the pharmaceutically acceptable form thereof is independently fluorine, chlorine, bromine, cyano, methyl, ethyl, isopropyl, tert-butyl, cyclopropyl, cyclopentyl, cyclohexyl, trifluoromethyl, methoxy, ethoxy, isopropoxy, trifluoromethoxy. —C(=O)—$OCH_3$, —C(=O)—$OCH_2CH_3$, phenyl, benzyl, pyridyl, —C(=O)—$NH_2$, —NH—C(=O)—$CH_3$, or —NH—C(=O)—$CH_2CH_3$.

In some preferred embodiments, each $R^5$ in the above-mentioned compound of formula II or the pharmaceutically acceptable form thereof is independently fluorine, chlorine, bromine, cyano, methyl, ethyl, isopropyl, trifluoromethyl, methoxy, trifluoromethoxy, —C(=O)—$OCH_3$, phenyl, benzyl, pyridyl, —C(=O)—$NH_2$, or —NH—C(=O)—$CH_3$.

In some more preferred embodiments, each $R^5$ in the above-mentioned compound of formula II or the pharmaceutically acceptable form thereof is independently cyano, methyl, trifluoromethyl, methoxy, trifluoromethoxy, —C(=O)—$OCH_3$, or —NH—C(=O)—$CH_3$.

In some embodiments, n in the above-mentioned compound of formula II or the pharmaceutically acceptable form thereof is 0, 1, 2 or 3.

In some embodiments, the above-mentioned compound of formula II or the pharmaceutically acceptable form thereof is a compound of any one of formula IIa-1 to formula IIa-5 or a pharmaceutically acceptable form thereof, IIa-1

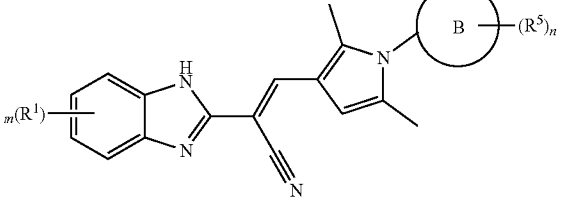

-continued

IIa-2

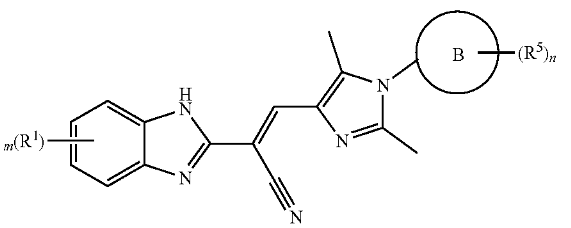

IIa-3

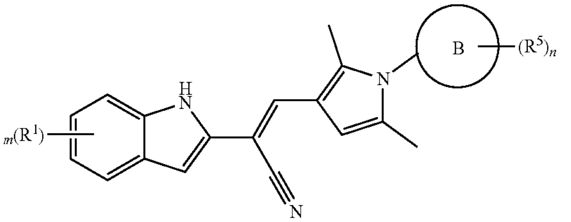

IIa-4

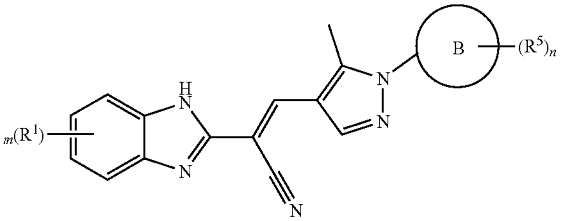

IIa-5

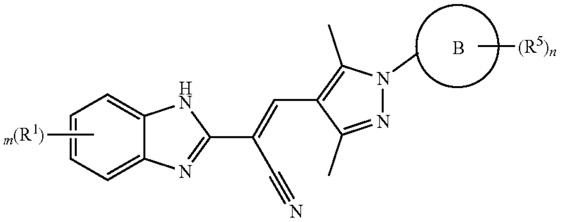

wherein B, $R^1$, R, m and n are as defined in formula II.

In some embodiments, the present disclosure provides a compound having the structure of formula I or a pharmaceutically acceptable form thereof,

III

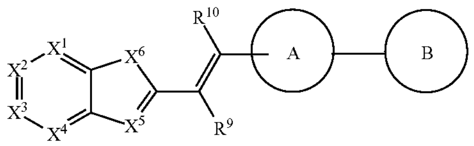

wherein $X^1$ is N or $CR^1$, $X^2$ is N or CR, $X^3$ is N or $CR^3$, $X^4$ is N or $CR^4$, provided that at least one of $X^1$, $X^2$, $X^3$ and $X^4$ is N;

$R^1$, $R^2$, $R^3$ and $R^4$ are each independently hydrogen, halogen, amino, nitro, hydroxyl, $C_{1-4}$ alkyl, $C_{1-4}$ haloalkyl, $C_{1-4}$ alkoxy, $C_{1-4}$ haloalkoxy, —NH($C_{1-4}$ alkyl), —N($C_{1-4}$ alkyl)$_2$, $C_{1-4}$ hydroxyalkyl, —O—($C_{1-4}$ alkylene)-O—($C_{1-4}$ alkyl), —C(=O)—NH—($C_{1-4}$ alkyl), —C(=O)—NH—($C_{1-4}$ alkylene)-N($C_{1-4}$ alkyl)$_2$, or —C(=O)—O—($C_{1-4}$ alkyl);

$X^5$ is N or $CR^5$, $X^6$ is Ne or $CR^7R^8$, provided that at least one of $X^5$ and $X^6$ is N or a nitrogen-containing group;

$R^5$ is hydrogen or $C_{1-4}$ alkyl; $R^6$ is hydrogen, $C_{1-4}$ alkyl, or —($C_{1-4}$ alkylene)-O—($C_{1-4}$ alkyl);

$R^7$ and $R^8$ are each independently hydrogen or $C_{1-4}$ alkyl;

$R^{10}$ is hydrogen, $C_{1-4}$ alkyl, or $C_{2-4}$ alkenyl, alternatively, $R^{10}$ and $X^6$ together with the atoms to which they are attached form a 5-7 membered ring;

$R^9$ is hydrogen, cyano, halogen, $C_{1-4}$ alkyl, or $C_{2-4}$ alkenyl;

ring A is a pyrrole ring, a pyrazole ring, an imidazole ring, a thiazole ring, or an oxazole ring, alternatively, ring A and $R^9$ together with the atoms to which they are attached form an indole ring, an isoindole ring, a benzimidazole ring, a benzothiazole ring, or a benzoxazole ring;

ring A is optionally substituted with one or more $R^{11}$;

each $R^{11}$ is independently halogen, $C_{1-4}$alkyl, or $C_{1-4}$ haloalkyl;

ring B is a pyrrole ring, a pyrazole ring, an imidazole ring, a triazole ring, a furan ring, an oxazole ring, an isoxazole ring, an oxadiazole ring, a thiophene ring, a thiazole ring, an isothiazole ring, a thiadiazole ring, a benzene ring, or a pyridine ring, ring B is optionally substituted with one or more $R^{12}$;

each $R^{12}$ is independently halogen, cyano, amino, nitro, hydroxyl, $C_{1-4}$ alkyl, $C_{1-4}$ haloalkyl, $C_{1-4}$ alkoxy, $C_{1-4}$ haloalkoxy, $C_{3-4}$ cycloalkyl, —C(═O)—O—($C_{1-4}$ alkyl), phenyl, benzyl, pyridyl, —C(═O)—$NH_2$, or —NH—C(═O)—($C_{1-4}$ alkyl), said phenyl, benzyl and pyridyl are optionally substituted with one or more substituents selected from hydrogen, halogen, cyano, amino, hydroxyl, $C_{1-4}$ alkyl and $C_{1-4}$ alkoxy; and said pharmaceutically acceptable form is selected from a pharmaceutically acceptable salt, an ester, a stereoisomer, a tautomer, a solvate, a N-oxide, an isotopically labeled form, a metabolite and a prodrug.

In some embodiments, $R^1$, $R^2$, $R^3$ and $R^4$ in the above-mentioned compound of formula III or the pharmaceutically acceptable form thereof are each independently hydrogen, fluorine, chlorine, bromine, amino, nitro, methyl, ethyl, isopropyl, trifluoromethyl, methoxy, ethoxy, isopropoxy, trifluoromethoxy, —$NH(CH_3)$, —$NH(CH_2CH_3)$, —$N(CH_3)_2$, —$N(CH_2CH_3)_2$, —$CH_2OH$, —$CH_2CH_2OH$, —O—$(CH_2)_2$—$OCH_3$, —C(═O)—NH—$CH_3$, —C(═O)—NH—$(CH_2)_2$—$N(CH_3)_2$, —C(═O)—NH—$(CH_2)_3$—$N(CH_3)_2$, —C(═O)—$OCH_3$, or —C(═O)—$OCH_2CH_3$.

In some preferred embodiments, $R^1$, $R^2$, $R^3$ and $R^4$ in the above-mentioned compound of formula III or the pharmaceutically acceptable form thereof are each independently hydrogen, fluorine, chlorine, bromine, amino, nitro, methyl, trifluoromethyl, methoxy, ethoxy, isopropoxy, trifluoromethoxy, —$NH(CH_3)$, —$N(CH_3)_2$, —$CH_2OH$, —O—$(CH_2)_2$—$OCH_3$, —C(═O)—NH—$CH_3$, —C(═O)—NH—$(CH_2)_2$—$N(CH_3)_2$, or —C(═O)—$OCH_2CH_3$.

In some more preferred embodiments, $R^1$, $R^2$, $R^3$ and $R^4$ in the above-mentioned compound of formula III or the pharmaceutically acceptable form thereof are each independently hydrogen, chlorine, trifluoromethyl, methoxy, trifluoromethoxy, —$NH(CH_3)$, —$N(CH_3)_2$, —C(═O)—NH—$CH_3$, or —C(═O)—NH—$(CH_2)_2$—$N(CH_3)_2$.

In some embodiments, $R^5$ in the above-mentioned compound of formula III or the pharmaceutically acceptable form thereof is hydrogen, methyl, ethyl, or isopropyl.

In some preferred embodiments, $R^5$ in the above-mentioned compound of formula III or the pharmaceutically acceptable form thereof is hydrogen or methyl.

In some embodiments, $R^6$ in the above-mentioned compound of formula III or the pharmaceutically acceptable form thereof is hydrogen, methyl, ethyl, isopropyl, —$(CH_2)_2$—$OCH_3$, or —$CH_2OCH_3$.

In some preferred embodiments, $R^6$ in the above-mentioned compound of formula m or the pharmaceutically acceptable form thereof is hydrogen, methyl, ethyl, or —$CH_2OCH_3$.

In some embodiments, $R^7$ and $R^8$ in the above-mentioned compound of formula III or the pharmaceutically acceptable form thereof are each independently hydrogen, methyl, ethyl, or isopropyl.

In some preferred embodiments, $R^7$ and $R^8$ in the above-mentioned compound of formula III or the pharmaceutically acceptable form thereof are each independently hydrogen or methyl.

In some embodiments, $R^{10}$ in the above-mentioned compound of formula III or the pharmaceutically acceptable form thereof is hydrogen, methyl, ethyl, or isopropyl.

In some preferred embodiments, $R^{10}$ in the above-mentioned compound of formula III or the pharmaceutically acceptable form thereof is hydrogen or methyl.

In some embodiments, $R^{10}$ and $X^6$ in the above-mentioned compound of formula III or the pharmaceutically acceptable form thereof, together with the atoms to which they are attached, form a 5-7 membered ring.

In some preferred embodiments, when $R^{10}$ and $X^6$ together with the atoms to which they are attached form a ring,

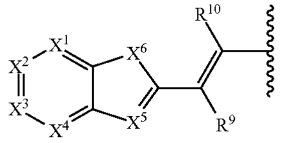

is

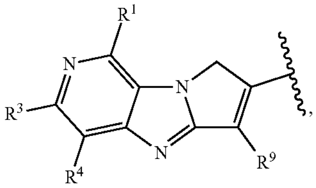

,

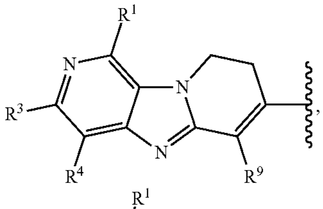

, or

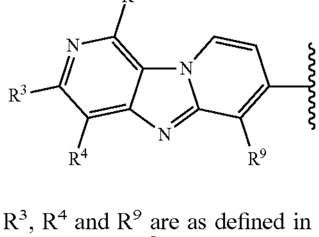

;

wherein $R^1$, $R^3$, $R^4$ and $R^9$ are as defined in formula III.

In some embodiments, $R^9$ in the above-mentioned compound of formula III or the pharmaceutically acceptable form thereof is hydrogen, fluorine, chlorine, bromine, cyano, methyl, ethyl, or isopropyl.

In some preferred embodiments, $R^9$ in the above-mentioned compound of formula III or the pharmaceutically acceptable form thereof is cyano.

In some embodiments, ring A in the above-mentioned compound of formula III or the pharmaceutically acceptable form thereof is

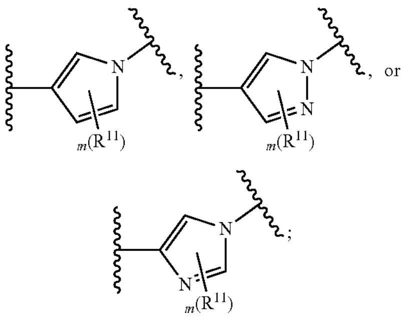

, or ;

wherein m is 0, 1, 2 or 3, and $R^9$ is as defined in formula M.

In some embodiments, ring A and $R^9$ in the above-mentioned compound of formula III or the pharmaceutically acceptable form thereof, together with the atoms to which they are attached, form

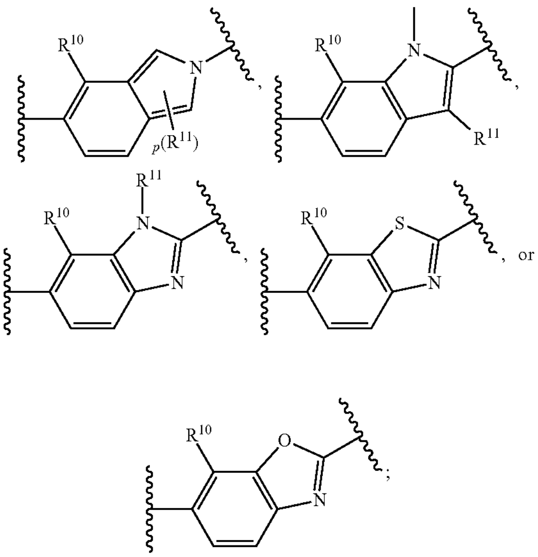

, , , or ;

wherein p is 0, 1 or 2, and $R^{10}$ and $R^{11}$ are as defined in formula III.

In some embodiments, each $R^{11}$ in the above-mentioned compound of formula III or the pharmaceutically acceptable form thereof is independently fluorine, chlorine, bromine, methyl, ethyl, isopropyl, or trifluoromethyl.

In some preferred embodiments, each $R^{11}$ in the above-mentioned compound of formula III or the pharmaceutically acceptable form thereof is independently chlorine, methyl, or trifluoromethyl.

In some preferred embodiments, ring B in the above-mentioned compound of formula III or the pharmaceutically acceptable form thereof is

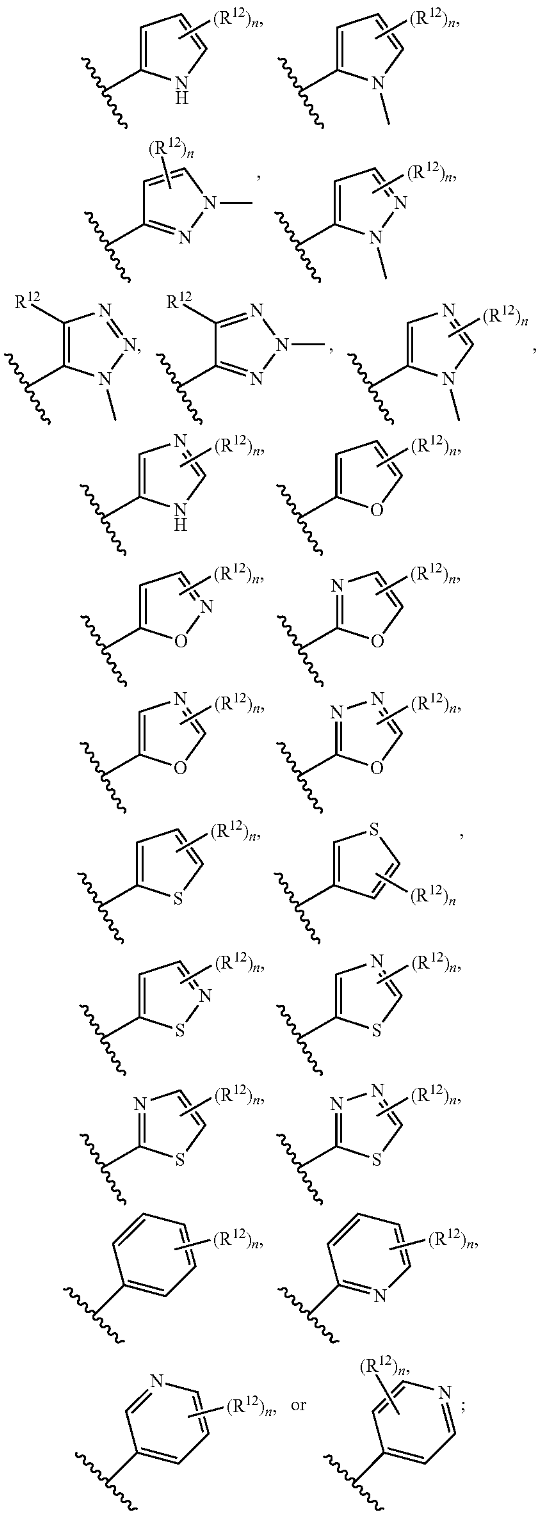

, or ;

wherein, n is 0, 1, 2, 3 or 4, and $R^{12}$ is as defined in formula III.

In some embodiments, each $R^{12}$ in the above-mentioned compound of formula III or the pharmaceutically acceptable form thereof is independently fluorine, chlorine, bromine, cyano, amino, nitro, methyl, ethyl, isopropyl, tert-butyl, cyclopropyl, cyclopentyl, cyclohexyl, trifluoromethyl, methoxy, ethoxy, isopropoxy, trifluoromethoxy, —C(═O)—$OCH_3$, —C(═O)—$OCH_2CH_3$, phenyl, benzyl, pyridyl, —C(═O)—$NH_2$, —NH—C(═O)—$CH_3$, or —NH—C(═O)—$CH_2CH_3$.

In some preferred embodiments, each $R^1$ in the above-mentioned compound of formula III or the pharmaceutically acceptable form thereof is independently fluorine, chlorine, bromine, cyano, amino, nitro, methyl, ethyl, isopropyl, tert-butyl, cyclopropyl, trifluoromethyl, methoxy, trifluoromethoxy, —C(═O)—$OCH_3$, —C(═O)—$OCH_2CH_3$, phenyl, benzyl, pyridyl, —C(═O)—$NH_2$, or —NH—C(═O)—$CH_3$.

In some embodiments, the above-mentioned compound of formula III or the pharmaceutically acceptable form thereof is a compound of any one of formula IIIa-1 to formula IIa-8 or a pharmaceutically acceptable form thereof, IIIa-1

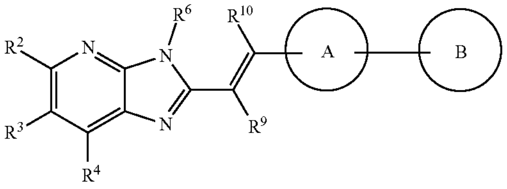

IIIa-2

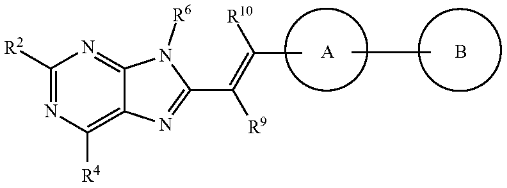

IIIa-3

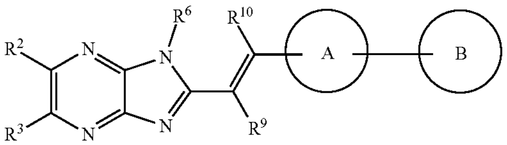

IIIa-4

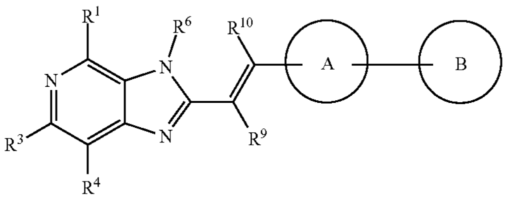

IIIa-5

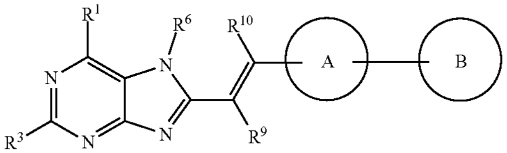

IIIa-6

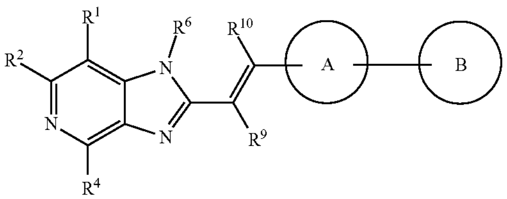

-continued

IIIa-7

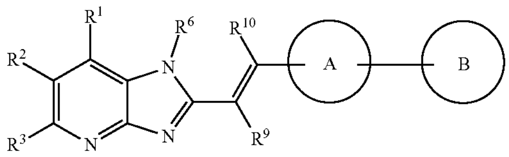

IIIa-8

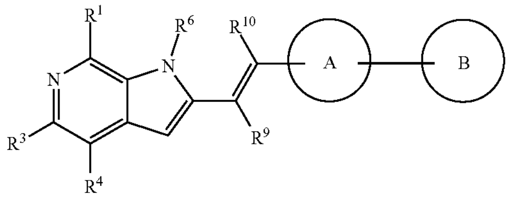

wherein ring A, ring B, $R^1$, $R^2$, $R^3$, $R^4$, $R^6$, $R^9$ and $R^{10}$ areas defined in formula II.

In some embodiments, the present disclosure provides a compound having the structure of formula IV or a pharmaceutically acceptable form thereof,

IV

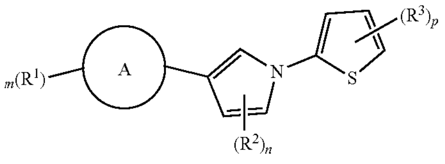

wherein ring A is a carbazole ring or a benzo[4,5]imidazo[1,2-a] pyridine ring:

each $R^1$ is independently halogen, amino, nitro, hydroxyl, $C_{1-4}$ alkyl, $C_{1-4}$ haloalkyl, $C_{1-4}$ alkoxy, $C_{1-4}$ haloalkoxy, —NH($C_{1-4}$ alkyl), —N($C_{1-4}$ alkyl)$_2$, or $C_{1-4}$ hydroxyalkyl;

each $R^2$ is independently halogen, $C_{1-4}$ alkyl, or $C_{1-4}$ haloalkyl;

each $R^3$ is independently halogen, cyano, amino, nitro, hydroxyl, $C_{1-4}$ alkyl, $C_{1-4}$ haloalkyl, $C_{1-4}$ alkoxy, or $C_{1-4}$ haloalkoxy;

m is 0, 1, 2, 3 or 4;

n and p are independently 0, 1, 2 or 3; and said pharmaceutically acceptable form is selected from a pharmaceutically acceptable salt, an ester, a stereoisomer, tautomer, a solvate, a N-oxide, an isotopically labeled form, a metabolite and a prodrug.

In some embodiments, ring A in the above-mentioned compound of formula IV or the pharmaceutically acceptable form thereof is

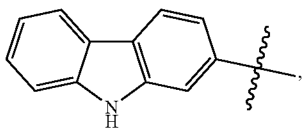

,

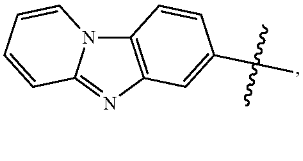

, or

-continued

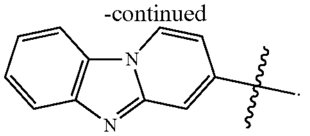

In some embodiments, each $R^1$ in the above-mentioned compound of formula IV or the pharmaceutically acceptable form thereof is independently halogen, amino, nitro, hydroxyl, $C_{1-4}$ alkyl, $C_{1-4}$ haloalkyl, $C_{1-4}$ alkoxy or $C_4$ haloalkoxy.

In some preferred embodiments, each $R^1$ in the above-mentioned compound of formula IV or the pharmaceutically acceptable form thereof is independently fluorine, chlorine, bromine, amino, nitro, hydroxyl, methyl, ethyl, isopropyl, trifluoromethyl, methoxy, ethoxy, isopropoxy, or trifluoromethoxy.

In some more preferred embodiments, each $R^1$ in the above-mentioned compound of formula IV or the pharmaceutically acceptable form thereof is independently methyl or methoxy.

In some embodiments, each $R^2$ in the above-mentioned compound of formula IV or the pharmaceutically acceptable form thereof is independently halogen or $C_{1-4}$ alkyl.

In some preferred embodiments, each $R^2$ in the above-mentioned compound of formula IV or the pharmaceutically acceptable form thereof is independently fluorine, chlorine, bromine, methyl, ethyl, or isopropyl.

In some more preferred embodiments, each $R^2$ in the above-mentioned compound of formula IV or the pharmaceutically acceptable form thereof is independently methyl.

In some embodiments, each $R^3$ in the above-mentioned compound of formula IV or the pharmaceutically acceptable form thereof is independently halogen, cyano, amino, nitro, hydroxyl, $C_{1-4}$ alkyl, or $C_{1-4}$ alkoxy.

In some preferred embodiments, each $R^3$ in the above-mentioned compound of formula IV or the pharmaceutically acceptable form thereof is independently fluorine, chlorine, bromine, cyano, amino, nitro, hydroxyl, methyl, ethyl, isopropyl, methoxy, ethoxy, or isopropoxy.

In some more preferred embodiments, each $R^3$ in the above-mentioned compound of formula IV or the pharmaceutically acceptable form thereof is independently cyano or methyl.

In some embodiments, m in the above-mentioned compound of formula IV or the pharmaceutically acceptable form thereof is 0, 1, 2 or 3.

In some preferred embodiments, m in the above-mentioned compound of formula IV or the pharmaceutically acceptable form thereof is 0, 1 or 2.

In some embodiments, n in the above-mentioned compound of formula IV or the pharmaceutically acceptable form thereof is 0, 1 or 2.

In some embodiments, p in the above-mentioned compound of formula IV or the pharmaceutically acceptable form thereof is 0, 1 or 2.

In some embodiments, the above-mentioned compound of formula IV or the pharmaceutically acceptable form thereof is a compound of any one of formula IV-1 to formula IV-3 or a pharmaceutically acceptable form thereof:

IV-1

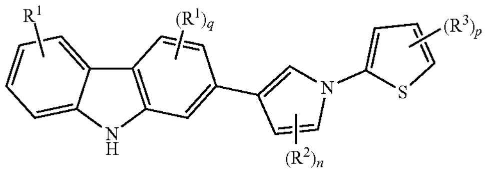

IV-2

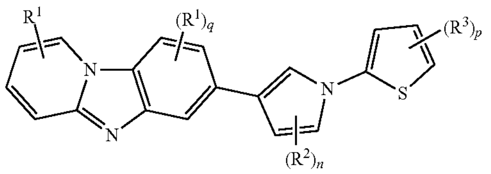

IV-3

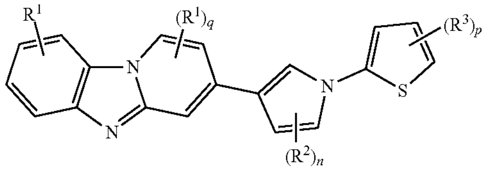

wherein $R^1$, $R^2$, $R^3$, n and p are as defined in formula IV and q is 0, 1 or 2.

In some embodiments, the present disclosure provides a compound having the structure of formula V or a pharmaceutically acceptable form thereof,

V

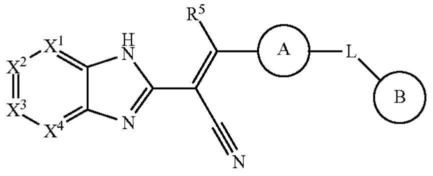

wherein

X is N or $CR^1$, $X^2$ is N or $CR^2$, $X^3$ is N or $CR^3$, $X^4$ is N or $CR^4$;

$R^1$, $R^2$, $R^3$ and $R^4$ are each independently hydrogen, halogen, amino, nitro, hydroxyl, $C_{1-4}$ alkyl, $C_{1-6}$ haloalkyl, $C_{1-6}$ alkoxy, $C_{1-6}$ haloalkoxy, —NH($C_{1-6}$ alkyl), —N($C_{1-6}$ alkyl)$_2$, $C_{1-6}$ hydroxyalkyl, —O—($C_{1-6}$ alkylene)-O—($C_{1-6}$ alkyl), —C(═O)—NH—($C_{1-6}$ alkyl), —C(═O)—NH—($C_{1-6}$ alkylene)-N(C alkyl)$_2$, or —C(═O)—O—($C_{1-4}$ alkyl);

$R^5$ is hydrogen, halogen, or $C_{1-4}$ alkyl;

ring A is a 5-10 membered heteroaryl or a 3-8 membered heterocyclyl, ring A is optionally substituted with one or more $R^6$;

each $R^6$ is independently halogen, $C_{1-4}$ alkyl, or $C_{1-6}$ haloalkyl;

L is O, S, or $CR^7R^8$;

$R^7$ and $R^8$ are each independently hydrogen, halogen, or $C_{1-6}$ alkyl;

ring B is $C_{6-10}$ aryl, a 5-12 membered heteroaryl, or a 3-8 membered heterocyclyl, ring B is optionally substituted with one or more $R^9$;

each $R^9$ is independently halogen, cyano, amino, nitro, hydroxyl, $C_{1-6}$ alkyl, $C_{1-6}$ haloalkyl, $C_{1-6}$ alkoxy, $C_{1-6}$ haloalkoxy, $C_{3-6}$ cycloalkyl, —C(═O)—O—($C_{1-6}$ alkyl), phenyl, benzyl, pyridyl, —C(═O)—$NH_2$, or —NH—C(═O)—($C_{1-6}$ alkyl), said phenyl, benzyl and pyridyl are optionally substituted with one or more substituents selected from hydrogen, halogen, cyano, amino, hydroxyl, $C_{1-6}$ alkyl and $C_{1-6}$ alkoxy; and said pharmaceutically acceptable form is selected from a pharmaceutically acceptable salt, ester, stereoisomer, tautomer, solvate, N-oxide, isotopically labeled form, metabolite and prodrug.

In some embodiments, $R^1$, $R^2$, $R^3$ and $R^4$ in the above-mentioned compound of formula V or the pharmaceutically acceptable form thereof are each independently hydrogen, halogen, amino, nitro, hydroxyl, $C_{1-6}$ alkyl, $C_{1-6}$ haloalkyl, $C_{1-6}$ alkoxy, $C_{1-6}$ haloalkoxy, —NH($C_{1-6}$ alkyl), —N($C_{1-4}$ alkyl)$_2$, or $C_{1-6}$ hydroxyalkyl.

In some preferred embodiments, $R^1$, $R^2$, $R^3$ and $R^4$ in the above-mentioned compound of formula V or the pharmaceutically acceptable form thereof are each independently hydrogen, halogen, amino, nitro, hydroxyl, $C_{1-4}$ alkyl, $C_{1-4}$ haloalkyl, $C_{1-4}$ alkoxy, or $C_{1-4}$ haloalkoxy.

In some more preferred embodiments, $R^1$, $R^2$, $R^3$ and $R^4$ in the above-mentioned compound of formula V or the pharmaceutically acceptable form thereof are each independently hydrogen, halogen, amino, nitro, hydroxyl, methyl, or methoxy.

In some embodiments, $R^5$ in the above-mentioned compound of formula V or the pharmaceutically acceptable form thereof is hydrogen, halogen, or $C_{1-4}$ alkyl.

In some preferred embodiments, $R^5$ in the above-mentioned compound of formula V or the pharmaceutically acceptable form thereof is hydrogen, halogen, or methyl.

In some embodiments, ring A in the above-mentioned compound of formula V or the pharmaceutically acceptable form thereof is a 5-10 membered heteroaryl, ring A is optionally substituted with one or more $R^6$, and each $R^6$ is independently halogen, $C_{1-4}$ alkyl, or $C_{1-4}$ haloalkyl.

In some preferred embodiments, ring A in the above-mentioned compound of formula V or the pharmaceutically acceptable form thereof is pyrrolyl, pyrazolyl, imidazolyl, thiazolyl, or oxazolyl, ring A is optionally substituted with one or more $R^6$, and each $R^6$ is independently halogen, methyl, ethyl, or trifluoromethyl.

In some more preferred embodiments, ring A in the above-mentioned compound of formula V or the pharmaceutically acceptable form thereof is pyrrolyl, ring A is optionally substituted with one or more $R^6$, and each $R^6$ is independently halogen or methyl.

In some particularly preferred embodiments, ring A in the above-mentioned compound of formula V or the pharmaceutically acceptable form thereof is

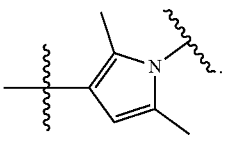 [SMILES: *c1cc(C)n(*)c1C]

In some embodiments, L in the above-mentioned compound of formula V or the pharmaceutically acceptable form thereof is $CR^7R^8$; and $R^7$ and $R^8$ are each independently hydrogen, halogen, or $C_{1-4}$ alkyl.

In some preferred embodiments, L in the above-mentioned compound of formula V or the pharmaceutically acceptable form thereof is $CR^7R^8$; and $R^7$ and $R^8$ are each independently hydrogen, halogen, or methyl.

In some embodiments, ring B in the above-mentioned compound of formula V or the pharmaceutically acceptable form thereof is $C_{6-10}$ aryl or a 5-12 membered heteroaryl, ring B is optionally substituted with one or more $R^9$, and each $R^9$ is independently halogen, cyano, amino, nitro, hydroxyl, $C_{1-6}$ alkyl, $C_{1-6}$ haloalkyl, $C_{1-6}$ alkoxy, $C_{1-6}$ haloalkoxy, or $C_{3-6}$ cycloalkyl.

In some preferred embodiments, ring B in the above-mentioned compound of formula V or the pharmaceutically acceptable form thereof is $C_{6-10}$ aryl or a 5-10 membered heteroaryl, ring B is optionally substituted with one or more $R^9$, each $R^9$ is independently halogen, cyano, amino, nitro, hydroxyl, $C_{1-4}$ alkyl, or $C_{1-4}$ alkoxy.

In some more preferred embodiments, ring B in the above-mentioned compound of formula V or the pharmaceutically acceptable form thereof is phenyl, pyrazinyl, pyridyl, pyrimidinyl, furanyl, thienyl, thiazolyl, pyrazolyl, or imidazolyl, ring B is optionally substituted with one or more $R^9$, and each $R^9$ is independently halogen, cyano, amino, nitro, hydroxyl, or methyl.

In some particularly preferred embodiments, ring B in the above-mentioned compound of formula V or the pharmaceutically acceptable form thereof is

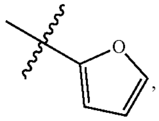, 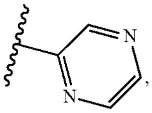, 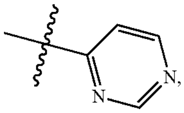,

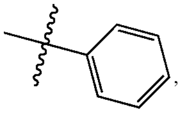, 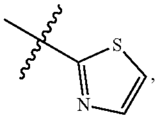, 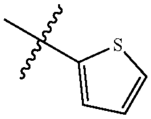,

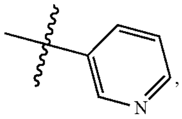, 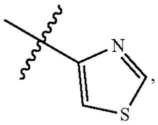, 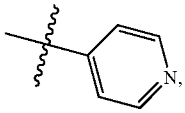,

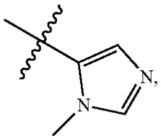, 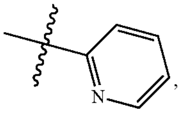,

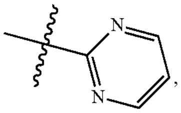, 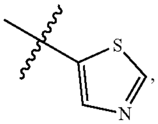, 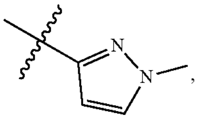,

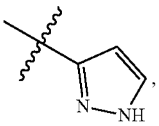, or 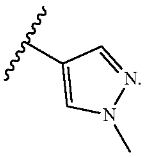.

In some embodiments, the above-mentioned compound of formula V or the pharmaceutically acceptable form thereof is a compound having the structure of any one of formula V-1 to formula V-3 or a pharmaceutically acceptable form thereof:

V-1

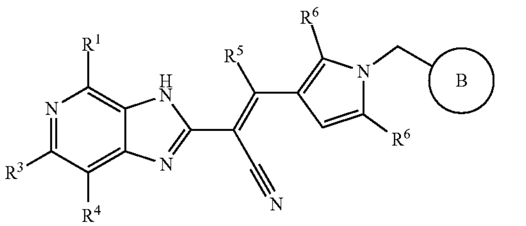

V-2

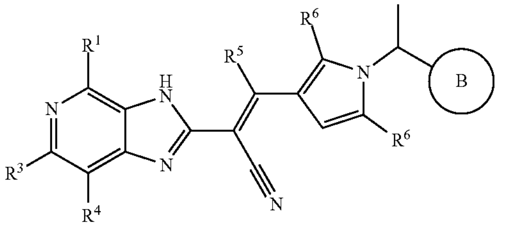

V-3

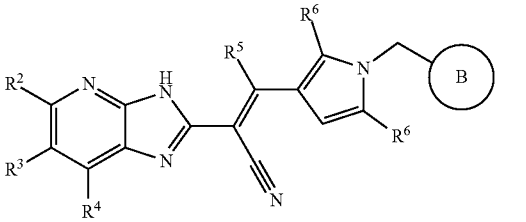

wherein $R^1$, $R^3$, $R^4$, $R^5$, $R^6$ and ring B are as defined in formula V.

In some preferred embodiments, the above-mentioned compound of formula V or the pharmaceutically acceptable form thereof is a compound having the structure of formula V-3 or formula V-4 or a pharmaceutically acceptable form thereof:

V-4

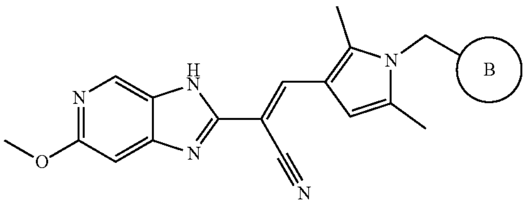

V-5

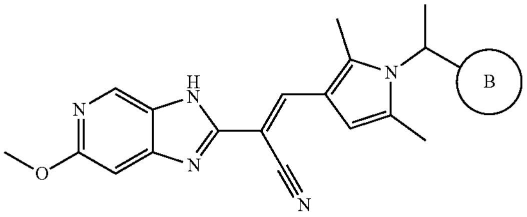

wherein ring B is as defined in formula V.

In some embodiments, the present disclosure provides a compound having the structure of formula VI or a pharmaceutically acceptable form thereof,

VI

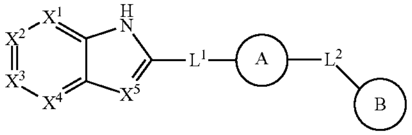

wherein $X^1$ is N or $CR^1$, $X^2$ is N or $CR^2$, $X^3$ is N or $CR^3$, X is N or $CR^4$;

$R^1$, $R^2$, $R^3$ and $R^4$ are each independently hydrogen, halogen, amino, nitro, hydroxyl, $C_{1-4}$ akyl, $C_{1-6}$ haloalkyl, $C_{1-6}$ alkoxy, $C_{1-6}$ haloalkoxy, —NH($C_{1-6}$ alkyl), —N($C_{1-6}$ alkyl)$_2$, $C_{1-4}$ hydroxyalkyl, —O—($C_{1-6}$ alkylene)-O—($C_{1-6}$ alkyl), —C(═O)—NH—($C_{1-6}$ alkyl), —C(═O)—NH—($C_{1-6}$ alkylene)-N($C_{1-6}$ alkyl)$_2$, or —C(═O)—O—($C_{1-6}$ alkyl);

$X^5$ is N or $CR^5$, $R^5$ is hydrogen, halogen, or $C_{1-6}$ alkyl;

$L^1$ is —$NR^6$C(═O)—, —$NR^6$S(═O)$_2$—, —$NR^6$S(═O)—, —C(═O)$NR^6$—, —S(═O)$_2$$NR^6$—, or —S(═O)$NR^6$—;

each $R^6$ is independently hydrogen, $C_{1-4}$ alkyl, $C_{3-8}$ cycloalkyl, or $C_{6-10}$ aryl;

ring A is a 5-10 membered heteroaryl or a 3-8 membered heterocyclyl, ring A is optionally substituted with one or more $R^7$;

each $R^7$ is independently halogen, $C_{1-6}$ alkyl, or $C_{1-6}$ haloalkyl;

$L^2$ is a single bond, O, S, or $CR^8R^9$;

$R^8$ and $R^9$ are each independently hydrogen, halogen, or $C_{1-6}$ alkyl;

ring B is $C_{6-10}$ aryl, a 5-12 membered heteroaryl, or a 3-8 membered heterocyclyl, ring B is optionally substituted with one or more $R^{10}$;

each $R^{10}$ is independently halogen, cyano, amino, nitro, hydroxyl, $C_{1-6}$ alkyl, $C_{1-6}$ haloalkyl, $C_{1-6}$ alkoxy, $C_{1-6}$ haloalkoxy, $C_{3-4}$ cycloalkyl, —C(═O)—O—($C_{1-6}$ alkyl), phenyl, benzyl, pyridyl, —C(═O)—$NH_2$, or —NH—C(═O)—($C_{1-6}$ alkyl), said phenyl, benzyl and pyridyl are optionally substituted with one or more substituents selected from hydrogen, halogen, cyano, amino, hydroxyl, $C_{1-4}$ alkyl and $C_{1-6}$ alkoxy; and said pharmaceutically acceptable form is selected from a pharmaceutically acceptable salt, an ester, a stereoisomer, a tautomer, a solvate, a N-oxide, an isotopically labeled form, a metabolite and a prodrug.

In some embodiments, $R^1$, $R^2$, $R^3$ and $R^4$ in the above-mentioned compound of formula VI or the pharmaceutically acceptable form thereof are each independently hydrogen, halogen, amino, nitro, hydroxyl, $C_{1-6}$ akyl, $C_{1-6}$ haloalkyl, $C_{1-6}$ alkoxy, $C_{1-6}$ haloalkoxy, —NH($C_{1-6}$ alkyl), —N($C_{1-6}$ alkyl)$_2$, or $C_{1-6}$ hydroxyalkyl.

In some preferred embodiments, $R^1$, $R^2$, $R^3$ and $R^4$ in the above-mentioned compound of formula VI or the pharmaceutically acceptable form thereof are each independently hydrogen, halogen, amino, nitro, hydroxyl, $C_{1-4}$ alkyl, $C_{1-4}$ haloalkyl, $C_{1-4}$ alkoxy, or $C_{1-4}$ haloalkoxy.

In some more preferred embodiments, $R^1$, $R^2$, $R^3$ and $R^4$ in the above-mentioned compound of formula VI or the pharmaceutically acceptable form thereof are each independently hydrogen, halogen, amino, nitro, hydroxyl, methyl, or methoxy.

In some embodiments, $R^5$ in the above-mentioned compound of formula VI or the pharmaceutically acceptable form thereof is hydrogen, halogen, or $C_{1-4}$ alkyl.

In some preferred embodiments, $R^5$ in the above-mentioned compound of formula VI or the pharmaceutically acceptable form thereof is hydrogen, halogen, or methyl.

In some embodiments, $L^1$ in the above-mentioned compound of formula VI or the pharmaceutically acceptable form thereof is —NRC(═O)—, —$NR^6S(═O)_2$—, —C(═O)$NR^6$—, or —$S(═O)_2NR^6$—, and each $R^6$ is independently hydrogen, $C_{1-4}$ alkyl, or $C_{3-4}$ cycloalkyl.

In some preferred embodiments, $L^1$ in the above-mentioned compound of formula VI or the pharmaceutically acceptable form thereof is —$NR^6C(═O)$—, —$NR^6S(═O)_2$—, —C(═O)$NR^6$—, or —$S(═O)_2NR^6$—, and each $R^6$ is independently hydrogen or $C_{1-4}$ alkyl.

In some more preferred embodiments, $L^1$ in the above-mentioned compound of formula VI or the pharmaceutically acceptable form thereof is —NHC(═O)—, —$N(CH_3)$—C(═O)—, —$NHS(═O)_2$—, —C(═O)NH—, or —$S(═O)_2$NH—.

In some embodiments, ring A in the above-mentioned compound of formula VI or the pharmaceutically acceptable form thereof is a 5-10 membered heteroaryl, ring A is optionally substituted with one or more $R^7$, and each $R^7$ is independently halogen, $C_{1-4}$ alkyl, or $C_{1-4}$ haloalkyl.

In some preferred embodiments, ring A in the above-mentioned compound of formula VI or the pharmaceutically acceptable form thereof is pyrrolyl, pyrazolyl, imidazolyl, thiazolyl, or oxazolyl, ring A is optionally substituted with one or more $R^7$, and each $R^7$ is independently halogen, methyl, ethyl, or trifluoromethyl.

In some more preferred embodiments, ring A in the above-mentioned compound of formula VI or the pharmaceutically acceptable form thereof is pyrrolyl or imidazolyl, ring A is optionally substituted with one or more $R^7$, and each $R^7$ is independently halogen or methyl.

In some particularly preferred embodiments, ring A in the above-mentioned compound of formula VI or the pharmaceutically acceptable form thereof is

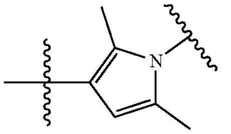 or 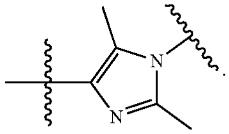.

In some embodiments, $L^2$ in the above-mentioned compound of formula VI or the pharmaceutically acceptable form thereof is a single bond or $CR^8R^9$; and $R^8$ and $R^9$ are each independently hydrogen, halogen, or Cia alkyl.

In some preferred embodiments, $L^2$ in the above-mentioned compound of formula VI or the pharmaceutically acceptable form thereof is a single bond.

In some embodiments, ring B in the above-mentioned compound of formula VI or the pharmaceutically acceptable form thereof is $C_{6-10}$ aryl or a 5-12 membered heteroaryl, ring B is optionally substituted with one or more $R^{10}$, and each $R^{10}$ is independently halogen, cyano, amino, nitro, hydroxyl, $C_{1-4}$ alkyl, $C_{1-6}$ haloalkyl, $C_{1-6}$ alkoxy, $C_{1-6}$ haloalkoxy, $C_{3-6}$ cycloalkyl, or —C(═O)—$NH_2$.

In some preferred embodiments, ring B in the above-mentioned compound of formula VI or the pharmaceutically acceptable form thereof is $C_{6-10}$ aryl or a 5-10 membered heteroaryl, ring B is optionally substituted with one or more $R^{10}$, and each $R^{10}$ is independently halogen, cyano, amino, nitro, hydroxyl, $C_{1-4}$ alkyl, $C_{1-4}$ alkoxy, or —C(═O)—$NH_2$.

In some more preferred embodiments, ring B in the above-mentioned compound of formula VI or the pharmaceutically acceptable form thereof is phenyl, pyrazinyl, pyridyl, pyrimidinyl, furanyl, oxazolyl, thienyl, thiazolyl, pyrazolyl, or imidazolyl, ring B is optionally substituted with one or more $R^{10}$, and each $R^{10}$ is independently halogen, cyano, amino, nitro, hydroxyl, methyl, or —C(═O)—$NH_2$.

In some particularly preferred embodiments, ring B in the above-mentioned compound of formula VI or the pharmaceutically acceptable form thereof is

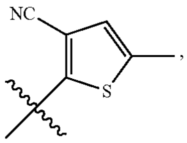, 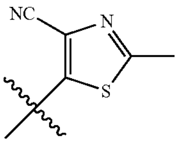, 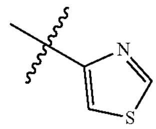,

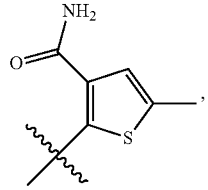, 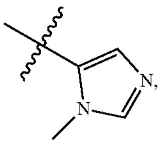, 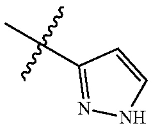,

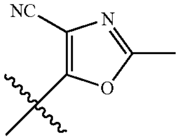, 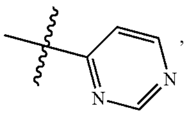, 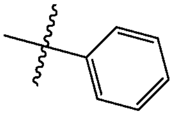,

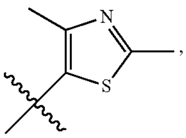, 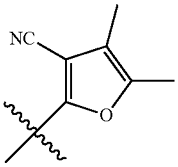, 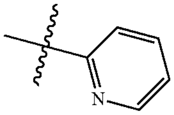,

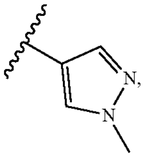, 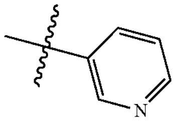, 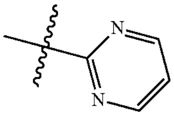,

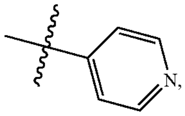, 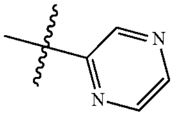,

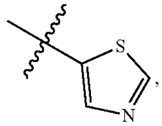, 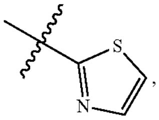, or 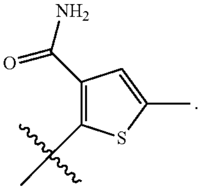.

In some embodiments, the above-mentioned compound of formula VI or the pharmaceutically acceptable form thereof is a compound having the structure of formula VI-1, formula VI-2, formula VI-3, formula VI-4, formula VI-5 or formula VI-6 or a pharmaceutically acceptable form thereof,

VI-1

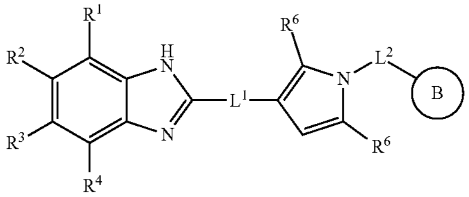

VI-2

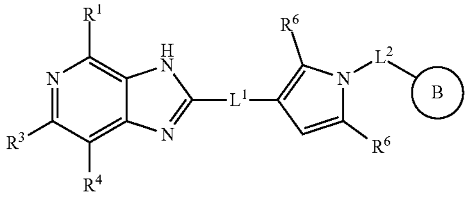

VI-3

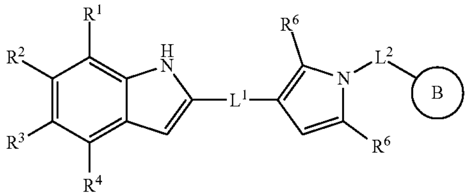

VI-4

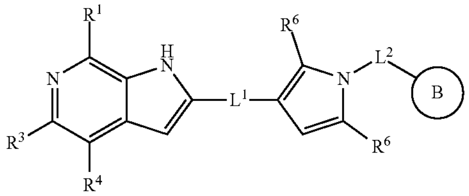

VI-5

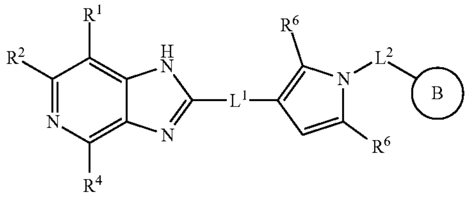

VI-6

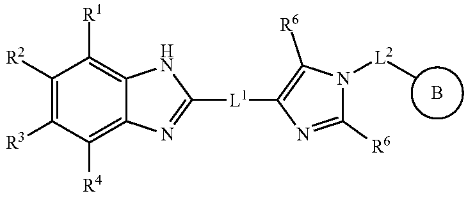

wherein $R^1$, $R^2$, $R^3$, $R^4$, $R^6$, $L^1$, $L^2$ and ring B are as defined in formula VI.

In some preferred embodiments, the above-mentioned compound of formula VI or the pharmaceutically acceptable form thereof is a compound having the structure of formula VI-7, formula VI-8, formula VI-9, formula VI-10, formula VI-11, formula VI-12, formula VI-13, formula VI-14, formula VI-15, formula VI-16, formula VI-17 or formula VI-18 or a pharmaceutically acceptable form thereof,

VI-7

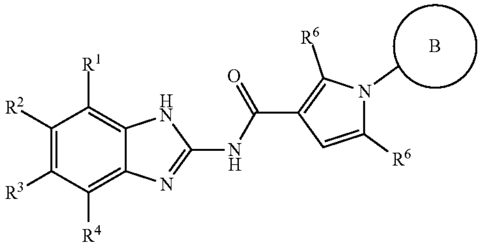

VI-8

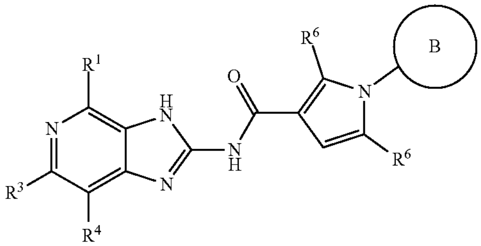

VI-9

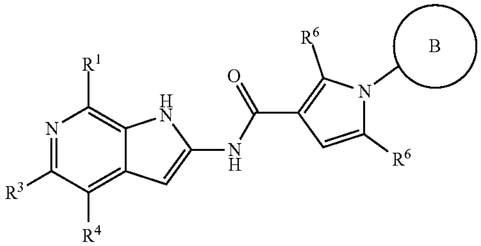

VI-10

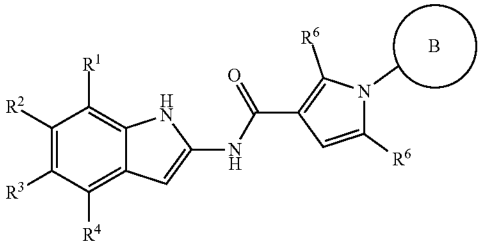

VI-11

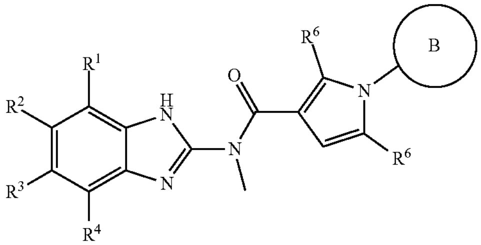

VI-12

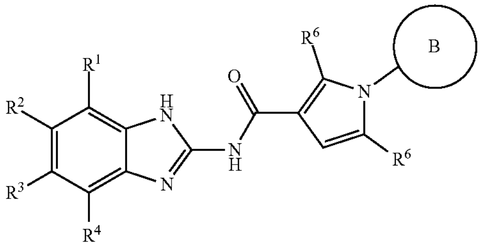

-continued

VI-13

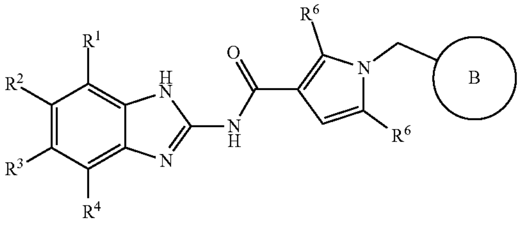

VI-14

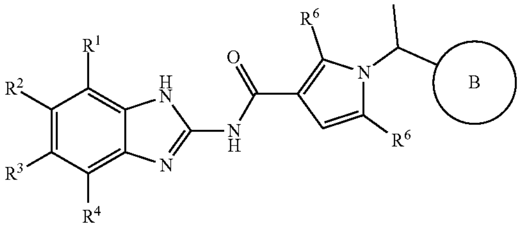

VI-15

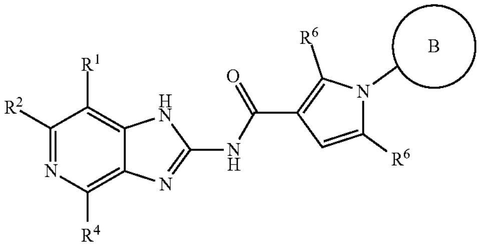

VI-16

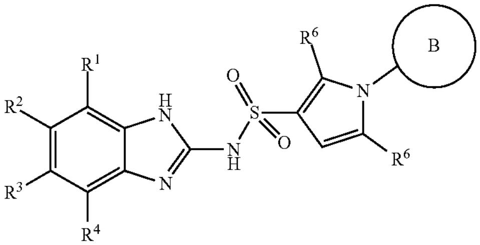

VI-17

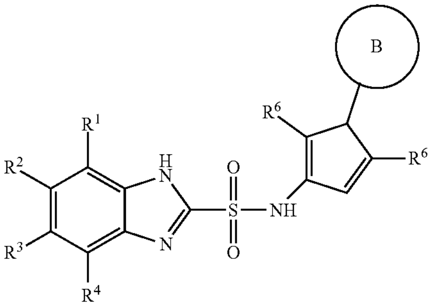

-continued

VI-18

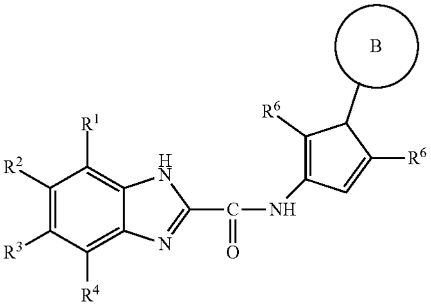

wherein $R^1$, $R^2$, $R^3$, $R^4$, $R^6$ and ring Bare as defined in formula VI.

It should be understood by those skilled in the art that the present disclosure encompasses compounds derived from any combination of various embodiments. Embodiments obtained by combining a technical feature or a preferred technical feature in one embodiment with a technical feature or a preferred technical feature in another embodiment are also included within the scope of the present disclosure.

In a second aspect, the present disclosure also provides the following compounds or the pharmaceutically acceptable salts, esters, stereoisomers, tautomers, solvates, N-oxides, isotopically labeled forms, metabolites or prodrugs thereof:

AB24242

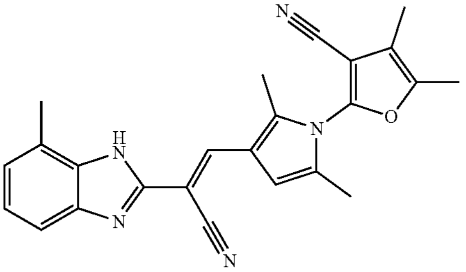 [SMILES: Cc1oc(-n2c(C)cc(/C=C(\C#N)c3nc4ccccc4[nH]3)c2C)c(C#N)c1C]

AB24241

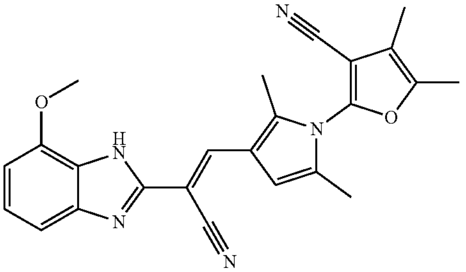

AB24218

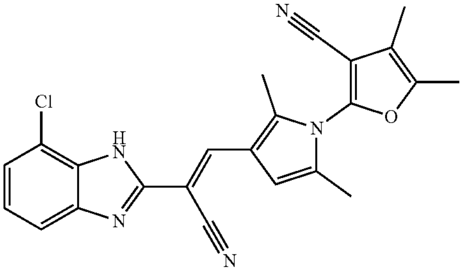

-continued
AB24239
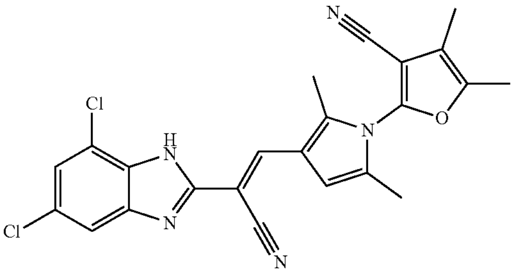
AB24203
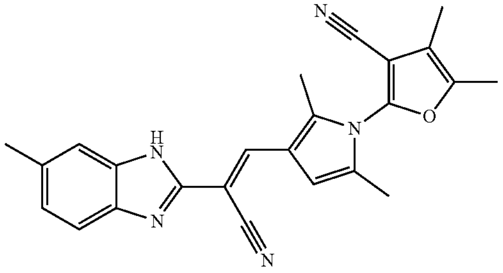
AB24202
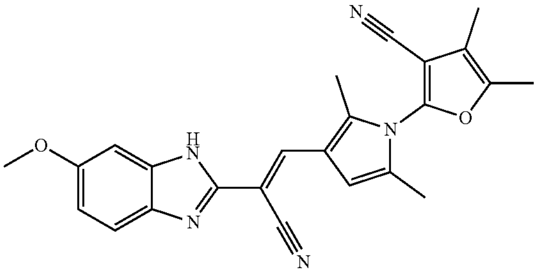
AB24297
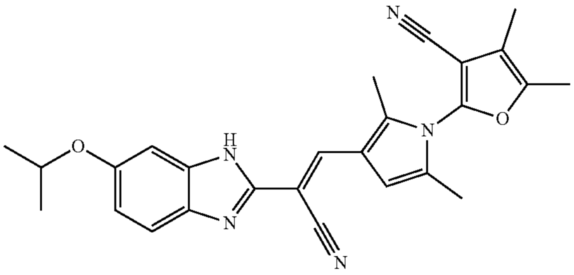
AB24225
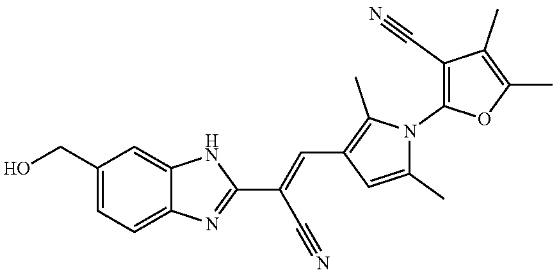
-continued
AB24230
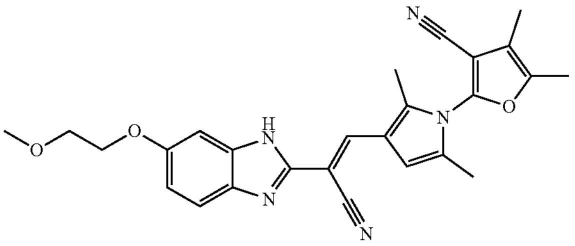
AB24221
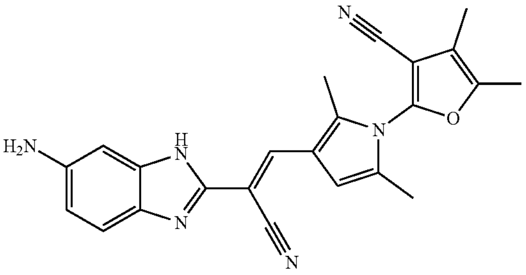
AB24222
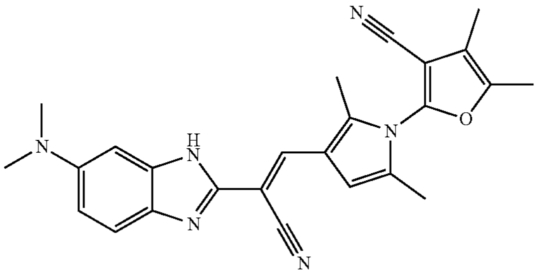
AB24206
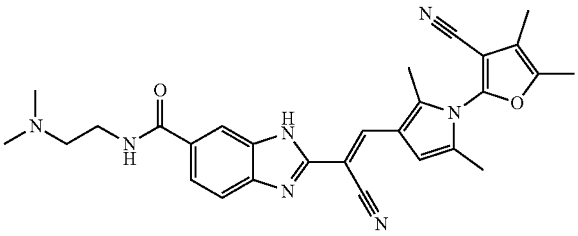
AB24208
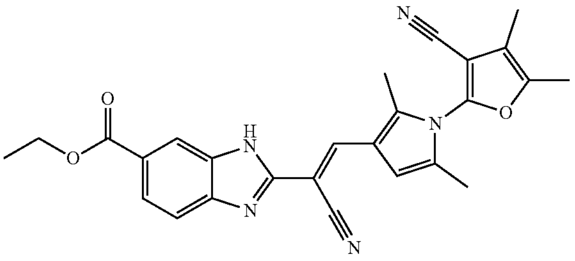

-continued
AB24205
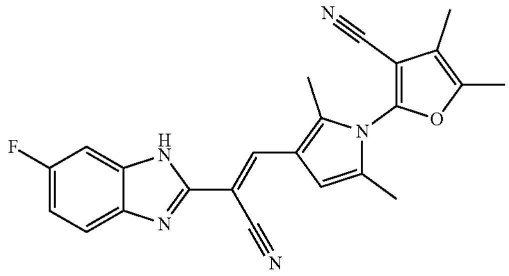
AB24201
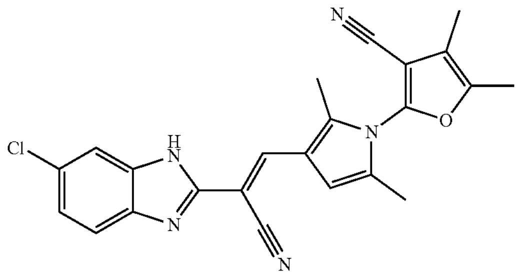
AB24213
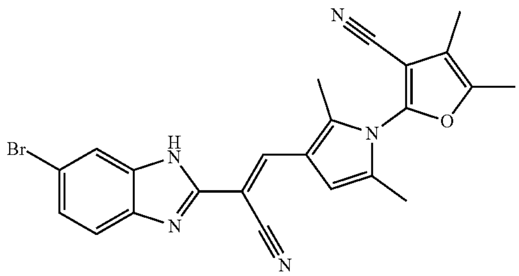
AB24243
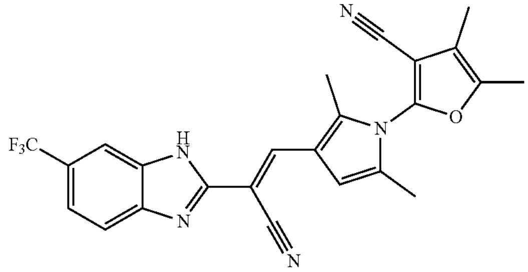
AB24255
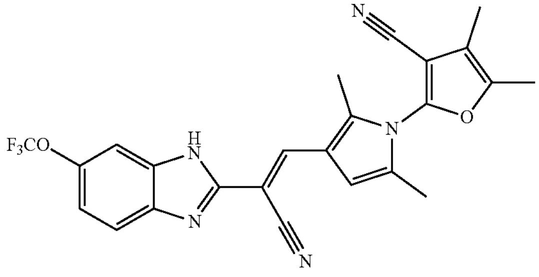
-continued
AB24217
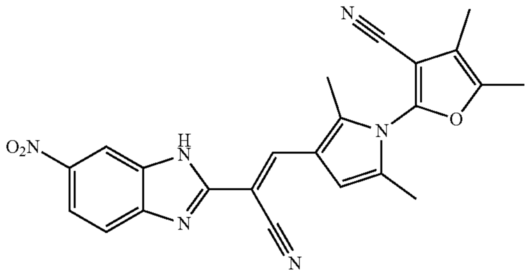
AB24229
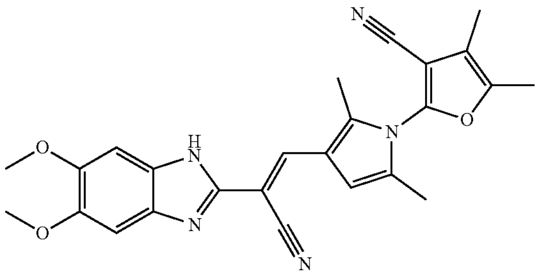
AB24287
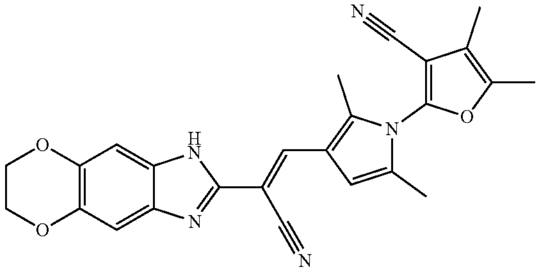
AB24246
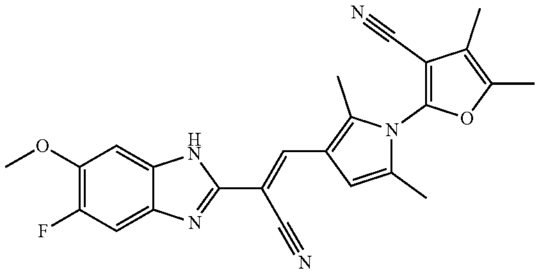
AB24266
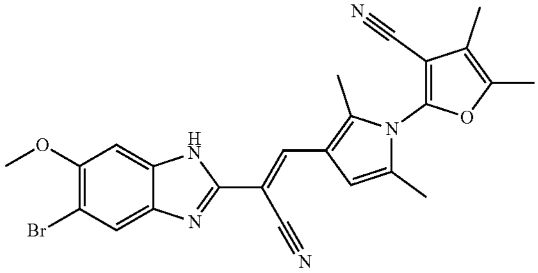

AB24214
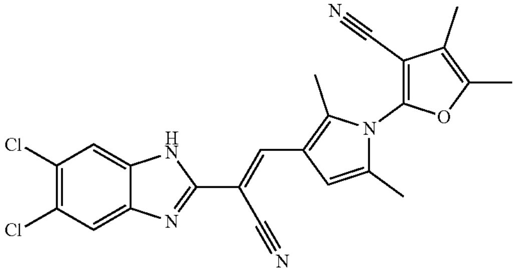
AB24231
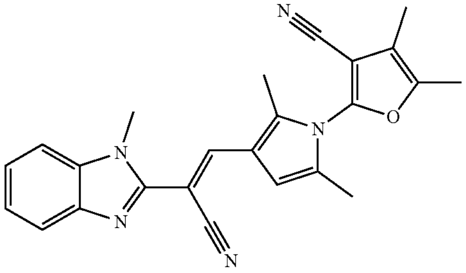
AB24263
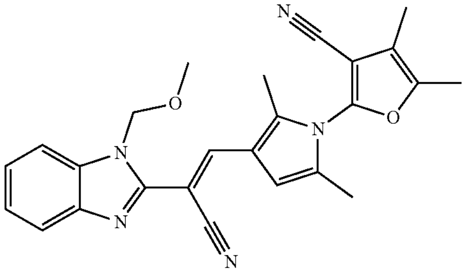
AB24283
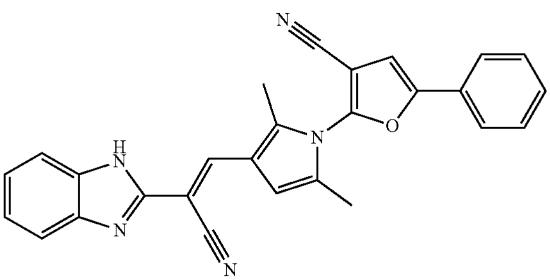
AB24264
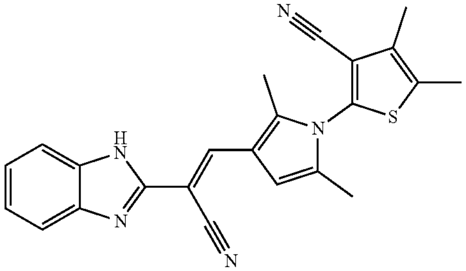
AB24270
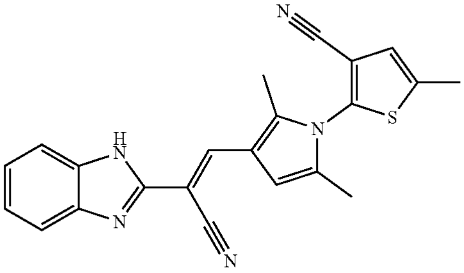
AB24273
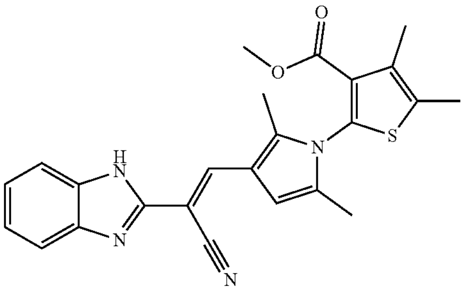
AB24274
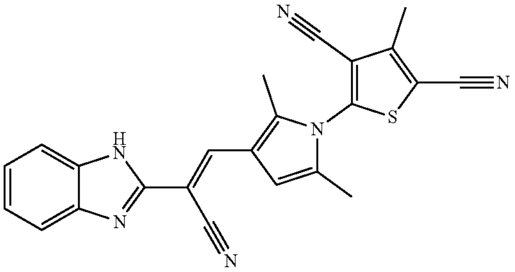
AB24284
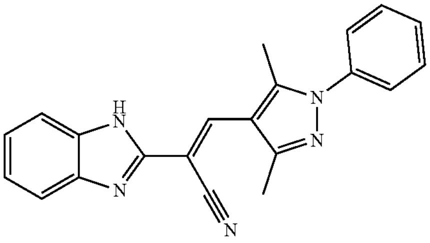
AB24285
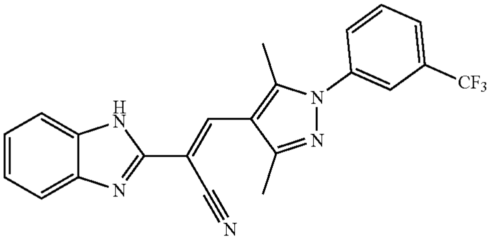

-continued
AB24290
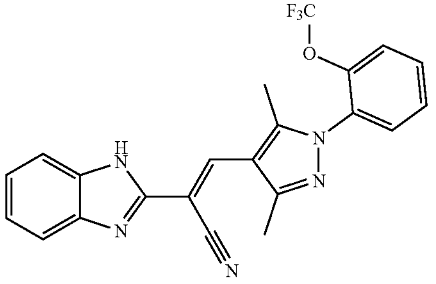
AB24307
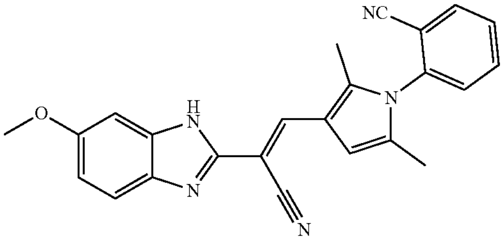
AB24331
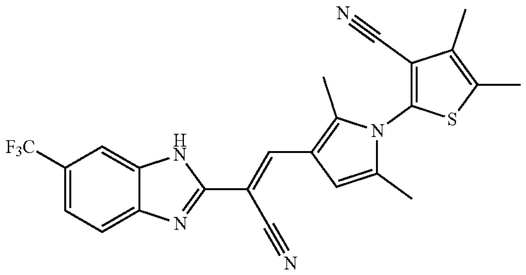
AB24343
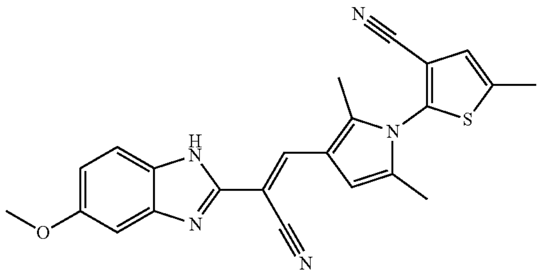
AB24339
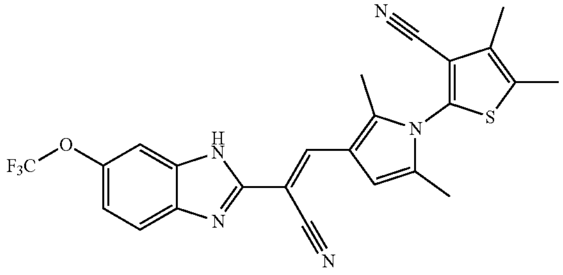
-continued
AB24322
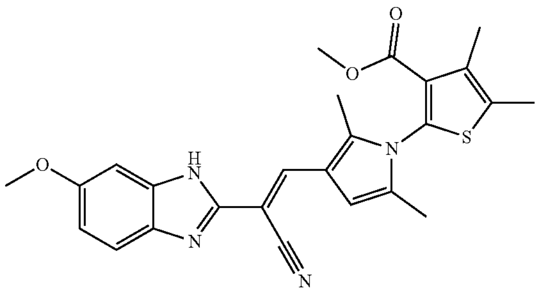
AB24354
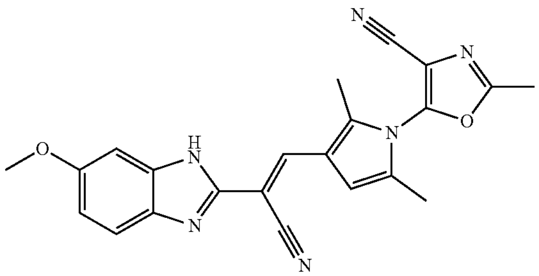
AB24386
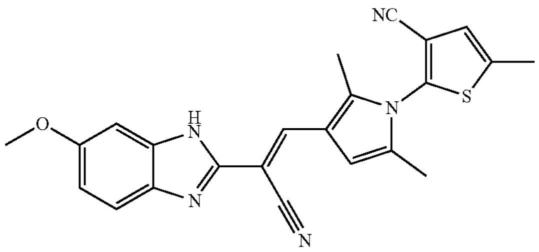
AB29520
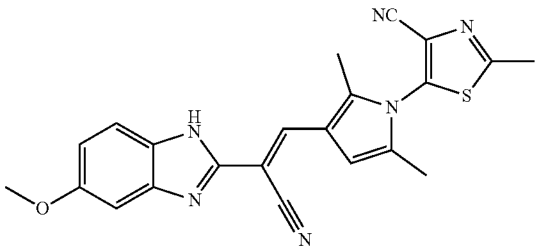
AB29515
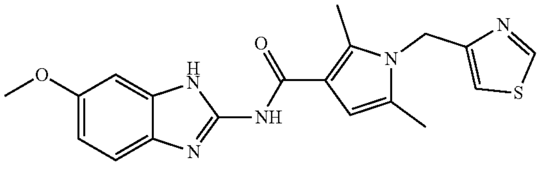
AB24387
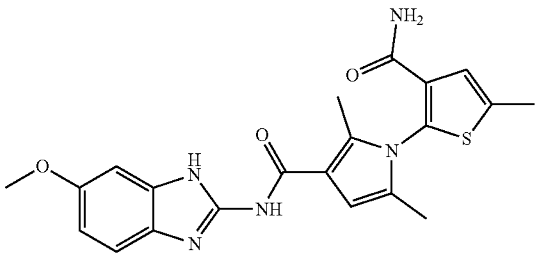

-continued
AB29509
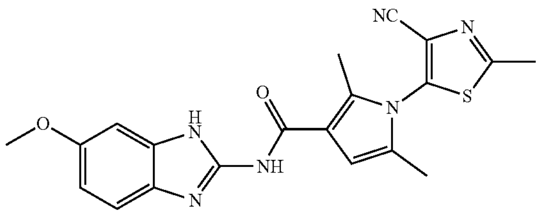
AB29524
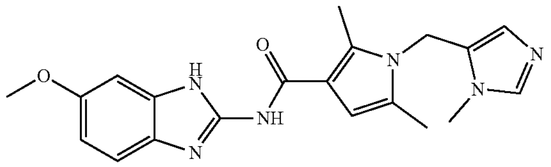
AB24396
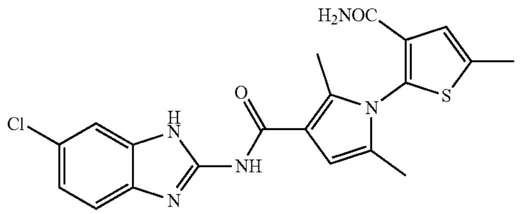
AB29521
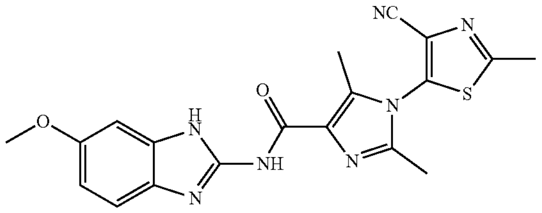
AB29525
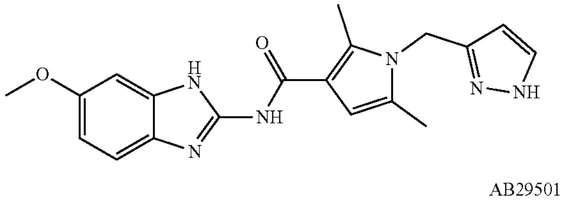
AB29501
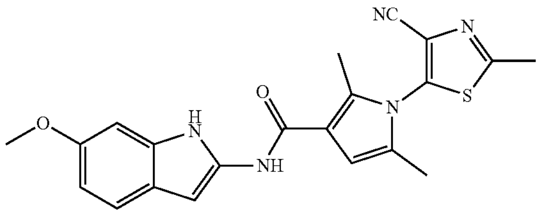
AB29522
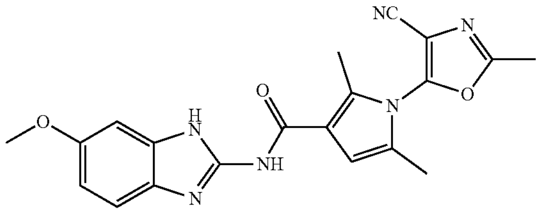
-continued
AB29526
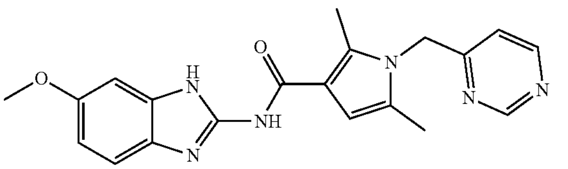
AB29502
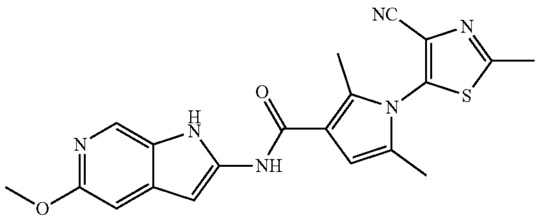
AB29523
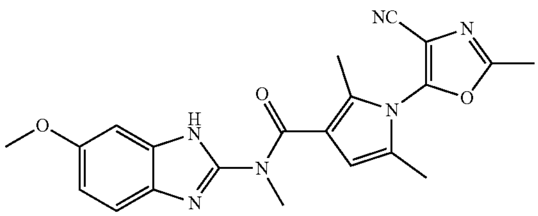
AB29727
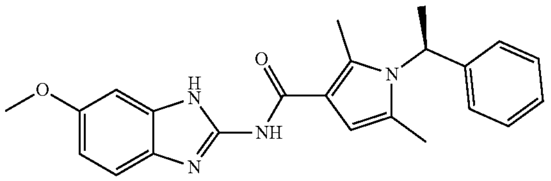
AB29505
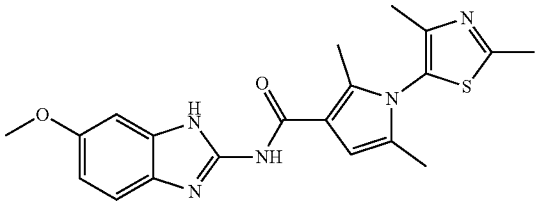
AB29510
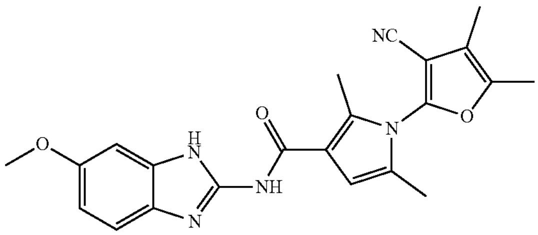
AB29528
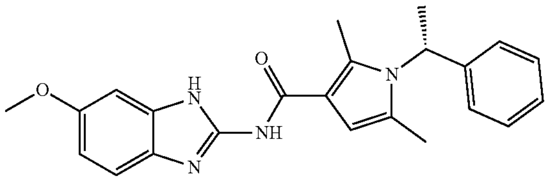

-continued
AB29529
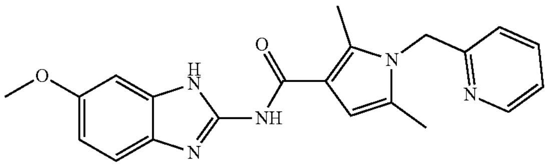
AB29513
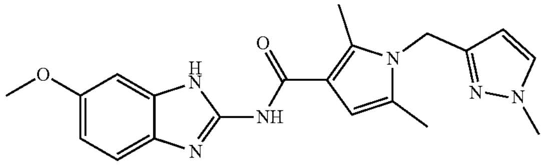
AN29536
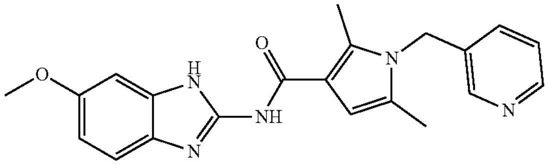
AB29538
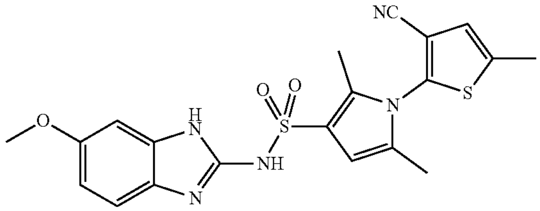
AB29539
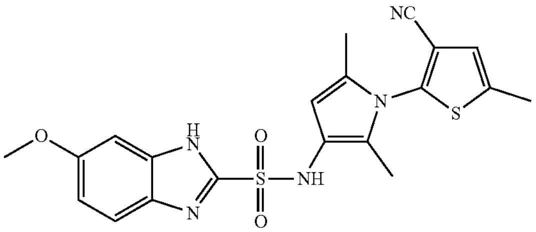
AB29540
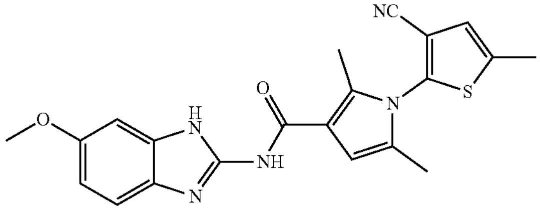
AB29531
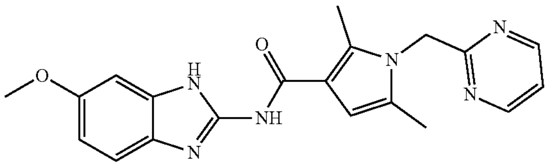
-continued
AB29530
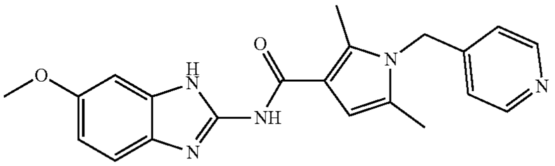
AB29532
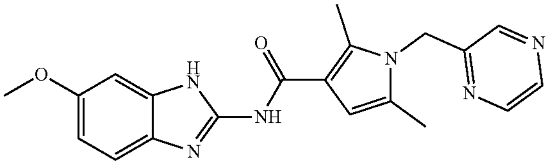
AB29533
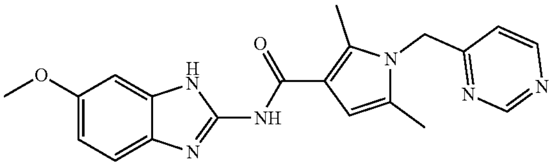
AB29535
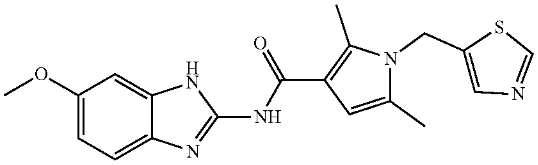
AB29534
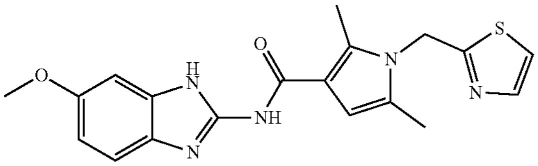
AAB29537
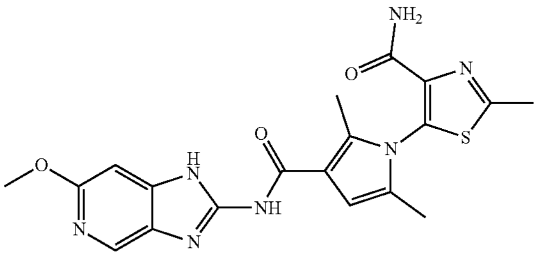
AB24281
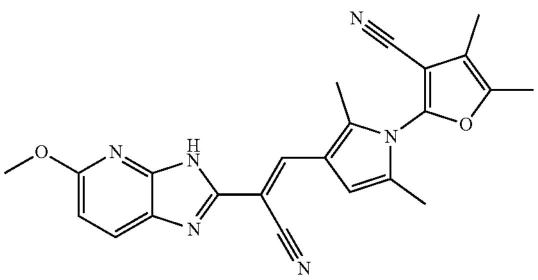

-continued
AB24254
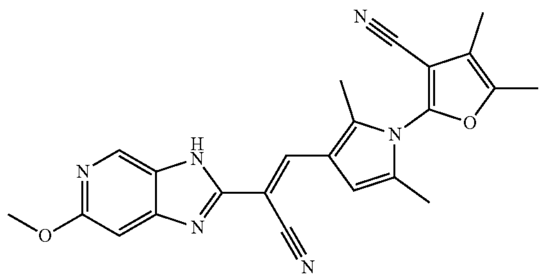
AB24288
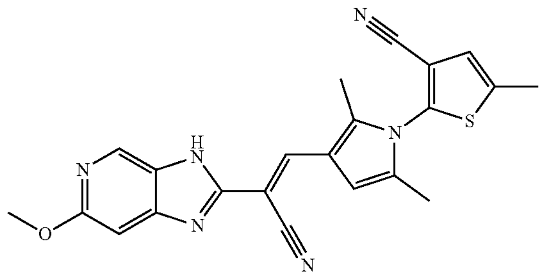
AB24289
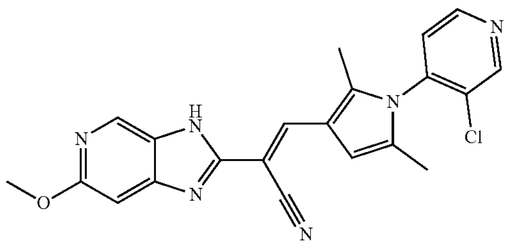
AB24295
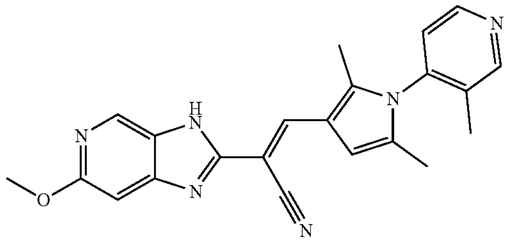
AB24300
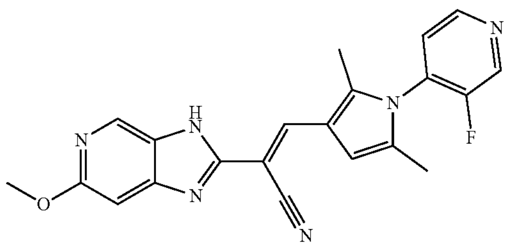
-continued
AB24301
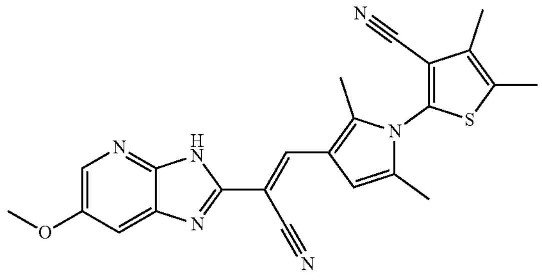
AB24302
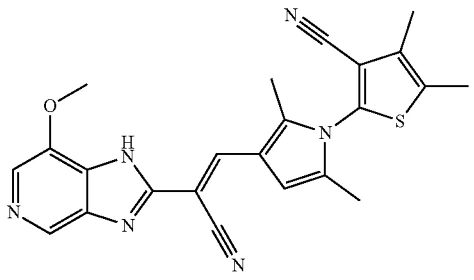
AB24308
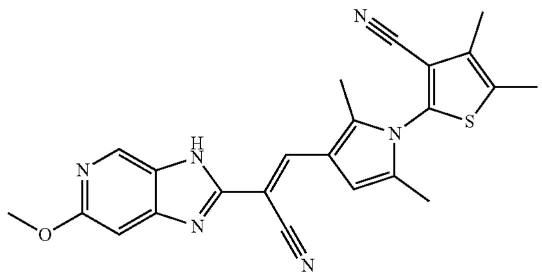
AB24310
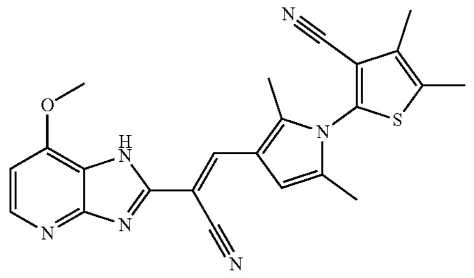
AB24311
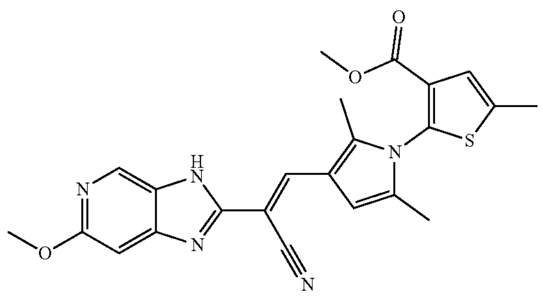

-continued
AB24313
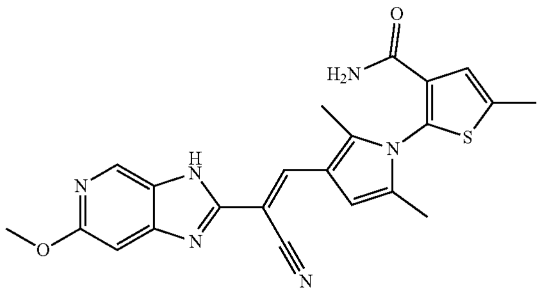
AB24314
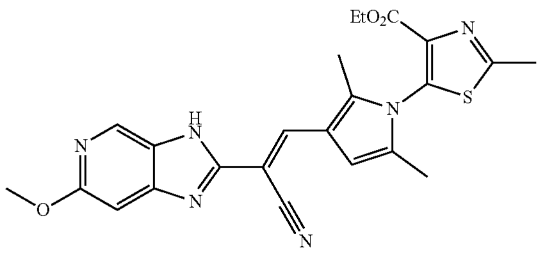
AB24351
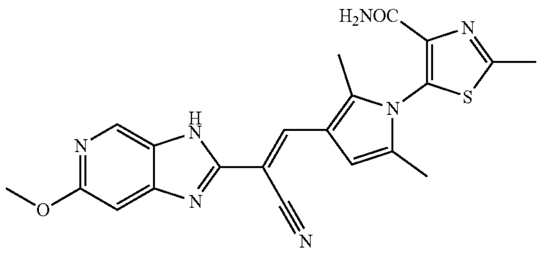
AB24325
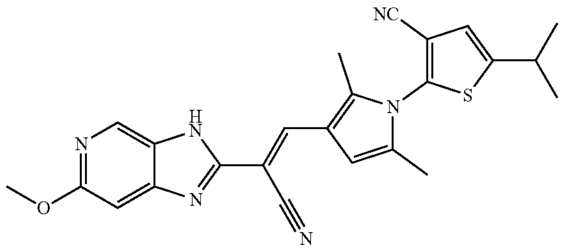
AB24333
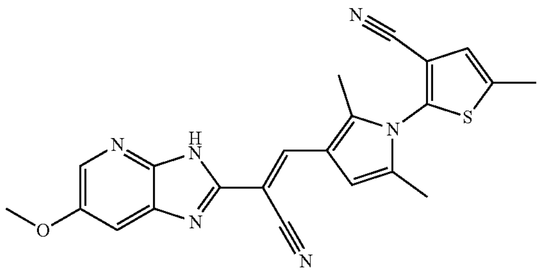
-continued
AB24348
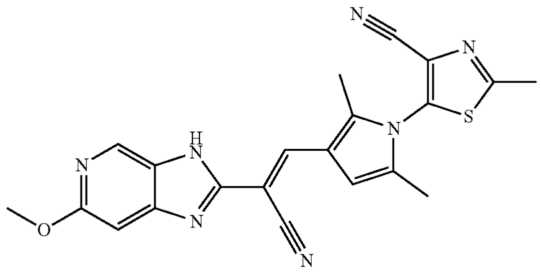
AB24317
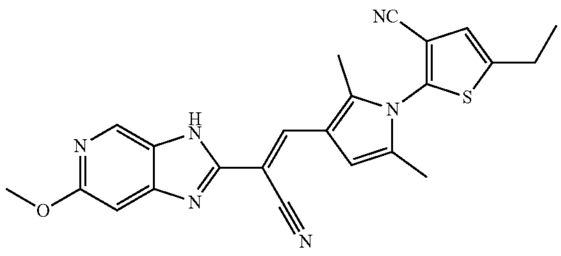
AB24318
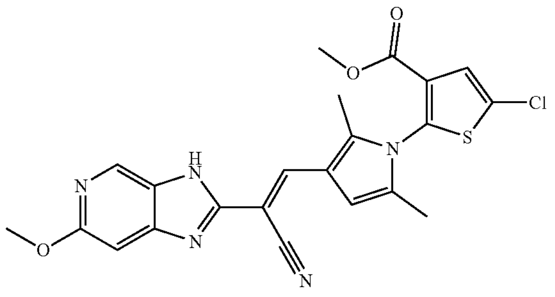
AB24323
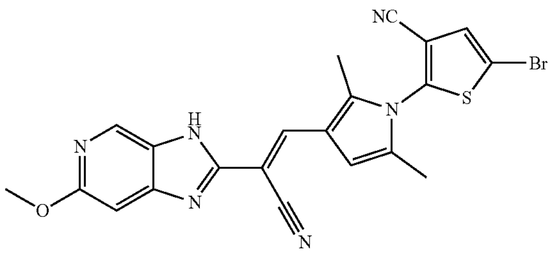
AB24324
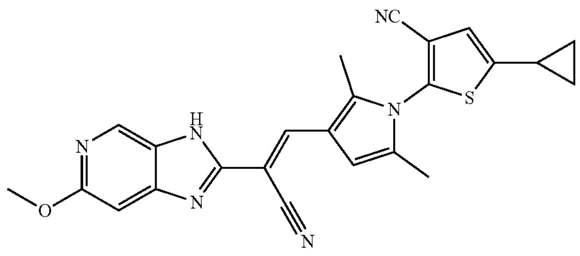

-continued
AB24328
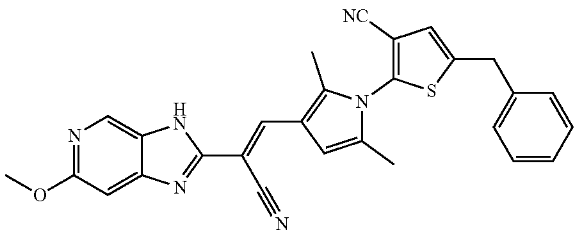
AB24327
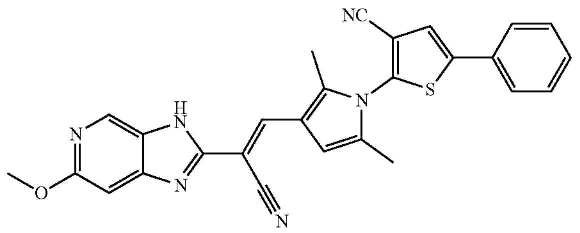
AB29504
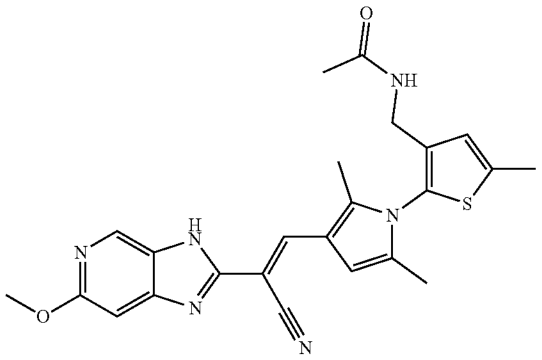
AB24334
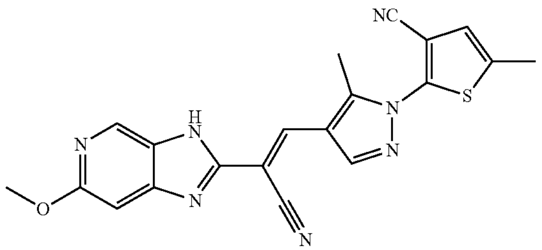
AB24336
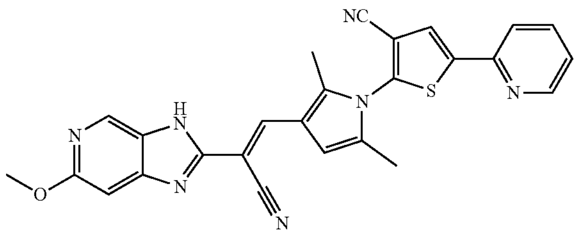
-continued
AB24341
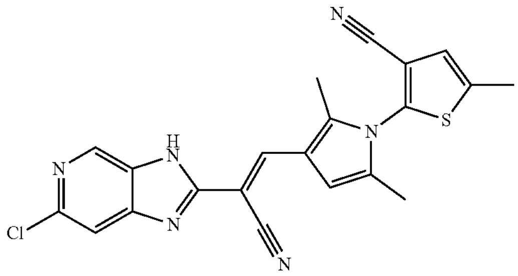
AB24342
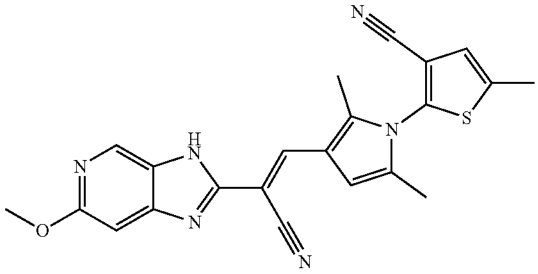
AB24347
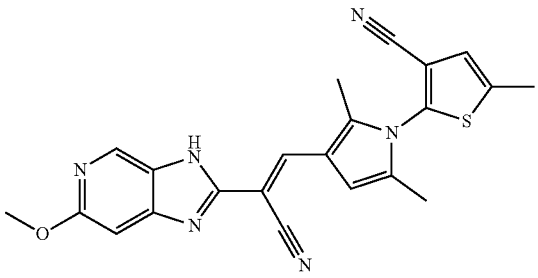
AB24352
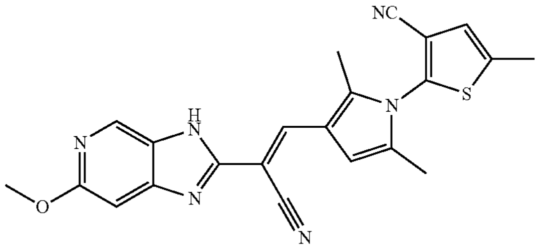
AB24358
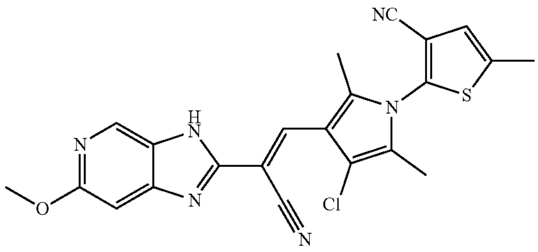

-continued
AB24359
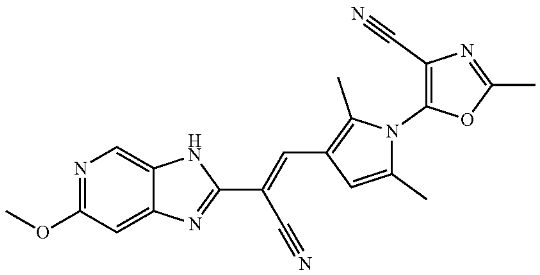
AB24361
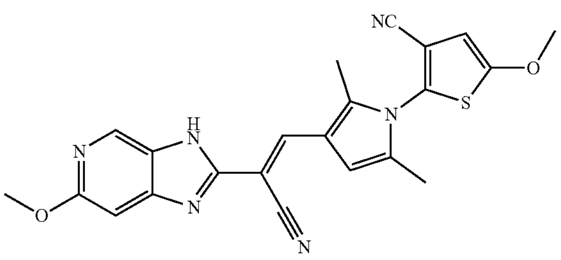
AB24363
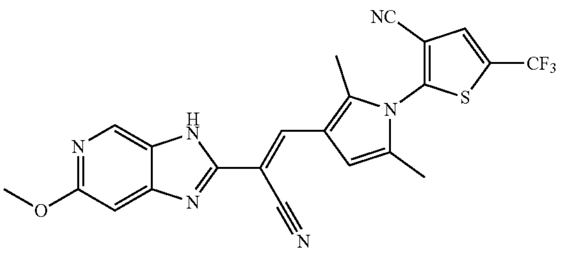
AB24366
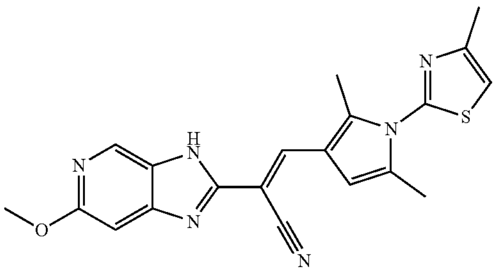
AB24367
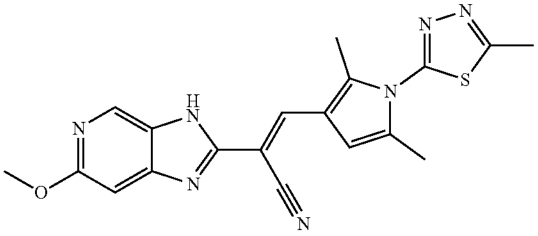
-continued
AB24368
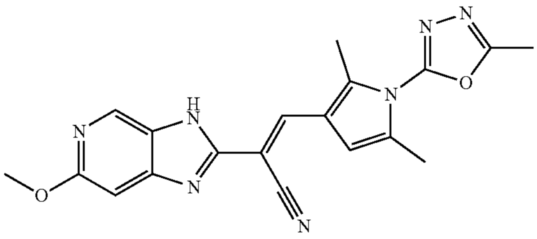
AB24369
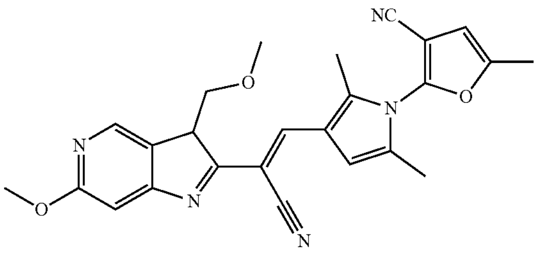
AB24370
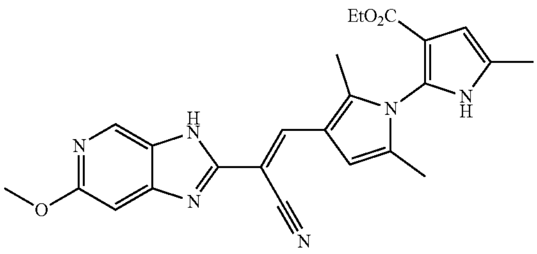
AB24355
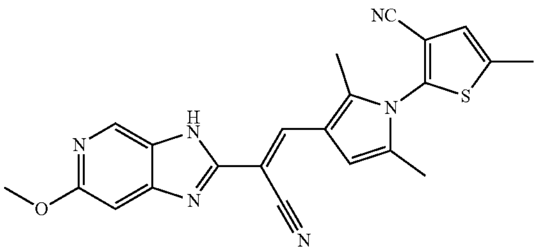
AB24376
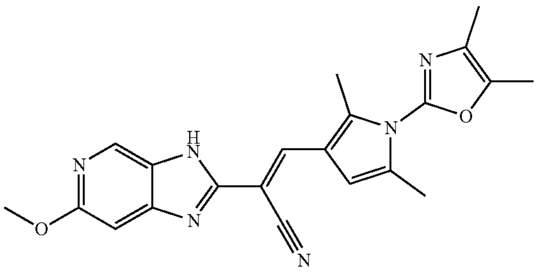

-continued
AB24395
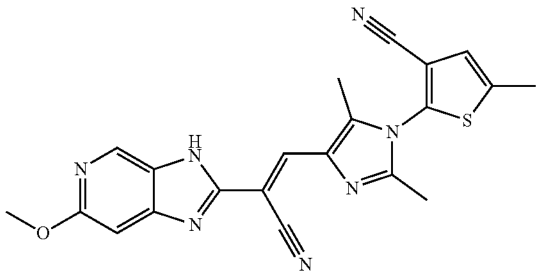
AC29601
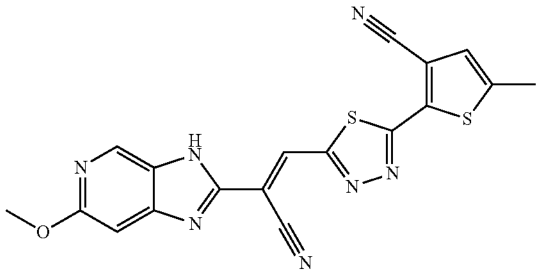
AC29602
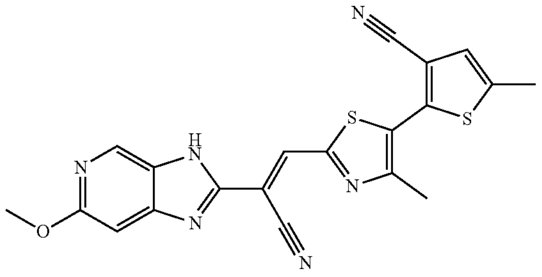
AC29603
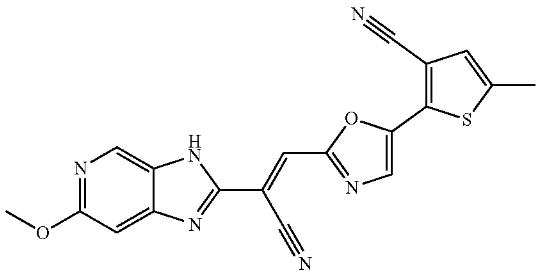
AC29604
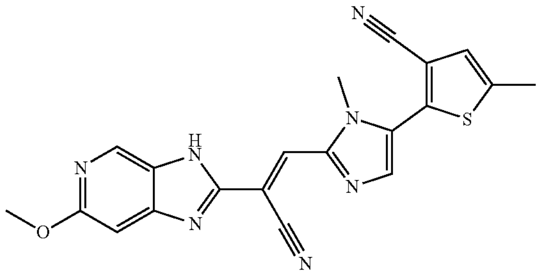
-continued
AC29605
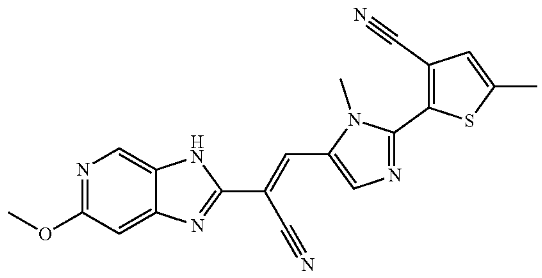
AB29511
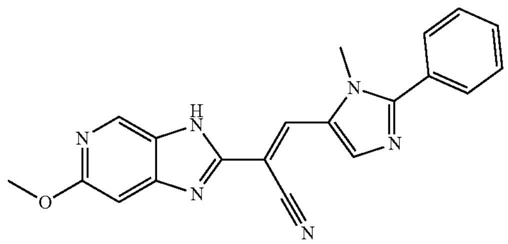
AB24310
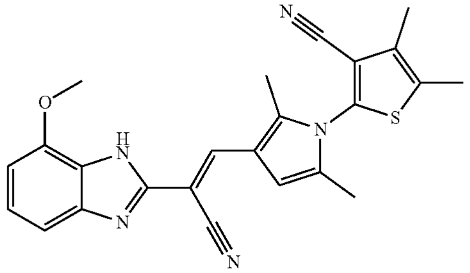
AB24350
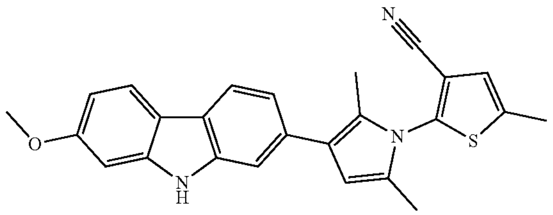
AB24374
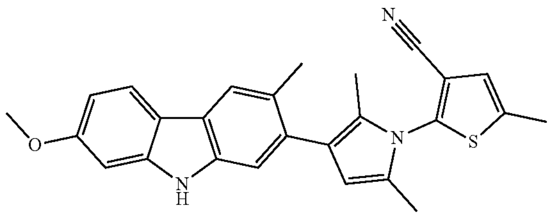
AB24375
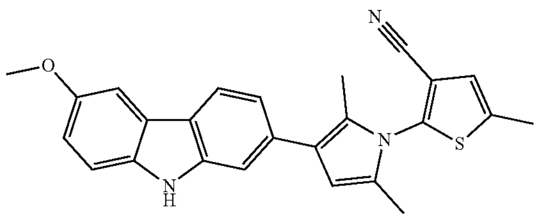

-continued
AB24385
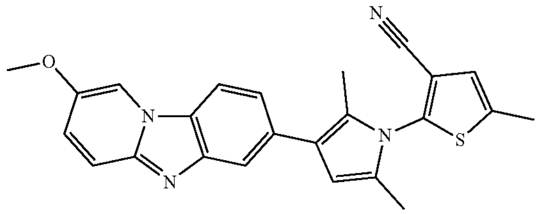
AB24379
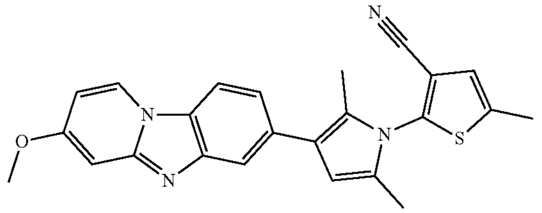
AB24397
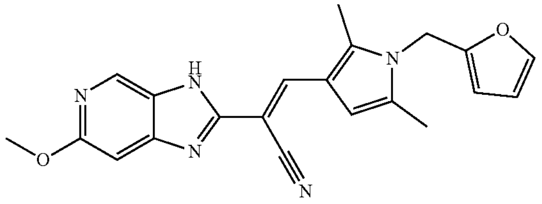
AB29508
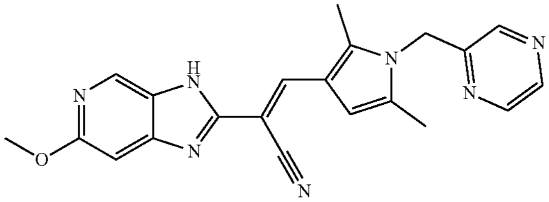
AB29544
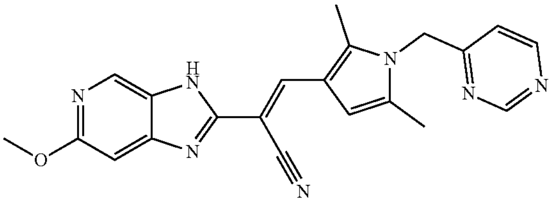
AB24398
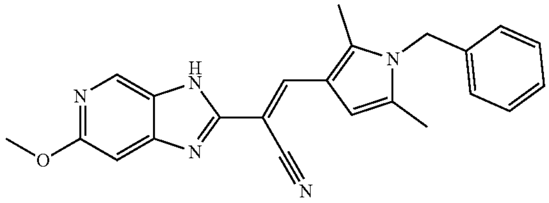
AB29541
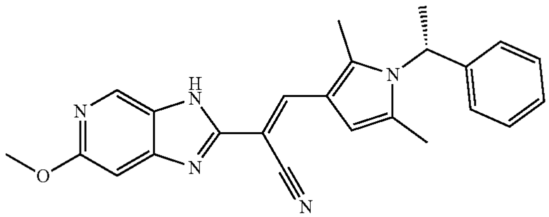
-continued
AB29545
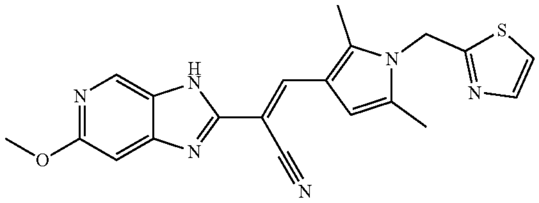
AB24399
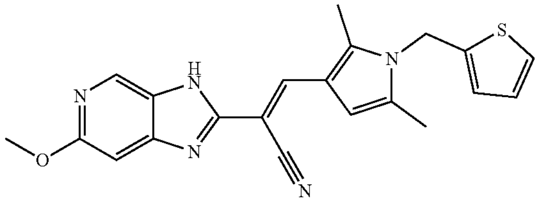
AB29542
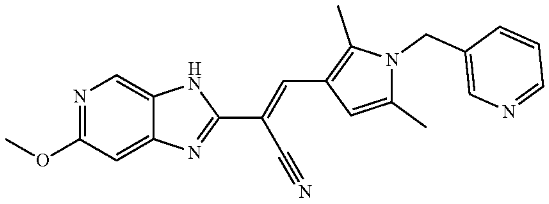
AB29546
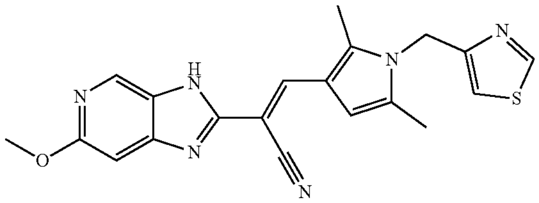
AB29506
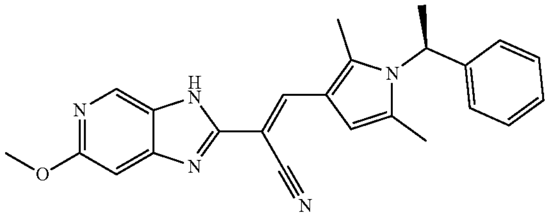
AB29512
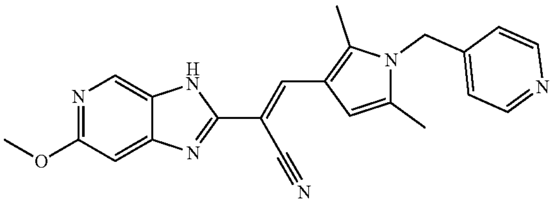
AB29547
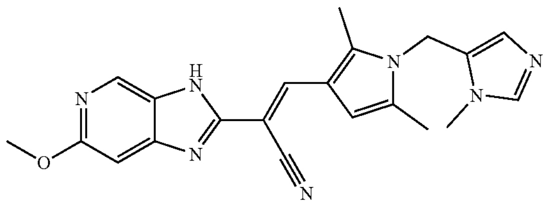

-continued

AB29507

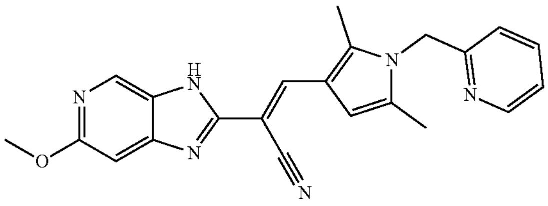

AB29543

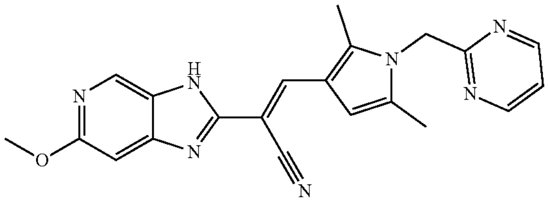

AB29548

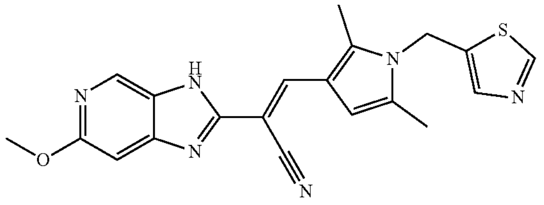

AB29549

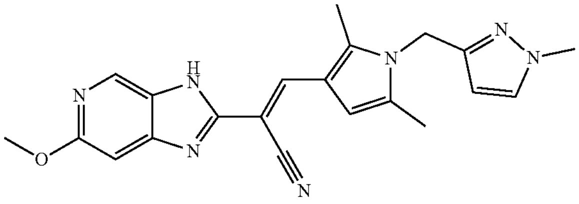

AB29550

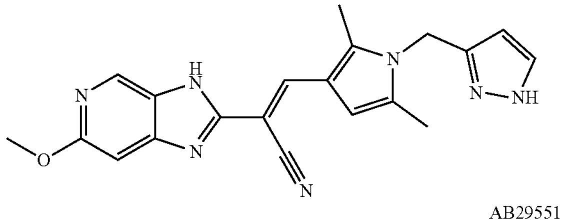

AB29551

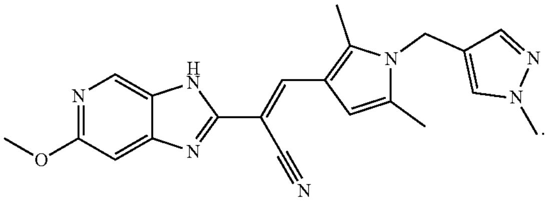

In a third aspect, the present disclosure provides a pharmaceutical composition, comprising at least one of the above-mentioned compounds of formula I to formula VII or the pharmaceutically acceptable form thereof, and one or more pharmaceutically acceptable carriers.

In a fourth aspect, the present disclosure provides the above-mentioned compounds of formula I to formula VII or the pharmaceutically acceptable form thereof or the above-mentioned pharmaceutical composition, for use as a DHX33 inhibitor for preventing and/or treating a disease or a disorder at least partially mediated by DHX33.

In a fifth aspect, the present disclosure provides the use of the above-mentioned compounds of formula I to formula VII or the pharmaceutically acceptable form thereof or the above-mentioned pharmaceutical composition in preparation of a drug for preventing and/or treating a disease or a disorder at least partially mediated by DHX33.

In a sixth aspect, the present disclosure provides a method for preventing and/or treating a disease or a disorder at least partially mediated by DHX33, comprising the following step of administering a prophylactically and/or a therapeutically effective amount of the above-mentioned compounds of formula I to formula VII or the pharmaceutically acceptable form thereof or the above-mentioned pharmaceutical composition to an individual in need thereof.

The present disclosure is not limited to the specific embodiments described herein. It should also be understood that the terms used herein are merely used for describing rather than limiting specific embodiments.

Definition of Terms

Unless otherwise specified, the meanings of the following terms in the present disclosure are as follows.

The terms "comprise", "include", "have" or "contain" or any other variation thereof are intended to encompass non-exclusive or open-ended inclusions. For example, a composition, method or device comprising a series of elements is not necessarily limited to the elements that have been explicitly listed, and may also comprise other elements that are not explicitly listed or the elements inherent to the above-described composition, method or device.

When the lower limit and the upper limit of a numerical range are disclosed, any numerical value or any subrange falling within this range is intended to be specifically disclosed. In particular, each numerical range (for example, in the form of "about a to b", or equivalent form of "approximately a to b", or equivalent form of "about a-b") of a parameter disclosed herein should be understood to encompass each numerical value and each subrange therein. For example, "$C_{1-4}$" should be understood to encompass any subrange and each point value therein, e.g., $C_{2-4}$, $C_{3-4}$, $C_{1-2}$, $C_{1-3}$, $C_{1-4}$ and the like, as well as $C_1$, $C_2$, $C_3$, $C_4$ and the like. For another example, "5-10 membered" should be understood to encompass any subrange and each point value therein, e.g., 5-6 membered, 5-7 membered, 5-8 membered, 5-9 membered, 6-7 membered, 6-8 membered and the like, as well as 5 membered, 6 membered, 7 membered, 8 membered, 9 membered, 10 membered and the like.

The term "pharmaceutical composition" refers to a composition that may be used as a drug and comprises a pharmaceutically active ingredient (or a therapeutic agent) and alternatively one or more pharmaceutically acceptable carriers. The term "pharmaceutically acceptable carrier" refers to an excipient that is administered together with a therapeutic agent and is suitable for contacting with the tissues of human beings and/or other animals without excessive toxicity, irritation, allergic response or other problems or complications corresponding to a reasonable benefit/risk ratio within the scope of reasonable medical judgment. Pharmaceutically acceptable carriers usable in the present disclosure include but are not limited to: a) diluents; b) lubricants; c) binders; d) disintegrants; e) absorbing agents, colorants, flavoring agents and/or sweeteners; f) emulsifying agents or dispersing agents; and/or g) substances that enhance the absorption of the compound, and the like.

The above-mentioned pharmaceutical composition may act systemically and/or locally. For this purpose, they may be administered via suitable routes such as parenteral route, topical route, intravenous route, oral route, subcutaneous route, intraarterial route, intradermal route, transdermal route, rectal route, intracranial route, intraperitoneal route, intranasal route, intramuscular route, or may be administered as an inhalant.

The administration via the above-mentioned routes may be realized via suitable dosage forms. Dosage forms usable in the present disclosure include but are not limited to: tablets, capsules, lozenges, hard candies, powders, sprays, creams, ointments, suppositories, gels, pastes, lotions, ointments, aqueous suspensions, injectable solutions, elixirs, syrups, and the like.

When administered orally, the above-mentioned pharmaceutical composition may be prepared into any orally acceptable formulation, including but not limited to tablets, capsules, aqueous solutions, aqueous suspensions, and the like.

The above-mentioned pharmaceutical composition may also be administered in the form of sterile injection, including sterile injectable aqueous suspensions or oily suspensions, or sterile injectable aqueous solutions or oily solutions. Among these, usable carriers include but are not limited to water, Ringer's solution and isotonic sodium chloride solution. In addition, sterile non-volatile oils such as monoglycerides or diglycerides may also be used as a solvent or a suspending medium.

The above-mentioned pharmaceutical composition may comprise 0.01 mg to 1000 mg of at least one of the above-mentioned compounds of formula I to formula VII or a pharmaceutically acceptable form thereof.

The term "a disease or a disorder at least partially mediated by DHX33" refers to a disease (such as cancer, viral infection and inflammation) of which the pathogeneses at least include DHX33-related factors in part.

The term "effective amount" refers to a dosage that is capable of inducing a cell, a tissue, an organ or an organism (e.g., an individual) to generate biological or medical response and is sufficient to achieve the desired prophylactic and/or therapeutic effects.

Dosing regimens may be adjusted to provide the optimal desired response. For example, the drug may be administered in a single dose, may be administered in divided doses over time, or may be administered in a dose that is reduced or increased proportionately according to the actual situation. It could be understood that, for any particular individual, the specific dosing regimen should be adjusted as needed and according to the professional judgment of the person administering the composition or supervising the administration of the composition.

The term "in need thereof" refers to a judgment of a physician or other nursing staff that an individual needs or will benefit from the prophylactic and/or therapeutic process, and this judgment is obtained based on various factors in the field of expertise of the physician or other nursing staff.

The term "individual" (or referred to as subject) refers to a human or a non-human animal. The individuals of the present disclosure include individuals suffering from a disease and/or disorder (patients) and normal individuals. The non-human animals of the present disclosure include all vertebrates, for example, non-mammals such as birds, amphibians and reptiles, and mammals such as non-human primates, livestock and/or domesticated animals (such as sheeps, dogs, cats, cows and pigs).

The term "treating" means alleviating or eliminating the targeted disease or disorder. If a subject receives a therapeutic amount of the compound or the pharmaceutically acceptable form thereof of the present disclosure or the pharmaceutical composition of the present disclosure and this subject exhibits observable and/or detectable remission and/or improvement in at least one indicator or symptom, it indicates that this subject has been successfully "treated". It could be understood that treatment not only includes the complete treatment, but also includes a case where the complete treatment has not been achieved while some biologically or medically relevant results have been achieved. To be specific, "treating" means that the compound or the pharmaceutically acceptable form thereof of the present disclosure or the pharmaceutical composition of the present disclosure is capable of realizing at least one of the following effects, for example, (1) preventing the occurrence of a disease in an animal that may be predisposed to the disease but have not yet experienced or exhibited the pathology or symptomatology of the disease, (2) inhibiting a disease (that is, preventing further progression of pathology and/or symptomatology) in an animal that is experiencing or exhibiting the pathology or symptomatology of the disease, and (3) ameliorating a disease (that is, reversing pathology and/or symptomatology) in an animal that is experiencing or exhibiting the pathology or symptomatology of the disease.

The term "pharmaceutically acceptable salt" refers to a salt of a compound of the present disclosure which is substantially non-toxic to an organism. Pharmaceutically acceptable salts generally include but are not limited to salts formed by the reaction of the compounds of the present disclosure with pharmaceutically acceptable inorganic/organic acids or inorganic/organic bases, and such salts are also referred to as acid addition salts or base addition salts. As for reviews of suitable salts, please refer to, for example, Jusiak, Soczewinski, et al., Remington's Pharmaceutical Sciences [M], *Mack Publishing Company,* 2005 and Stahl, Wermuth, Handbook of Pharmaceutical Salts: Properties, Selection, and Use [M], *Wiley-VCH,* 2002. A method for preparing the pharmaceutically acceptable salts of the compounds of the present disclosure is known to those skilled in the art.

The term "pharmaceutically acceptable ester" refers to an ester that is substantially non-toxic to an organism and is hydrolyzed to a compound of the present disclosure or a salt thereof in the organism. Pharmaceutically acceptable esters generally include but are not limited to esters formed by the compounds of the present disclosure and pharmaceutically acceptable carboxylic acids or sulfonic acids, and such esters are also referred to as carboxylic acid esters or sulfonic acid esters.

The term "isomers" refers to compounds that have the same molecular weight due to the same number and type of atoms while having different spatial arrangement of atoms or configurations.

The term "stereoisomer" (or referred to as "optical isomer") refers to a stable isomer that has a vertical asymmetric plane resulting from at least one chiral factor (including a chiral center, a chiral axis, a chiral plane, and the like) and thus is capable of enabling the rotation of the plane-polarized light. Since asymmetric center(s) and other chemical structures that may result in stereoisomerism exist in the compounds of the present disclosure, the present disclosure also includes these stereoisomers and the mixtures thereof.

Unless otherwise indicated, all stereoisomeric forms of the compounds of the present disclosure are within the scope of the present disclosure.

The term "tautomers" (or referred to as "tautomeric forms") refers to structural isomers that have different energy and are interconvertible via a low energy barrier. If tautomerism is possible (for example, in solution), a chemical equilibrium of tautomers may be achieved. For example, proton tautomers (or referred to as proton-transfer tautomers) include but are not limited to those obtained by the interconversion via proton transfer such as keto-enol tautomerism, imine-enamine tautomerism and amide-iminol tautomerism. Unless otherwise indicated, all tautomeric forms of the compounds of the present disclosure are within the scope of the present disclosure.

The term "solvate" refers to a substance formed by the association of a compound of the present disclosure (or a pharmaceutically acceptable salt thereof) with at least one kind of solvent molecule via non-covalent intermolecular force. For example, solvates include but are not limited to hydrates (including hemihydrates, monohydrates, dihydrates, trihydrates, and the like), ethanolates, acetonates, and the like.

The term "N-oxide" refers to a compound formed by the oxidation of the nitrogen atom(s) in the structure of a tertiary amine-based compound or a nitrogen-containing (aromatic) heterocyclic compound. For example, the nitrogen atoms in the parent structure of the compound of formula I may be oxidized, so that the corresponding N-oxide may be formed.

The term "isotopically labeled form" refers to a derivative compound formed by replacing a particular atom in a compound of the present disclosure with an isotope thereof.

Unless otherwise indicated, the compounds of the present disclosure comprise various isotopes of H, C, N, O, F, P, S and Cl, such as, but not limited to, $^{2}H$(D). $^{3}H$(T), $^{13}C$, $^{14}C$, $^{15}N$, $^{17}O$, $^{18}O$, $^{18}F$, $^{31}P$, $^{32}P$, $^{35}S$, $^{36}S$ $^{37}Cl$.

The term "metabolite" refers to a derivative compound formed by the metabolism of a compound of the present disclosure. As for further information on metabolism, please refer to Goodman and Gilman's: The Pharmacological Basis of Therapeutics ($9^{th}$ ed.) [M], McGraw-Hill International Editions, 1996. The present disclosure encompasses all possible forms of the metabolites of the compounds of the present disclosure, that is, substances formed in an individual to whom the compound(s) of the present disclosure is administered. The metabolites of compounds may be identified by techniques well known in the art, and the activity thereof may be characterized by assays.

The term "prodrug" refers to a derivative compound capable of directly or indirectly providing a compound of the present disclosure upon administration to an individual. Particularly preferred derivative compounds or prodrugs are compounds that are capable of improving the bioavailability of the compounds of the present disclosure (e.g., enabling easier absorption into blood) or facilitating the delivery of the parent compounds to the sites of action (e.g., the lymphatic system) when administered to an individual. Unless otherwise indicated, all forms of the prodrugs of the compounds of the present disclosure are within the scope of the present disclosure, and various forms of the prodrugs are known in the art, for example, see T. Higuchi, V. Stella, Pro-drugs as Novel Drug Delivery Systems [J], *American Chemical Society,* Vol. 14, 1975. In addition, the present disclosure also encompasses the compounds of the present disclosure that contain protecting groups. In any process of preparing the compounds of the present disclosure, it may be essential and/or desirable to protect the sensitive group(s) or reactive group(s) on any relevant molecule, and the chemically protected forms of the compounds of the present disclosure are thus formed. It could be achieved by conventional protecting groups, such as the protecting groups described in T. W. Greene, P. G M. Wuts, Protective Groups in Organic Synthesis [M], *John Wiley & Sons,* 2006. These protecting groups may be removed at an appropriate subsequent stage using methods known in the art.

The term "each independently" means that at least two groups (or cyclic systems) that are present in the structure and have the same or similar range of values may have the same or different meanings under certain circumstances. For example, substituent X and substituent Y are each independently hydrogen, halogen, hydroxyl, cyano, alkyl or aryl, then when substituent X is hydrogen, substituent Y may be hydrogen, and may also be halogen, hydroxyl, cyano, alkyl or aryl; similarly, when substituent Y is hydrogen, substituent X may be hydrogen, and may also be halogen, hydroxyl, cyano, alkyl or aryl.

When used herein alone or in combination with other groups, the term "halogen" refers to fluorine (F), chlorine (Cl), bromine (Br) and iodine (I).

When used herein alone or in combination with other groups, the term "alkyl" refers to a linear or branched aliphatic hydrocarbon group. For example, the term "$C_{1-6}$ alkyl" used in the present disclosure refers to an alkyl group having 1 to 6 carbon atoms. For example, alkyl groups include but are not limited to methyl, ethyl, n-propyl, isopropyl, n-butyl, sec-butyl, isobutyl, tert-butyl, or the like. Alkyl groups may be optionally substituted or unsubstituted.

When used herein alone or in combination with other groups, the term "alkylene" refers to a linear or branched divalent saturated aliphatic hydrocarbon group, and the two groups (or fragments) attached to alkylene may be attached to either the same carbon atom or different carbon atoms. For example, the term "$C_{1-4}$ alkylene" used herein refers to an alkylene group having 1 to 6 carbon atoms (e.g., methylene, 1,1-ethylene, 1,2-ethylene, 1,2-propylene, 1,3-butylene, and the like). Alkylene groups may be optionally substituted or unsubstituted.

When used herein alone or in combination with other groups, the term "haloalkyl" refers to an alkyl group substituted with one or more (such as 1 to 3) same or different halogen atoms. For example, the term "$C_{1-6}$ haloalkyl" used in the present disclosure refers to a haloalkyl group having 1 to 6 carbon atoms. For example, haloalkyl groups include but are not limited to $-CH_2F$, $-CHF_2$, $-CF_3$, $-CH_2CF_3$, $-CF_2CF_3$, $-CH_2CH_2CF_3$, $-CH_2Cl$, and the like. Haloalkyl groups may be optionally substituted or unsubstituted.

When used herein alone or in combination with other groups, the term "hydroxyalkyl" refers to an alkyl group substituted with one or more (such as 1 to 3) hydroxyl groups. For example, the term "$C_{1-6}$ hydroxyalkyl" used in the present disclosure refers to a hydroxyalkyl group having 1 to 6 carbon atoms. For example, hydroxyalkyl groups include but are not limited to

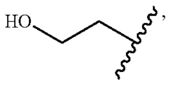,
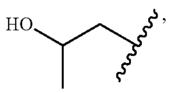,
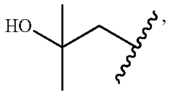,
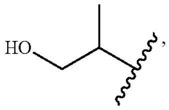,
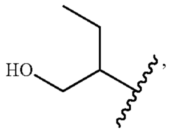,
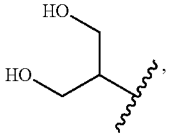,

-continued

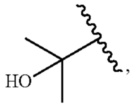

or the like.

Hydroxyalkyl groups may be optionally substituted or unsubstituted. When used herein alone or in combination with other groups, the term "alkoxy" refers to an alkyl group that is attached to the remaining part of the molecule via an oxygen atom. For example, alkoxy groups include but are not limited to methoxy, ethoxy, n-propoxy, isopropoxy, n-butoxy, isobutoxy, tert-butoxy, and the like. Alkoxy groups may be optionally substituted or unsubstituted.

When used herein alone or in combination with other groups, the term "haloalkoxy" refers to a monovalent linear or branched haloalkyl-O-group, which is substituted with at least one atom selected from fluorine, chlorine, bromine and iodine, may comprise degree(s) of unsaturation, and is attached to other groups via a single bond attached to an oxygen atom, such as $C_{1-6}$haloalkoxy. For example, haloalkoxy groups include but are not limited to fluoromethoxy ($—OCH_2F$), difluoromethoxy ($—OCHF_2$), trifluoromethoxy($—OCF_3$), 1-fluoroethoxy ($—OCHFCH_3$), 2-fluoroethoxy ($—OCH_2CH_2F$), 1,2-difluoroethoxy ($—OCHFCH_2F$), 2,2-difluoroethoxy ($—OCH_2CHF_2$), 1,2,2-trifluoroethoxy ($—OCHFCHF_2$), 2,2,2-trifluoroethoxy ($—OCH_2CF_3$), and the like.

When used herein alone or in combination with other groups, the term "alkylthio" refers to an alkyl group that is attached to the remaining part of the molecule via a sulfur atom. For example, alkylthio groups include but are not limited to methylthio, ethylthio, n-propylthio, isopropylthio, and the like. Alkylthio groups may be optionally substituted or unsubstituted.

When used herein alone or in combination with other groups, the term "haloalkylthio" refers to a monovalent linear or branched haloalkyl-S-group, which is substituted with at least one atom selected from fluorine, chlorine, bromine and iodine, may comprise degree(s) of unsaturation, and is attached to other groups via a single bond attached to a sulfur atom, such as $C_{1-6}$ haloalkylthio. For example, haloalkylthio groups include but are not limited to fluoroethylthio ($—SCH_2F$), difluoromethylthio ($—SCHF_2$), trifluoromethylthio ($—SCF_3$), and the like.

When used herein alone or in combination with other groups, the term "cycloalkyl" refers to a monocyclic or polycyclic (such as bicyclic) non-aromatic hydrocarbon group that is saturated or partially saturated. For example, the term "$C_4$ cycloalkyl" used in the present disclosure refers to a cycloalkyl group having 3 to 6 carbon atoms. For example, cycloalkyl groups include but are not limited to cyclopropyl, cyclobutyl, cyclopentyl, cyclohexyl, or the like. Cycloalkyl groups may be optionally substituted or unsubstituted.

When used herein alone or in combination with other groups, the term "heterocyclyl" refers to a monocyclic or polycyclic (for example, bicyclic such as fused cyclic, bridged cyclic or spiro cyclic) non-aromatic group that is saturated or partially saturated and has ring atoms consisting of carbon atoms and at least one heteroatom selected from N, O and S, wherein the sulfur atom is optionally substituted to form S(═O), $S(═O)_2$ or $S(═O)(═NR^x)$ and $R^x$ is independently H or $C_{1-4}$ alkyl. A heterocyclyl group may be attached to the remaining part of the molecule via any one of the ring atoms if the requirements of valence are satisfied. For example, the term "3-8 membered heterocyclyl" used in the present disclosure refers to a heterocyclic group having 3 to 8 ring atoms. Common heterocyclyl groups include (but are not limited to) oxiranyl, aziridinyl, azetidinyl, oxetanyl, tetrahydrofuranyl, dioxolyl, pyrolidinyl, pyrrolidonyl, imidazolidinyl, pyrazolidinyl, tetrahydropyranyl, piperidinyl, piperazinyl, morpholinyl, thiomorpholinyl, dithianyl or trithianyl. A heterocyclic group in the present disclosure is optionally substituted with one or more substituents as described in the present disclosure.

When used herein alone or in combination with other groups, the term "aryl" refers to a monocyclic or fused polycyclic aromatic hydrocarbon group that has a conjugated system of π electrons. For example, the term "$C_{6-10}$ aryl" used in the present disclosure refers to an aryl group having 6 to 10 carbon atoms. Common aryl group include (but are not limited to) phenyl, naphthyl, anthryl, phenanthryl, acenaphthenyl, azulenyl, fluorenyl, indenyl, pyrenyl, and the like. An aryl group in the present disclosure is optionally substituted with one or more substituents as described in the present disclosure.

When used herein alone or in combination with other groups, the term "heteroaryl" refers to a monocyclic or fused polycyclic aromatic group that has a conjugated system of π electrons and has ring atoms consisting of carbon atoms and at least one heteroatom selected from N, O and S. A heteroaryl group may be attached to the remaining part of the molecule via any one of the ring atoms if the requirements of valence are satisfied. For example, the term "5-10 membered heteroaryl" used in the present disclosure refers to a heteroaryl group having 5 to 10 ring atoms. Common heteroaryl groups include (but are not limited to) thienyl, furanyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, triazinyl and the benzo derivatives thereof, pyrrolopyridyl, pyrrolopyridinyl, pyrazolopyridyl, imidazolopyridyl, pyrrolopyrimidinyl, pyrazolopyrimidinyl, purinyl, and the like. A heteroaryl group in the present disclosure is optionally substituted with one or more substituents as described in the present disclosure (e.g., halogen, $C_1$ alkyl, and the like).

When used herein alone or in combination with other groups, the term "hydroxyl" refers to —OH.

When used herein alone or in combination with other groups, the term "cyano" refers to —CN.

When used herein alone or in combination with other groups, the term "amino" refers to $—NH_2$.

When used herein alone or in combination with other groups, the term "nitro" refers to $—NO_2$.

DETAILED DESCRIPTION

Figure 1:
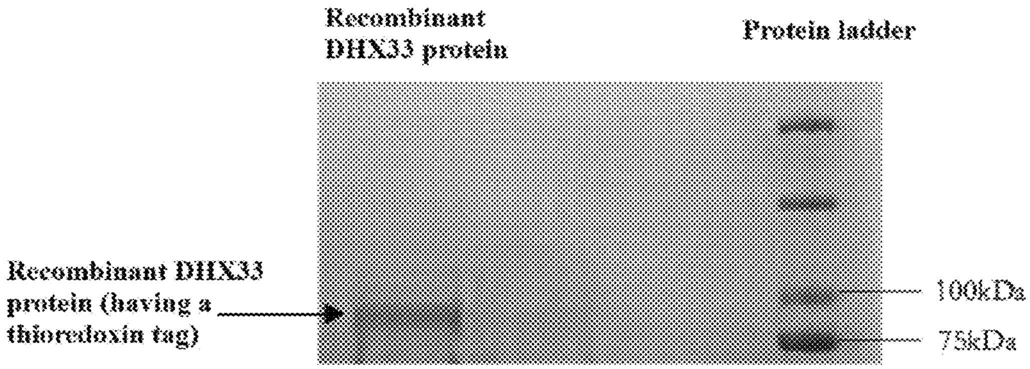
FIG. 1 shows the analysis of the results obtained after the SDS-PAGE separation and Coomassie brilliant blue staining of the recombinant DHX33 protein prepared by using the method of the present disclosure.

In order to make the objects and technical solutions of the present disclosure more explicit, the embodiments of the present disclosure are described in detail below with reference to examples. However, those skilled in the art would understand that the following examples are merely for the illustration of the present disclosure and should not be construed as limiting the scope of the present disclosure.

The reagents or instruments used in the examples are all conventional products that are commercially available. If no specific conditions are specified, the routine conditions or the conditions suggested by the manufacturer shall be followed. The term "room temperature" used in the present disclosure refers to 20° C.±5° C. When used for modifying certain numerical value or numerical range, the term "about" used in the present disclosure is intended to include this numerical value or numerical range as well as the error range (acceptable to those skilled in the art) of this numerical value or numerical range, for example, this error range is ±10%, ±5%, ±4%, ±3%, ±2%, ±1%, ±0.5%, and the like.

The structures of the compounds described in the following examples are determined by nuclear magnetic resonance (NMR) and/or mass spectrometry (MS).

A Bruker 400 MHz NMR spectrometer is used as the measurement instrument of nuclear magnetic resonance (NMR), the solvents used for determination are deuterated methanol ($CD_3OD$), deuterated chloroform ($CDCl_3$) and hexadeuterated dimethyl sulfoxide (DMSO-$d_6$), and the internal standard substance is tetramethylsilane (TMS). In $^1$H NMR, some of the hydrogen atoms may not give rise to peaks due to interference from a salt or a solvent.

The meanings of the abbreviations in the nuclear magnetic resonance (NMR) data in the following examples are as follows.

s: singlet, d: doublet, t: triplet, q: quartet, dd: doublet of doublets, qd: quartet of doublets, ddd: doublet of doublet of doublets, ddt: doublet of doublet of triplets, dddd: doublet of doublet of doublet of doublets, m: multiplet, br: broad singlet, J: coupling constant, Hz: Hertz, δ: chemical shift.

All chemical shift (δ) values are given in parts per million (ppm).

An Agilent 6120B mass spectrometer is used as the measurement instrument of mass spectrometry (MS), and the ion source is an electrospray ion source (ESI).

An Agilent 1200DAD high-pressure liquid chromatograph (chromatographic column: Sunfire C18, 150×4.6 mm, 5 μm) and a Waters 2695-2996 high-pressure liquid chromatograph (chromatographic column: Gimini C18, 150×4.6 mm, 5 μm) are used for HPLC assay.

GF254 silica gel plates manufactured by Qingdao Marine Chemical Inc. are used as the silica gel plates for thin layer chromatography, the specification of the silica gel plates used for thin layer chromatography (TLC) is 0.15 mm to 0.2 mm, and the specification of the silica gel plates used for the separation and purification of the product via thin layer chromatography is 0.4 mm to 0.5 mm.

Silica gel (200 mesh to 300 mesh) manufactured by Qingdao Marine Chemical Inc. is generally used as the carrier in column chromatography.

Thin layer chromatography (TLC) is adopted to monitor the reaction progress in the examples. The solvent systems used in thin layer chromatography include (A) dichloromethane/methanol system and (B) petroleum ether/ethyl acetate system. The volume ratio of solvents is adjusted according to the polarity of the compound.

The eluent systems for column chromatography and the solvent systems for thin layer chromatography adopted for the purification of compounds include (A) dichloromethane/methanol system and (B) petroleum ether/ethyl acetate system. The volume ratio of solvents is adjusted according to the polarity of the compound, and a small amount of triethylamine or an acidic or basic reagent may also be added for adjustment.

Synthesis of Compounds

Example 1: Synthesis of Compound AB29502 (1-(4-cyano-2-methylthiazol-5-yl)-N-(6-methoxy-3H-imidazo[4,5-c]pyridin-2-yl)-2,5-dimethyl-1H-pyrrole-3-carboxamide)

(1) Preparation Method of Compound 3 (ethyl 5-(2,5-dimethyl-1H-pyrrol-1-yl)-2-methylthiazole-4-carboxylate)

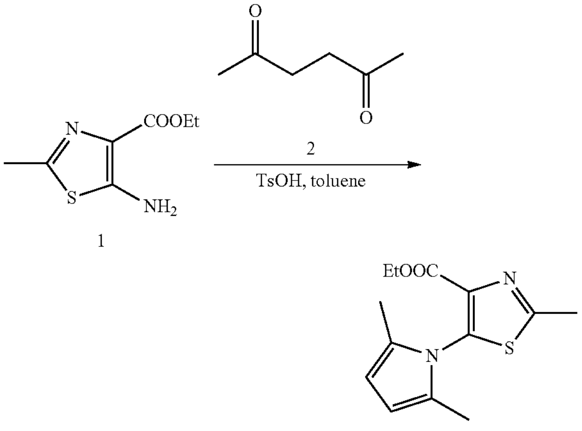

1
3

Compound 1 (ethyl 5-amino-2-methyl-1,3-thiazole-4-carboxylate) (5 g, 26.84 mmol, 1.0 eq) was dissolved in toluene (100 mL). Compound 2 (2,5-hexanedione) (4.6 g, 40.26 mmol, 1.5 eq), 3 A molecular sieve (10 g) and p-toluenesulfonic acid (1.8 g, 10.73 mmol, 0.4 eq) were added thereto. The mixture was heated under reflux and stirred overnight. The solid was filtered and concentrated and the residue was separated by flash column chromatography (petroleum ether/ethyl acetate=10/1), so as to obtain Compound 3 (ethyl 5-(2,5-dimethyl-1H-pyrrol-1-yl)-2-methylthiazole-4-carboxylate) as a white solid (3 g, yield: 42.8%). MS (ESI) m/z: 265 $[M+H]^+$. TLC:petroleum ether/ethyl acetate (5/1); $R_f$ (Compound 1)=0.2; $R_f$ (Compound 3)=0.5.

(2) Preparation Method of Compound 4 (5-(2,5-dimethyl-1H-pyrrol-1-yl)-2-methylthiazole-4-carboxamide)

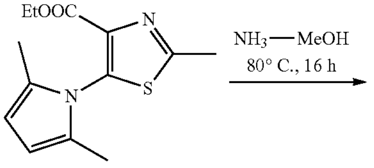

3

-continued

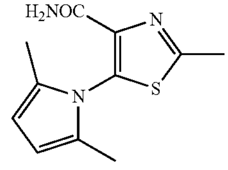

4

Compound 3 (ethyl 5-(2,5-dimethyl-1H-pyrrol-1-yl)-2-methylthiazole-4-carboxylate) (3.0 g, 11.4 mmol, 1.0 eq) was dissolved in a mixed solution of ammonia/methanol (40 mL). The mixture was sealed in a reaction tube and heated and stirred at 80° C. for 16 hours. The solid was filtered so as to obtain Compound 4 (5-(2,5-dimethyl-1H-pyrrol-1-yl)-2-methylthiazole-4-carboxamide) as a white solid (1.9 g, yield: 71.2%). MS (ESI) m/z: 236 $[M+H]^+$. TLC:petroleum ether/ethyl acetate (3/1); $R_f$ (Compound 3)=0.6; $R_f$ (Compound 4)=0.4.

(3) Preparation Method of Compound 5 (5-(3-formyl-2,5-dimethyl-1H-pyrrol-1-yl)-2-methylthiazole-4-carbonitrile)

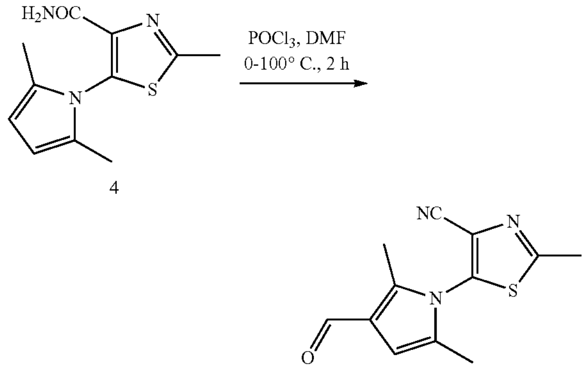

4

5

Phosphorus oxychloride (2.48 g, 16.2 mmol, 2.0 eq) was added dropwise to dimethylformamide (30 mL) at 0° C. under the protection of nitrogen gas. The mixture was stirred at 0° C. for 30 minutes and then warmed to room temperature. Compound 4 (5-(2,5-dimethyl-1H-pyrrol-1-yl)-2-methylthiazole-4-carboxamide) (1.9 g, 8.09 mmol, 1.0 eq) in dimethylformamide (4 mL) was added to the above-mentioned reaction system. Afterwards, the above-mentioned reaction solution was heated to 100° C. and stirred for one hour under the protection of nitrogen gas. After the reaction solution was cooled, the mixture was poured into ice water and the pH of the resulting mixture was then adjusted to 10 with 30% NaOH aqueous solution. The mixture was extracted with ethyl acetate and washed with brine. Afterwards, the organic layer was dried over anhydrous sodium sulfate and concentrated. The residue was purified by flash column chromatography (petroleum ether/ethyl acetate=2/1) so as to obtain Compound 5 (5-(3-formyl-2,5-dimethyl-1H-pyrrol-1-yl)-2-methylthiazole-4-carbonitrile) as a white solid (1.3 g, yield: 65.6%). MS (ESI) m/z: 246 $[M+H]^+$. TLC:petroleum ether/ethyl acetate (2/1); $R_f$ (Compound 4)=0.3; $R_f$ (Compound 5)=0.5.

(4) Preparation Method of Compound 6 (1-(4-cyano-2-methylthiazol-5-yl)-2,5-dimethyl-1H-pyrrole-3-carboxylic acid)

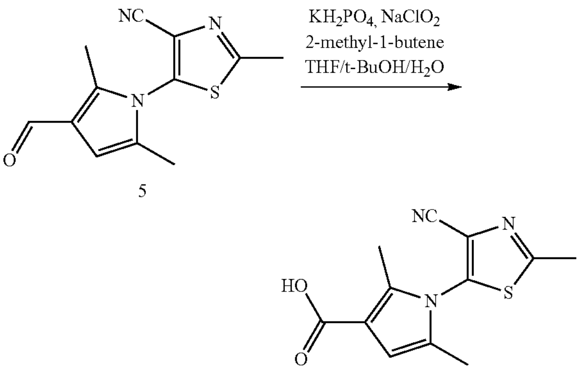

5

6

Compound 5 (5-(3-formyl-2,5-dimethyl-1H-pyrrol-1-yl)-2-methylthiazole-4-carbonitrile) (1.7 g, 6.93 mmol, 1.0 eq) was dissolved in tetrahydrofuran/tert-butanol/water (1/1/1, 45 mL). Potassium dihydrogen phosphate (4.71 g, 34.65 mmol, 5.0 eq), 2-methyl-1-butene (4.86 g, 69.3 mmol, 10.0 eq) and sodium chlorite (3.76 g, 41.58 mmol, 6.0 eq) were added thereto at 0° C. The reactants were stirred and refluxed at room temperature for 16 hours. After the completion of the reaction, the mixture was concentrated and then purified by preparative high-pressure liquid chromatography so as to obtain Compound 6 (1-(4-cyano-2-methylthiazol-5-yl)-2,5-dimethyl-1H-pyrrole-3-carboxylic acid) as a white solid (450 mg, yield: 25%). MS (ESI) m/z: 262 $[M+H]^+$.

(5) Preparation Method of Compound AB29502 (1-(4-cyano-2-methylthiazol-5-yl)-N-(6-methoxy-3H-imidazo[4,5-c]pyridin-2-yl)-2,5-dimethyl-1H-pyrrole-3-carboxamide)

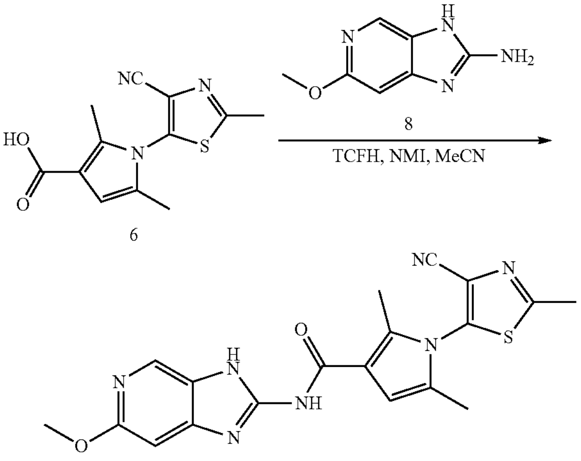

6

AB29502

Compound 6 (1-(4-cyano-2-methylthiazol-5-yl)-2,5-dimethyl-1H-pyrrole-3-carboxylic acid) (55 mg, 0.21 mmol, 1.0 eq) was dissolved in acetonitrile (2.0 mL). Compound 8

(6-methoxy-3H-imidazo[4,5-c]pyridin-2-amine) (46 mg, 0.273 mmol, 1.3 eq), 2-methylimidazole NMI (69 mg, 0.84 mmol, 4.0 eq) and tetramethylchloroformamidinium hexafluorophosphate TCFH (71 mg, 0.25 mmol, 1.2 eq) were added thereto. The mixture was stirred at room temperature for 1 hour. After the completion of the reaction, the mixture was concentrated and then separated and purified by preparative high-pressure liquid chromatography, so as to obtain Compound AB29502 (1-(4-cyano-2-methylthiazol-5-yl)-N-(6-methoxy-3H-imidazo[4,5-c]pyridin-2-yl)-2,5-dimethyl-1H-pyrrole-3-carboxamide) as a yellow solid (2.5 mg, yield: 2.9%). MS (ESI) m/z: 408.3 [M+H$^+$]. $^1$H NMR (400 MHz, $CD_3OD$-d4) δ 8.33 (s, 1H), 7.21 (s, 1H), 6.70 (s, 1H), 4.09 (s, 3H), 2.78 (s, 3H), 2.48 (s, 3H), 2.15 (s, 3H).

Example 2: Preparation method of Compound AB29509 (1-(4-cyano-2-methylthiazol-5-yl)-N-(6-methoxy-1H-benzo[d]imidazol-2-yl)-2,5-dimethyl-1H-pyrrole-3-carboxamide)

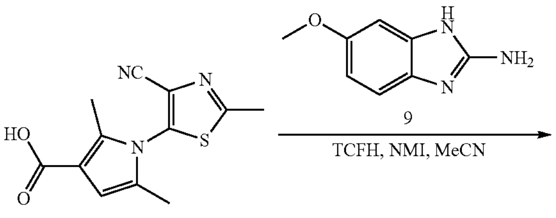

9

6

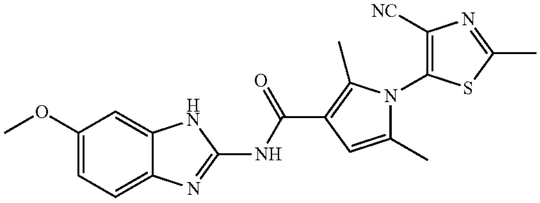

AB29509

Compound 6 (1-(4-cyano-2-methylthiazol-5-yl)-2,5-dimethyl-1H-pyrrole-3-carboxylic acid) (100 mg, 0.38 mmol, 1.0 eq) was dissolved in acetonitrile (5.0 mL). Compound 9 (6-methoxy-1H-benzo[d]imidazole-2-amine) (81 mg, 0.50 mmol, 1.3 eq), 2-methylimidazole NMI (126 mg, 1.53 mmol, 4.0 eq) and tetramethylchloroformamidinium hexafluorophosphate TCFH (129 mg, 0.46 mmol, 1.2 eq) were added thereto. The mixture was stirred at room temperature for 1 hour. After the completion of the reaction, the mixture was concentrated and purified by preparative high-pressure liquid chromatography, so as to obtain Compound AB29509 (1-(4-cyano-2-methylthiazol-5-yl)-N-(6-methoxy-1H-benzo[d]imidazol-2-yl)-2,5-dimethyl-1H-pyrrole-3-carboxamide) as a yellow solid (3.0 mg, yield: 1.9%). MS (ESI) m/z: 407.10 [M+H$^+$]. $^1$H NMR (400 MHz, DMSO-$d_6$) δ 7.45 (d, J=10 Hz, 1H), 7.10 (s, 1H), 6.88 (d, J=8.8 Hz, 1H), 6.81 (s, 1H), 3.76 (s, 3H), 2.76 (s, 3H), 2.42 (s, 3H), 2.09 (s, 3H).

Example 3: Synthesis of Compound AB24386 (1-(3-cyano-5-methylthiophen-2-yl)-N-(6-methoxy-1H-benzo[d]imidazol-2-yl)-2,5-dimethyl-1H-pyrrole-3-carboxamide)

(1) Preparation Method of Compound 3 (ethyl 2-acetyl-4-levulinate)

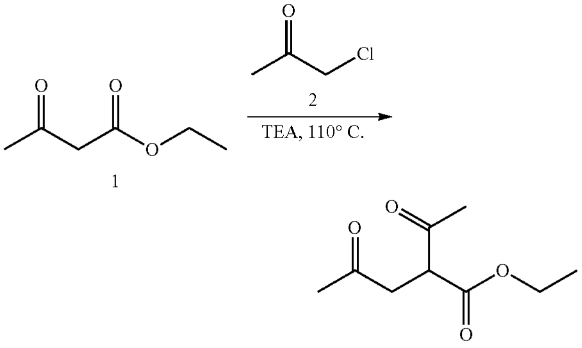

2

1

3

Compound 1 (ethyl acetoacetate) (5 g, 38.42 mmol, 1.0 eq) was dissolved in triethylamine (75 mL), and Compound 2 (chloroacetone) (3.5 g, 38.42 mmol, 1.0 eq) was added thereto. The reactants were reacted at 110° C. for 2 hours under the protection of nitrogen gas. After being concentrated, the residue was dissolved in water (100 mL) and then extracted twice with dichloromethane (50 mL for each extraction). The organic layers were washed with brine, dried over anhydrous sodium sulfate, filtered and then concentrated. The residue was purified by flash column chromatography (petroleum ether/ethyl acetate=100/1 to 50/1 to 20/1), so as to obtain Compound 3 (ethyl 2-acetyl-4-levulinate) as a colorless oil (1.3 g, yield: 18.3%). MS (ESI) m/z: 187 [M+H$^+$]. TLC:PE/EA (2/1); $R_f$ (Compound 1)=0.6; $R_f$(Compound 3)=0.4.

(2) Preparation Method of Compound 5 (ethyl 1-(3-cyano-5-methylthiophen-2-yl)-2,5-dimethyl-1H-pyrrole-3-carboxylate)

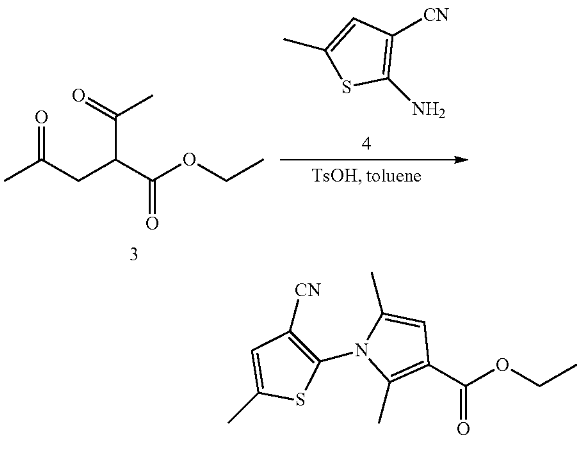

4

3

5

Compound 3 (ethyl 2-acetyl-4-levulinate) (1 g, 7.23 mmol, 1.0 eq) was dissolved in toluene (20 mL). Compound 4 (2-amino-3-cyano-5-methylthiophene) (1.6 g, 8.68 nmol, 1.2 eq) and p-toluenesulfonic acid (249 mg, 1.45 mmol, 0.2 eq) were added thereto. The reactants were stirred at 110° C. for 16 hours. The solid was filtered and then concentrated. The residue was purified by flash column chromatography (petroleum ether/ethyl acetate=50/1 to 30/1), so as to obtain Compound 5 (ethyl 1-(3-cyano-5-methylthiophen-2-yl)-2,5-dimethyl-1H-pyrrole-3-carboxylate) as a yellow oil (860 mg, yield: 41%). MS (ESI) m/z: 289 [M+H$^+$]. TLC:petroleum ether/ethyl acetate (10/1); $R_f$ (Compound 3)=0.2; $R_f$ (Compound 5)=0.4.

(3) Preparation Method of Compound AB24386 (1-(3-cyano-5-methylthiophen-2-yl)-N-(6-methoxy-1H-benzo[d]imidazol-2-yl)-2,5-dimethyl-1H-pyrrole-3-carboxamide)

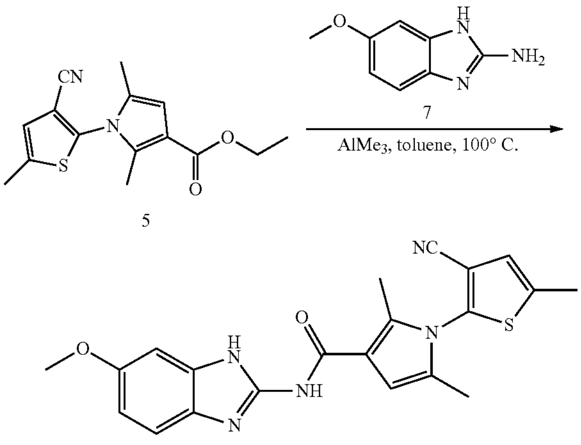

7

5

AB24386

Trimethylaluminum (0.15 mL, 0.306 mmol, 1.0 eq, 2 M in toluene) was added into the mixture of Compound 5 (ethyl 1-(3-cyano-5-methylthiophen-2-yl)-2,5-dimethyl-1H-pyrrole-3-carboxylate) (50 mg, 0.306 mmol, 1.0 eq) and Compound 7 (5-methoxy-1H-benzimidazole-2-amine) (88 mg, 0.306 mmol, 1.0 eq) that was dissolved in 1 mL of toluene. The reactants were stirred at 100° C. for 16 hours. The mixture was cooled to room temperature and quenched with methanol (10 mL), and the pH of the resulting mixture was then adjusted to 3 with 3 M hydrochloric acid. The mixture was diluted with water (30 mL) and then extracted three times with ethyl acetate (20 ml for each extraction). The organic layers were washed with brine, dried over anhydrous sodium sulfate, filtered and then concentrated. The residue was purified by preparative high-pressure liquid chromatography Prep-HPLC (acetonitrile/water (containing 0.1% formic acid)) so as to obtain Compound AB24386 (1-(3-cyano-5-methylthiophen-2-yl)-N-(6-methoxy-1H-benzo[d]imidazol-2-yl)-2,5-dimethyl-1H-pyrrole-3-carboxamide) as a white solid (5 mg, yield: 4%). MS (ESI) m/z: 406 [M+H$^+$]. $^1$H NMR (400 MHz, DMSO-d$_6$): δ 12.04 (s, 1H), 11.20 (s, 1H), 7.32 (s, 1H), 7.29 (s, 1H), 6.98 (s, 1H), 6.89 (s, 1H), 6.69 (d, J=7.2 Hz, 1H), 3.73 (s, 3H), 2.47 (s, 3H), 2.38 (s, 3H), 2.04 (s, 3H).

Example 4: Preparation Method of Compound AB24387 (1-(3-carbamoyl-5-methylthiophen-2-yl)-N-(6-methoxy-1H-benzo[d]imidazol-2-yl)-2,5-dimethyl-1H-pyrrole-3-carboxamide)

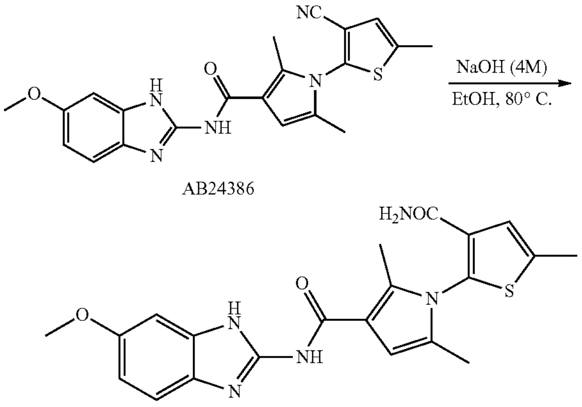

AB24386

AB24387

Compound AB24386 (1-(3-cyano-5-methylthiophen-2-yl)-N-(6-methoxy-1H-benzo[d]imidazol-2-yl)-2,5-dimethyl-1H-pyrrole-3-carboxamide) (15 mg, 0.037 mmol, 1.0 eq) was dissolved in ethanol (4 mL), and sodium hydroxide (0.5 mL, 4 M in $H_2O$) was added thereto. The mixture was stirred at 80° C. for 2 hours. After the reaction mixture was cooled, the mixture was diluted with water (10 mL) and the pH of the resulting mixture was then adjusted to 6 to 7 with 3 N hydrochloric acid. The mixture was extracted three times with ethyl acetate (20 mL×3). The organic layers were dried over anhydrous sodium sulfate, filtered and concentrated. The residue was purified by preparative high-pressure liquid chromatography (acetonitrile/water/0.1% formic acid) so as to obtain Compound AB24387 (1-(3-carbamoyl-5-methylthiophen-2-yl)-N-(6-methoxy-1H-benzo[d]imidazol-2-yl)-2,5-dimethyl-1H-pyrrole-3-carboxamide) as a white solid (6 mg, yield: 38.4%). MS (ESI) m/z: 424 [M+H$^+$]. $^1$H NMR (400 MHz, DMSO-d$_6$): δ 11.98 (s, 1H), 11.02 (s, 1H), 7.27 (s, 2H), 7.23 (s, 1H), 6.95 (s, 1H), 6.76 (s, 1H), 6.66 (d, J=8.4 Hz, 1H), 3.71 (s, 3H), 3.31 (s, 3H), 2.31 (s, 3H), 1.94 (s, 3H).

Example 5: Synthesis of Compound AB29505 (1-(2,4-dimethylthiazol-5-yl)-N-(6-methoxy-1H-benzo[d]imidazol-2-yl)-2,5-dimethyl-1H-pyrrole-3-carboxamide)

(1) Synthetic Method of Compound 2 (tert-butyl (2,4-dimethylthiazol-5-yl)carbamate)

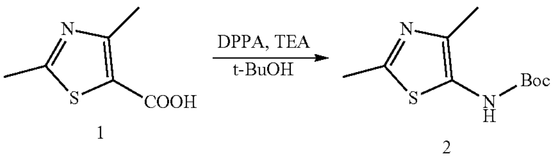

1

2

Compound 1 (2,4-dimethyl-1,3-thiazole-5-carboxylic acid) (2 g, 12.72 mmol; 1.0 eq) was dissolved in tert-butanol (40 mL). Diphenylphosphoryl azide DPPA (4.5 g, 16.53 mmol, 1.3 eq) and triethylamine (TEA) (3.2 g, 31.8 mmol, 2.5 eq) were added thereto. The mixture was stirred at 85° C. for 3 hours under the protection of nitrogen gas, and then the resulting mixture was concentrated. The residue was dissolved in water (80 mL), and the resulting mixture was then extracted three times with ethyl acetate (80 mL×3). Afterwards, the organic layers were combined, dried over anhydrous $Na_2SO_4$, filtered and then concentrated. The residue was purified by flash column chromatography (dichloromethane/methanol=200/1 to 150/1) so as to obtain Compound 2 (tert-butyl (2,4-dimethylthiazol-5-yl)carbamate) as a yellow solid (2.7 g, yield: 93.1%). MS (ESI) m/z: 229.0 $[M+H]^+$. TLC:dichloromethane/methanol (20:1); $R_f$(Compound 1)=0.2; $R_f$(Compound 2)=0.7.

(2) Preparation Method of Compound 3 (2,4-dimethylthiazole-5-amine hydrochloride)

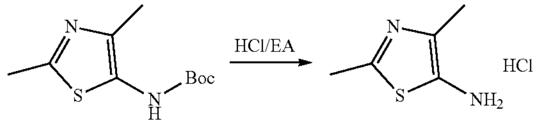

2 3

Compound 2 (tert-butyl (2,4-dimethylthiazol-5-yl)carbamate) (1.7 g, 7.44 mmol, 1.0 eq) was dissolved in a mixed solution of ethyl acetate/hydrochloric acid HCl/EA (20 mL, 4 M), and the resulting mixture was stirred at room temperature for 3 hours. Afterwards, the solid was filtered, washed twice with diethyl ether (5 mL×2), and then concentrated to obtain Compound 3 (2,4-dimethylthiazole-5-amine hydrochloride) as a yellow solid (1.1 g, yield: 91.6%). MS (ESI) m/z: 129.0 $[M+H]^+$. TLC:petroleum ether/ethyl acetate (1:1); $R_f$(Compound 2)=0.5; $R_f$(Compound 3)=0.2.

(3) Preparation Method of Compound 5 (methyl 1-(2,4-dimethylthiazol-5-yl)-2,5-dimethyl-1H-pyrrole-3-carboxylate)

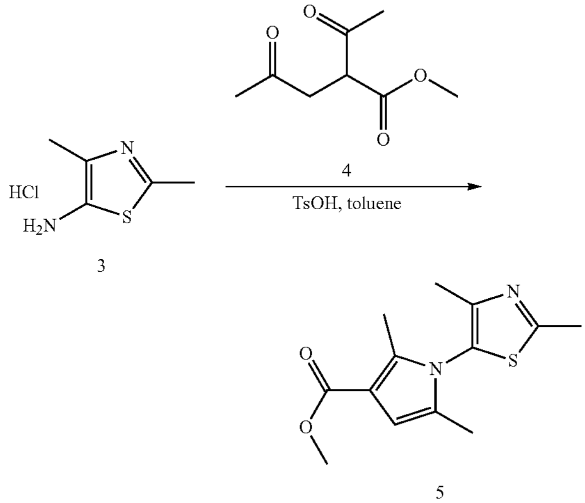

3 4 5

Compound 3 (2,4-dimethylthiazole-5-amine hydrochloride) (1.1 g, 6.68 mmol, 1.0 eq) was dissolved in toluene (20 mL). Compound 4 (methyl 2-acetyl-4-levulinate) (1.7 g, 10.02 mmol, 1.5 eq), 3 A molecular sieve (2 g) and p-toluenesulfonic acid (459 mg, 2.67 mmol, 0.4 eq) were added thereto. The mixture was stirred at 85° C. for 4 hours, and then the solid was filtered and concentrated. The residue was purified by flash column chromatography (petroleum ether/ethyl acetate=30/1) so as to obtain Compound 5 (methyl 1-(2,4-dimethylthiazol-5-yl)-2,5-dimethyl-1H-pyrrole-3-carboxylate) as a yellow solid (1.6 g, yield: 90.9%). MS (ESI) m/z: 265 $[M+H]^+$. TLC:petroleum ether/ethyl acetate (5:1); $R_f$(Compound 3)=0.1; $R_f$(Compound 5)=0.7.

(4) Preparation Method of Compound 6 (1-(2,4-dimethylthiazol-5-yl)-2,5-dimethyl-1H-pyrrole-3-carboxylic acid)

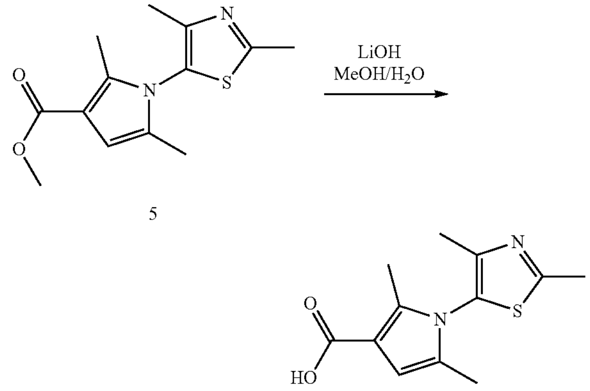

5 6

Compound 5 (1.6 g, 6.05 mmol, 1 eq) was dissolved in a solution of methanol/water MeOH/$H_2O$ (10 mL/10 mL), and then lithium hydroxide LiOH (579 mg, 24.2 mmol, 4 eq) was added thereto. The mixture was stirred at 50° C. for 1 hour. After the completion of the reaction, the resulting mixture was concentrated and diluted with water (50 mL), and the pH of the mixture was then adjusted to 5 with 3 N hydrochloric acid. The solid was filtered and concentrated, so as to obtain Compound 6 (1-(2,4-dimethylthiazol-5-yl)-2,5-dimethyl-1H-pyrrole-3-carboxylic acid) as a yellow solid (950 mg, yield: 62.7%). MS (ESI) m/z: 251 $[M+H]^+$. TLC:petroleum ether/ethyl acetate (5:1); $R_f$ (Compound 5)=0.7; $R_f$(Compound 6)=0.2.

(5) Preparation Method of Compound AB29505 (1-(2,4-dimethylthiazol-5-yl)-N-(6-methoxy-1H-benzo[d]imidazol-2-yl)-2,5-dimethyl-1H-pyrrole-3-carboxamide)

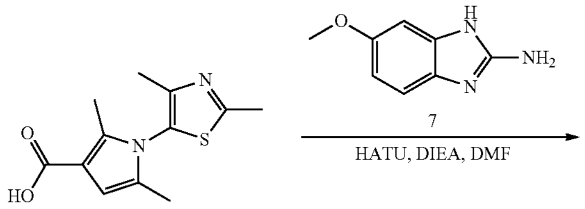

6 7

-continued

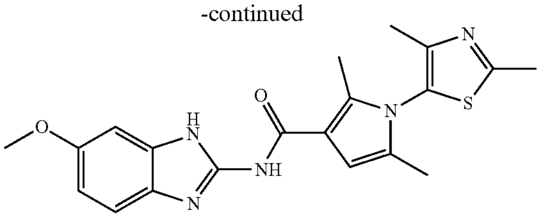

AB29505

Compound 6 (1-(2,4-dimethylthiazol-5-yl)-2,5-dimethyl-1H-pyrrole-3-carboxylic acid) (100 mg, 0.399 mmol, 1.0 eq) was dissolved in dimethylformamide (5 mL). Thereafter, Compound 7 (6-methoxy-1H-benzo[d]imidazole-2-amine) (65 mg, 0.399 mmol, 1.0 eq), N,N-diisopropylethylamine DIEA (206 mg, 1.596 mmol, 4.0 eq), and O-(7-azabenzotriazol-1-yl)-N,N,N',N'-tetramethyluronium HATU (167 mg, 0.439 mmol, 1.1 eq) were added thereto. The mixture was stirred at room temperature for 16 hours. After the completion of the reaction, the resulting mixture was diluted with ethyl acetate (30 mL) and washed three times with saturated aqueous sodium chloride solution (20 mL×3). The organic layers were dried, filtered and concentrated. The residue was purified by preparative high-pressure liquid chromatography so as to obtain Compound AB29505 (1-(2,4-dimethylthiazol-5-yl)-N-(6-methoxy-1H-benzo[d]imidazol-2-yl)-2,5-dimethyl-1H-pyrrole-3-carboxamide) as a yellow solid (10.8 mg, yield: 6.8%). MS (ESI) m/z: 395 $[M+H]^+$. $^1$H NMR (400 MHz, DMSO-$d_6$) δ 7.30 (d, J=8.8 Hz, 1H), 6.98 (s, 1H), 6.83 (s, 1H), 6.70-6.68 (m, 1H), 3.73 (s, 3H), 2.64 (s, 3H), 2.31 (s, 3H), 2.01 (s, 3H), 1.96 (s, 3H).

Example 6: Synthesis of Compound AB29510 (1-(3-cyano-4,5-dimethylfuran-2-yl)-N-(6-methoxy-1H-benzo[d]imidazol-2-yl)-2,5-dimethyl-1H-pyrrole-3-carboxamide)

(1) Preparation Method of Compound 2 (1-(3-cyano-4,5-dimethylfuran-2-yl)-2,5-dimethyl-1H-pyrrole-3-carboxylic acid)

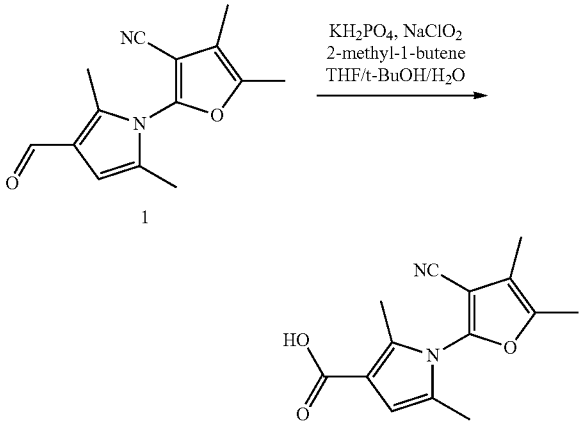

Compound 1 (2-(3-formyl-2,5-dimethyl-1H-pyrrol-1-yl)-4,5-dimethylfuran-3-carbonitrile) (1.2 g, 4.9 mmol, 1.0 eq) was dissolved in a mixed solution of tetrahydrofuran, tert-butanol and water THF/t-BuOH/$H_2O$ (1/1/1, 30 mL). Potassium dihydrogen phosphate $KH_2PO_4$ (2.9 g, 24.7 mmol, 5.0 eq), 2-methyl-1-butene (3.0 g, 49.5 mmol, 10.0 eq) and sodium chlorite (2.4 g, 29.7 mmol, 6.0 eq) were added thereto at 0° C. The mixture was stirred at room temperature for 16 hours. After the completion of the reaction, the mixture was concentrated and then purified by preparative high-pressure liquid chromatography, so as to obtain Compound 6 (1-(3-cyano-4,5-dimethylfuran-2-yl)-2,5-dimethyl-H-pyrrole-3-carboxylic acid) as a white solid (1.0 g, yield: 78.1%). MS (ESI) m/z: 259 $[M+H^+]$.

(2) Preparation Method of Compound AB29510 (1-(3-cyano-4,5-dimethylfuran-2-yl)-N-(6-methoxy-1H-benzo[d]imidazol-2-yl)-2,5-dimethyl-1H-pyrrole-3-carboxamide)

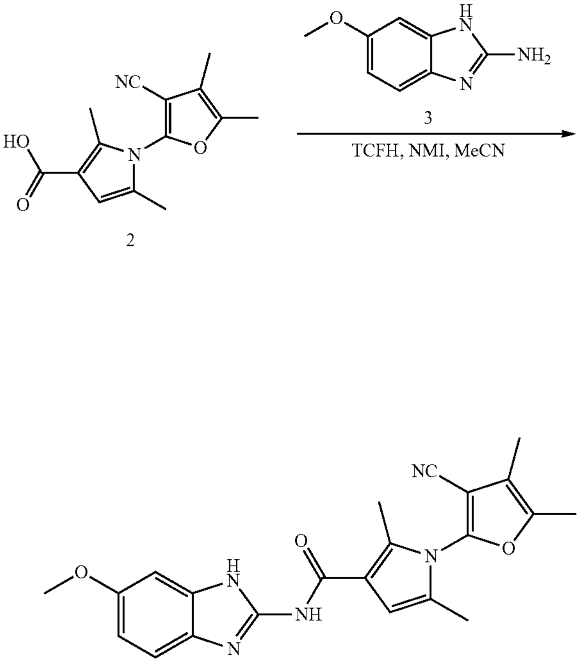

AB29510

Compound 2 (1-(3-cyano-4,5-dimethylfuran-2-yl)-2,5-dimethyl-1H-pyrrole-3-carboxylic acid) (60 mg, 0.23 mmol, 1.0 eq) was dissolved in acetonitrile (2.0 mL). Compound 3 (6-methoxy-1H-benzo[d]imidazole-2-amine hydrochloride) (50 mg 0.30 mmol, 1.3 eq), N-methylimidazole NMI (77 mg, 0.94 mmol, 4.0 eq) and N,N,N',N'-tetramethylchloroformamidinium hexafluorophosphate TCFH (79 mg, 0.28 mmol, 1.2 eq) were added thereto. The mixture was stirred at room temperature for 16 hours. After the completion of the reaction, the mixture was concentrated and then purified by preparative high-pressure liquid chromatography, so as to obtain Compound AB29510 (1-(3-cyano-4,5-dimethylfuran-2-yl)-N-(6-methoxy-1H-benzo[d]imidazol-2-yl)-2,5-dimethyl-1H-pyrrole-3-carboxamide) as a yellow solid (2.4 mg, yield: 78.1%). MS (ESI) m/z: 404.30 $[M+H^+]$. $^1$H NMR (400 MHz, DMSO-$d_6$) 7.49 (d, J=8.8 Hz, 1H), 7.11 (s, 1H), 6.91 (d, J=8.8 Hz, 1H), 6.74 (s, 1H), 3.77 (s, 3H), 2.41 (s, 3H), 2.29 (s, 3H), 2.10 (s, 3H), 2.07 (s, 3H).

Example 7: Synthesis of Compound AB29513 (N-(6-methoxy-1H-benzo[d]imidazol-2-yl)-2,5-dimethyl-1-((1-methyl-1H-pyrazol-4-yl)methyl)-1H-pyrrole-3-carboxamide)

(1) Synthetic Method of Compound 3 (methyl 2,5-dimethyl-1-(((1-methyl-1H-pyrazol-4-yl)methyl)-1H-pyrrole-3-carboxylate)

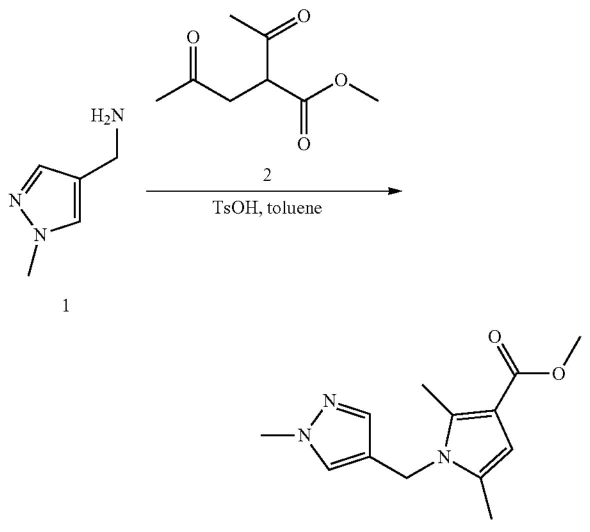

Compound 1 (4-(aminomethyl)-1-methylpyrazole) (500 mg, 4.5 mmol, 1.0 eq) was dissolved in toluene (20 mL). Compound 2 (methyl 2-acetyl-4-levulinate) (1.16 g, 6.75 mmol, 1.5 eq), 3 A molecular sieve (1 g) and p-toluenesulfonic acid (310 mg, 1.8 mmol, 0.4 eq) were added thereto. The mixture was stirred at 100° C. for 8 hours. The solid was filtered and concentrated. The residue was purified by flash column chromatography (petroleum ether/ethyl acetate=10/1 to 5/1) so as to obtain Compound 3 (methyl 2,5-dimethyl-1-(((1-methyl-1H-pyrazol-4-yl)methyl)-1H-pyrrole-3-carboxylate) as a yellow solid (650 mg, yield: 58.4%). MS (ESI) m/z: 248 [M+H]+. TLC:petroleum ether/ethyl acetate (2:1); $R_f$ (Compound 1)=0.1; $R_f$ (Compound 3)=0.6.

(2) Preparation Method of Compound 4 (2,5-dimethyl-1-(((1-methyl-1H-pyrazol-4-yl)methyl)-1H-pyrrole-3-carboxylic acid)

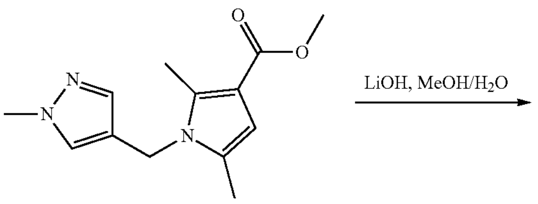

3

-continued

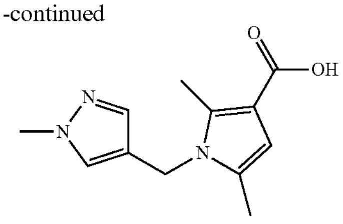

4

Compound 3 (methyl 2,5-dimethyl-1-(((1-methyl-1H-pyrazol-4-yl)methyl-1H-pyrrole-3-carboxylate) (300 mg, 1.21 mmol, 1 eq) was dissolved in a solution of methanol/water (10 mL/10 mL), and lithium hydroxide (43 mg, 1.81 mmol, 1.5 eq) was then added thereto. The mixture was heated to 85° C. and then stirred for 3 hours. The resulting mixture was concentrated and diluted with water (20 mL), and the pH of the mixture was then adjusted to 5 with 3 N hydrochloric acid. The solid was filtered and concentrated, so as to obtain Compound 4 (2,5-dimethyl-1-(((1-methyl-1H-pyrazol-4-yl)methyl)-1H-pyrrole-3-carboxylic acid) as a yellow solid (110 ng, yield: 39%). MS (ESI) m/z: 234 $[M+H]^+$. TLC:dichloromethane/methanol (20:1); $R_f$ (Compound 3)=0.7; $R_f$ (Compound 4)=0.3.

(3) Preparation Method of Compound AB29513 (N-(6-methoxy-1H-benzo[d]imidazol-2-yl)-2,5-dimethyl-1-((1-methyl-1H-pyrazol-4-yl)methyl)-1H-pyrrole-3-carboxamide)

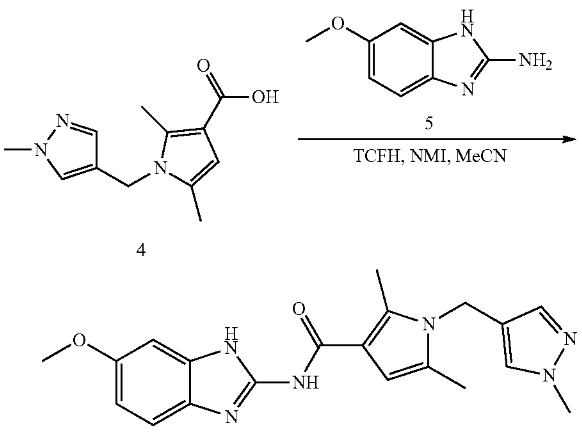

AB29513

Compound 4 (2,5-dimethyl-1-(((1-methyl-1H-pyrazol-4-yl)methyl)-1H-pyrrole-3-carboxylic acid) (110 mg, 0.47 mmol, 1.0 eq) was dissolved in acetonitrile (5 mL). Compound (6-methoxy-1H-benzo[d]imidazole-2-amine) (100 mg, 0.61 mmol, 1.0 eq), N-methylimidazole NMI (154 mg, 1.88 mmol, 4.0 eq) and tetramethylchloroformamidinium hexafluorophosphate TCFH (158 mg, 0.56 mmol, 1.2 eq) were added thereto. The mixture was stirred at room temperature for 16 hours. After the completion of the reaction, the mixture was diluted with ethyl acetate (30 mL) and washed three times with saturated aqueous sodium chloride solution (20 mL×3). The organic layers were dried, filtered and concentrated. The residue was purified by preparative high-pressure liquid chromatography so as to obtain Compound AB29513 (N-(6-methoxy-1H-benzo[d]imidazol-2-yl)-2,5-dimethyl-1-((1-methyl-1H-pyrazol-4-yl)methyl)-1H-pyrrole-3-carboxamide) as a yellow solid (35 mg, yield: 19.6%). MS (ESI) m/z: 379 $[M+H]^+$. $^1H$ NMR (400 MHz, DMSO-$d_6$) δ 7.55 (s, 1H), 7.49 (d, J=8.8 Hz, 1H), 7.25 (s, 1H), 7.13 (s, 1H), 6.93 (d. J=8.8 Hz, 1H), 6.52 (s, 1H), 4.90 (s, 2H), 3.76 (d, J 10.8 Hz, 6H), 2.59 (s, 3H), 2.23 (s, 3H).

Example 8: Synthesis of Compound (E)-2-(3-(2-cyano-2-(6-methoxy-3H-imidazo[4,5-c]pyridin-2-yl)vinyl)-2,5-dimethyl-1H-pyrrol-1-yl)-4,5-dimethylfuran-3-carbonitrile (AB24254)

(1) Synthesis of Compound 6 (6-methoxypyridine-3,4-diamine)

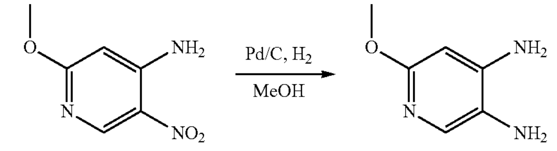

5 6

Compound 5 (2-methoxy-5-nitropyridine-4-amine) (3.0 g, 17.74 mmol, 1.0 eq) was dissolved in methanol (30 mL), and palladium on carbon (300 mg, 0.1 wt %) was added as a catalyst. The mixture was stirred at room temperature under hydrogen atmosphere for 16 hours. The solid was filtered off, and the filtrate was then concentrated to obtain Compound 6 (6-methoxypyridine-3,4-diamine) as a brown solid (2.6 g, yield: 100%). MS (ESI) m/z: 140$[M+H]^+$. TLC:DCM:MeOH (10:1); $R_f$ (Compound 5)=0.7; $R_f$ (Compound 6)=0.5.

(2) Synthesis of Compound 7 (2-(6-methoxy-3H-imidazo[4,5-c]pyridin-2-yl)acetonitrile)

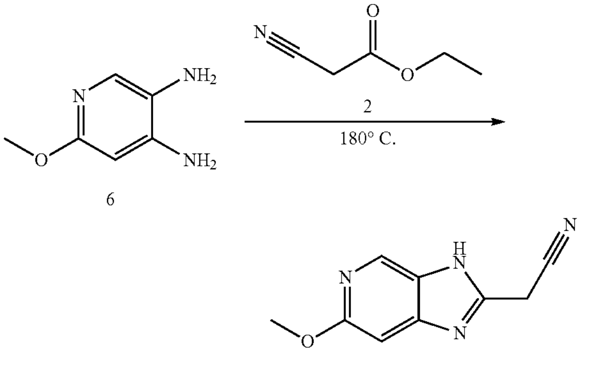

2

6

7

Compound 6 (6-methoxypyridine-3,4-diamine) (1.5 g, 10.2 mmol, 1.0 eq) and Compound 2 (ethyl cyanoacetate) (3.5 g, 30.6 mmol, 3.0 eq) were dissolved in dimethylformamide (6 mL), and the mixture was stirred at 180° C. for 5 hours. The solvent was removed after cooling. The residue was purified by flash column chromatography (dichloromethane:methanol=200:1 to 50:1) so as to obtain Compound 7 (2-(6-methoxy-3H-imidazo[4,5-c]pyridin-2-yl)acetonitrile) as a brown solid powder (500 mg, yield: 26.0%). MS (ESI) m/z: 188 [M+H]+. TLC:petroleum ether/ethyl acetate (1:1); $R_f$ (Compound 6)=0.5; $R_f$ (Compound 7)=0.2.

(3) Synthesis of Compound AB24254 (E)-2-(3-(2-cyano-2-(6-methoxy-3H-imidazo[4,5-c]pyridin-2-yl)vinyl)-2,5-dimethyl-1H-pyrrol-1-yl)-4,5-dimethylfuran-3-carbonitrile

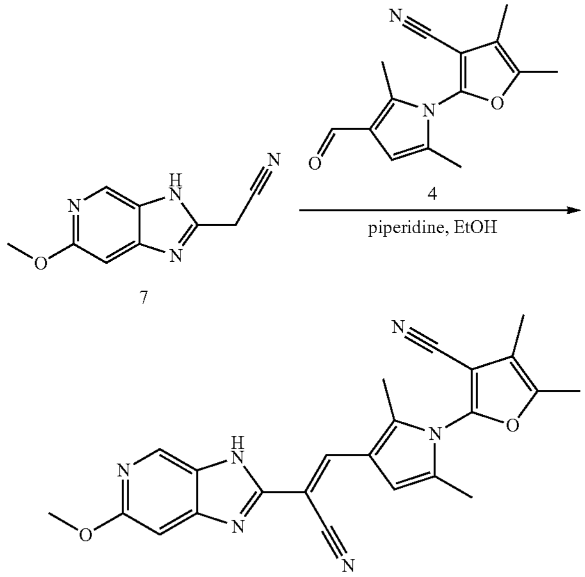

4

7

AB24254

Compound 7 (2-(6-methoxy-3H-imidazo[4,5-c]pyridin-2-yl)acetonitrile) (80 mg, 0.42 mmol, 1.0 eq) was dissolved in 1 mL of ethanol. Compound 4 (2-(3-formyl-2,5-dimethyl-1H-pyrrol-1-yl)-4,5-dimethylfuran-3-carbonitrile) (103 mg, 0.42 mmol, 1.0 eq) and piperidine (36 mg, 0.42 mmol, 1.0 eq) were added thereto. The mixture was heated under reflux and stirred for 1 hour. After the completion of the reaction, the resulting mixture was cooled to room temperature and filtered. The solid was collected and dried so as to obtain Compound AB24254 ((E)-2-(3-(2-cyano-2-(6-methoxy-3H-imidazo[4,5-c]pyridin-2-yl)vinyl)-2,5-dimethyl-1H-pyrrol-1-yl)-4,5-dimethylfuran-3-carbonitrile) as a yellow powder (95 mg, yield: 54.3%). MS (ESI) m/z: 382 [M+H]+. $^1H$ NMR (400 MHz, DMSO) δ 8.48 (s, 1H), 8.13 (s, 1H), 6.95 (s, 1H), 6.79 (s, 1H), 3.85 (s, 3H), 2.31 (d, J=15.1 Hz, 6H), 2.10 (d, J=20.0 Hz, 6H).

Example 9: Synthesis of Compound (E)-2-(3-(2-cyano-2-(6-methoxy-3H-imidazo[4,5-c]pyridin-2-yl)vinyl)-2,5-dimethyl-1H-pyrrol-1-yl)-5-methylthiophene-3-carbonitrile (AB24288)

AB24288 was synthesized in the same manner as in Example 8 (yield: 13.6%). $^1H$ NMR (400 MHz, DMSO-d6) δ 8.53 (s, 1H), 8.16 (s, 1H), 7.31 (s, 1H), 6.96 (s, 1H), 6.89 (s, 1H), 3.89 (s, 3H), 2.51 (s, 3H), 2.30 (s, 3H), 2.08 (s, 3H).

Example 10: Synthesis of Compound (E)-3-(1-(3-chloropyridin-4-yl)-2,5-dimethyl-1H-pyrrol-3-yl)-2-(6-methoxy-3H-imidazo[4,5-c]pyridin-2-yl)acrylonitrile (AB24289)

AB24289 was synthesized in the same manner as in Example 8 (yield: 40.3%). $^1H$ NMR (400 MHz, DMSO-d6)

δ 8.96 (s, 1H), 8.77 (d, J=4.2 Hz, 1H), 8.45 (s, 1H), 8.14 (s, 1H), 7.71 (d, J=4.1 Hz, 1H), 6.96 (s, 1H), 6.77 (s, 1H), 3.84 (s, 3H), 2.16 (s, 3H), 1.95 (s, 3H).

Example 11: Synthesis of Compound (E)-3-(2,5-dimethyl-1-(3-methylpyridin-4-yl)-1H-pyrrol-3-yl)-2-(6-methoxy-3H-imidazo[4,5-c]pyridin-2-yl)acrylonitrile (AB24295)

AB24295 was synthesized in the same manner as in Example 8 (yield: 52.3%). $^1$H NMR (400 MHz, DMSO-d6) δ 8.72 (s, 1H), 8.62 (s, 1H), 8.45 (s, 1H), 8.15 (s, 1H), 7.39 (s, 1H), 6.96 (s, 1H), 6.78 (s, 1H), 3.84 (s, 3H), 2.12 (s, 3H), 1.93 (d, J=19.2 Hz, 611).

Example 12: Synthesis of Compound (E)-3-(1-(3-fluoropyridin-4-yl)-2,5-dimethyl-1H-pyrrol-3-yl)-2-(6-methoxy-3H-imidazo[4,5-c]pyridin-2-yl)acrylonitrile (AB24300)

AB24300 was synthesized in the same manner as in Example 8 (yield: 50%). $^1$H NMR (400 MHz, DMSO-d6) δ 12.91 (s, 1H), 8.91 (s, 1H), 8.67 (d, J=4.5 Hz, 1H), 8.47 (s, 1H), 8.16 (s, 1H), 7.72 (s, 1H), 6.98 (s, 1H), 6.79 (s, 1H), 3.85 (s, 3H), 2.24 (s, 3H), 2.03 (s, 3H).

Example 13: Synthesis of Compound (E)-2-(3-(2-cyano-2-(5-methoxy-3H-imidazo[4,5-b]pyridin-2-yl)vinyl)-2,5-dimethyl-1H-pyrrol-1-yl)-4,5-dimethylfuran-3-carbonitrile (AB24281)

(1) Synthesis of Compound 9 (6-methoxy-2,3-diaminopyridine)

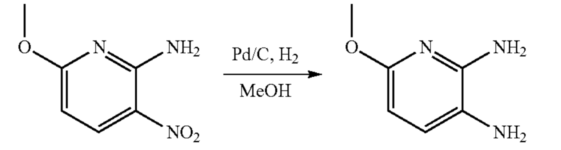

8 9

Compound 8 (2-amino-3-nitro-6-methoxypyridine) (3.0 g, 17.76 mmol, 1.0 eq) was dissolved in methanol (30 mL), and palladium on carbon (450 mg, 0.15 wt %) was added as a catalyst. The mixture was stirred at room temperature in the presence of hydrogen gas for 16 hours. The solid was filtered off, and the filtrate was concentrated to afford Compound 9 (6-methoxy-2,3-diaminopyridine) as a brown solid powder (2.6 g, yield: 100%). MS (ESI) m/z: 140 [M+H]$^+$. TLC:DCM/MeOH (10:1); $R_f$ (Compound 8)=0.7; $R_f$ (Compound 9)=0.3.

(2) Synthesis of Compound 10 (2-(5-methoxy-3H-imidazo[4,5-b]pyridin-2-yl)acetonitrile)

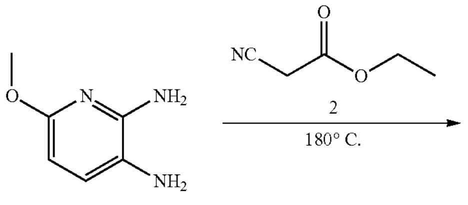

9

-continued

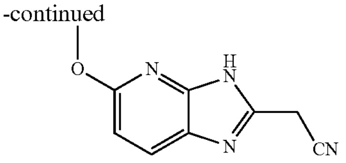

10

Compound 9 (6-methoxy-2,3-diaminopyridine) (300 mg, 2.16 mmol, 1.0 eq) and Compound 2 (ethyl cyanoacetate) (732 mg, 6.47 mmol, 3.0 eq) were dissolved in dimethylformamide (3 mL), heated to 180° C. and stirred for 5 hours. The solvent was removed after cooling. The residue was purified by flash column chromatography (dichloromethane: methanol=200:1 to 50:1) so as to obtain Compound 10 (2-(5-methoxy-3H-imidazo [4,5-b]pyridin-2-yl)acetonitrile) as a brown solid powder (90 mg, yield: 22.2%). MS (ESI) m/z: 188[M+H]$^+$. TLC:petroleum ether/ethyl acetate (1:1); $R_f$ (Compound 9)=0.6; $R_f$ (Compound 10)=0.5.

(3) Synthesis of Compound AB24281 ((E)-2-(3-(2-cyano-2-(5-methoxy-3H-imidazo[4,5-b]pyridin-2-yl)vinyl)-2,5-dimethyl-1H-pyrrol-1-yl)-4,5-dimethylfuran-3-carbonitrile)

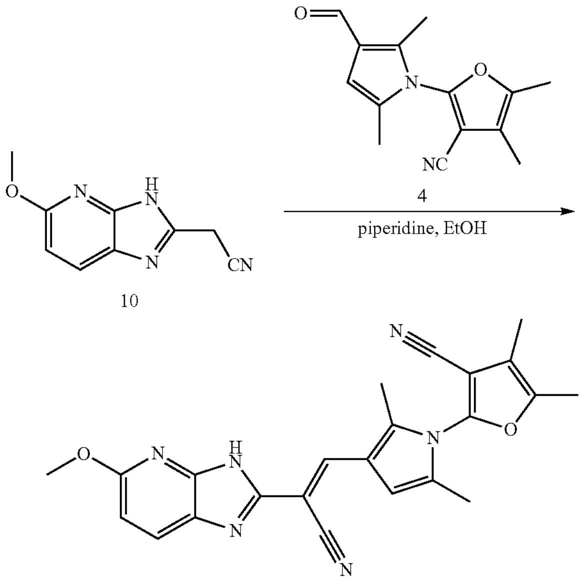

AB24281

Compound 10 (2-(5-methoxy-3H-imidazo[4,5-b]pyridin-2-yl)acetonitrile) (90 mg, 0.48 mmol, 1.0 eq) was dissolved in ethanol (1.5 mL). Compound 4 (2-(3-formyl-2,5-dimethyl-1H-pyrrol-1-yl)-4,5-dimethylfuran-3-carbonitrile) (116 mg, 0.48 mmol, 1.0 eq) and piperidine (40 mg, 0.48 mmol, 1.0 eq) were added thereto. The mixture was heated under reflux for one hour. After the completion of the reaction, the mixture was cooled to room temperature and filtered. The solid was collected and dried so as to obtain Compound AB24281 ((E)-2-(3-(2-cyano-2-(5-methoxy-3H-imidazo[4,5-b]pyridin-2-yl)vinyl)-2,5-dimethyl-1H-pyrrol-1-yl)-4,5-dimethylfuran-3-carbonitrile) as a yellow solid powder (100 mg, yield: 54.3%). MS (ESI) m/z: 411.0 [M−H]$^-$. $^1$H NMR (400 MHz, DMSO-d6) δ 8.08 (s, 1H), 7.90 (d, J=8.2 Hz, 1H), 6.93 (s, 1H), 6.66 (d, J=8.6 Hz, 1H), 3.87 (s, 3H), 2.31 (d, J=11.5 Hz, 6H), 2.10 (d, J=18.4 Hz, 6H).

Example 14: Synthesis of Compound (E)-2-(3-(2-cyano-2-(7-methoxy-1H-imidazo[4,5-c]pyridyl-2-yl) vinyl)-2,5-dimethyl-H-pyrrol-1-yl)-4,5-dimethylthiophene-3-carbonitrile (AB24302)

(1) Synthesis of Compound 12 (3-methoxy-5-nitropyridine-4-amine)

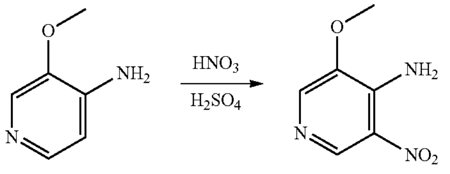

11 12

After sulfuric acid (15 mL) and nitric acid (1.1 g, 15.48 mmol, 1.2 eq) were cooled to 0° C., Compound 11 (4-amino-3-methoxypyridine) (1.6 g, 12.90 mmol, 1.0 eq) was added thereto. The mixture was stirred at room temperature for 2 hours. The reaction mixture was quenched with aqueous sodium hydroxide solution at 0° C. The filtrate was concentrated to obtain Compound 12 (3-methoxy-5-nitropyridine-4-amine) as a brown solid powder (1.2 g, yield: 55%). MS (ESI) m/z: 170[M+H]$^+$. TLC:DCM/MeOH (50:1); $R_f$(Compound 11)=0.2; $R_f$ (Compound 12)=0.5.

(2) Synthesis of Compound 13 (5-methoxypyridine-3,4-diamine)

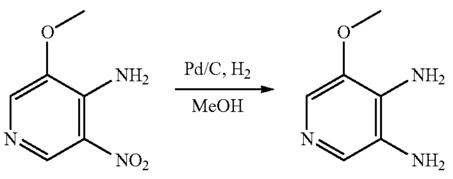

12 13

Compound 12 (3-methoxy-5-nitropyridine-4-amine) (700 mg, 4.14 mmol, 1.0 eq) was dissolved in methanol (10 mL), and palladium on carbon (200 mg, 0.3 wt %) was added as a catalyst. The mixture was stirred at room temperature under hydrogen atmosphere for 16 hours. The solid was filtered off, and the filtrate was concentrated and dried so as to obtain Compound 13 (5-methoxypyridine-3,4-diamine) as a brown solid (520 mg, yield: 90%). MS (ESI) m/z: 140 [M+H]$^+$. TLC:DCM/MeOH (20:1); $R_f$(Compound 12)=0.5; $R_f$(Compound 13)=0.1.

(3) Synthesis of Compound 14 (2-(7-methoxy-1H-imidazo[4,5-c]pyridin-2-yl)acetonitrile)

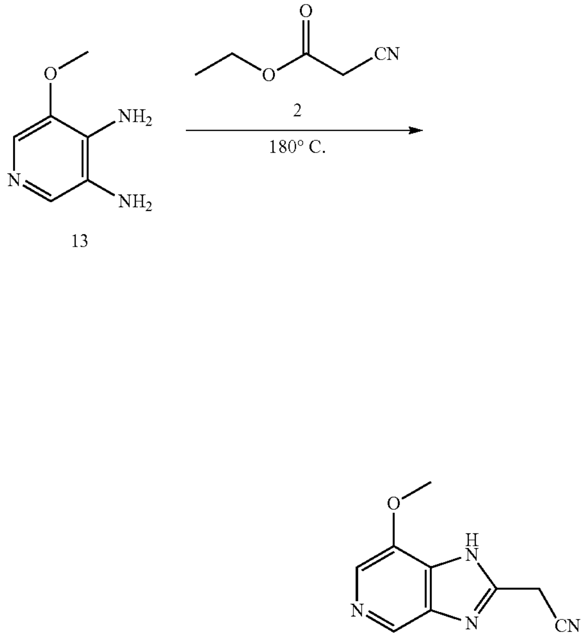

13 2 14

Compound 13 (5-methoxypyridine-3,4-diamine) (580 mg, 4.17 mmol, 1.0 eq) and Compound 2 (ethyl cyanoacetate) (950 mg, 8.34 mmol, 2.0 eq) were dissolved in dimethylformamide (6 mL), heated to 180° C. and stirred for 5 hours. The solvent was removed after cooling. The residue was purified by flash column chromatography (dichloromethane:methanol=200:1 to 50:1) so as to obtain Compound 14 (2-(7-methoxy-1H-imidazo[4,5-c]pyridin-2-yl)acetonitrile) as a brown solid powder (200 mg, yield: 26.0%). MS (ESI) m/z: 189 [M+H]$^+$. TLC:DCM/MeOH (20:1); $R_f$ (Compound 13)=0.1; $R_f$(Compound 14)=0.3.

(4) Synthesis of Compound AB24302 ((E)-2-(3-(2-cyano-2-(7-methoxy-1H-imidazo[4,5-c]pyridyl-2-yl) vinyl)-2,5-dimethyl-1H-pyrrol-1-yl)-4,5-dimethylthiophene-3-carbonitrile)

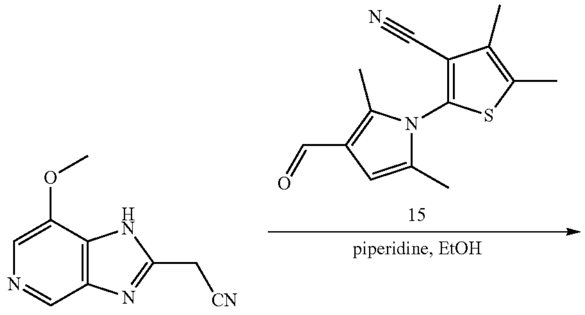

15 14

-continued

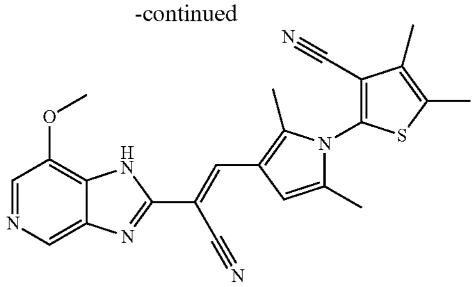

AB24302

Compound 14 (2-(7-methoxy-1H-imidazo[4,5-c]pyridin-2-yl)acetonitrile)(58 mg, 0.31 mmol, 1.0 eq) was dissolved in ethanol (2.0 mL). Compound 15 (2-(3-formyl-2,5-dimethyl-1H-pyrrol-1-yl)-4,5-dimethylthiophene-3-carbonitrile) (79 mg, 0.31 mmol, 1.0 eq) and piperidine (52 mg, 0.62 mmol, 2.0 eq) were added thereto. The mixture was heated under reflux and stirred for 1 hour. After the completion of the reaction, the resulting mixture was cooled and concentrated. The solid was collected and dried so as to obtain Compound AB24302 ((E)-2-(3-(2-cyano-2-(7-methoxy-1H-imidazo[4,5-c]pyridyl-2-yl)vinyl)-2,5-dimethyl-1H-pyrrol-1-yl)-4,5-dimethylthiophene-3-carbonitrile) as a yellow solid powder (50 mg, yield: 37.8%). MS (ESI) m/z: 429 $[M+H]^+$. $^1H$ NMR (400 MHz, dmso) δ 8.55 (s, 1H), 8.27 (s, 1H), 8.02 (s, 1H), 6.97 (s, 1H), 4.03 (s, 3H), 2.42 (s, 3H), 2.31 (s, 3H), 2.24 (s, 3H), 2.09 (s, 3H).

Example 15: Synthesis of Compound (E)-2-(3-(2-cyano-2-(6-methoxy-3H-imidazo[4,5-b]pyridin-2-yl)vinyl)-2,5-dimethyl-1H-pyrrol-1-yl)-4,5-dimethylthiophene-3-carbonitrile (AB24301)

(1) Synthesis of Compound 17 (5-methoxypyridine-2,3-diamine)

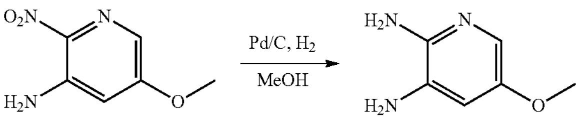

16 17

Compound 16 (5-methoxy-2-nitropyridine-3-amine) (1.0 g, 5.91 mmol, 1.0 eq) was dissolved in methanol (30 mL), and palladium on carbon (300 mg, 0.3 wt %) was added as a catalyst. The mixture was stirred at room temperature in the presence of hydrogen gas for 16 hours. The solid was filtered off, and the filtrate was concentrated to obtain Compound 17 (5-methoxypyridine-2,3-diamine) as a brown solid powder (700 mg, yield: 85%). MS (ESI) m/z: 140 $[M+H]^+$. TLC:EA; $R_f$ (Compound 16)=0.4; $R_f$ (Compound 17)=0.1.

(2) Synthesis of Compound 18 (2-(6-methoxy-3H-imidazo[4,5-b]pyridin-2-yl)acetonitrile)

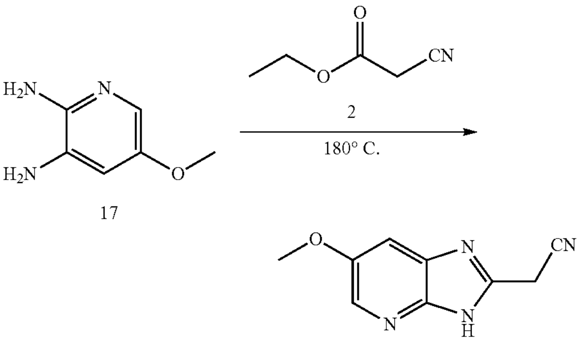

17

18

Compound 17 (5-methoxypyridine-2,3-diamine) (500 mg, 3.59 mmol, 1.0 eq) and Compound 2 (ethyl cyanoacetate) (812 mg, 7.19 mmol, 2.0 eq) were dissolved in dimethylformamide (2 mL) and stirred at 180° C. for 5 hours. The solvent was removed after cooling. The residue was purified by flash column chromatography (dichloromethane:methanol=200:1 to 50:1) so as to obtain Compound 18 (2-(6-methoxy-3H-imidazo[4,5-b]pyridin-2-yl)acetonitrile) as a brown solid powder (500 mg, yield: 73.9%). MS (ESI) m/z: 189 $[M+H]^+$. TLC:DCM/MeOH (20:1); $R_f$ (Compound 17)=0.2; $R_f$ (Compound 18)=0.5.

(3) Preparation Method of Compound AB24301 ((E)-2-(3-(2-cyano-2-(6-methoxy-3H-imidazo[4,5-b]pyridin-2-yl)vinyl)-2,5-dimethyl-1H-pyrrol-1-yl)-4,5-dimethylthiophene-3-carbonitrile)

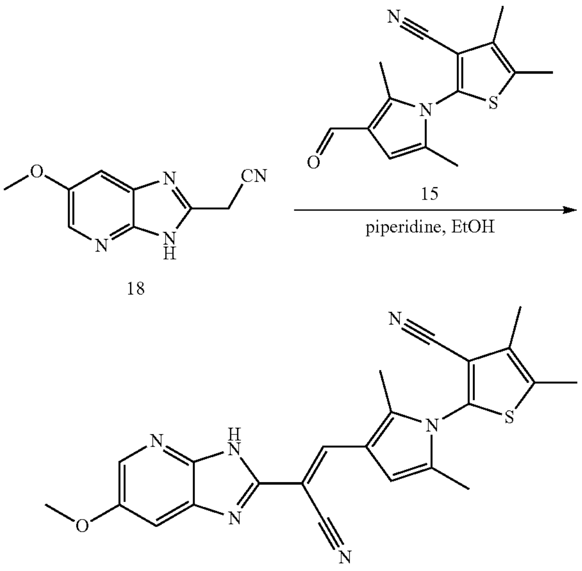

18

AB24301

Compound 18 (50 mg, 0.265 mmol, 1.0 eq) was dissolved in ethanol (1.0 mL). Compound 15 (2-(3-formyl-2,5-dimethyl-1H-pyrrol-1-yl)-4,5-dimethylthiophene-3-carbonitrile) (68.6 mg, 0.265 mmol, 1.0 eq) and piperidine (45 mg, 0.530 mmol, 2.0 eq) were added thereto. The mixture was heated under reflux and stirred for 1 hour. After the completion of the reaction, the resulting mixture was cooled to room temperature and filtered. The solid was collected and dried so as to obtain Compound AB24301 ((E)-2-(3-(2-cyano-2-(6-methoxy-3H-imidazo[4,5-b]pyridin-2-yl)vinyl)-2,5-dimethyl-1H-pyrrol-1-yl)-4,5-dimethylthiophene-3-carbonitrile) as a yellow solid powder (10 mg, yield-9.66%). MS (ESI) m/z: 429 $[M+H]^+$. $^1H$ NMR (400 MHz, DMSO-d6) δ 13.16 (s, 1H), 8.15 (s, 1H), 8.06 (s, $1H_1$), 7.55 (s, 1H), 6.97 (s, 1H), 3.83 (s, 3H), 2.42 (s, $3H_1$), 2.30 (s, $3H_1$), 2.24 (s, 3H), 2.09 (s, 3H).

Example 16: Synthesis of Compound ethyl (E)-5-(3-(2-cyano-2-(6-methoxy-3H-imidazo[4,5-c]pyridin-2-yl)vinyl)-2,5-dimethyl-1H-pyrrol-1-yl)-2-methylthiazole-4-carboxylate (AB24314)

(1) Synthesis of Compound 21 (ethyl 5-(2,5-dimethyl-1H-pyrrol-1-yl)-2-methylthiazole-4-carboxylate)

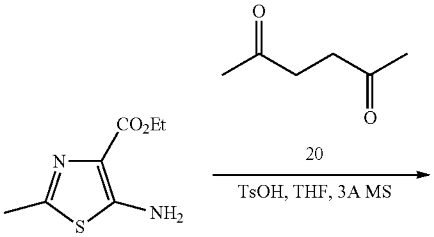

19

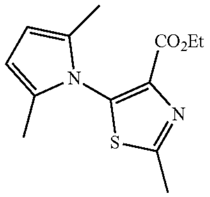

21

Compound 19 (ethyl 5-amino-2-methyl-1,3-thiazole-4-carboxylate) (0.5 g, 2.7 mmol, 1.0 eq) was dissolved in tetrahydrofuran (5 mL), and 2,5-hexanedione (456 mg, 4 mmol, 1.5 eq), p-toluenesulfonic acid monohydrate (TsOH—$H_2O$) (186 mg, 1.04 mmol, 0.4 eq) and 3 A molecular sieve (1 g) were added thereto. The mixture was heated under reflux and stirred overnight. The solid was filtered off and the filtrate was concentrated. The residue was purified by using flash column chromatography (FCC) (petroleum ether:ethyl acetate=10:1), and a yellow solid, i.e. Compound 21 (ethyl 5-(2,5-dimethyl-1H-pyrrol-1-yl)-2-methylthiazole-4-carboxylate) (462 mg, yield: 64.8%) was obtained. MS (ESI) m/z: 265 $[M+H]^+$. TLC:PE/EA (5/1); $R_f$ (Compound 19)=0.2; $R_f$(Compound 21)=0.5. $^1H$ NMR (400 MHz, $CDCl_3$) δ 5.89 (s, 2H), 4.22 (q, J=7.1 Hz, 2H), 2.75 (s, 3H), 2.01 (s, 6H), 1.16 (t, J=7.1 Hz, 3H).

(2) Synthesis of Compound 22 (ethyl 5-(3-formyl-2,5-dimethyl-1H-pyrrol-1-yl)-2-methylthiazole-4-carboxylate)

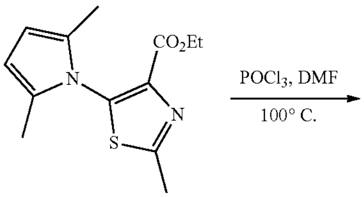

21

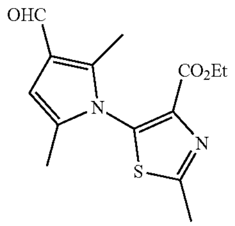

22

Phosphorus oxychloride (690 mg, 4.51 mmol, 1.0 eq) was added dropwise to dimethylformamide (5 mL) under conditions of 0° C. and nitrogen atmosphere. The mixture was stirred at 0° C. for 30 minutes and then warmed to room temperature. Afterwards, Compound 21 (ethyl 5-(2,5-dimethyl-1H-pyrrol-1-yl)-2-methylthiazole-4-carboxylate) (1.19 g, 4.51 mmol, 1.0 eq) in dimethylformamide (5 mL) was added to the above-mentioned mixture. The mixture was heated to 100° C. and was stirred under nitrogen atmosphere for 5 hours. After cooling, the mixture was poured into ice water, and the pH of the resulting mixture was adjusted to 9 with $Na_2CO_3$ solution. The mixture was extracted with ethyl acetate and washed with brine. The organic phase was dried over $Na_2SO_4$, filtered and concentrated. The residue was purified by using flash column chromatography (FCC) (petroleum ether:ethyl acetate=2:1), and a yellow solid, i.e. Compound 22 (ethyl 5-(3-formyl-2,5-dimethyl-1H-pyrrol-1-yl)-2-methylthiazole-4-carboxylate) (285 mg, yield 78.5%) was obtained. MS (ESI) m/z: 293 $[M+H]^+$. TLC:petroleum ether/ethyl acetate (2/1); $R_f$ (Compound 21)=0.7; $R_f$(Compound 22)=0.3. $^1H$ NMR (400 MHz, $CDCl_3$) δ 9.87 (s, 1H), 6.40 (d, J=0.9 Hz, 1H), 4.23 (q, J=7.1 Hz, 2H), 2.80 (s, 3H), 2.32 (s, 3H), 2.02 (d, J=0.5 Hz, 3H), 1.15 (t, J=7.1 Hz, 3H).

(3) Synthesis of Compound AB24314 (ethyl (E)-5-(3-(2-cyano-2-(6-methoxy-3H-imidazo[4,5-c]pyridin-2-yl)vinyl)-2,5-dimethyl-1H-pyrol-1-yl)-2-methylthiazole-4-carboxylate)

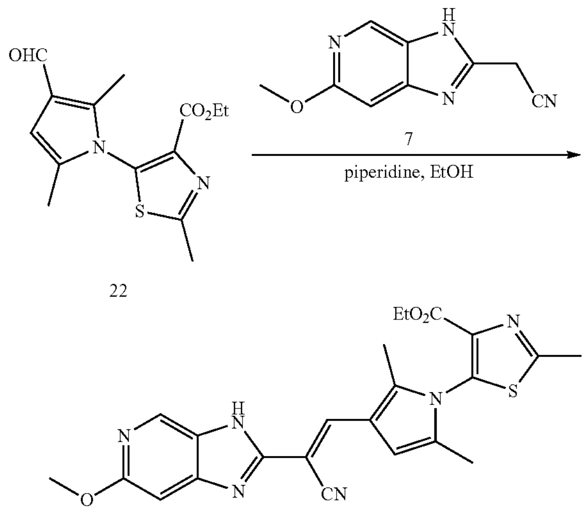

22

AB24314

Compound 22 (ethyl 5-(3-formyl-2,5-dimethyl-1H-pyrrol-1-yl)-2-methylthiazole-4-carboxylate) (77.6 mg, 0.266 mmol, 1.0 eq) was dissolved in ethanol (1 mL), and Compound 7 (2-(6-methoxy-3H-imidazo[4,5-c]pyridin-2-yl)acetonitrile) (50 mg, 0.266 mmol, 1.0 eq) and two drops of piperidine were added thereto. The mixture was heated under reflux and stirred for 2 hours. The mixture was cooled to room temperature and filtered. The residue was purified by using preparative high performance liquid chromatograph, and a yellow solid, i.e. AB24314 (10 mg, yield: 8.15%) was obtained. MS (ESI) m/z: 463.0 $[M+H]^+$. $^1H$ NMR (400 MHz, DMSO-$d_6$) δ 8.59 (s, 1H), 8.21 (s, 1H), 6.96 (d, J=7.0 Hz, 2H), 4.11 (q, J=6.6 Hz, 2H), 3.94 (s, 3H), 2.75 (s, 3H), 2.27 (s, 3H), 2.03 (s, 3H), 1.06 (t, J=6.8 Hz, 3H).

Example 17: Synthesis of Compound (E)-2-(3-(2-cyano-2-(6-methoxy-3H-imidazo[4,5-c]pyridin-2-yl)vinyl)-2,5-dimethyl-1H-pyrrol-1-yl)-4,5-dimethylthiophene-3-carbonitrile (AB24308)

AB24308 (78 mg, yield: 69.2%) was synthesized in the same manner as in Example 8. $^1H$ NMR (400 MHz, DMSO-d6) δ 12.99 (s, 1H), 8.51 (s, 1H), 8.17 (s, 1H), 7.00 (s, 1H), 6.83 (s, 1H), 3.89 (s, 3H), 2.45 (s, 3H), 2.33 (s, 3H), 2.27 (s, 3H), 2.12 (s, 3H).

Example 18: Synthesis of Compound methyl (E)-2-(3-(2-cyano-2-(6-methoxy-3H-imidazo[4,5-c]pyridin-2-yl)vinyl)-2,5-dimethyl-1H-pyrrol-1-yl)-5-methylthiophene-3-carboxylate (AB24311)

AB24311 (30 mg, yield: 37.2%) was synthesized in the same manner as in Example 8. $^1H$ NMR (400 MHz, DMSO-d6) δ 8.57 (s, 1H), 8.16 (s, 1H), 7.24 (s, 1H), 6.90 (s, 1H), 6.86 (s, 1H), 3.92 (s, 3H), 3.66 (s, 3H), 2.53 (s, 3H), 2.25 (s, 3H), 2.02 (s, 3H).

Example 19: Synthesis of Compound (E)-2-(3-(2-cyano-2-(6-methoxy-3H-imidazo[4,5-c]pyridin-2-yl)vinyl)-2,5-dimethyl-1H-pyrrol-1-yl)-5-ethylthiophene-3-carbonitrile (AB24317)

AB24317 (40 mg, yield: 48.1%) was synthesized in the same manner as in Example 8. $^1H$ NMR (400 MHz, DMSO-d6) δ 8.51 (s, 1H), 8.17 (s, 1H), 7.41 (s, 1H), 7.01 (s, 1H), 6.83 (s, 1H), 3.89 (s, 3H), 2.51 (s, 3H), 2.34 (s, 3H), 2.13 (s, 3H).

Example 20: Synthesis of Compound methyl (E)-5-chloro-2-(3-(2-cyano-2-(6-methoxy-3H-imidazo[4,5-c]pyridin-2-yl)vinyl)-2,5-dimethyl-1H-pyrrol-1-yl)thiophene-3-carboxylate (AB24318)

(1) Synthesis of Compound 24 (methyl 2-amino-5-chlorothiophene-3-carboxylate)

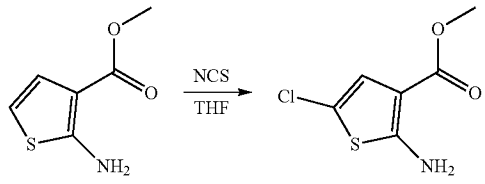

23 24

Compound 23 (methyl 2-aminothiophene-3-carboxylate) (1 g, 6.369 mmol, 1.0 eq) was dissolved in tetrahydrofuran (10 mL), N-chlorosuccinimide (0.847 g, 6.369 mmol, 1.0 eq) was added thereto, and the mixture was stirred overnight. The solid was filtered off and the filtrate was concentrated. The residue was purified by using flash column chromatography (petroleum ether:ethyl acetate=20:1), and a white solid, i.e. Compound 24 (methyl 2-amino-5-chlorothiophene-3-carboxylate) (420 mg, yield: 34.4%) was obtained. MS (ESI) m/z: 192 $[M+H]^+$. TLC:PE/EA (5:1); $R_f$ (Compound 23)=0.5; $R_f$(Compound 24)=0.4; $^1H$ NMR (400 MHz, $CDCl_3$) δ 6.87-6.71 (m, 1H), 5.83 (s, 2H), 3.78 (s, 3H).

(2) Synthesis of Compound 25 (methyl 5-chloro-2-(2,5-dimethyl-1H-pyrrol-1-yl)thiophene-3-carboxylate)

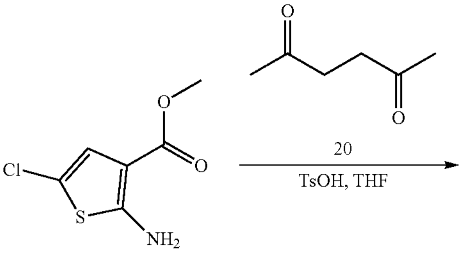

24

-continued

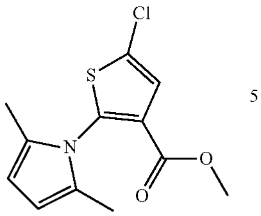

25

Compound 24 (methyl 2-amino-5-chlorothiophene-3-carboxylate) (420 mg, 2.356 mmol, 1.0 eq) was added to toluene (10 mL), and 2,5-hexanedione (403 mg, 3.534 mmol, 1.5 eq), p-toluenesulfonic acid monohydrate (81 mg, 0.2 mmol, 0.471 eq) and 3 A molecular sieve (500 mg) were added thereto. The mixture was heated under reflux and stirred overnight. The solid was filtered off and the filtrate was concentrated. The residue was purified by using flash column chromatography (petroleum ether:ethyl acetate=50:1), and a colorless liquid, i.e. Compound 25 (methyl 5-chloro-2-(2,5-dimethyl-1H-pyrrol-1-yl)thiophene-3-carboxylate) (480 mg yield: 81.2%) was obtained. MS (ESI) m/z: 270 $[M+H]^+$. TLC:petroleum ether/ethyl acetate (20:1); $R_f$ (Compound 24)=0.2; $R_f$ (Compound 25)=0.7; $^1H$ NMR (400 MHz, $CDCl_3$) δ 7.29 (s, 1H), 5.89 (s, 2H), 3.69 (s, 3H), 2.03 (s, 6H).

(3) Synthesis of Compound 26 (methyl 5-chloro-2-(3-formyl-2,5-dimethyl-1H-pyrrol-1-yl)thiophene-3-carboxylate)

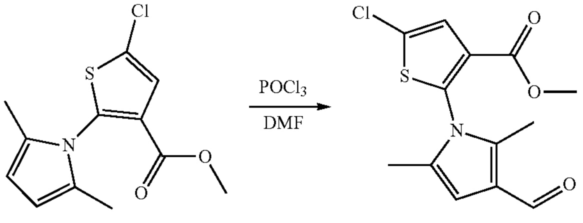

25 26

Phosphorus oxychloride (340 mg, 2.319 mmol, 1.2 eq) was added dropwise to dimethylformamide (30 mL) under conditions of 0° C. and nitrogen atmosphere. The mixture was stirred at 0° C. for 30 minutes and then warmed to room temperature. Compound 25 (methyl 5-chloro-2-(2,5-dimethyl-1H-pyrrol-1-yl)thiophene-3-carboxylate) (520 mg, 1.933 mmol, 1.0 eq) was added to dimethylformamide (4 mL). The mixture was heated to 100° C. and was stirred under nitrogen atmosphere for 1 hour. After cooling, the mixture was poured into ice water and the pH of the resulting mixture was adjusted to 10 with 30% NaOH solution. The mixture was extracted with ethyl acetate and washed with brine. The organic phase was dried over $Na_2SO_4$, filtered and concentrated. The residue was purified by using flash column chromatography (petroleum ether: ethyl acetate=100:1), and a yellow solid. i.e. Compound 26 (methyl 5-chloro-2-(3-formyl-2,5-dimethyl-1H-pyrrol-1-yl) thiophene-3-carboxylate) (300 mg, yield: 52.8%) was obtained. MS (ESI) m/z: 298 $[M+H]^+$. TLC:petroleum ether/ethyl acetate (20:1); $R_f$(Compound 25)=0.2; $R_f$(Compound 26)=0.7; H NMR (400 MHz, $CDCl_3$) δ 9.85 (s, 1H), 7.34 (s, 1H), 6.37 (s, 1H), 3.69 (s, 3H), 2.02 (d, J=4.2 Hz, 6H).

(4) Synthesis of Compound AB24318 (methyl (E)-5-chloro-2-(3-(2-cyano-2-(6-methoxy-3H-imidazo[4,5-c]pyridin-2-yl)vinyl)-2,5-dimethyl-1H-pyrrol-1-yl) thiophene-3-carboxylate)

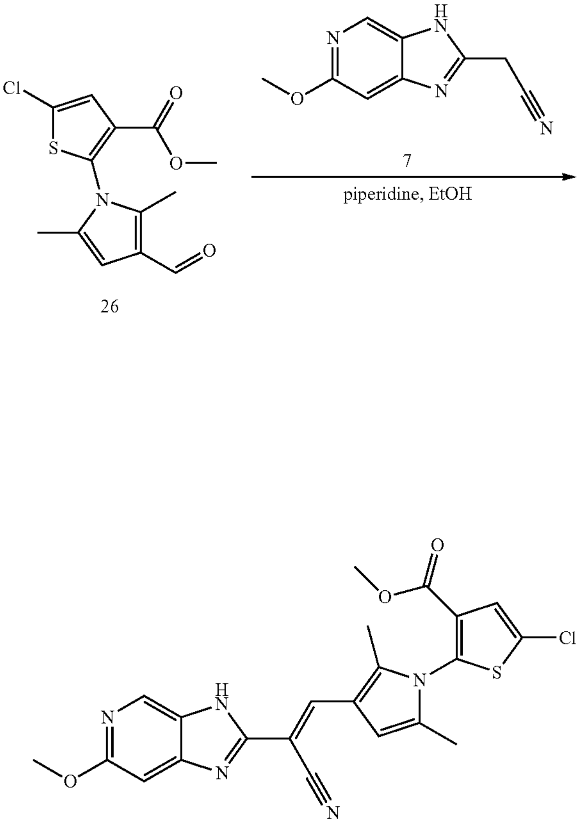

26 7

AB24318

Compound 26 (methyl 5-chloro-2-(3-formyl-2,5-dimethyl-1H-pyrrol-1-yl)thiophene-3-carboxylate) (84 mg, 0.38 mmol, 1.0 eq) was dissolved in ethanol (1 mL), and Compound 7 (2-(6-methoxy-3H-imidazo[4,5-c]pyridin-2-yl)acetonitrile) (53 mg, 0.32 mmol, 1.0 eq) and piperidine (47 mg, 0.32 mmol, 2.0 eq) were added thereto. The mixture was heated under reflux and stirred for 1 hour. The mixture was cooled to room temperature and filtered. The solid was collected and dried to obtain a yellow solid, i.e. AB24318 methyl (E)-5-chloro-2-(3-(2-cyano-2-(6-methoxy-3H-imidazo[4,5-c]pyridin-2-yl)vinyl)-2,5-dimethyl-1H-pyrrol-1-yl)thiophene-3-carboxylate) (40 mg, yield 28.8%). MS (ESI) m/z: 468 $[M+H]^+$. $^1H$ NMR (400 MHz, DMSO-d6) δ 12.96 (s, 1H), 8.49 (s, 1H), 8.12 (s, 1H), 7.68-7.47 (m, 1H), 6.92 (s, 1H), 6.78 (s, 1H), 3.86 (s, 3H), 3.65 (s, 3H), 2.27 (s, 3H), 2.04 (s, 3H).

Example 21: Synthesis of Compound (E)-2-(3-(2-cyano-2-(7-methoxy-1H-imidazo[4,5-b]pyridin-2-yl)vinyl)-2,5-dimethyl-1H-pyrrol-1-yl)-4,5-dimethylthiophene-3-carbonitrile (AB24310)

(1) Synthesis of Compound 31 (4-methoxy-3-nitropyridine-2-amine)

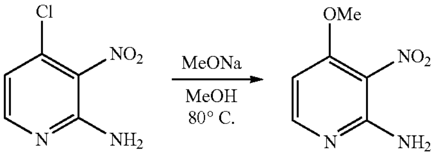

30

31

Compound 30 (2-amino-3-nitro-4-chloropyridine) (1.5 g, 8.64 mmol, 1.0 eq) was dissolved in methanol (30 mL), and sodium methoxide (933 mg, 17.3 mmol, 2.0 eq) was added thereto. The mixture was stirred at 80° C. under nitrogen atmosphere for 16 hours and cooled, and was then subjected to vacuum concentration. The residue was extracted with ethyl acetate and water. The combined organic layers were washed with saturated sodium chloride solution, dried over anhydrous sodium sulfate, filtered and concentrated in vacuum, so as to obtain the crude product, which was purified by silica gel chromatography (dichloromethane: methanol=100:1) to obtain yellow Compound 31 (4-methoxy-3-nitropyridine-2-amine) (1248 mg, 7.38 mmol, 85.4%). MS (ESI) m/z: 170 $[M+H]^+$. TLC:DCM: MeOH=10:1. $R_f$ (Compound 30)=0.7; $R_f$ (Compound 31)=0.6. $^1H$ NMR (400 MHz, DMSO-$d_6$): δ 7.97 (s, 1H), 6.84 (s, 2H), 6.43 (s, 1H), 3.80 (s, 3H).

(2) Synthesis of Compound 32 (4-methoxypyridine-2,3-diamine)

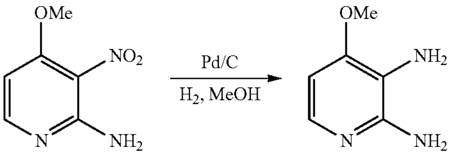

31

32

To a methanol solution (20 mL) of Compound 31 (4-methoxy-3-nitropyridine-2-amine) (1.248 g, 7.38 mmol, 1.0 eq) was added palladium on carbon (120 mg, 0.2 wt %). The resulting mixture was stirred for 16 hours under conditions of hydrogen atmosphere and room temperature. The solid was filtered off. After filtration, the filtrate was concentrated to obtain Compound 32 (4-methoxypyridine-2,3-diamine) as a brown solid (940 mg, yield: 91.6%). MS (ESI) m/z: 140 $[M+H]^+$. TLC:DCM-MeOH (10:1); $R_f$(Compound 31)=0.7; $R_f$ (Compound 32)=0.2. $^1H$ NMR (400 MHz, DMSO-$d_6$) J 7.22 (s, 1H), 6.24 (s, 1H), 5.16 (s, 2H), 3.99 (s, 2H), 3.68 (s, 3H).

(3) Synthesis of Compound 33 (2-(7-methoxy-1H-imidazo[4,5-b]pyridin-2-yl)acetonitrile)

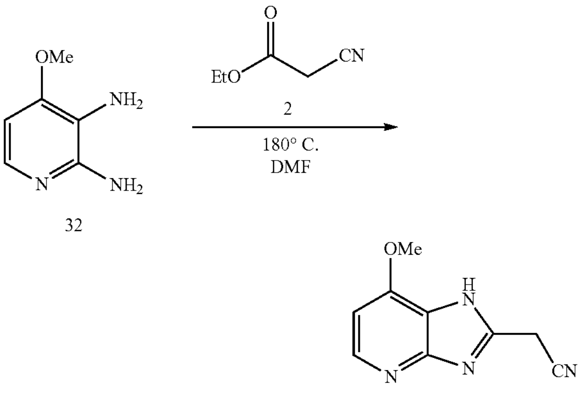

32

33

Compound 32 (4-methoxypyridine-2,3-diamine) (300 mg, 2.16 mmol, 1.0 eq) and Compound 2 (ethyl cyanoacetate) (488 mg, 4.32 mmol, 2.0 eq) were stirred and reacted in dimethylformamide (2 mL) at 180° C. for 5 hours. The solvent was removed after cooling. The residue was purified by flash column chromatography (dichloromethane:methanol=100:1 to 30:1) so as to obtain Compound 33 (2-(7-methoxy-1H-imidazo[4,5-b]pyridin-2-yl)acetonitrile) as a brown solid (193 mg, yield: 47.5%). MS (ESI) m/z: 189 $[M+H]^+$. TLC:DCM/MeOH (10:1); $R_f$(Compound 32)=0.2; $R_f$(Compound 33)=0.5.

(4) Synthesis of Compound AB24310 ((E)-2-(3-(2-cyano-2-(7-methoxy-1H-imidazo[4,5-b]pyridin-2-yl)vinyl)-2,5-dimethyl-1H-pyrrol-1-yl)-4,5-dimethylthiophene-3-carbonitrile)

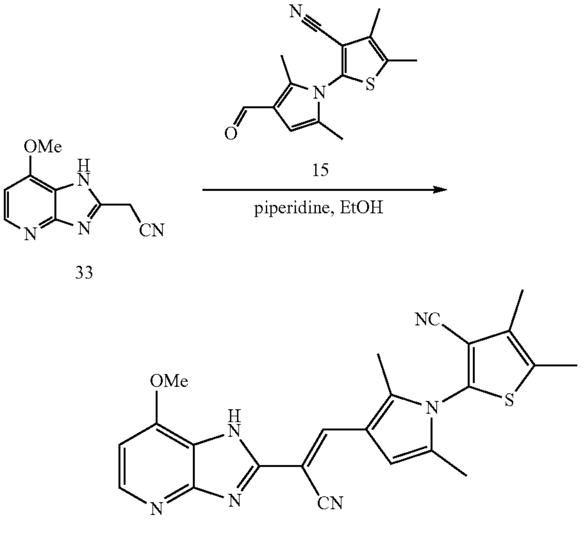

33

AB24310

To an ethanol solution (1.0 mL) of Compound 33 (2-(7-methoxy-1H-imidazo[4,5-b]pyridin-2-yl)acetonitrile) (45 mg, 0.24 mmol, 1.0 eq), Compound 15 (2-(3-formyl-2,5-dimethyl-1H-pyrrol-1-yl)-4,5-dimethylthiophene-3-carbonitrile) (62 mg, 0.24 mmol, 1.0 eq) and two drops of piperidine were added. The mixture was heated under reflux and stirred for 2 hours. After that, the resulting mixture was cooled and filtered. AB24310 ((E)-2-(3-(2-cyano-2-(7-methoxy-1H-imidazo[4,5-b]pyridin-2-yl)vinyl)-2,5-dimethyl-1H-pyrrol-1-yl)-4,5-dimethylthiophene-3-carbonitrile) (10 mg, yield, 8.8%) was collected and obtained as a yellow solid. MS (ESI) m/z: 429.0 $[M+H]^+$. $^1H$ NMR (400 MHz, DMSO-$d_6$) δ 13.19 (s, 1H), 8.17 (s, 2H), 6.97 (s, 1H), 6.83 (s, 1H), 4.02 (s, 3H), 2.42 (s, 3H), 2.30 (s, 3H), 2.24 (s, 3H), 2.09 (s, 3H).

Example 22: Synthesis of Compound (E)-2-(3-(2-cyano-2-(6-methoxy-3H-imidazo[4,5-c]pyridin-2-yl)vinyl)-2,5-dimethyl-1H-pyrrol-1-yl)-5-methylthiophene-3-carboxamide (AB24313)

(1) Synthesis of Compound 35 (2-(3-formyl-2,5-dimethyl-1H-pyrrol-1-yl)-5-methylthiophene-3-carboxamide)

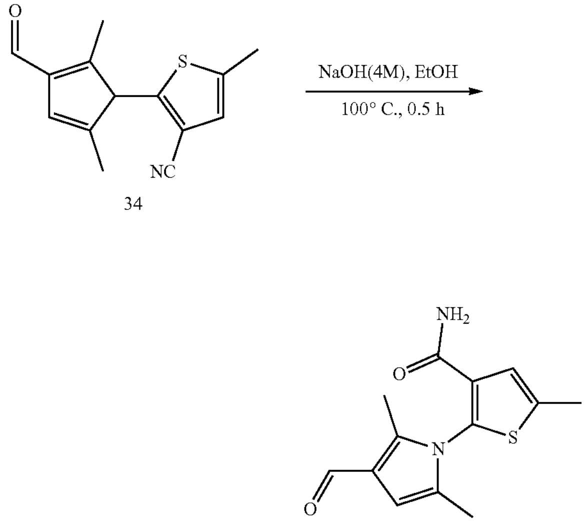

34

35

To a solution of Compound 34 (2-(3-formyl-2,5-dimethyl-1H-pyrrol-1-yl)-5-methylthiophene-3-carbonitrile) (200 mg, 0.82 mmol, 1.0 eq) in 4 mL of ethanol was added 4 M sodium hydroxide (2 mL). The mixture was stirred at 100° C. for 0.5 hours. After the completion of the above operation, collection and concentration were conducted. The residue was diluted with water and washed with ethyl acetate. The aqueous layer was adjusted to have a pH of 6 with 6 N HCl and extracted with ethyl acetate. The organic layer was dried, filtered and concentrated to obtain Compound 35 (2-(3-formyl-2,5-dimethyl-1H-pyrrol-1-yl)-5-methylthiophene-3-carboxamide) as a yellow solid (200 mg, yield: 93%). MS (ESI) m/z: 263 $[M+H]^+$. TLC:DCM:MeOH (10:1); $R_f$ (Compound 34)=0.7; $R_f$ (Compound 35)=0.1. $^1H$ NMR (400 MHz, DMSO-d6) δ 9.74 (s, 1H), 7.40 (s, 1H), 7.28 (s, 1H), 7.15 (s, 1H), 6.19 (s, 1H), 3.30 (s, 3H), 2.22 (s, 3H), 1.93 (s, 3H).

(2) Synthesis of Compound AB24313 ((E)-2-(3-(2-cyano-2-(6-methoxy-3H-imidazo[4,5-c]pyridin-2-yl)vinyl)-2,5-dimethyl-1H-pyrrol-1-yl)-5-methylthiophene-3-carboxamide)

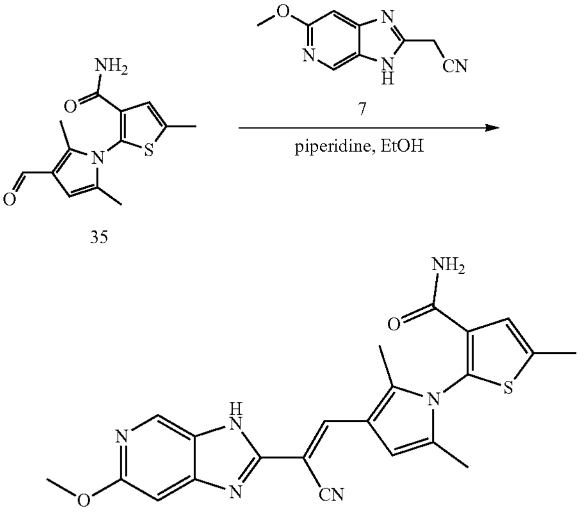

7

35

AB24313

To a solution of Compound 35 (2-(3-formyl-2,5-dimethyl-1H-pyrrol-1-yl)-5-methylthiophene-3-carbonitrile) (50 mg, 0.19 mmol, 1.0 eq) in 1 mL of ethanol. Compound 7 (2-(6-methoxy-3H-imidazo[4,5-c]pyridin-2-yl)acetonitrile) (36 mg, 0.19 mmol, 1.0 eq) and piperidine (20 mg, 0.24 mmol, 1.0 eq) were added. The mixture was heated under reflux and stirred for 1 h. After the completion of the above operation, the mixture was cooled to room temperature and filtered. The solid was collected and dried, so as to obtain Compound AB24313 (E)-2-(3-(2-cyano-2-(6-methoxy-3H-imidazo[4,5-c]pyridin-2-yl)vinyl)-2,5-dimethyl-1H-pyrrol-1-yl)-5-methylthiophene-3-carboxamide) as a yellow solid (30 mg, yield: 36.5%). MS (ESI) m/z: 433 $[M+H]^+$. $^1H$ NMR (400 MHz, DMSO) δ 12.92 (s, 1H), 8.48 (s, 1H), 8.14 (s, 1H), 7.52 (s, 1H), 7.35 (s, 1H), 7.21 (s, 1H), 6.88 (s, 1H), 6.81 (s, 1H) 3.88 (s, 3H), 2.51 (s, 3H), 2.29 (s, 3H), 2.04 (s, 3H).

Example 23: Synthesis of Compound AB24333 ((E)-2-(3-(2-cyano-2-(6-methoxy-3H-imidazo[4,5-b]pyridin-2-yl)vinyl)-2,5-dimethyl-1H-pyrrol-1-yl)-5-methylthiophene-3-carbonitrile)

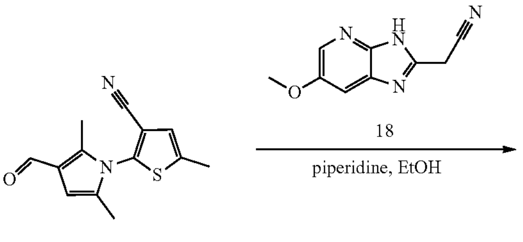

18

34

-continued

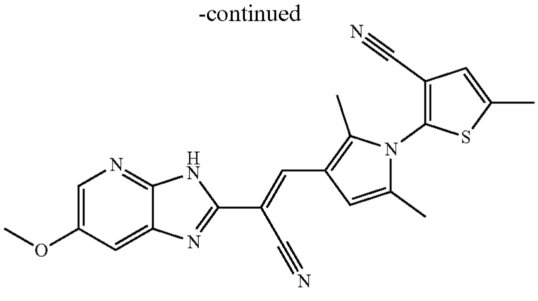

AB24333

Compound 34 (2-(3-formyl-2,5-dimethyl-1H-pyrrol-1-yl)-5-methylthiophene-3-carbonitrile) (105 mg, 0.425 mmol, 1 eq) was dissolved in 2 ml of ethanol. Compound 18 (2-(6-methoxy-3H-imidazo[4,5-b]pyridin-2-yl)acetonitrile) (80 mg, 0.425 mmol, 1 eq) and two drops of piperidine were added thereto. The mixture was heated under reflux and stirred for 1 hour. After the completion of the reaction, the mixture was cooled to room temperature and filtered. The solid was collected and dried, so as to obtain Compound AB24333 ((E)-2-(3-(2-cyano-2-(6-methoxy-3H-imidazo[4,5-b]pyridin-2-yl)vinyl)-2,5-dimethyl-1H-pyrrol-1-yl)-5-methylthiophene-3-carbonitrile) as a brown solid (150 mg, yield 68.6%). MS (ESI) m/z: 415 [M+H$^+$]. $^1$H NMR (400 MHz, DMSO-d6) δ 13.15 (s, 1H), 8.16 (s, 1H), 8.06 (s, 1H), 7.55 (s, 1H), 7.33 (s, 1H), 6.98 (s, 1H), 3.84 (s, 3H), 2.53 (s, 3H), 2.31 (s, 3H), 2.10 (s, 3H).

Example 24: Synthesis of Compound AB24334 ((E)-2-(4-(2-cyano-2-(6-methoxy-3H-imidazo[4,5-c]pyridin-2-yl)vinyl)-5-methyl-1H-pyrazol-1-yl)-5-methylthiophene-3-carbonitrile)

(1) Synthesis of Compound 42 (2-methyl-4-cyanothiophene)

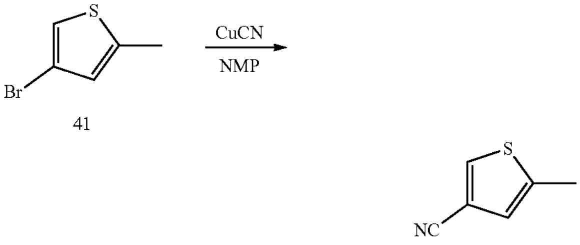

41

42

Compound 41 (4-bromo-2-methylthiophene) (10 g, 56.497 mmol, 1 eq) was suspended in N-methylpyrrolidone NMP (100 mL), and cuprous cyanide (10 g, 112.994 mmol, 2 eq) was added thereto. The mixture was heated to 160° C., and was stirred for 6 hours under the protection of nitrogen gas. After the completion of the reaction, the resulting mixture was quenched with hydrated sodium carbonate and was extracted twice with dichloromethane. Afterwards, the organic layers were dried, filtered and concentrated, so as to obtain the crude Compound 42 (2-methyl-4-cyanothiophene) as a colorless liquid (5.6 g, yield: 80%). TLC:PE/EA (20/1); $R_f$(Compound 41)=0.6; $R_f$(Compound 42)=0.3; $^1$H NMR (400 MHz, $CDCl_3$): δ 7.68 (s, 1H), 6.93 (s, 1H), 2.50 (d, J=5.0 Hz, 3H).

(2) Synthesis of Compound 43 (2-iodo-5-methylthiophene-3-carbonitrile)

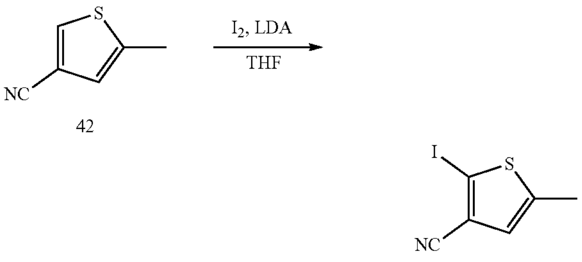

42

43

The crude Compound 42 (2-methyl-4-cyanothiophene) (5 g, 40.650 mmol, 1.0 eq) was dissolved in tetrahydrofuran (50 mL). At −78° C., lithium diisopropylamide (24.4 ml, 48.780 mmol, 1.2 eq) was added thereto, and the resulting mixture was stirred for 30 minutes. Thereafter, iodine was added thereto, and the mixture was stirred for 1 hour. Thin layer chromatography (PE/EA=20/1) showed the complete consumption of Compound 3. The reaction mixture was quenched with saturated aqueous ammonium chloride solution. The aqueous layer was extracted with dichloromethane. The residue was purified by flash column chromatography (petroleum ether/ethyl acetate=50/1), so as to obtain Compound 43 (2-iodo-5-methylthiophene-3-carbonitrile) as a white solid (6.9 g, yield: 68.2%). TLC:petroleum ether/ethyl acetate (2011); $R_f$ (Compound 42)=0.6; $R_f$ (Compound 43)=0.7; $^1$H NMR (400 MHz, $CDCl_3$): δ 6.76 (d, J=6.1 Hz, 1H), 2.48 (d, J=6.0 Hz, 3H).

(3) Synthesis of Compound 45 (ethyl 1-(3-cyano-5-methylthiophen-2-yl)-5-methyl-1H-pyrazole-4-carboxylate)

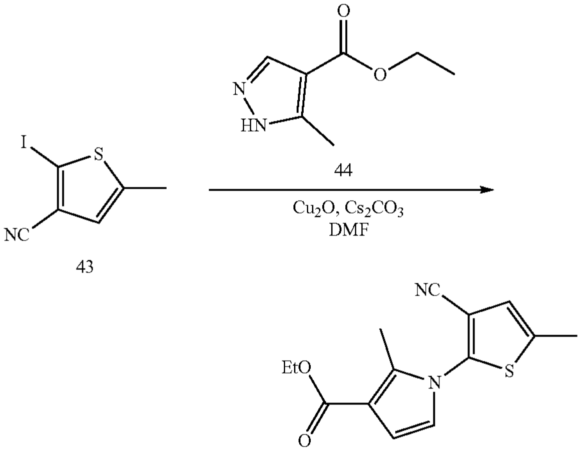

43

45

Cuprous oxide (0.18 g, 1.299 mmol, 0.2 eq), cesium carbonate (4.2 g, 12.987 mmol, 2 eq), Compound 43 (2-iodo-5-methylthiophene-3-carbonitrile) (1.9 g, 7.792 mmol, 1.2 eq) and Compound 44 (ethyl 3-methylpyrazole-4-carboxylate) (1 g, 6.493 mmol, 1.0 eq) were mixed in 20 mL of dimethylformamide. The mixture was purged with nitrogen gas three times and stirred at 110° C. for 8 hours. The progress of the reaction was monitored by thin layer chromatography. After the completion of the reaction, the resulting mixture was filtered, and the filtrate was dried over anhydrous sodium sulfate and concentrated under reduced pressure condition to obtain the crude product, which was then purified by column chromatography (petroleum ether: ethyl acetate=20:1 to 10:1) so as to obtain Compound 45 (ethyl 1-(3-cyano-5-methylthiophen-2-yl)-5-methyl-1H-pyrazole-4-carboxylate) as a yellow oil (160 mg, yield: 7.4%). TLC:petroleum ether/ethyl acetate (1011); $R_f$ (Compound 45)=0.4; $^1$H NMR (400 MHz, $CDCl_3$) δ 8.66 (d, J=7.0 Hz, 1H), 6.76 (s, 1H), 4.32 (t, J=7.1 Hz, 2H), 2.53 (d, J=6.9 Hz, 3H), 2.46 (d, J=6.9 Hz, 3H), 1.35 (t, J=7.1 Hz, 3H).

(4) Synthesis of Compound 46 (2-(4-(hydroxymethyl)-5-methyl-1H-pyrazol-1-yl)-5-methylthiophene-3-carbonitrile)

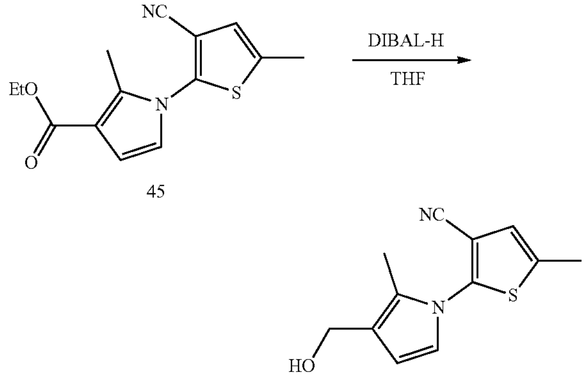

45

46

Compound 45 (ethyl 1-(3-cyano-5-methylthiophen-2-yl)-5-methyl-1H-pyrazole-4-carboxylate) (125 mg, 0.454 mmol, 1 eq) was dissolved in tetrahydrofuran (10 mL). Diisobutylaluminum hydride (1.2 ml, 1.816 mmol, 4 eq) was added thereto at −5° C. Under the protection of nitrogen gas, the mixture was warmed to room temperature and reacted for 3 hours. The reactants were monitored by liquid chromatography-mass spectrometry. The resulting mixture was filtered and concentrated. The residue was purified by flash column chromatography (petroleum ether/ethyl acetate=3/1), so as to obtain Compound 46 (2-(4-(hydroxymethyl)-5-methyl-1H-pyrazol-1-yl)-5-methylthiophene-3-carbonitrile) (80 mg, yield: 75.5%). MS (ESI) m/z: 234 [M+H$^+$]. $R_f$ (Compound 45)=0.8; $R_f$ (Compound 46)=0.4.

(5) Synthesis of Compound 47 (2-(4-formyl-5-methyl-1H-pyrazol-1-yl)-5-methylthiophene-3-carbonitrile)

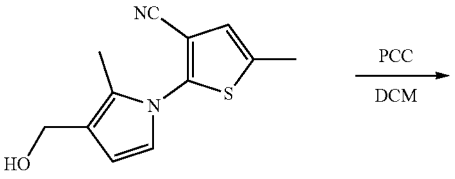

46

-continued

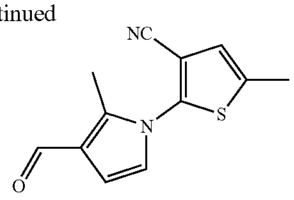

47

Compound 46 (2(4-(hydroxymethyl)-5-methyl-1H-pyrazol-1-yl)-5-methylthiophene-3-carbonitrile) (120 mg, 0.515 mmol, 1 eq) was dissolved in dichloromethane (10 mL). Pyridinium chlorochromate (332 mg, 1.545 mmol, 3 eq) was added thereto at 0° C. The mixture was warmed to room temperature and reacted for 2 hours, and the progress of the reaction was monitored by liquid chromatography-mass spectrometry. The mixture was filtered, concentrated, and purified by flash column chromatography (petroleum ether/ethyl acetate=3/1), so as to obtain Compound 47 (2-(4-formyl-5-methyl-1H-pyrazol-1-yl)-5-methylthiophene-3-carbonitrile) as a yellow solid (60 mg, yield=50%). MS (ESI) m/z: 232 [M+H$^+$]. $R_f$ (Compound 46)=0.6; $R_f$ (Compound 47)=0.4; $^1$H NMR (400 MHz, $CDCl_3$) δ 9.99 (s, 1H), 8.72 (s, 1H), 6.78 (s, 1H), 2.55 (d, J=6.4 Hz, 3H), 2.47 (d, J=6.9 Hz, 3H).

(6) Synthesis of Compound AB24334 ((E)-2-(4-(2-cyano-2-(6-methoxy-3H-imidazo[4,5-c]pyridin-2-yl)vinyl)-5-methyl-1H-pyrazol-1-yl)-5-methylthiophene-3-carbonitrile)

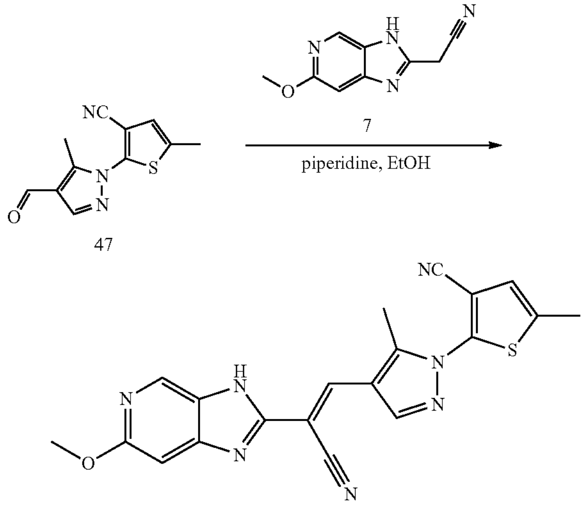

7

47

AB24334

Compound 47 (2-(4-formyl-5-methyl-1H-pyrazol-1-yl)-5-methylthiophene-3-carbonitrile) (55 mg, 0.238 mmol, 1 eq) was dissolved in 2 mL of ethanol. Compound 7 (2-(6-methoxy-3H-imidazo[4,5-c]pyridin-2-yl)acetonitrile) (45 mg, 0.238 mmol. 1 eq) and two drops of piperidine were added thereto. The mixture was heated under reflux and stirred for 1 hour. After the completion of the reaction, the mixture was cooled to room temperature and filtered. The solid was collected and dried so as to obtain Compound AB24334 ((E)-2-(4-(2-cyano-2-(6-methoxy-3H-imidazo[4, 5-c]pyridin-2-yl)vinyl)-5-methyl-1H-pyrazol-1-yl)-5-methylthiophene-3-carbonitrile)) as a yellow solid (65 mg, yield: 68%). MS (ESI) m/z: 402 [M+H$^+$]. 1H NMR (400 MHz, DMSO-d6) δ 13.09 (s, 1H), 9.14 (s, 1H), 8.55 (s, 1H), 8.10 (s, 11H), 7.14 (s, 1H), 6.83 (s, 1H), 3.86 (s, 3H), 2.44 (s, 6H).

Example 25: Synthesis of Compound AB24341 ((E)-2-(3-(2-(6-chloro-3H-imidazo[4,5-c]pyridin-2-yl)-2-cyanovinyl)-2,5-dimethyl-1H-pyrrol-1-yl)-5-methylthiophene-3-carbonitrile)

(1) Synthesis of Compound 56 (3,4-diamino-6-chloropyridine)

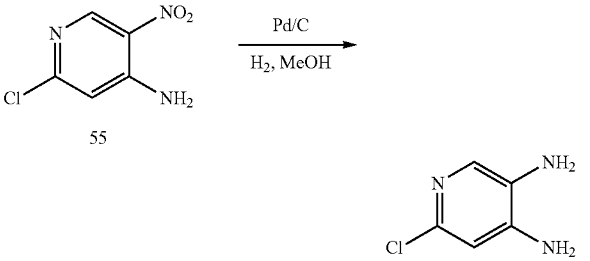

55

56

Compound 55 (2-chloro-4-amino-5-nitropyridine) (2 g, 11.52 mmol, 1 eq) was dissolved in 30 mL of methanol, and palladium on carbon Pd/C (400 mg, 0.2 wt %) was added thereto. The mixture was stirred and reacted at room temperature for 16 hours under the protection of hydrogen gas. After the resulting mixture was filtered and concentrated, the crude Compound 56 (3,4-diamino-6-chloropyridine) (1.8 g, yield 100%) was obtained as a brown solid without the need of further purification. MS (ESI) m/z: 144 [M+H$^+$]. TLC: dichloromethane/methanol (10/1); $R_f$ (Compound 55)=0.5; $R_f$ (Compound 56)=0.8.

(2) Synthesis of Compound 58 (N-(4-amino-6-chloropyridin-3-yl)-2-cyanoacetamide)

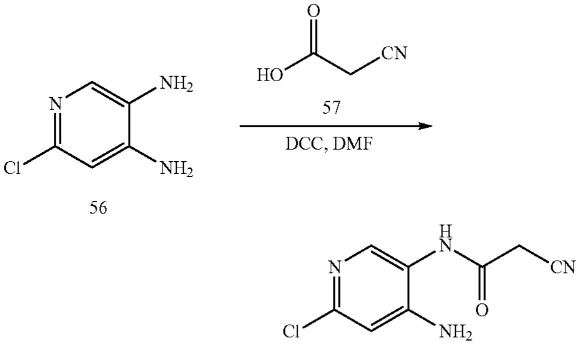

57

56

58

Compound 56 (3,4-diamino-6-chloropyridine) (1.3 g, 9.09 mmol, 1.0 eq) was dissolved in dimethylformamide (20 mL). Compound 57 (cyanoacetic acid) (1.16 g, 13.64 mmol, 1.5 eq) and dicyclohexylcarbodiimide (2.1 g, 10.0 mmol, 1.1 eq) were added thereto. The mixture was stirred at room temperature for 16 hours. After the resulting mixture was concentrated, the residue was purified by flash column chromatography (dichloromethane/methanol=100/1 to 50/1 to 30/1), so as to obtain Compound 58 (N-(4-amino-6-chloropyridin-3-yl)-2-cyanoacetamide) as a yellow oil (1.1 g, yield: 21.1%). MS (ESI) m/z: 211 [M+H$_1$]. TLC:dichloromethane/methanol (10/1); $R_f$ (Compound 56)=0.6; $R_f$ (Compound 58)=0.2.

(3) Synthesis of Compound 59 (2-(6-chloro-3H-imidazo[4,5-c]pyridin-2-yl)acetonitrile)

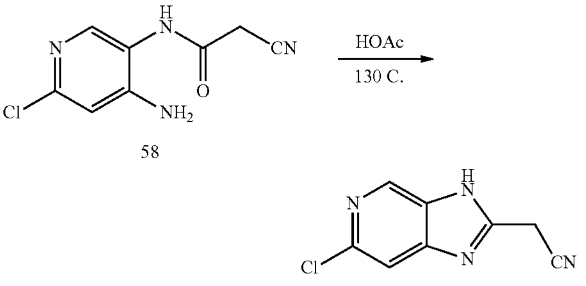

58

59

Compound 58 (N-(4-amino-6-chloropyridin-3-yl)-2-cyanoacetamide) (1.1 g, 5.22 mmol, 1.0 eq) was dissolved in acetic acid (20 mL), and the mixture was stirred at 100° C. for 3 hours. After the resulting mixture was concentrated, the residue was purified by flash column chromatography (dichloromethane/methanol=100/1 to 50/1 to 20/1 to 10/1), so as to obtain Compound 59 (2-(6-chloro-3H-imidazo[4,5-c]pyridin-2-yl)acetonitrile) as a brown solid (730 mg, yield: 72.6%). MS (ESI) m/z: 193 [M+H$^+$]. TLC:dichloromethane/methanol (10/1); $R_f$ (Compound 58)=0.5; $R_f$ (Compound 59)=0.45.

(4) Synthesis of Compound AB24341 ((E)-2-(3-(2-(6-chloro-3H-imidazo[4,5-c]pyridin-2-yl)-2-cyanovinyl)-2,5-dimethyl-1H-pyrrol-1-yl)-5-methylthiophene-3-carbonitrile)

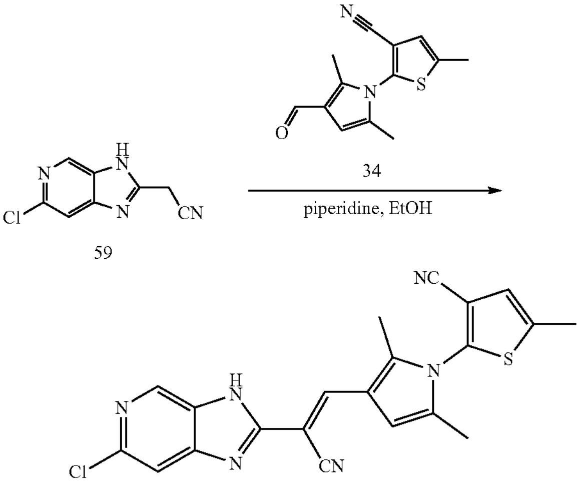

34

59

AB24341

Compound 59 (2-(6-chloro-3H-imidazo[4,5-c]pyridin-2-yl)acetonitrile) (60 mg, 0.314 mmol, 1 eq) was dissolved in ethanol (1.5 mL). Compound 34 (2-(3-formyl-2,5-dimethyl-1H-pyrrol-1-yl)-5-methylthiophene-3-carbonitrile) (74 mg, 0.314 mmol, 1 eq) and piperidine (27 mg, 0.314 mmol, 1 eq) were added thereto. The mixture was heated under reflux and stirred for 2 hours. After the completion of the reaction, the mixture was concentrated and purified by preparative high-pressure liquid chromatography, so as to obtain Compound AB24341 ((E)-2-(3-(2-(6-chloro-3H-imidazo[4,5-c]pyridin-2-yl)-2-cyanovinyl)-2,5-dimethyl-1H-pyrrol-1-yl)-5-methylthiophene-3-carbonitrile) as a yellow solid (55 mg, yield: 41.8%). MS (ESI) m/z: 419 [M+H$^+$]. $^1$H NMR (400 MHz, DMSO-$d_6$) δ 8.68 (s, 1H), 8.25 (s, 1H), 7.63 (s, 1H), 7.34 (s, 1H), 6.99 (s, 1H), 2.53 (s, 3H), 2.32 (s, 31H), 2.10 (s, 3H).

Example 26: Synthesis of Compound AB24336 ((E)-2-(3-(2-cyano-2-(6-methoxy-3H-imidazo[4,5-c]pyridin-2-yl)vinyl)-2,5-dimethyl-1H-pyrrol-1-yl)-5-(pyridin-2-yl)thiophene-3-carbonitrile)

(1) Synthesis of Compound 62 (2-(3-formyl-2,5-dimethyl-1H-pyrrol-1-yl)-5-(pyridin-2-yl)thiophene-3-carbonitrile)

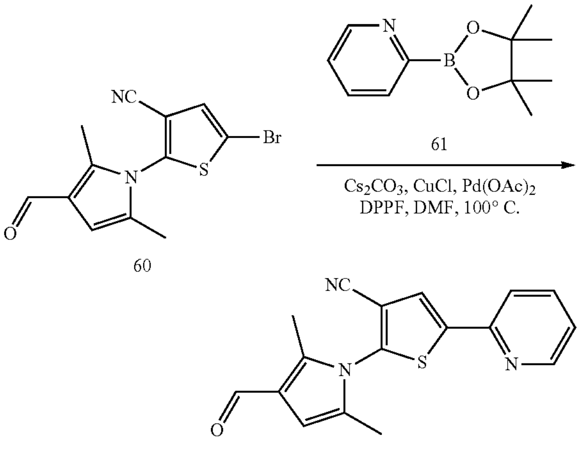

60 61 62

Compound 60 (5-bromo-2-(3-formyl-2,5-dimethyl-1H-pyrrol-1-yl)thiophene-3-carbonitrile) (50 mg, 0.162 mmol, 1.0 eq) was dissolved in 1 mL of dimethylformamide. Compound 61 (2-pyridineboronic acid pinacol ester) (40 mg, 0.323 mmol, 2.0 eq), cesium carbonate (105 mg, 0.323 mmol, 2.0 eq), cuprous chloride (16 mg, 0.162 mmol, 1.0 eq), palladium acetate (2 mg, 0.0081 mmol, 0.05 eq) and 1,1'-bis(diphenylphosphino)ferrocene DPPF (9 mg, 0.0162 mmol, 0.1 eq) were added thereto. The mixture was reacted in a sealed tube at 100° C. for 16 hours. The solid was collected, filtered and concentrated. The residue was purified by preparative thin layer chromatography (petroleum ether/ethyl acetate=1/1), so as to obtain Compound 62 (2-(3-formyl-2,5-dimethyl-1H-pyrol-1-yl)-5-(pyridin-2-yl)thiophene-3-carbonitrile) as a yellow oil (23 mg, yield: 46%). MS (ESI) m/z: 308 [M+H]+. TLC:petroleum ether/ethyl acetate (3/1); $R_f$ (Compound 60)=0.6; $R_f$ (Compound 62)=0.3.

(2) Synthesis of Compound AB24336 ((E)-2-(3-(2-cyano-2-(6-methoxy-3H-imidazo[4,5-c]pyridin-2-yl)vinyl)-2,5-dimethyl-1H-pyrrol-1-yl)-5-(pyridin-2-yl)thiophene-3-carbonitrile)

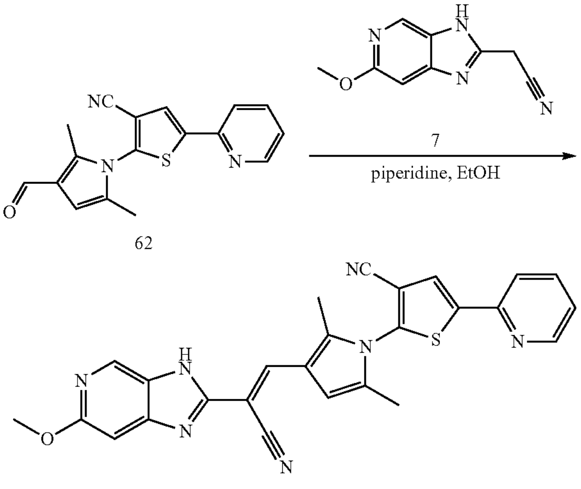

62 7 AB24336

To a solution of Compound 62 (2-(3-formyl-2,5-dimethyl-1H-pyrrol-1-yl)-5-(pyridin-2-yl)thiophene-3-carbonitrile) (21 mg, 0.068 mmol, 1.0 eq) in 1 mL of ethanol, Compound 7 (2-(6-methoxy-3H-imidazo[4,5-c]pyridin-2-yl)acetonitrile) (13 mg, 0.068 mmol, 1.0 eq) and piperidine (6 mg, 0.068 mmol, 1.0 eq) were added. The mixture was heated under reflux for 1 hour. After the completion of the reaction, the mixture was cooled to room temperature and filtered. The solid was collected and dried so as to obtain Compound AB24336 ((E)-2-(3-(2-cyano-2-(6-methoxy-3H-imidazo[4,5-c]pyridin-2-yl)vinyl)-2,5-dimethyl-1H-pyrrol-1-yl)-5-(pyridin-2-yl)thiophene-3-carbonitrile) as a yellow solid (19 mg, yield: 58%). MS (ESI) m/z: 478 [M+H]+. $^1$H NMR (400 MHz, DMSO-d6) δ 12.96 (s, 1H), 8.58 (d, J=4.8 Hz, 1H), 8.49 (s, 1H), 8.37 (s, 1H), 8.17-8.09 (m, 2H), 7.99-7.95 (m, 1H), 7.45-7.42 (m, 1H), 7.02 (s, 1H), 6.80 (s, 1H), 3.86 (s, 3H), 2.38 (s, 3H), 2.17 (s, 3H).

Example 27: Synthesis of Compound AB24342 ((Z)-2-(3-(2-cyano-2-(5-methoxy-1H-pyrrolo[2,3-c]pyridin-2-yl)vinyl)-2,5-dimethyl-1H-pyrrol-1-yl)-5-methylthiophene-3-carbonitrile)

(1) Synthesis of Compound 64 (2-methoxy-4-methyl-5-nitropyridine)

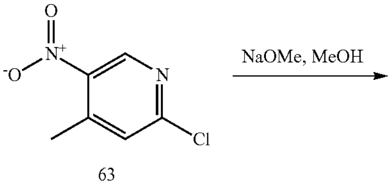

63

-continued

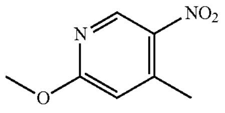

64

Compound 63 (2-chloro-5-nitro-4-methylpyridine) (7.8 g, 45.348 mmol, 1 eq) was dissolved in methanol (80 mL), and sodium methoxide (2.93 g, 54.418 mmol, 1.2 eq) was added thereto at 0° C. The mixture was stirred at room temperature for 8 hours. After the completion of the reaction, the mixture was concentrated to obtain the crude Compound 64 (2-methoxy-4-methyl-5-nitropyridine) (7 g, yield: 92.1%) as a brown solid without the need of further purification. TLC:petroleum ether/ethyl acetate (10/1); MS (ESI) m/z: 169 [M+H$^+$]. $R_f$(Compound 63)=0.3; $R_f$ (Compound 64)=0.5; $^1$H NMR (400 MHz, $CDCl_3$) δ 8.93 (d, J=3.3 Hz, 1H), 6.63 (d, J=3.4 Hz, 1H), 4.00 (d, J=3.1 Hz, 3H), 2.61 (d, J=3.3 Hz, 3H).

(2) Synthesis of Compound 65 (ethyl 3-(2-methoxy-5-nitropyridin-4-yl)-2-oxopropanoate)

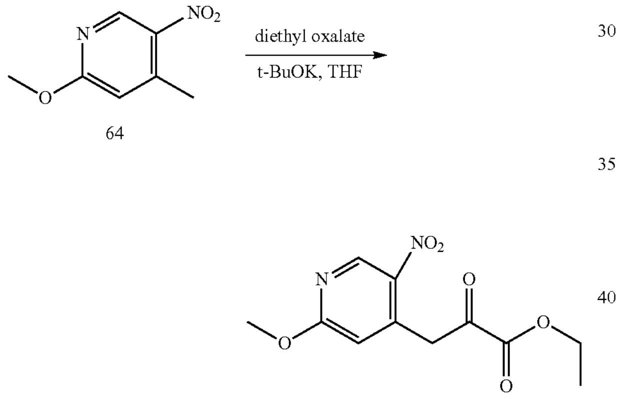

64

65

Potassium tert-butoxide (3.4 g, 29.761 mmol, 1.0 eq) was dissolved in tetrahydrofuran (50 mL), and diethyl oxalate (4.4 g, 29.761 mmol, 1.0 eq) was added thereto under the protection of nitrogen gas. The reactants were stirred at room temperature for 15 minutes, a solution of Compound 64 (2-methoxy-4-methyl-5-nitropyridine) (5 g, 29.761 mmol, 1.0 eq) was then added into the above-mentioned reaction system, and the mixture was heated under reflux for 4 hours. The resulting mixture was cooled to room temperature and the pH of the mixture was adjusted to 3 to 4 with 2N hydrochloric acid. The aqueous layer was extracted three times with ethyl acetate. The residue was purified by flash column chromatography (petroleum ether/ethyl acetate=5/1), so as to obtain Compound 65 (ethyl 3-(2-methoxy-5-nitropyridin-4-yl)-2-oxopropanoate) (2.8 g, yield: 25%). TLC:petroleum ether/ethyl acetate (5/1). MS (ESI) m/z: 269 [M+H$^+$]. $R_f$ (Compound 64)=0.8; $R_f$ (Compound 65)=0.2; $^1$H NMR (400 MHz, $CDCl_3$) δ 8.89 (d, J=4.0 Hz, 1H), 7.54 (d, J=4.0 Hz, 1H), 7.06 (d, J=12.7 Hz, 2H), 4.61-4.34 (m, 2H), 4.02 (d, J=4.1 Hz, 3H), 1.39 (t, J=6.7 Hz, 3H).

(3) Synthesis of Compound 66 (ethyl 5-methoxy-1H-pyrrolo[2,3-c]pyridine-2-carboxylate)

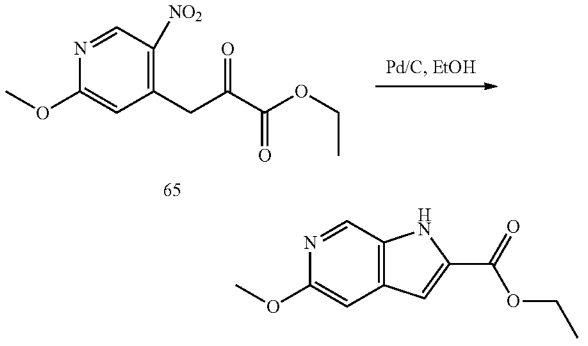

65

66

Compound 65 (ethyl 3-(2-methoxy-5-nitropyridin-4-yl)-2-oxopropanoate) (2.5 g, 8.741 mmol, 1 eq) was dissolved in ethanol (30 mL), and palladium on carbon Pd/C (0.5 g, 0.2 wt %) was added thereto. The mixture was stirred at room temperature for 8 hours in the presence of hydrogen gas. The solid was filtered off and the filtrate was concentrated. The residue was purified by flash column chromatography (petroleum ether/ethyl acetate=2/1), so as to obtain Compound 66 (ethyl 5-methoxy-1H-pyrrolo[2,3-c]pyridine-2-carboxylate) (1 g, yield: 48.7%). TLC:petroleum ether/ethyl acetate (2:1); MS (ESI) m/z: 221 [M+H$^+$]. $R_f$(Compound 65)=0.4; $R_f$(Compound 66)=0.6; $^1$H NMR (400 MHz, $CDCl_3$) δ 9.34 (s, 1H), 8.53 (s, 1H), 7.07 (s, 1H), 6.94 (s, 1H), 4.43 (d, J=7.3 Hz, 2H), 3.96 (d, J=2.8 Hz, 3H), 1.41 (t, J=7.1 Hz, 3H).

(4) Synthesis of Compound 67 ((5-methoxy-1H-pyrrolo[2,3-c]pyridin-2-yl)methanol)

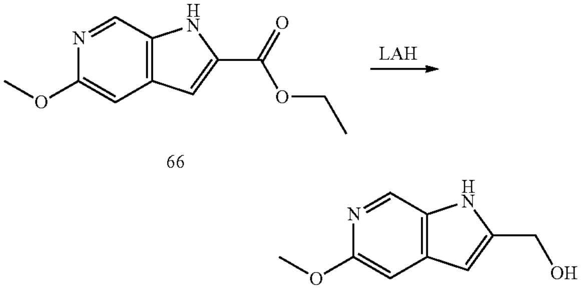

66

67

Compound 66 (ethyl 5-methoxy-1H-pyrrolo[2,3-c]pyridine-2-carboxylate) (935 mg, 3.488 mmol, 1 eq) was dissolved in tetrahydrofuran (10 mL), and lithium aluminum hydride (123 mg, 3.523 mmol, 1.1 eq) was added thereto at −5° C. The reaction was carried out at room temperature for 1 hour under the protection of nitrogen gas. The progress of the reaction was monitored by liquid chromatography-mass spectrometry. After the completion of the reaction, the reaction was quenched with sodium bicarbonate and the resulting mixture was filtered to collect the solid, which was purified by flash column chromatography (petroleum ether/ethyl acetate=1/1) so as to obtain Compound 67 ((5-methoxy-1H-pyrrolo[2,3-c]pyridin-2-yl)methanol) (700 mg, yield 92.5%). MS (ESI) m/z: 179 [M+H$^+$]. $R_f$ (Compound 66)=0.2; $R_f$ (Compound 67)=0.6. $^1$H NMR (400 MHz, DMSO-d6) δ 11.16 (s, 1H), 8.22 (s, 1H), 6.73 (s, 111), 6.17 (s, 1H), 5.40 (d, J=5.8 Hz, 1H), 4.59 (d, J=5.4 Hz, 2H), 3.78 (s, 3H).

(5) Synthesis of Compound 68 (2-(chloromethyl)-5-methoxy-1H-pyrrolo[2,3-c]pyridine)

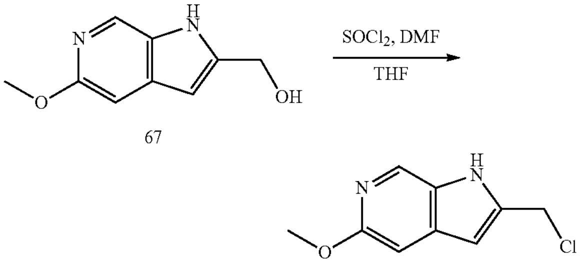

67

68

Compound 67 ((5-methoxy-1H-pyrrolo[2,3-c]pyridin-2-yl)methanol) (300 mg, 1.685 mmol, 1 eq) was dissolved in tetrahydrofuran (10 mL). Thionyl chloride (407 mg, 3.370 mmol, 2 eq) and two drops of dimethylformamide were added thereto at 0° C. Under the protection of nitrogen gas, the reactants were warmed to room temperature and reacted for 8 hours. The progress of the reaction was monitored by liquid chromatography-mass spectrometry. After the completion of the reaction, the pH of the resulting mixture was adjusted to 9 to 10 with sodium bicarbonate solution, and was then extracted three times with dichloromethane. The organic layers were dried, filtered and concentrated, so as to obtain Compound 68 (2-(chloromethyl)-5-methoxy-1H-pyrrolo[2,3-c]pyridine) (300 mg, yield, 90.6%). TLC: petroleum ether/ethyl acetate (1:1); MS (ESI) m/z: 197 [M+H$^+$]. $R_f$ (Compound 67)=0.2; $R_f$(Compound 68)=0.4.

(6) Synthesis of Compound 69 (2-(5-methoxy-1H-pyrrolo[2,3-c]pyridin-2-yl)acetonitrile)

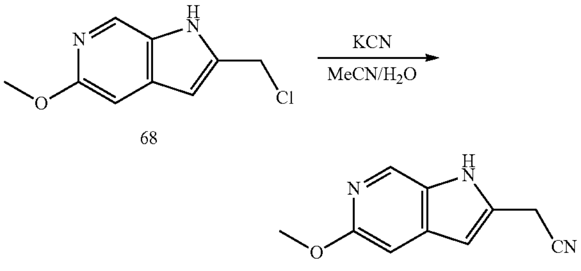

68

69

Compound 68 (2-(chloromethyl)-5-methoxy-1H-pyrrolo[2,3-c]pyridine) (300 mg, 0.16 mmol, 1 eq) was dissolved in a mixed solution of acetonitrile/water (10:1) (10 mL), and potassium cyanide (132 mg, 2.215 mmol, 1.3 eq) was added thereto. The reactants were stirred at room temperature for 2 hours. The progress of the reaction was monitored by liquid chromatography-mass spectrometry. After the completion of the reaction, the aqueous phase was extracted three times with dichloromethane. The organic layers were dried, filtered and concentrated. The residue was purified by flash column chromatography (petroleum ether/ethyl acetate=1/1), so as to obtain Compound 69 (2-(5-methoxy-1H-pyrrolo[2,3-c]pyridin-2-yl)acetonitrile) (60 mg, yield=21%). MS (ESI) m/z: 188 [M+H$^+$]. TLC:petroleum ether/ethyl acetate (1:1); $R_f$ (Compound 68)=0.4; $R_f$ (Compound 69)=0.6.

(7) Synthesis of Compound AB24342 ((Z)-2-(3-(2-cyano-2-(5-methoxy-1H-pyrrolo[2,3-c]pyridin-2-yl) vinyl)-2,5-dimethyl-1H-pyrol-1-yl)-5-methylthiophene-3-carbonitrile)

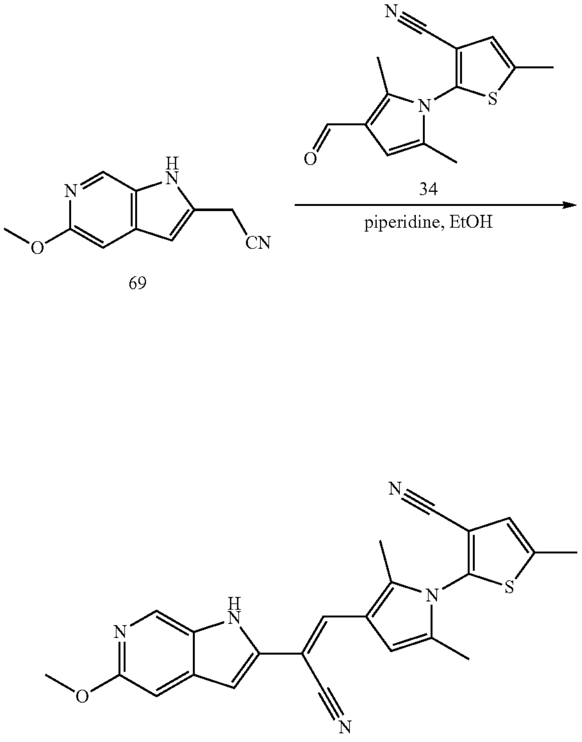

34

69

AB24342

Compound 69 (2-(5-methoxy-1H-pyrrolo[2,3-c]pyridin-2-yl)acetonitrile) (50 mg, 0.267 mmol, 1 eq) was dissolved in ethanol (2 mL). Compound 34 (2-(3-formyl-2,5-dimethyl-1H-pyrrol-1-yl)-5-methylthiophene-3-carbonitrile) (65 mg, 0.267 mmol, 1 eq) and two drops of piperidine were added thereto. The mixture was heated under reflux and stirred for 1 hour. After the completion of the reaction, the mixture was cooled to room temperature and filtered to collect the solid, which was dried to obtain Compound AB24342 ((Z)-2-(3-(2-cyano-2-(5-methoxy-1H-pyrrolo[2,3-c]pyridin-2-yl)vinyl)-2,5-dimethyl-1H-pyrol-1-yl)-5-methylthiophene-3-carbonitrile) as a yellow solid (27 mg, yield: 22.2%). MS (ESI) m/z: 414 [M+H]$^+$, 1H NMR (400 MHz, DMSO-d6) δ 11.75 (s, 1H), 8.32 (d, J=7.0 Hz, 1H), 7.89 (s, 1H), 7.32 (s, 1H), 6.91 (s, 1H), 6.82 (s, 1H), 6.51 (s, 1H), 3.81 (d, J=7.0 Hz, 3H), 2.52 (s, 3H), 2.29 (s, 3H), 2.09 (s, 3H).

Example 28: Synthesis of Compound AB24324 ((E)-2-(3-(2-cyano-2-(6-methoxy-3H-imidazo[4,5-c] pyridin-2-yl)vinyl)-2,5-dimethyl-1H-pyrrol-1-yl)-5-cyclo propylthiophene-3-carbonitrile)

(1) Synthesis of Compound 75 (2-amino-5-bromothiophene-3-carbonitrile)

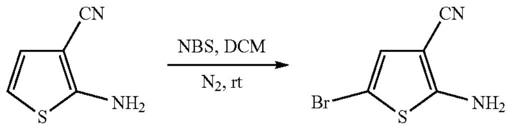

74 75

Compound 74 (2-aminothiophene-3-carbonitrile) (2 g, 16.1 mmol, 1 eq) was suspended in dichloromethane (40 mL), and then N-bromosuccinimide (2.87 mg, 16.1 mmol, 1 eq) was added thereto. The mixture was stirred at room temperature for two hours under the protection of nitrogen gas. After the completion of the reaction, the reaction was quenched with sodium carbonate, the resulting mixture was extracted twice with dichloromethane, and then the organic layers were concentrated to obtain the crude Compound 75 (2-amino-5-bromothiophene-3-carbonitrile) (3.2 g) as a brown solid without the need of further purification. TLC: petroleum ether/ethyl acetate (5/1); $R_f$(Compound 74)=0.3; $R_f$(Compound 75)=0.32; $^1$H NMR (400 MHz, DMSO-$d_6$) δ 6.93 (s, 1H), 7.40 (br s, 2H).

(2) Synthesis of Compound 76 (5-bromo-2-(2,5-dimethyl-1H-pyrrol-1-yl)thiophene-3-carbonitrile)

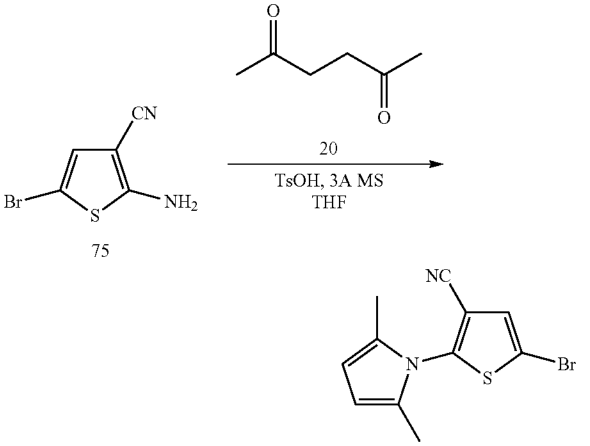

75

76

The crude Compound 75 (2-amino-5-bromothiophene-3-carbonitrile) (3.2 g, 1.0 eq) was dissolved in tetrahydrofuran (16 mL). Compound 20 (2,5-hexanedione) (3.63 g, 31.8 mmol, 2 eq), 3 A molecular sieve (3 g) and p-toluenesulfonic acid hydrate (1.2 g, 6.36 nmol, 0.4 eq) were added thereto. The mixture was heated under reflux and stirred for 4 hours. The solid was filtered off, and the filtrate was concentrated. The residue was purified by flash column chromatography (petroleum ether/ethyl acetate=100/1), so as to obtain Compound 76 (5-bromo-2-(2,5-dimethyl-1H-pyrol-1-yl)thiophene-3-carbonitrile) as a yellow oil (945 mg, overall yield for the two steps of the reaction: 21.1%). TLC:petroleum ether/ethyl acetate (5/1); $R_f$(Compound 75)=0.55; $R_f$(Compound 76)=0.7; $^1$H NMR (400 MHz, $CDCl_3$) δ 7.22 (s, 1H), 5.93 (s, 2H), 2.12 (s, 6H).

(3) Synthesis of Compound 77 (5-bromo-2-(3-formyl-2,5-dimethyl-1H-pyrol-1-yl)thiophene-3-carbonitrile)

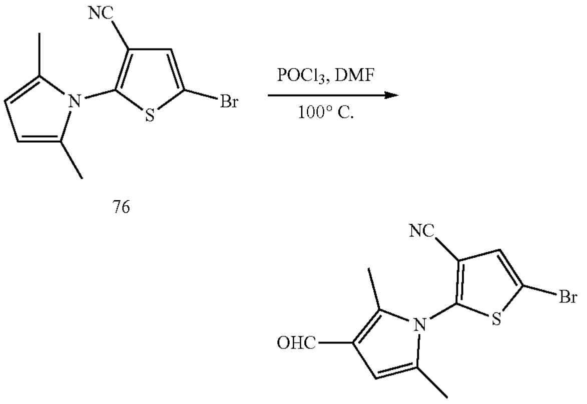

76

77

Under the protection of nitrogen gas, phosphorus oxychloride (514 mg, 3.36 mmol, 1.0 eq) was added dropwise to dimethylformamide (5 mL) at 0° C., and then the resulting mixture was warmed to room temperature. Compound 76 (5-bromo-2-(2,5-dimethyl-1H-pyrrol-1-yl)thiophene-3-carbonitrile) (944 mg, 3.36 mmol, 1.0 eq) in dimethylformamide (3 mL) was added into the above-mentioned mixture. The reactants were heated to 100° C., and was then stirred for 3 hours in the presence of nitrogen gas. After the reactants were cooled, the mixture was poured into ice water and the pH of the resulting mixture was adjusted to 10 with 30% NaOH. The mixture was extracted with ethyl acetate and washed with saturated aqueous sodium chloride solution. Afterwards, the organic layer was dried over anhydrous sodium sulfate, filtered and concentrated. The residue was purified by flash column chromatography (petroleum ether/ethyl acetate=20/1), so as to obtain Compound 77 (5-bromo-2-(3-formyl-2,5-dimethyl-1H-pyrrol-1-yl)thiophene-3-carbonitrile) as a yellow solid powder (667 mg, yield: 64.5%). TLC:petroleum ether/ethyl acetate (5:1); $R_f$ (Compound 76)=0.8; $R_f$ (Compound 77)=0.3; $^1$H NMR (400 MHz, $CDCl_3$) δ 9.89 (s, 1H), 7.30 (s, 1H), 6.43 (s, 1H), 2.41 (s, 3H), 2.12 (s, 3H).

(4) Synthesis of Compound 79 (5-cyclopropyl-2-(3-formyl-2,5-dimethyl-1H-pyrrol-1-yl)-thiophene-3-carbonitrile)

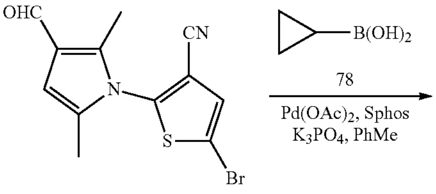

77

-continued

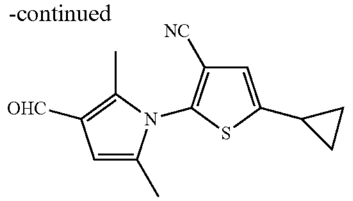

79

Compound 77 (5-bromo-2-(3-formyl-2,5-dimethyl-1H-pyrrol-1-yl)thiophene-3-carbonitrile) (50 mg, 0.16 mmol, 1 eq) was dissolved in 2 mL of toluene. Cyclopropylboronic acid (41 mg, 0.48 mmol, 3 eq), palladium acetate (16 mg, 0.012 mmol, 7.5%), Sphos (10 mg, 0.024 mmol, 0.15 eq) and potassium phosphate (71 mg, 0.336 mmol, 2.1 eq) were added thereto. The reactants were heated to 100° C. in the presence of nitrogen gas. The mixture was monitored by liquid chromatography-mass spectrometry, filtered and then concentrated. The residue was purified by flash column chromatography (petroleum ether/ethyl acetate=5/1), so as to obtain Compound 79 (5-cyclopropyl-2-(3-formyl-2,5-dimethyl-1H-pyrrol-1-yl)thiophene-3-carbonitrile) as a yellow solid (35 mg, yield 83%). MS (ESI) m/z: 271 [M+H$^+$]. $^1$H NMR (400 MHz, $CDCl_3$) δ 9.86 (s, 1H), 6.89 (s, 1H), 6.39 (s, 1H), 2.36 (s, 3H), 2.07 (s, 4H), 1.13 (d, J=7.3 Hz, 2H), 0.81 (d, J=4.6 Hz, 2H).

(5) Synthesis of Compound AB24324 ((E)-2-(3-(2-cyano-2-(6-methoxy-3H-imidazo[4,5-c]pyridin-2-yl)vinyl)-2,5-dimethyl-1H-pyrrol-1-yl)-5-cyclopropylthiophene-3-carbonitrile)

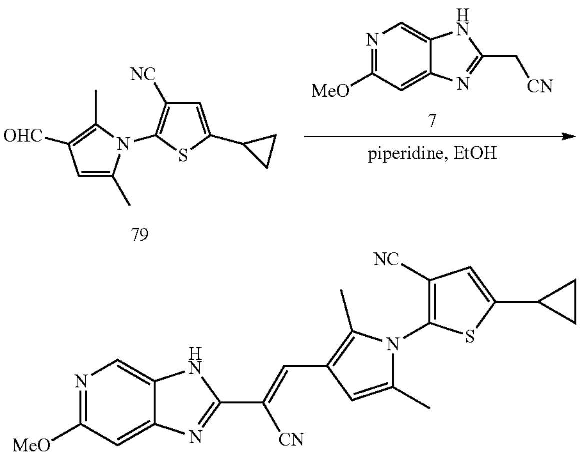

79

AB24324

Compound 79 (5-cyclopropyl-2-(3-formyl-2,5-dimethyl-1H-pyrrol-1-yl)thiophene-3-carbonitrile) (35 mg, 0.133 mmol, 1 eq) was dissolved in 2 mL of ethanol. Compound 7 (2-(6-methoxy-3H-imidazo[4,5-c]pyridin-2-yl)acetonitrile) (25 mg, 0.133 mmol, 1 eq) and two drops of piperidine were added thereto. The mixture was heated under reflux and stirred for 2 hours. After the completion of the reaction, the mixture was cooled to room temperature and filtered. The solid was collected and dried so as to obtain Compound AB24324 ((E)-2-(3-(2-cyano-2-(6-methoxy-3H-imidazo[4,5-c]pyridin-2-yl)vinyl)-2,5-dimethyl-1H-pyrrol-1-yl)-5-cyclopropylthiophene-3-carbonitrile) as a yellow solid powder (33 mg, yield: 57.7%). MS (ESI) m/z: 441 [M+H$^+$]. $^1$H NMR (400 MHz, DMSO-$d_6$) δ 8.44 (s, 1H), 8.09 (s, 1H), 7.27 (s, 1H), 6.92 (s, 1H), 6.75 (s, 1H), 3.81 (s, 3H), 2.26 (s, 3H), 2.24-2.15 (m, 1H), 2.05 (s, 3H), 1.04 (d, J=6.1 Hz, 2H), 0.79 (d, J=6.0 Hz, 2H).

Example 29: Synthesis of Compound (E)-5-bromo-2-(3-(2-cyano-2-(6-methoxy-3H-imidazo[4,5-c]pyridin-2-yl)vinyl)-2,5-dimethyl-1H-pyrrol-1-yl)thiophene-3-carbonitrile (AB24323)

The compound was obtained in the same manner as in Example 28 (yield: 21.2%), $^1$H NMR (400 MHz, DMSO-d6) δ 8.51 (s, 1H), 8.15 (s, 1H), 7.93 (s, 1H), 6.99 (s, 1H), 6.81 (s, 1H), 3.88 (s, 3H), 2.35 (s, 3H), 2.14 (s, 3H).

Example 30: Synthesis of Compound (E)-2-(3-(2-cyano-2-(6-methoxy-3H-imidazo[4,5-c]pyridin-2-yl)vinyl)-2,5-dimethyl-1H-pyrrol-1-yl)-5-isopropylthiophene-3-carbonitrile (AB24325)

(1) Synthesis of Compound 81 (2-(2,5-dimethyl-1H-pyrrol-1-yl)-5-isopropylthiophene-3-carbonitrile)

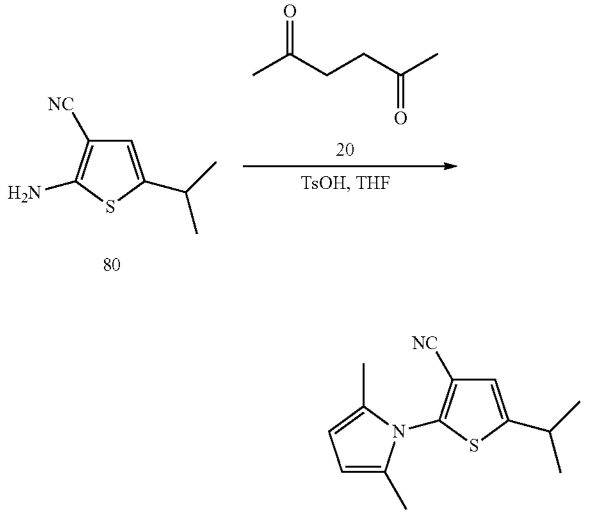

80

81

Compound 80 (2-amino-5-isopropylthiophene-3-carbonitrile) (250 mg, 1.506 mmol, 1.0 eq) was dissolved in tetrahydrofuran (10 mL). Compound 20 (2,5-hexanedione) (257 mg, 2.259 mmol, 1.5 eq), 3 A molecular sieve (500 mg) and p-toluenesulfonic acid hydrate (52 mg, 0.211 mmol, 0.2 eq) were added thereto. The reactants were heated under reflux for 4 hours. The solid was filtered off. The filtrate was concentrated and then purified by flash column chromatography (petroleum ether/ethyl acetate=50/1), so as to obtain Compound 81 (2-(2,5-dimethyl-1H-pyrrol-1-yl)-5-isopropylthiophene-3-carbonitrile) as a colorless liquid (270 mg, yield: 73.4%). MS (ESI) m/z: 245 [M+H]$^+$. TLC:petroleum ether/ethyl acetate (50/1); Rf (Compound 80)=0.2; $R_f$(Compound 81)=0.6.

(2) Synthesis of Compound 82 (2-(3-formyl-2,5-dimethyl-1H-pyrrol-1-yl)-5-isopropylthiophene-3-carbonitrile)

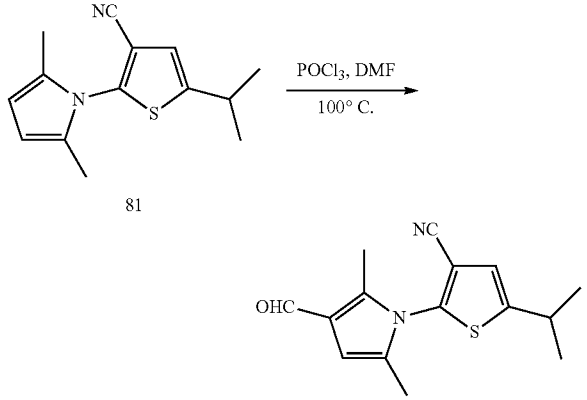

81

82

Under the protection of nitrogen gas, phosphorus oxychloride (242 mg, 1.598 mmol, 1.5 eq) was added dropwise to dimethylformamide (30 mL) at 0° C. The reactants were stirred at 0° C. for 30 minutes and then warmed to room temperature. Compound 81 (2-(2,5-dimethyl-1H-pyrrol-1-yl)-5-isopropylthiophene-3-carbonitrile) (260 mg, 1.065 mmol, 1.0 eq) in 4 mL of dimethylformamide was added into the above-mentioned mixture. The reactants were heated to 100° C., and were stirred for 1 hour in the presence of nitrogen gas. After the reaction mixture was cooled, the resulting mixture was poured into ice water and the pH of the resulting mixture was adjusted to 10 with 30% NaOH solution. The mixture was extracted with ethyl acetate and washed with saturated sodium chloride solution. Afterwards, the organic layer was separated, dried over anhydrous sodium sulfate, filtered, concentrated, and then purified by flash column chromatography (petroleum ether/ethyl acetate=10/1), so as to obtain Compound 82 (2-(3-formyl-2,5-dimethyl-1H-pyrrol-1-yl)-5-isopropylthiophene-3-carbonitrile) (200 mg, yield, 69%). MS (ESI) m/z: 273 [M+H]+. TLC:petroleum ether/ethyl acetate (5:1); $R_f$(Compound 81)=0.8; $R_f$ (Compound 82)=0.2; $^1$H NMR (400 MHz, $CDCl_3$) δ 9.88 (s, 1H), 6.96 (s, 1H), 6.41 (s, 1H), 3.18 (s, 1H), 2.38 (s, 3H), 2.09 (s, 3H), 1.38 (d, J=4.3 Hz, 6H).

(3) Synthesis of Compound AB24325 ((E)-2-(3-(2-cyano-2-(6-methoxy-3H-imidazo[4,5-c]pyridin-2-yl)vinyl)-2,5-dimethyl-1H-pyrol-1-yl)-5-isopropylthiophene-3-carbonitrile)

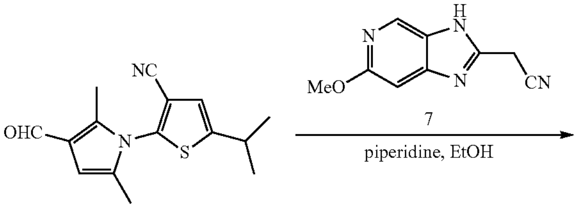

7

82

-continued

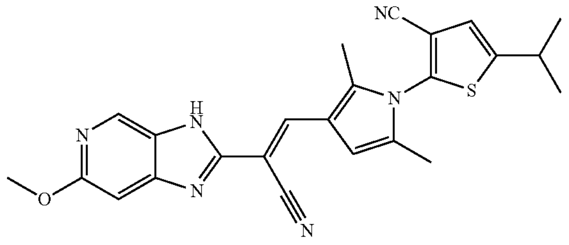

AB24325

Compound 7 (2-(6-methoxy-3H-imidazo[4,5-c]pyridin-2-yl)acetonitrile) (54 mg, 0.287 mmol, 1.0 eq) was dissolved in 1.5 mL of ethanol. Compound 82 (2-(3-formyl-2,5-dimethyl-1H-pyrrol-1-yl)-5-isopropylthiophene-3-carbonitrile) (78 mg, 0.287 mmol, 1.0 eq) and piperidine (48 mg, 0.574 mmol, 2.0 eq) were added thereto. The mixture was heated under reflux and stirred for 1 hour. After the completion of the reaction, the mixture was cooled to room temperature and filtered. The solid was collected and dried, so as to obtain Compound AB24325 ((E)-2-(3-(2-cyano-2-(6-methoxy-3H-imidazo[4,5-c]pyridin-2-yl)vinyl)-2,5-dimethyl-1H-pyrrol-1-yl)-5-isopropylthiophene-3-carbonitrile) as a yellow solid (80 mg, yield: 63%). MS (ESI) m/z: 443 [M+H]$^+$. $^1$H NMR (400 MHz, DMSO-d6) δ 12.95 (s, 1H), 8.48 (s, 1H), 8.13 (s, 1H), 7.41 (s, 1H), 6.97 (s, 1H), 6.79 (s, 1H), 3.85 (s, 3H), 3.22 (m, 1H), 2.30 (s, 3H), 2.09 (s, 3H), 1.31 (d, J=6.8 Hz, 6H).

Example 31: Synthesis of Compound (E)-2-(3-(2-cyano-2-(6-methoxy-3H-imidazo[4,5-c]pyridin-2-yl)vinyl)-2,5-dimethyl-1H-pyrol-1-yl)-5-phenylthiophene-3-carbonitrile (AB24327)

Compound AB24327 was obtained in the same manner as in Example 30 (yield: 64.3%), $^1$H NMR (400 MHz, DMSO-d6) δ 8.49 (s, 1H), 8.13 (s, JH), 8.01 (s, 1H), 7.75 (s, 2H), 7.50-7.44 (m, 3H), 7.01 (s, 1H), 6.80 (s, 1H), 3.86 (s, 3H), 2.37 (s, 3H), 2.16 (s, 3H).

Example 32: Synthesis of Compound (E)-5-benzyl-2-(3-(2-cyano-2-(6-methoxy-3H-imidazo[4,5-c]pyridin-2-yl)vinyl)-2,5-dimethyl-1H-pyrrol-1-yl)thiophene-3-carbonitrile (AB24328)

Compound AB24328 was obtained in the same manner as in Example 30 (yield: 53.8%), $^1$H NMR (400 MHz, DMSO-d6) δ 12.95 (s, 1H), 8.48 (s, 1H), 8.12 (s, 1H), 7.41 (s, 1H), 7.34 (d, J=7.2 Hz, 4H), 7.28-7.24 (m, 1H), 6.96 (s, 1H), 6.78 (s, 1H), 4.24 (s, 2H), 3.85 (s, 3H), 2.28 (s, 3H), 2.07 (s, 3H).

Example 33: Synthesis of Compound AB24351 ((E)-5-(3-(2-cyano-2-(6-methoxy-3H-imidazo[4,5-c]pyridin-2-yl)vinyl)-2,5-dimethyl-1H-pyrrol-1-yl)-2-methylthiazole-4-carboxamide)

(1) Synthetic Method of Compound 88 ((E)-ethyl 5-(3-(2-cyano-2-(6-methoxy-3H-imidazo[4,5-c]pyridin-2-yl)vinyl)-2,5-dimethyl-1H-pyrrol-1-yl)-2-methylthiazole-4-carboxylate)

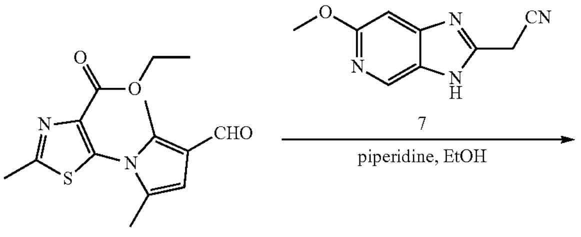

87

7

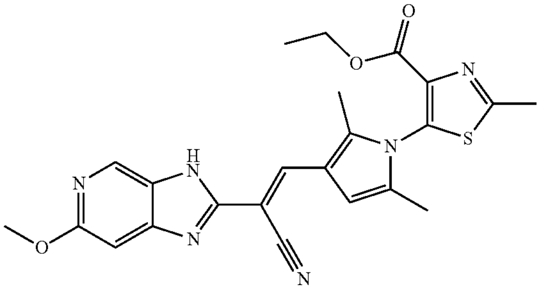

88

To a solution of Compound 87 (ethyl 5-(3-formyl-2,5-dimethyl-1H-pyrrol-1-yl)-2-methylthiazole-4-carboxylate) (160 mg, 0.548 mmol, 1 eq) in 2 mL of ethanol, Compound 7 (2-(6-methoxy-3H-imidazo[4,5-c]pyridin-2-yl)acetonitrile) (103 ng, 0.548 mmol, 1 eq) and piperidine (46 mg, 0.548 mmol, 1 eq) were added. The mixture was heated under reflux and stirred for 2 hours. After the completion of the reaction, the mixture was cooled to room temperature and filtered. The solid was collected and then dried, so as to obtain Compound 88 ((E)-ethyl 5-(3-(2-cyano-2-(6-methoxy-3H-imidazo[4,5-c]pyridin-2-yl)vinyl)-2,5-dimethyl-1H-pyrrol-1-yl)-2-methylthiazole-4-carboxylate) as a yellow solid (130 mg, yield: 51.3%). MS (ESI) m/z: 463 [M+H$^+$].

(2) Preparation Method of Compound AB24351 ((E)-5-(3-(2-cyano-2-(6-methoxy-3H-imidazo[4,5-c]pyridin-2-yl)vinyl)-2,5-dimethyl-1H-pyrrol-1-yl)-2-methylthiazole-4-carboxamide)

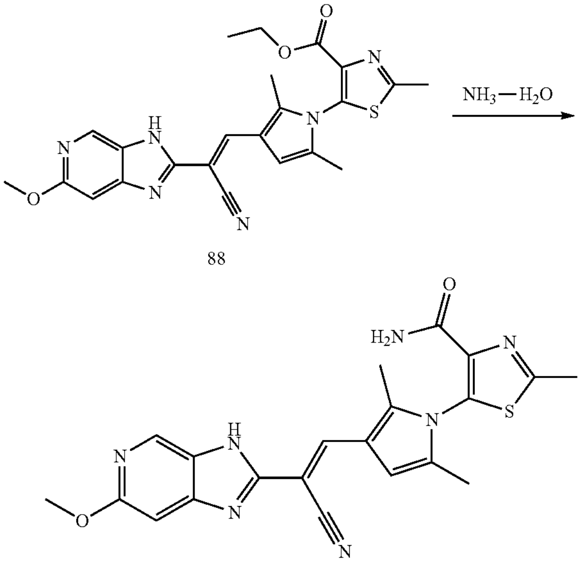

88

AB24351

Compound 88 ((E)-ethyl 5-(3-(2-cyano-2-(6-methoxy-3H-imidazo[4,5-c]pyridin-2-yl)vinyl)-2,5-dimethyl-H-pyrol-1-yl)-2-methylthiazol-4-carboxylate) (50 mg, 0.108 nmol, 1.0 eq) was dissolved in $NH_3$-MeOH (2 mL), and the mixture was stirred at 80° C. for 16 hours. The reactants were cooled to room temperature and concentrated. The residue was purified by preparative high-pressure liquid chromatography so as to obtain Compound AB24351 ((E)-5-(3-(2-cyano-2-(6-methoxy-3H-imidazo[4,5-c]pyridin-2-yl)vinyl)-2,5-dimethyl-1H-pyrrol-1-yl)-2-methylthiazole-4-carboxamide) as a yellow solid (61 mg, yield: 85.9%). MS (ESI) m/z: 434 [M+H$^+$]. $^1$H NMR (400 MHz, DMSO-$d_6$) δ 8.46 (s, 1H), 8.12 (s, 1H), 7.82 (s, 1H), 7.64 (s, 1H), 6.88 (s, 1H), 6.78 (s, 1H), 3.85 (s, 3H), 2.72 (s, 3H), 2.23 (s, 3H), 2.01 (s, 3H).

Example 34: Synthesis of Compound AB24347 ((E)-2-(3-(1-cyano-1-(6-methoxy-3H-imidazo[4,5-c]pyridin-2-yl)prop-1-en-2-yl)-2,5-dimethyl-1H-pyrrol-1-yl)-5-methylthiophene-3-carbonitrile)

(1) Synthetic Method of Compound 90 (2-(3-acetyl-2,5-dimethyl-1H-pyrrol-1-yl)-5-methylthiophene-3-carbonitrile)

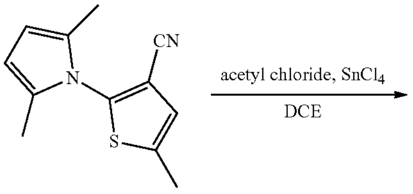

89

-continued

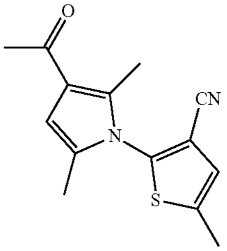

90

At 0° C., acetyl chloride (412 mg, 5.278 mmol, 1.2 eq) was dissolved in anhydrous dichloroethylene DCE (20 mL), and tin tetrachloride (1.14 g, 4.398 mmol, 1 eq) was added carefully. The mixture was stirred at 0° C. for 10 minutes, and then a solution of Compound 89 (2-(2,5-dimethyl-1H-pyrrol-1-yl)-5-methylthiophene-3-carbonitrile) (950 mg, 4.398 mmol, 1 eq) in 20 mL of dichloroethylene was added to the above-mentioned mixture. The mixture was stirred at 0° C. for 30 minutes and then warmed to room temperature for 3 hours. The reaction mixture was cooled with 50 mL of water and then extracted three times with dichloromethane (50 mL for each extraction). Thereafter, the organic layers were dried over anhydrous sodium sulfate and concentrated. The residue was purified by flash column chromatography (petroleum ether/ethyl acetate=5:1 to 2:1), so as to obtain Compound 90 (2-(3-acetyl-2,5-dimethyl-1H-pyrrol-1-yl)-5-methylthiophene-3-carbonitrile) as a yellow solid (888 mg, yield: 78.3%). TLC:petroleum ether/ethyl acetate (1/1); $R_f$ (Compound 89)=0.6; $R_f$(Compound 90)=0.3. $^1$H NMR (400 MHz, $CDCl_3$) δ 6.93 (s, 1M), 6.33 (s, 1H), 2.53 (s, 3H), 2.40 (s, 3H), 2.39 (s, 3H), 2.08 (s, 3H).

(2) Preparation Method of Compound AB24347 ((E)-2-(3-(1-cyano-1-(6-methoxy-3H-imidazo[4,5-c]pyridin-2-yl)prop-1-en-2-yl)-2,5-dimethyl-1H-pyrrol-1-yl)-5-methylthiophene-3-carbonitrile)

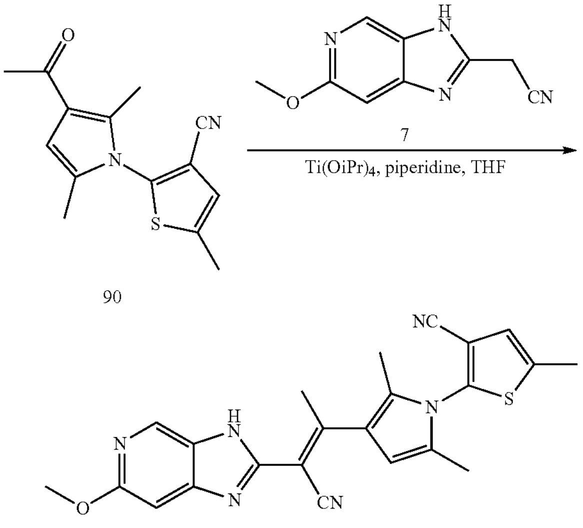

90 7 AB24347

Compound 90 (2-(3-acetyl-2,5-dimethyl-1H-pyrrol-1-yl)-5-methylthiophene-3-carbonitrile) (50 mg, 0.265 mmol, 1 eq) was dissolved in tetrahydrofuran (1 mL). Compound 7 (2-(6-methoxy-3H-imidazo[4,5-c]pyridin-2-yl)acetonitrile) (68 mg, 0.265 mmol, 1 eq), tetraisopropyl titanate (225 mg, 0.795 mmol, 3 eq) and two drops of piperidine were added thereto. The mixture was stirred at room temperature for 12 hours. The solid was filtered and washed with ethyl acetate. Afterwards, the filtrate was concentrated and purified by preparative high-pressure liquid chromatography, so as to obtain Compound AB24347 ((E)-2-(3-(1-cyano-1-(6-methoxy-3H-imidazo[4,5-c]pyridin-2-yl)prop-1-en-2-yl)-2,5-dimethyl-1H-pyrrol-1-yl)-5-methylthiophene-3-carbonitrile) as a yellow solid (30 mg, yield: 36.1%). MS (ESI) m/z: 429.14 [M+H$^+$]. $^1$H NMR (400 MHz, DMSO-$d_6$) δ 8.43 (s, 1H), 7.19 (s, 1H), 6.66 (s, 1H), 6.27 (s, 1H), 3.81 (s, 3H), 3.14 (s, 3H), 2.44 (s, 3H), 2.04 (s, 3H), 1.33 (s, 3H).

Example 35: Synthesis of Compound AB24348 ((E)-5-(3-(2-cyano-2-(6-methoxy-3H-imidazo[4,5-c]pyridin-2-yl)vinyl)-2,5-dimethyl-1H-pyrrol-1-yl)-2-methylthiazole-4-carbonitrile)

(1) Preparation Method of Compound 92 (5-(2,5-dimethyl-1H-pyrrol-1-yl)-2-methylthiazol-4-carboxamide)

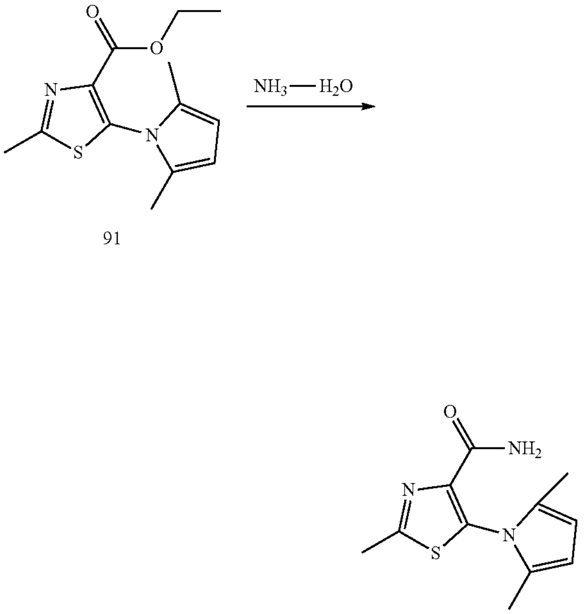

91 92

Compound 91 (ethyl 5-(2,5-dimethyl-1H-pyrrol-1-yl)-2-methylthiazole-4-carboxylate) (1.5 g, 5.68 mmol, 1.0 eq) was dissolved in aqueous ammonia $NH_3$—$H_2O$ (100 mL). The reactants were heated to 70° C. and stirred for 3 hours. After the completion of the reaction, the resulting mixture was cooled to room temperature and filtered. The solid was collected and dried, so as to obtain Compound 92 (5-(2,5-dimethyl-1H-pyrrol-1-yl)-2-methylthiazol-4-carboxamide) as a white solid (1.0 g, yield: 74.9%). MS (ESI) m/z: 236 [M+H$^+$]. TLC:petroleum ether/ethyl acetate (3/1); $R_f$(Compound 91)=0.6; $R_E$(Compound 92)=0.3.

(2) Preparation Method of Compound 93 (5-(2,5-dimethyl-1H-pyrrol-1-yl)-2-methylthiazole-4-carbonitrile)

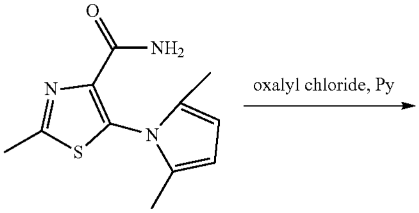

92

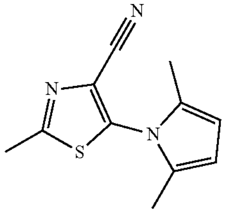

93

Compound 92 (5-(2,5-dimethyl-1H-pyrrol-1-yl)-2-methylthiazol-4-carboxamide) (500 mg, 2.10 mmol, 1.0 eq) and piperidine (198 mg, 2.50 mmol, 1.2 eq) were dissolved in acetonitrile (40 mL). Oxalyl chloride (406 mg, 3.20 mmol, 1.5 eq) was added dropwise at 0° C. The mixture was reacted at 0° C. for half an hour. After the completion of the reaction, the residue was purified by flash column chromatography (petroleum ether/ethyl acetate=3/1), so as to obtain Compound 93 (5-(2,5-dimethyl-1H-pyrrol-1-yl)-2-methylthiazole-4-carbonitrile) as a colorless oil (180 mg, yield: 38.9%). MS (ESI) m/z: 218 [M+$H_1$]. TLC:petroleum ether/ethyl acetate (2/1); $R_f$ (Compound 92)=0.5; $R_E$(Compound 93)=0.6.

(3) Preparation Method of Compound 94 (5-(3-formyl-2,5-dimethyl-JH-pyrrol-1-yl)-2-methylthiazole-4-carbonitrile)

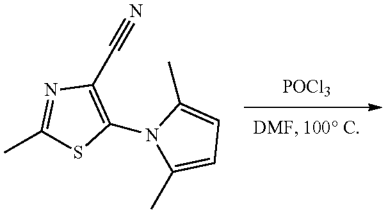

93

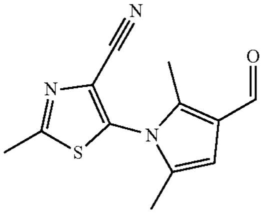

94

Dimethyl formamide (10 mL) was added dropwise to phosphorus oxychloride (105 mg, 0.69 mmol, 1.0 eq) under the conditions of nitrogen gas protection and 0° C., and then the resulting mixture was warmed to room temperature. A solution of Compound 93 (5-(2,5-dimethyl-1H-pyrrol-1-yl)-2-methylthiazole-4-carbonitrile) (150 mg, 0.69 mmol, 1.0 eq) in 5 mL of dimethylformamide was added to the above-mentioned system. Under the protection of nitrogen gas, the mixture was heated to 100° C. and stirred for 3 hours. After the reaction mixture was cooled, the mixture was poured into ice water and the pH of the resulting mixture was adjusted to 9 with 30% sodium hydroxide solution. The mixture was extracted with ethyl acetate and then washed with brine. The organic layer was dried over anhydrous sodium sulfate, filtered and concentrated. The residue was purified by flash column chromatography (petroleum ether/ethyl acetate=3/1), so as to obtain Compound 94 (5-(3-formyl-2,5-dimethyl-1H-pyrrol-1-yl)-2-methylthiazole-4-carbonitrile) as a white solid (60 mg, yield: 35.6%). MS (ESI) m/z: 246 [M+$H^+$]. TLC:petroleum ether/ethyl acetate (3:1); $R_f$ (Compound 93)=0.4; $R_f$ (Compound 94)=0.2.

(4) Synthesis of Compound AB24348 ((E)-5-(3-(2-cyano-2-(6-methoxy-3H-imidazo[4,5-c]pyridin-2-yl)vinyl)-2,5-dimethyl-1H-pyrrol-1-yl)-2-methylthiazole-4-carbonitrile)

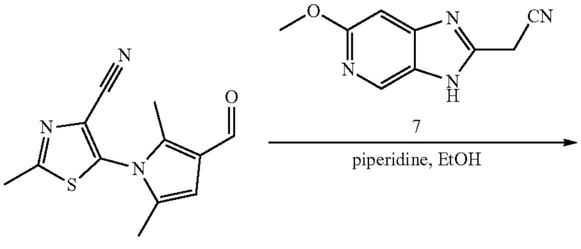

94

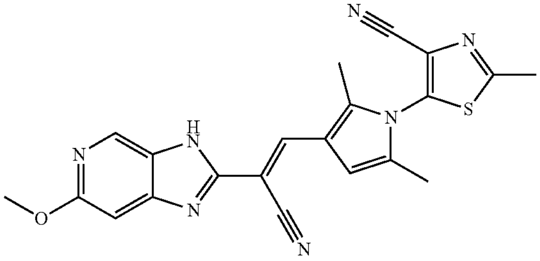

AB24348

To a system of Compound 94 (5-(3-formyl-2,5-dimethyl-1H-pyrrol-1-yl)-2-methylthiazole-4-carbonitrile) (20 mg, 0.08 mmol, 1 eq) in 4 mL of ethanol, Compound 7 (2-(6-methoxy-3H-imidazo[4,5-c]pyridin-2-yl)acetonitrile) (15 mg, 0.08 mmol, 1 eq) and piperidine (3 mg, 0.08 mmol, 1 eq) were added. The mixture was heated under reflux and stirred for 2 hours. After the completion of the reaction, the mixture was cooled to room temperature and filtered. The solid was collected, dried and filtered, so as to obtain Compound AB24348 ((E)-5-(3-(2-cyano-2-(6-methoxy-3H-imidazo[4,5-c]pyridin-2-yl)vinyl)-2,5-dimethyl-1H-pyrrol-1-yl)-2-methylthiazole-4-carbonitrile) as a yellow solid (13 mg, yield: 38.4%). MS (ESI) m/z: 416.3 $[M+H]^+$. $^1$H NMR (400

MHz, DMSO-$d_6$) δ 12.99 (s, 1H), 8.49 (s, 1H), 8.15 (s, 1H), 7.00 (s, 1H), 6.80 (s, 1H), 3.86 (s, 3H), 2.77 (s, 3H), 2.33 (s, 3H), 2.13 (s, 3H).

Example 36: Synthesis of Compound AB24355 ((E)-2-(3-(2-cyano-2-(6-(dimethylamino)-3H-imidazo[4,5-c]pyridin-2-yl)vinyl)-2,5-dimethyl-1H-pyrrol-1-yl)-5-methylthiophene-3-carbonitrile)

(1) Synthetic Method of Compound 97 (N,N-dimethyl-5-nitropyridine-2,4-diamine)

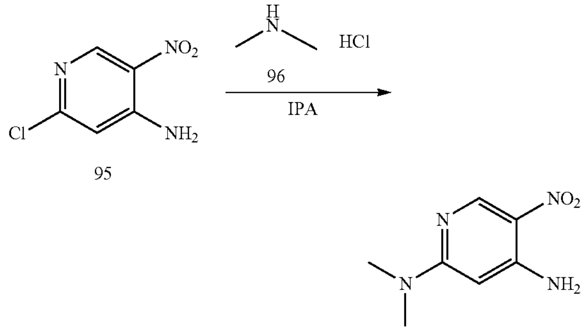

95

97

Compound 95 (2-chloro-4-amino-5-nitropyridine) (300 mg, 1.57 mmol, 1 eq) was dissolved in isopropanol (5 mL). Compound 96 (636 mg, 7.85 mmol, 5.0 eq) and triethylamine (1.1 g, 11.0 mmol, 7.0 eq) were added thereto. The mixture was stirred at 100° C. for 12 h. After the completion of the reaction, the resulting mixture was concentrated, and the residue was purified by flash column chromatography (using a system of petroleum ether and ethyl acetate (10:1) and a system of dichloromethane and ethyl acetate (10:1) successively), so as to obtain the crude Compound 97 (N,N-dimethyl-5-nitropyridine-2,4-diamine) as a brown solid (270 mg, yield: 94.5%). MS (ESI) m/z: 183.20 $[M+H]^+$. TLC:petroleum ether/ethyl acetate (1/I); $R_f$(Compound 95)=0.6; $R_f$ (Compound 97)=0.5.

(2) Preparation Method of Compound 98 (N,N-dimethylpyridine-2,4,5-triamine)

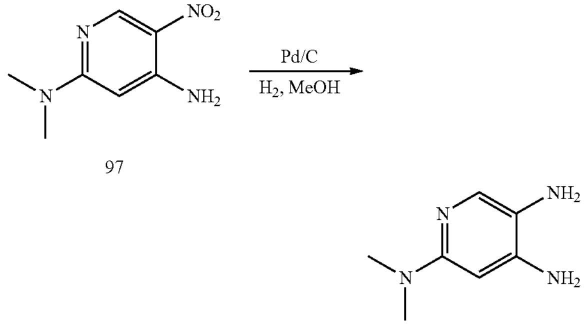

97

98

Compound 97 (N,N-dimethyl-5-nitropyridine-2,4-diamine) (270 mg, 1.48 mmol, 1 eq) was dissolved in methanol (10 mL), and palladium on carbon (50 mg, 0.2 wt %) was added thereto. The mixture was stirred at room temperature for 16 h in the presence of nitrogen gas. The solid was filtered off and the filtrate was concentrated, so as to obtain the crude Compound 98 (N,N-dimethylpyridine-2,4,5-triamine) as a brown solid (270 mg, yield: 100%). MS (ESI) m/z: 153.25 $[M+H^+]$. TLC:dichloromethane/methanol (10/1); $R_f$ (Compound 97)=0.6; $R_f$(Compound 98)=0.1.

(3) Preparation Method of Compound 99 (2-(6-(dimethylamino)-3H-imidazo[4,5-c]pyridin-2-yl) acetonitrile)

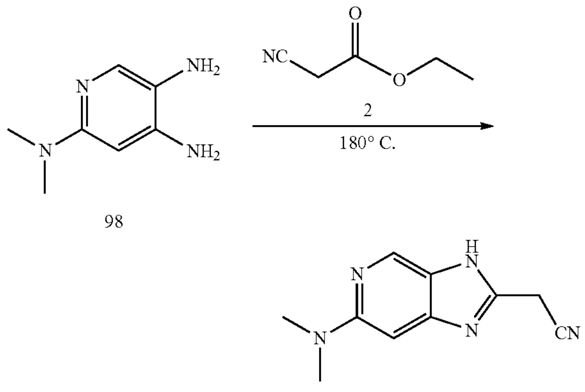

98

99

Compound 98 (N,N-dimethylpyridine-2,4,5-triamine) (130 mg, 0.855 mmol, 1.0 eq) was dissolved in dimethylformamide (2 mL), and Compound 2 (ethyl cyanoacetate) (290 mg, 2.56 mmol, 3.0 eq) was added thereto. The mixture was stirred at 150° C. for 5 h. After the completion of the reaction, the resulting mixture was concentrated to obtain the residue, which was purified by preparative high-pressure liquid chromatography to obtain Compound 99 (2-(6-(dimethylamino)-3H-imidazo[4,5-c]pyridin-2-yl)acetonitrile) as a brown solid (78 mg, yield: 45.4%). MS (ESI) m/z: 202.25 $[M+H^+]$. TLC:dichloromethane/methanol (10/1); $R_f$(Compound 98)=0.1; $R_E$ (Compound 99)=0.5.

(4) Preparation Method of Compound AB24355 ((E)-2-(3-(2-cyano-2-(6-(dimethylamino)-3H-imidazo[4,5-c]pyridin-2-yl)vinyl)-2,5-dimethyl-1H-pyrrol-1-yl)-5-methylthiophene-3-carbonitrile)

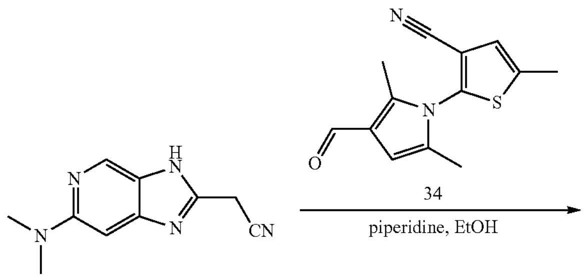

99

-continued

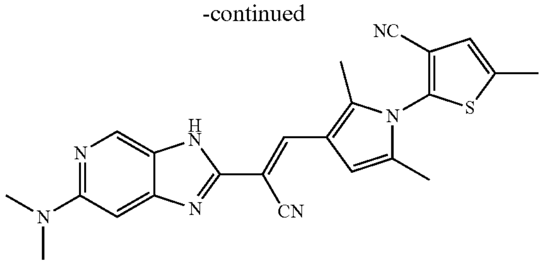

AB24355

Compound 99 (2-(6-(dimethylamino)-3H-imidazo[4,5-c]pyridin-2-yl)acetonitrile) (78 mg, 0.388 mmol, 1.0 eq) was dissolved in ethanol (1.5 mL). Compound 34 (2-(3-formyl-2,5-dimethyl-1H-pyrrol-1-yl)-5-methylthiophene-3-carbonitrile) (94.7 mg, 0.388 mmol, 1 eq) and piperidine (33 mg, 0.388 mmol, 1 eq) were added thereto. The mixture was heated under reflux and stirred for 1 h. After the completion of the reaction, the resulting mixture was concentrated and purified by preparative high-pressure liquid chromatography, so as to obtain Compound AB24355 ((E)-2-(3-(2-cyano-2-(6-(dimethylamino)-3H-imidazo [4,5-c]pyridin-2-yl)vinyl)-2,5-dimethyl-1H-pyrrol-1-yl)-5-methylthiophene-3-carbonitrile) as a yellow solid (60 mg, yield: 36.2%). MS (ESI) m/z: 428.35 [M+H$^+$]. $^1$H NMR (400 MHz, DMSO-d$_6$) δ 12.51 (s, 1H), 8.46 (s, 1H), 8.04 (s, 1H), 7.33 (s, 1H), 6.96 (s, 1H), 6.45 (s, 1H), 3.02 (s, 6H), 2.52 (s, 3H), 2.30 (s, 3H), 2.09 (s, 3H).

Example 37: Synthesis of Compound AB24352 ((E)-2-(3-(2-cyano-2-(6-methoxy-3-methyl-3H-imidazo[4,5-c]pyridin-2-yl)vinyl)-2,5-dimethyl-1H-pyrrol-1-yl)-5-methylthiophene-3-carbonitrile)

(1) Preparation Method of Compound 101 (2-(6-methoxy-3-methyl-3H-imidazo[4,5-c]pyridin-2-yl) acetonitrile)

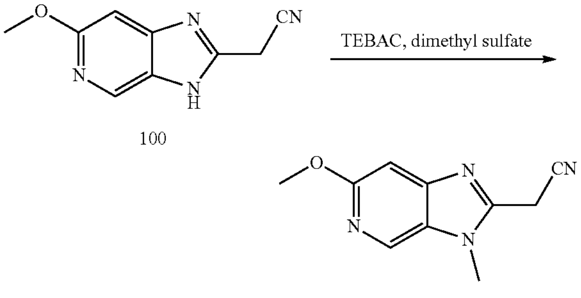

100

101

Compound 100 (2-(6-methoxy-3H-imidazo[4,5-c]pyridin-2-yl)acetonitrile) (100 mg, 0.532 mmol, 1 eq) was dissolved in a mixed solution (4 mL) of dimethylformamide and acetonitrile (3:1). Triethylbenzylammonium chloride TEBAC (9.7 mg, 0.04 nmol, 0.075 eq), potassium carbonate (73 mg, 0.532 mmol, 1.0 eq) and dimethyl sulfate (74 mg, 0.585 mmol, 1.1 eq) were added thereto. The reactants were stirred at room temperature for 16 hours. After the completion of the reaction, the resulting mixture was extracted with ethyl acetate, dried over anhydrous sodium sulfate and concentrated, so as to obtain the residue, which was purified by flash column chromatography (petroleum ether/ethyl acetate=5:1 to 1:2) to obtain Compound 101 (2-(6-methoxy-3-methyl-3H-imidazo[4,5-c]pyridin-2-yl)acetonitrile) as a black solid (80 mg, yield: 75%). TLC:petroleum ether/ethyl acetate (0/1); $R_f$(Compound 100)=0.3; $R_f$(Compound 101)=0.5. MS (ESI) m/z: 203 [M+H$^+$].

(2) Preparation Method of Compound AB24352 ((E)-2-(3-(2-cyano-2-(6-methoxy-3-methyl-3H-imidazo[4,5-c]pyridin-2-yl)vinyl)-2,5-dimethyl-1H-pyrol-1-yl)-5-methylthiophene-3-carbonitrile)

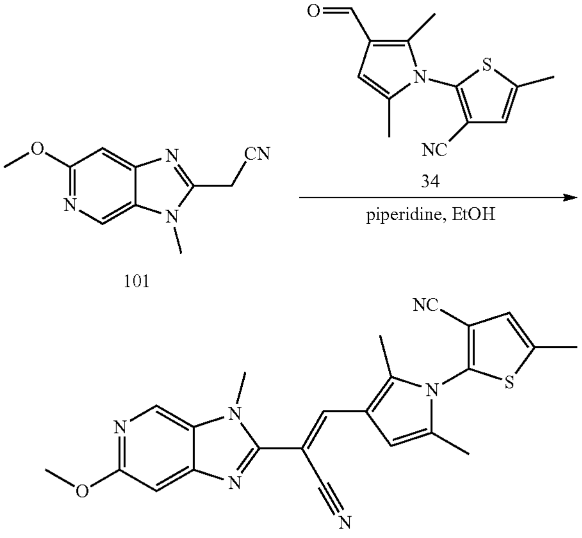

101

AB24352

Compound 101 (2-(6-methoxy-3-methyl-3H-imidazo[4,5-c]pyridin-2-yl)acetonitrile) (80 mg, 0.396 mmol, 1 eq) was dissolved in ethanol (1 mL). Compound 34 (2-(3-formyl-2,5-dimethyl-1H-pyrrol-1-yl)-5-methylthiophene-3-carbonitrile) (93 mg, 0.396 mmol, 1 eq) and two drops of piperidine were added thereto. The mixture was heated under reflux and stirred for 1 hour. After the completion of the reaction, the mixture was cooled to room temperature and filtered. The solid was collected and dried so as to obtain Compound AB24352 ((E)-2-(3-(2-cyano-2-(6-methoxy-3-methyl-3H-imidazo[4,5-c]pyridin-2-yl)vinyl)-2,5-dimethyl-1H-pyrrol-1-yl)-5-methylthiophene-3-carbonitrile) as a yellow solid (61 mg, yield: 35.9%). MS (ESI) m/z: 429.10 [M+H$^+$]. $^1$H NMR (400 MHz, DMSO-d$_6$) δ 8.53 (s, 1H), 7.98 (s, 1H), 7.34 (s, 1H), 6.99 (s, 2H), 3.87 (s, 6H), 2.52 (s, 3H), 2.25 (s, 31H), 2.10 (s, 31H).

Example 38: Synthesis of Compound (E)-2-(3-(2-(1H-benzo[d]imidazol-2-yl)-2-cyanovinyl)-2,5-dimethyl-1H-pyrrol-1-yl)-5-methylthiophene-3-carbonitrile (AB24270)

Compound AB24270 was obtained in the same manner as in Example 23 (yield: 82.3%), $^1$H NMR (400 MHz, DMSO-d6) δ 12.83 (s, 1H), 8.13 (s, 1H), 7.55 (s, 2H), 7.33 (s, 1H), 7.19 (s, 2H), 6.98 (s, 1H), 2.47 (s, 3H), 2.31 (s, 3H), 2.09 (s, 3H).

Example 39: Synthesis of Compound methyl (E)-2-(3-(2-(1H-benzo[d]imidazol-2-yl)-2-cyanovinyl)-2,5-dimethyl-1H-pyrrol-1-yl)-4,5-dimethylthiophene-3-carboxylate (AB24273)

Compound AB24273 was obtained in the same manner as in Example 23 (yield: 65.7%), $^{1}H$ NMR (400 MHz, DMSO-d6) δ 12.77 (s, 1H), 8.09 (s, 1H), 7.51 (d, J=1.6 Hz, 2H), 7.16 (s, 2H), 6.88 (s, 1H), 3.56 (s, 3H), 2.36 (s, 3H), 2.21 (d, J=11.0 Hz, 6H), 1.97 (s, 3H).

Example 40: Synthesis of Compound (E)-5-(3-(2-(1H-benzo[d]imidazol-2-yl)-2-cyanovinyl)-2,5-dimethyl-1H-pyrrol-1-yl)-3-methylthiophene-2,4-dicarbonitrile (AB24274)

Compound AB24274 was obtained in the same manner as in Example 23 (yield: 76.9%), 1H NMR (400 MHz, DMSO-d6) δ 12.87 (s, 1H), 8.14 (s, 1H), 7.55 (s, 2H), 7.21 (s, 2H), 7.01 (s, 1H), 2.48 (s, 3H), 2.35 (s, 3H), 2.15 (s, 3H).

Example 41: Synthesis of Compound (E)-2-(3-(2-cyano-2-(6-methoxy-1H-benzo[d]imidazol-2-yl]vinyl)-2,5-dimethyl-1H-pyrrol-1-yl)benzonitrile (AB24307)

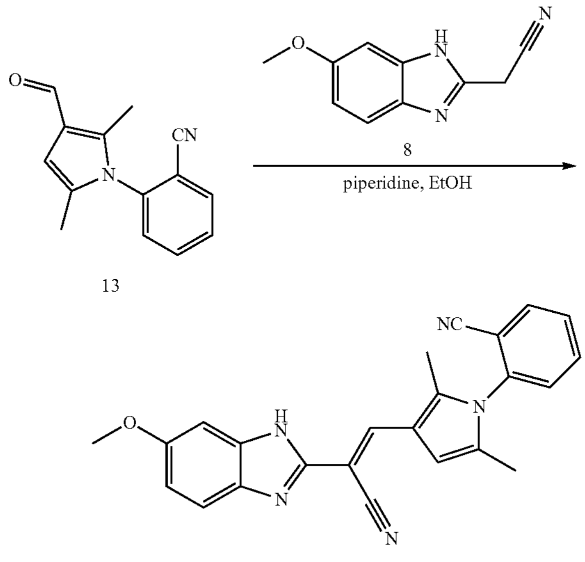

13

AB24307

To a solution of Compound 8 (2-(6-methoxy-1H-benzo[d]imidazol-2-yl)acetonitrile) (84 mg, 0.45 mmol, 1.0 eq) in 2 mL of ethanol, Compound 13 (2-(3-formyl-2,5-dimethyl-1H-pyrrol-1-yl)benzonitrile) (100 mg, 0.45 mmol, 1.0 eq) and piperidine (39 mg, 0.45 mmol, 1.0 eq) were added. The mixture was heated under reflux and stirred for 1 hour. After the completion of the above operation, the mixture was cooled to room temperature and filtered. The solid was collected and dried, so as to obtain Compound AB24307 (E)-2-(3-(2-cyano-2-(6-methoxy-1H-benzo[d]imidazol-2-yl]vinyl)-2,5-dimethyl-1H-pyrrol-1-yl)benzonitrile as a yellow solid (100 mg, yield: 47.6%). MS (ESI) m/z: 394 $[M+H]^{+}$. $^{1}H$ NMR (DMSO-d6, 400 Hz); δ 12.68 (s, 1H), 8.14 (s, 1H), 8.09 (s, 1H), 7.96 (s, 1H), 7.78 (s, 1H), 7.71 (s, 1H), 7.45 (s, 1H), 7.10-6.97 (m, 2H), 6.81 (s, 1H), 3.78 (s, 3H), 2.20 (s, 3H), 1.99 (s, 3H).

Example 42: Synthesis of Compound methyl (E)-2-(3-(2-cyano-2-(6-methoxy-1H-benzo[d]imidazol-2-yl)vinyl)-2,5-dimethyl-1H-pyrrol-1-yl)-4,5-dimethylthiophene-3-carboxylate (AB24322)

Compound AB24322 was obtained in the same manner as in Example 41 (yield: 52.0%), $^{1}H$ NMR (DMSO-d6, 400 Hz); δ 12.58 (s, 1H), 8.03 (s, 1H), 7.42 (s, 1H), 7.00 (s, 1H), 6.87 (s, 1H), 6.80 (s, 1H), 3.77 (s, 3H), 3.57 (s, 3H), 2.38 (s, 3H), 2.22 (d, J=14.8 Hz, 61H), 1.98 (s, 3H).

Example 43: Synthesis of Compound (E)-2-(1H-benzo[d]imidazol-2-yl)-3-(3,5-dimethyl-1-(3-(trifluoromethyl)phenyl)-1H-pyrazol-4-yl)acrylonitrile (AB24285)

(1) Synthesis of Compound 16 (3,5-dimethyl-1-(3-(trifluoromethyl)phenyl)-1H-pyrazole)

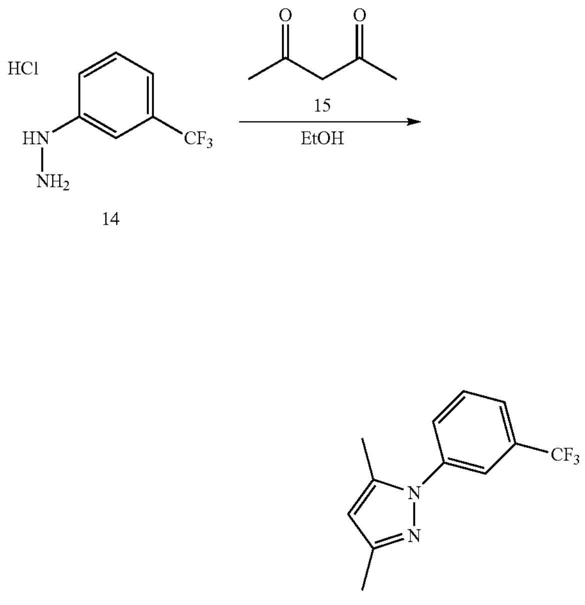

16

Compound 14 (3-(trifluoromethyl)phenylhydrazine hydrochloride) (1.0 g, 4.7 mmol, 1.0 eq) was dissolved in ethanol (15 mL), and Compound 15 (acetylacetone) (471 mg, 4.7 mmol, 1.0 eq) was added thereto. The mixture was heated under reflux for 3 hours. After the mixture was concentrated, the residue was dissolved in water (20 mL) and extracted three times with ethyl acetate (20 mL×3). The organic layers were dried, filtered and concentrated. The residue was purified by flash column chromatography (petroleum ether/ethyl acetate=20/1), so as to obtain Compound 16 (3,5-dimethyl-1-(3-(trifluoromethyl)phenyl)-1H-pyrazole) as a yellow solid powder (900 mg, yield: 79.7%). MS (ESI) m/z: 241 $[M+H]^{+}$. TLC:petroleum ether/ethyl acetate (3:1); $R_f$ (Compound 14)=0.3; $R_f$ (Compound 16)=0.6.

(2) Synthesis of Compound 17 (3,5-dimethyl-1-(3-(trifluoromethyl)phenyl)-1H-pyrazole-4-carbaldehyde)

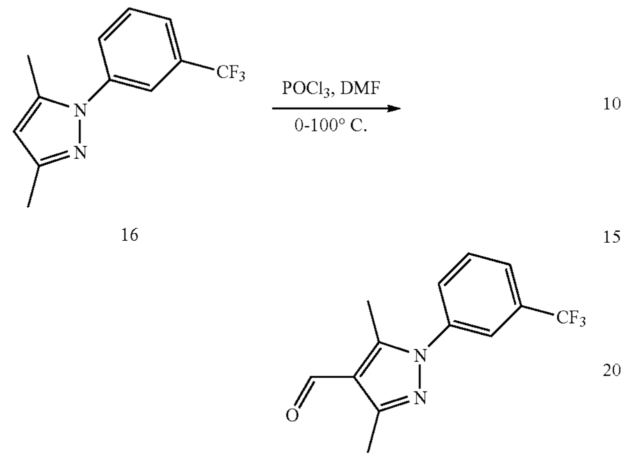

16

17

Phosphorus oxychloride (400 mg, 2.63 mmol, 0.7 eq) was added to dimethylformamide (10 mL, 0° C.) in the presence of nitrogen gas. The mixture was stirred at 0° C. for 30 minutes and then heated to room temperature. A solution of Compound 16 (3,5-dimethyl-1-(3-(trifluoromethyl)phenyl)-1H-pyrazole) (900 mg, 3.75 mmol, 1.0 eq) in 10 mL of dimethylformamide was added to the above-mentioned reaction system. The mixture was heated to 100° C., and was stirred for 1 hour in the presence of nitrogen gas. After the reaction mixture was cooled, all the reaction products were poured into ice water, and the pH of the resulting mixture was adjusted to 10 with 30% sodium hydroxide solution. The mixture was extracted with ethyl acetate and then washed with brine. The organic layer was dried over sodium sulfate, filtered and concentrated. The residue was purified by flash column chromatography (petroleum ether/ethyl acetate=50/1 to 10/1), so as to obtain Compound 17 (3,5-dimethyl-1-(3-(trifluoromethyl)phenyl)-1H-pyrazole-4-carbaldehyde) as a yellow solid powder (320 mg, yield: 31.8%). MS (ESI) m/z: 269 $[M+H]^+$. TLC:petroleum ether/ethyl acetate (3:1); $R_f$ (Compound 16)=0.6; $R_f$ (Compound 17)=0.4.

(3) Synthesis of Compound AB24285 ((E)-2-(1H-benzo[d]imidazol-2-yl)-3-(3,5-dimethyl-1-(3-(trifluoromethyl)phenyl)-1H-pyrazol-4-yl)acrylonitrile)

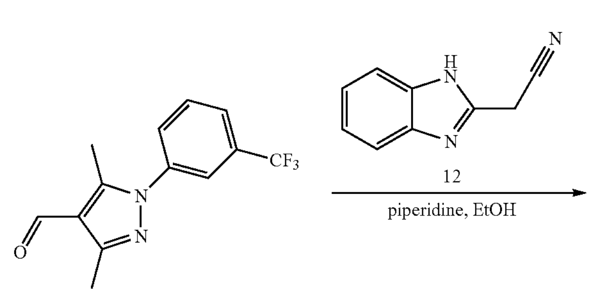

17

12

-continued

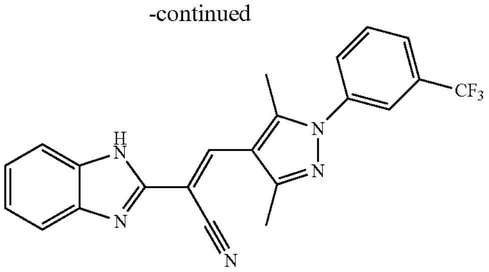

AB24285

Compound 17 (3,5-dimethyl-1-(3-(trifluoromethyl)phenyl)-1H-pyrazole-4-carbaldehyde) (100 mg, 0.37 mmol, 1.0 eq) was dissolved in ethanol (2.0 mL). Compound 12 (2-cyano methylbenzimidazole) (59 mg, 0.37 mmol, 1.0 eq) and piperidine (32 mg, 0.371 nmol, 1.0 eq) were added thereto. The mixture was heated under reflux and stirred for 1 hour. After the completion of the reaction, the resulting mixture was cooled to room temperature, filtered and concentrated. The solid was collected and dried so as to obtain AB24285 ((E)-2-(1H-benzo[d]imidazol-2-yl)-3-(3,5-dimethyl-1-(3-(trifluoromethyl)phenyl)-1H-pyrazol-4-yl)acrylonitrile) as a yellow solid powder (40 mg, yield: 26.3%). MS (ESI) m/z: 408 [M+H]+. $^1$H NMR (400 MHz, DMSO) δ 8.11 (s, 1H), 7.80 (s, 3H), 7.75-7.61 (m, 5H), 7.55-7.40 (m, 4H), 7.22 (s, 4H), 2.37 (s, 6H), 2.01 (s, 1H), 1.80 (s, 1H).

Example 44: Synthesis of Compound (E)-2-(1H-benzo[d]imidazol-2-yl)-3-(3,5-dimethyl-1-phenyl-1H-pyrazol-4-yl)acrylonitrile (AB24284)

AB24284 was obtained in the same manner as in Example 43 (yield: 50%), $^1$H NMR (400 MHz, CDCl3) δ 9.59 (s, 1H), 8.45 (s, 1H), 7.78 (s, 1H), 7.58-7.39 (m, 6H), 7.32 (d, J=6.6 Hz, 2H), 2.48 (s, 6H).

Example 45: Synthesis of Compound (E)-2-(1H-benzo[d]imidazol-2-yl)-3-(3,5-dimethyl-1-(2-(trifluoromethoxy)phenyl)-1H-pyrazol-4-yl)acrylonitrile (AB24290)

AB24290 was obtained in the same manner as in Example 43 (yield: 20%), $^1$H NMR (400 MHz, dmso) δ 8.21 (s, 2H), 7.82 (s, 1H), 7.75-7.35 (m, 20H), 7.21-7.19 (m, 8H), 7.05 (s, 1H), 6.92 (s, 1H), 2.37 (s, 6H), 2.00 (s, 3H), 1.79 (s, 3H).

Example 46: Synthesis of Compound AB24331 ((E)-2-(3-(2-cyano-2-(6-(trifluoromethyl)-1H-benzo[d]imidazol-2-yl)vinyl)-2,5-dimethyl-1H-pyrrol-1-yl)-4,5-dimethylthiophene-3-carbonitrile)

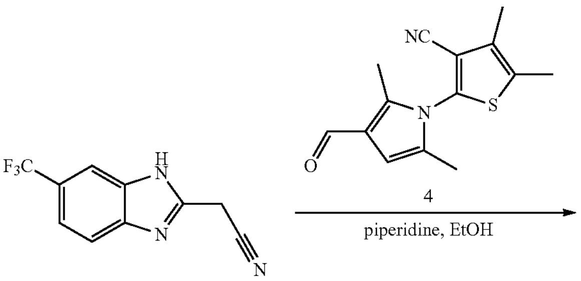

18

4

-continued

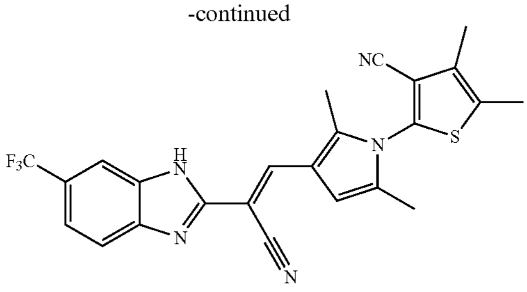

AB24331

Compound 18 (2-(6-(trifluoromethyl)-1H-benzo[d]imidazol-2-yl)acetonitrile) (50 mg, 0.222 mmol, 1 eq) was dissolved in 2 mL of ethanol. Compound 4 (2-(3-formyl-2,5-dimethyl-1H-pyrrol-1-yl)-4,5-diethylthiophene-3-carbonitrile) (68 mg, 0.222 mmol, 1 eq) and two drops of piperidine were added thereto. The mixture was heated under reflux and stirred for 2 hours. After the completion of the reaction, the mixture was cooled to room temperature and filtered. The yellow solid was collected and dried, so as to obtain AB24331 ((E)-2-(3-(2-cyano-2-(6-(trifluoromethyl)-1H-benzo[d]imidazol-2-yl)vinyl)-2,5-dimethyl-1H-pyrrol-1-yl)-4,5-dimethylthiophene-3-carbonitrile) (74 mg, yield: 71.8%). MS (ESI) m/z: 466.25 $[M+H]^+$. $^1H$ NMR (400 MHz, DMSO-$d_6$) δ 8.21 (s, 1H), 7.90 (s, 1H), 7.73-7.71 (m, 1H), 7.50 (d, J=8.4 Hz, 1H), 6.98 (s, 1H), 2.42 (s, 3H), 2.32 (s, 3H), 2.24 (s, 3H), 2.10 (s, 3H).

Example 47: Synthesis of Compound (E)-2-(3-(2-cyano-2-(6-(trifluoromethoxy)-1H-benzo[d]imidazol-2-yl)vinyl)-2,5-dimethyl-1H-pyrrol-1-yl)-4,5-dimethylthiophene-3-carbonitrile (AB24339)

AB24339 was obtained in the same manner as in Example 46 (yield: 73.7%). $^1H$ NMR (400 MHz, DMSO-d) δ 8.16 (s, 1H), 7.61-7.55 (m, 2H), 7.18 (d, J=7.6 Hz, 1H), 6.97 (s, 1H), 2.42 (s, 3H), 2.28 (d, J=25.2 Hz, 6H), 2.10 (s, 3H).

Example 48: Synthesis of Compound AB24343 ((Z)-2-(3-(2-cyano-2-(5-methoxy-1H-indol-2-yl)vinyl)-2,5-dimethyl-1H-pyrrol-1-yl)-5-methylthiophene-3-carbonitrile)

(1) Synthesis of Compound 21 ((5-methoxy-1H-indol-2-yl)methanol)

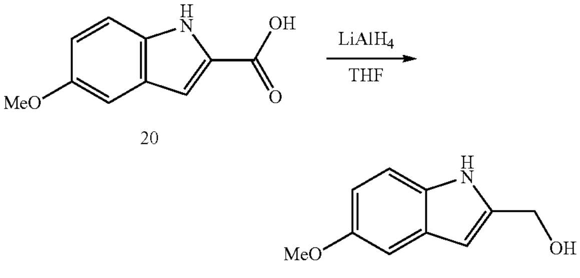

20

21

Compound 20 (5-methoxyindole-2-carboxylic acid) (2 g, 10.5 mmol, 1 eq) was dissolved in anhydrous tetrahydrofuran THF (20 mL). Lithium aluminum hydride (0.438 g, 11.05 mmol, 1.05 eq) was slowly added at 0° C. The mixture was stirred at room temperature for 5 hours. The reaction mixture was cooled to 0° C., 5 mL of NaOH solution was added thereto, and the resulting mixture was stirred at 25° C. for 5 min. The mixture was extracted with ethyl acetate, dried over anhydrous sodium sulfate and concentrated. The residue was purified by flash column chromatography (petroleum ether/ethyl acetate=5:1 to 2:1), so as to obtain Compound 21 ((5-methoxy-1H-indol-2-yl)methanol) (956 mg, yield: 51.4%). TLC:petroleum ether/ethyl acetate (1/1); $R_f$ (Compound 20)=0.3; $R_f$ (Compound 21)=0.6; $^1H$ NMR (400 MHz, $CDCl_3$) δ 8.26 (s, 1H), 7.30-7.16 (m, 1H), 7.03 (s, 1H), 6.84 (d, J=8.9 Hz, 1H), 6.33 (s, 1H), 4.79 (s, 2H), 3.84 (s, 3H).

(2) Synthesis of Compound 22 (methyl (5-methoxy-1H-indol-2-yl)benzoate)

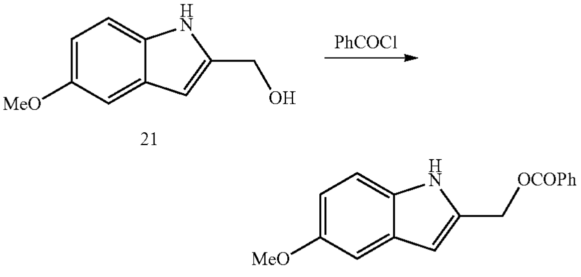

21

22

Compound 21 ((5-methoxy-1H-indol-2-yl)methanol) (356 mg, 2.03 mmol, 1.0 eq) and triethylamine TEA (410 mg, 4.06 mmol, 2 eq) were dissolved in tetrahydrofuran (5 mL), and benzoyl chloride (430 g, 3.05 mmol, 1.5 eq) was added thereto. The mixture was stirred and reacted at room temperature for 10 minutes. Afterwards, the reaction was quenched with sodium bicarbonate hydrate, and the resulting mixture was extracted with ethyl acetate. The organic layer was washed with brine, dried over anhydrous sodium sulfate and filtered. The filtrate was concentrated to obtain Compound 22 (methyl (5-methoxy-1H-indol-2-yl)benzoate) (478 mg, yield: 83.7%), which was directly used in the next step without the need of further purification. TLC:petroleum ether/ethyl acetate (3/1); $R_f$ (Compound 21)=0.2; $R_f$ (Compound 22)=0.7; $^1H$ NMR (400 MHz, DMSO-d6) δ 11.11 (s, 1H), 7.95 (d, J=7.7 Hz, 2H), 7.61 (t, J=7.6 Hz, 1H), 7.48 (t, J=7.7 Hz, 2H), 7.22 (d, J=8.8 Hz, 1H), 6.97 (s, 1H), 6.70 (d, J=8.7 Hz, 1H), 6.42 (s, 1H), 5.38 (s, 2H), 3.68 (s, 3H).

(3) Synthesis of Compound 23 (2-(5-methoxy-1H-indol-2-yl)acetonitrile)

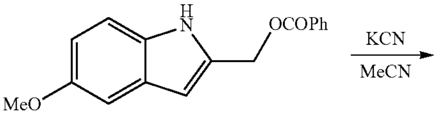

22

-continued

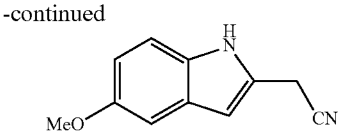

23

Compound 22 (methyl (5-methoxy-1H-indol-2-yl)benzoate) (250 mg, 0.89 mmol, 1.0 eq) was dissolved in acetonitrile (3 mL), and potassium cyanide (116 mg, 1.78 mmol, 2.0 eq) was added thereto. The mixture was stirred at 80° C. for 24 hours. After the completion of the reaction, the resulting mixture was cooled to room temperature, and saturated aqueous sodium bicarbonate solution was added thereto. The mixture was extracted with ethyl acetate, and the organic layer was dried over anhydrous sodium sulfate and concentrated. The residue was purified by flash column chromatography (petroleum ether/ethyl acetate=3:1 to 1:1), so as to obtain Compound 23 (2-(5-methoxy-1H-indol-2-yl) acetonitrile) (30 mg, yield: 18.1%). TLC:petroleum ether/ethyl acetate (3/1); $R_f$ (Compound 22)=0.25; $R_f$ (Compound 23)=0.5; $^1$H NMR (400 MHz, $CDCl_3$) δ 8.12 (s, 1H), 7.41-7.12 (m, 1H), 7.03 (s, 1H), 6.87 (d, J=8.5 Hz, 1H), 6.41 (s, 1H), 3.90 (s, 2H), 3.85 (s, 3H).

(4) Synthesis of Compound AB24343 ((Z)-2-(3-(2-cyano-2-(5-methoxy-1H-indol-2-yl)vinyl)-2,5-dimethyl-1H-pyrrol-1-yl)-5-methylthiophene-3-carbonitrile)

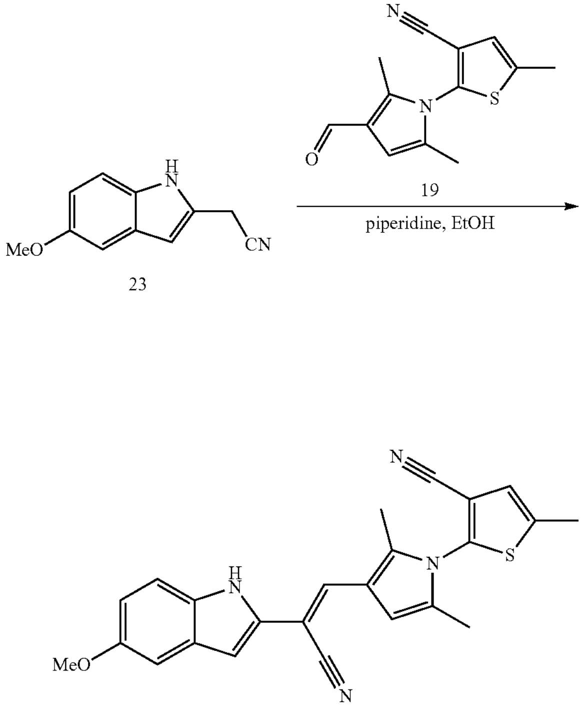

AB24343

Compound 23 (2-(5-methoxy-1H-indol-2-yl)acetonitrile) (30 mg, 0.16 mmol, 1 eq) was dissolved in ethanol (1 mL). Compound 19 (2-(3-formyl-2,5-dimethyl-1H-pyrrol-1-yl)-5-methylthiophene-3-carbonitrile) (39 mg, 0.16 mmol, 1 eq) and two drops of piperidine were added thereto. The mixture was heated under reflux and stirred for 2 hours. After the completion of the reaction, the resulting mixture was cooled to room temperature and filtered. The solid was collected and dried, so as to obtain Compound AB24343 ((Z)-2-(3-(2-cyano-2-(5-methoxy-1H-indol-2-yl)vinyl)-2,5-dimethyl-1H-pyrrol-1-yl)-5-methylthiophene-3-carbonitrile) as a yellow solid (20 mg, yield: 30.3%). MS (ESI) m/z: 413.05 [M+H$^+$]. $^1$H NMR (400 MHz, DMSO-$d_6$) δ 11.41 (s, 1H), 7.68 (s, 1H), 7.29 (s, 1H), 7.21 (d, J=8.6 Hz, 1H), 6.99 (s, 1H), 6.86 (s, 1H), 6.73 (d, J=8.4 Hz, 1H), 6.49 (s, 1H), 3.70 (s, 3H), 2.49 (s, 3H), 2.24 (s, 3H), 2.06 (s, 3H).

Example 49: Synthesis of Compound (E)-2-(3-(2-cyano-2-(6-methoxy-1H-benzo[d]imidazol-2-yl]vinyl)-2,5-dimethyl-1H-pyrrol-1-yl)-4,5-dimethylfuran-3-carbonitrile (AB24202)

(1) Synthesis of Compound 3 (2-(2,5-dimethyl-1H-pyrrol-1-yl)-4,5-dimethylfuran-3-carbonitrile)

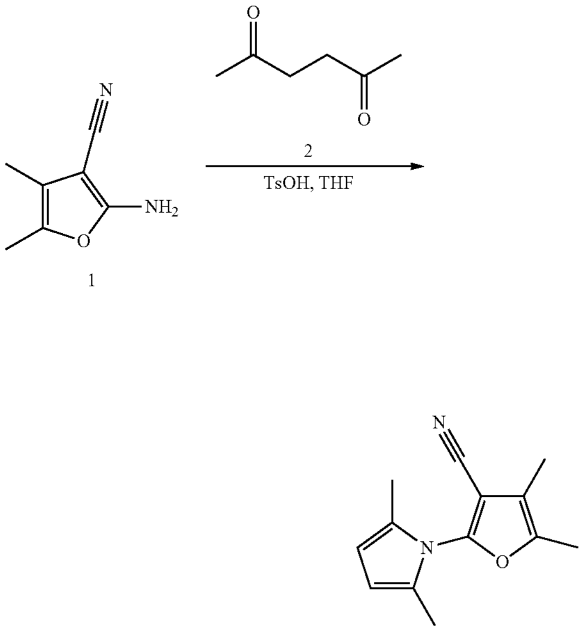

3

To a solution of Compound 1 (2-amino-4,5-dimethyl-3-furancarbonitrile) (2.5 g, 18.36 mmol, 1.0 eq) in 50 mL of tetrahydrofuran (THF), 2 (2,5-hexanedione) (3.3 g, 29.38 mmol, 1.6 eq), 3 A molecular sieve (50 g) and p-toluenesulfonic acid (TsOH—$H_2O$, 1.4 g, 7.44 mmol, 0.4 eq) were added. The mixture was heated under reflux and stirred overnight. The solid was filtered off and the filtrate was concentrated. The residue was purified by flash column chromatography (petroleum ether/ethyl acetate=100/1), so as to obtain Compound 3 (2-(2,5-dimethyl-1H-pyrrol-1-yl)-4,5-dimethylfuran-3-carbonitrile) as a white solid (2.8 g, yield: 71.2%). MS (ESI) m/z: 215.3 [M+H]$^+$. TLC:petroleum ether/ethyl acetate (10:1); $R_f$(Compound 1)=0.1; $R_f$ (Compound 3)=0.7. $^1$H NMR ($CDCl_3$, 400 Hz); δ 5.87 (s, 2H), 2.24 (s, 3H), 2.11 (s, 6H), 2.08 (s, 3H).

(2) Synthesis of Compound 4 (2-(3-formyl-2,5-dimethyl-1H-pyrrol-1-yl)-4,5-dimethylfuran-3-carbonitrile)

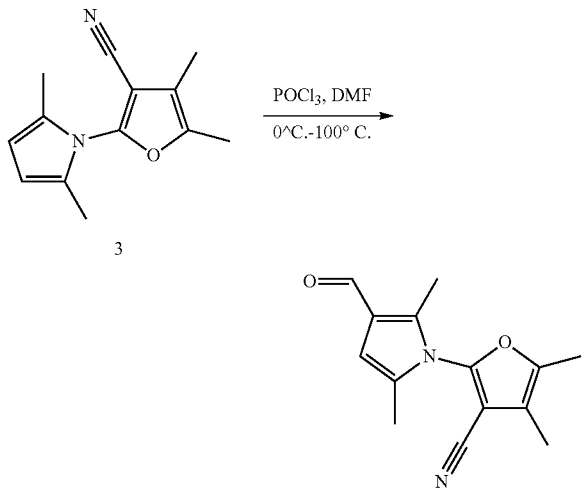

3

4

Phosphorus oxychloride ($POCl_3$, 5.3 g, 35.04 mmol, 3.0 eq) was added dropwise to 30 mL of dimethylformamide (DMF) under conditions of 0° C. and nitrogen ($N_2$) atmosphere. The mixture was stirred at 0° C. for 30 minutes and was then warmed to room temperature. A solution of Compound 3 (2-(2,5-dimethyl-1H-pyrrol-1-yl)-4,5-dimethylfuran-3-carbonitrile) (2.5 g, 11.68 mmol, 1.0 eq) in 4 mL of DMF was added thereto. The mixture was heated to 100° C. and stirred for 2 hours under $N_2$ atmosphere. After being cooled, the mixture was placed in ice water and basified with 30% NaOH aqueous solution until the pH of the mixture was 10. The mixture was extracted with ethyl acetate (EA) and washed with brine. The organic layer was dried over $Na_2SO_4$, filtered and concentrated. The residue was purified by flash column chromatography (petroleum ether/ethyl acetate=100/1), so as to obtain Compound 4 (2-(3-formyl-2,5-dimethyl-1H-pyrrol-1-yl)-4,5-dimethylfuran-3-carbonitrile) as a yellow solid (2.2 g, yield: 78.5%). MS (ESI) m/z: 243 $[M+H]^+$. TLC:petroleum ether/ethyl acetate (20:1); $R_f$ (Compound 3)=0.7; $R_f$ (Compound 4)=0.5. $^1H$ NMR ($CDCl_3$, 400 Hz); δ 9.86 (s, 1H), 6.35 (s, 1H), 2.38 (s, 3H), 2.27 (s, 3H), 2.10 (s, 6H).

(3) Synthesis of Compound 7 (N-(2-amino-4-methoxyphenyl)-2-cyanoacetamide)

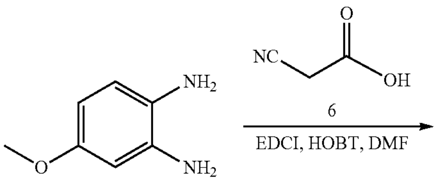

5

-continued

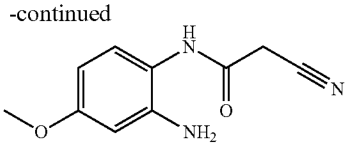

7

To a solution of Compound 5 (4-methoxy-o-phenylenediamine) (2.0 g, 14.5 mmol, 1.1 eq) in dimethylformamide (20 mL), 6 (cyanoacetic acid) (1.36 g, 15.95 mmol, 1.1 eq), 1-(3-dimethylaminopropyl)-3-ethylcarbodiimide hydrochloride EDCI (3.34 g, 17.4 mmol, 1.2 eq) and 1-hydroxybenzotriazole HOBT (1.96 g, 14.5 mmol, 1.0 eq) were added. The mixture was stirred at room temperature overnight. The mixture was diluted with water and extracted with dichloromethane. The organic layer was washed with brine, dried over sodium sulfate, filtered and concentrated. The residue was purified by flash column chromatography (dichloromethane/methanol=200/1 to 30/1), so as to obtain Compound 7 (N-(2-amino-4-methoxyphenyl)-2-cyanoacetamide) as a black solid (1.3 g, yield: 43.7%). MS (ESI) m/z: 206 $[M+H]^+$. TLC:dimethylformamide/methanol (10:1); $R_f$ (Compound 5)=0.2; $R_f$ (Compound 7)=0.4.

(4) Synthesis of C und 8 (2-(6-methoxy-1H-benzo d imidazol-2-yl)acetonitrile)

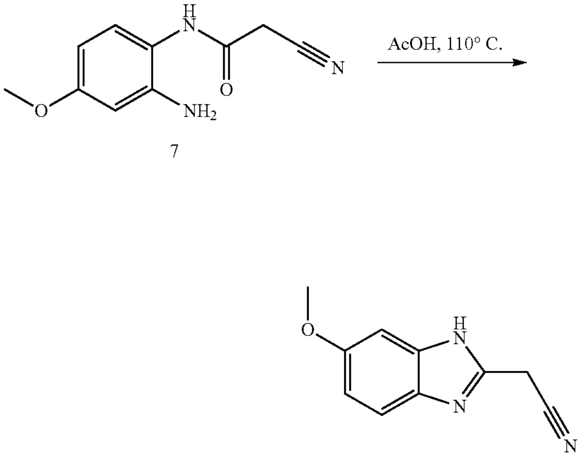

7

8

Compound 7 (N-(2-amino-4-methoxyphenyl)-2-cyanoacetamide) (490 mg, 2.38 mmol, 1.0 eq) was dissolved in acetic acid (5 mL) and stirred at 110° C. overnight. The mixture was diluted with water and extracted with dichloromethane. The organic layer was washed with brine, dried over sodium sulfate, filtered and concentrated. The residue was purified by flash column chromatography (petroleum ether/ethyl acetate=50/1 to 1/1), so as to obtain a black Compound 8 (2-(6-methoxy-1H-benzo[d]imidazol-2-yl)acetonitrile) (290 mg, yield: 64.8%). MS (ESI) m/z: 188 $[M+H]^+$. TLC:petroleum ether/ethyl acetate (10:1); $R_f$ (Compound 7)=0.7; $R_f$ (Compound 18)=0.75. $^1H$ NMR (DMSO-$d_6$, 400 Hz): δ 12.35 (s, 1H), 7.44-7.31 (m, 1H), 7.01 (s, 1H), 6.80-6.74 (m, 1H), 4.28 (s, 2H), 3.73 (s, 3H).

(5) Synthesis of Compound AB24202 ((E)-2-(3-(2-cyano-2-(6-methoxy-1H-benzo[d]imidazol-2-yl]vinyl)-2,5-dimethyl-1H-pyrrol-1-yl)-4,5-dimethyl-furan-3-carbonitrile)

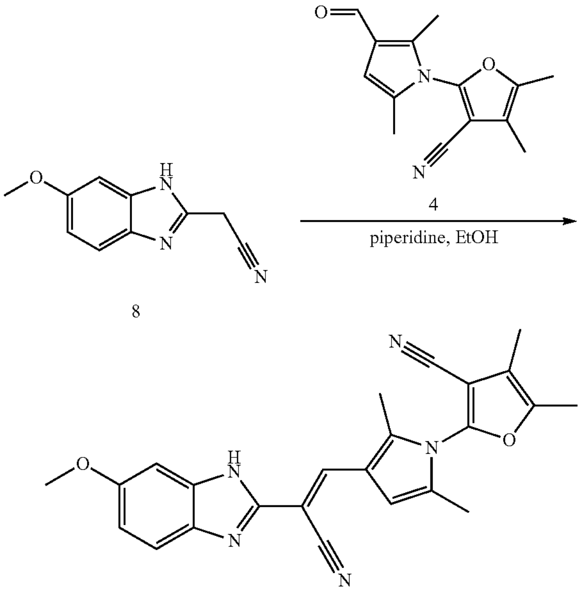

4

8

AB24202

To a solution of Compound 8 (2-(6-methoxy-1H-benzo[d]imidazol-2-yl)acetonitrile) (46 mg, 0.24 mmol, 1.0 eq) in ethanol (1 mL), Compound 4 (2-(3-formyl-2,5-dimethyl-1H-pyrrol-1-yl)-4,5-dimethylfuran-3-carbonitrile) (60 mg, 0.24 mmol, 1.0 eq) and piperidine (20 mg, 0.24 mmol, 1.0 eq) were added. The mixture was heated under reflux and stirred for 1 hour. After the completion of the above operation, the mixture was cooled to room temperature and filtered. The solid was collected and dried, so as to obtain Compound AB24202 (E)-2-(3-(2-cyano-2-(6-methoxy-1H-benzo[d]imidazol-2-yl)vinyl)-2,5-dimethyl-1H-pyrrol-1-yl)-4,5-dimethylfuran-3-carbonitrile) as a yellow solid (30 mg, yield: 30.3%). MS (ESI) m/z: 412.3 $[M+H]^+$. $^1$H NMR (DMSO-d6, 400 Hz): δ 12.72 (s, 1H), 8.04 (s, 1H), 7.45 (s, 1H), 7.01 (s, 1H), 6.94 (s, 1H), 6.82 (d, J=8.4 Hz, 1H), 3.77 (s, 3H), 2.32 (s, 3H), 2.29 (s, 3H), 2.13 (s, 3H), 2.08 (s, 3H).

Example 50: Synthesis of Compound (E)-2-(3-(2-(6-chloro-1H-benzo[d]imidazol-2-yl)-2-cyanovinyl)-2,5-dimethyl-1H-pyrrol-1-yl)-4,5-dimethylfuran-3-carbonitrile (AB24201)

Compound AB24201 was obtained in the same manner as in Example 49 (yield: 58.3%), $^1$H NMR ($CDCl_3$, 400 Hz): δ 9.49 (s, 1H), 8.32 (d, J=4.4 Hz, 1H), 7.68-7.60 (m, 1H), 7.36-7.24 (m, 1H), 6.99 (s, 1H), 2.32 (s, 3H), 2.28 (s, 3H), 2.15 (s, 3H), 2.11 (s, 3H).

Example 51: Synthesis of Compound (E)-2-(3-(2-cyano-2-(6-methyl-1H-benzo[d]imidazol-2-yl]vinyl)-2,5-dimethyl-1H-pyrrol-1-yl)-4,5-dimethyl-furan-3-carbonitrile (AB24203)

Compound AB24203 was obtained in the same manner as in Example 49 (yield: 30.6%), H NMR (DMSO-$d_6$, 400 Hz): δ 12.70 (s, 1H), 8.07 (s, 1H), 7.39-7.26 (m, 2H), 7.00-6.94 (m, 2H), 2.40 (s, 3H), 2.33 (s, 3H), 2.29 (s, 3H), 2.13 (s, 3H), 2.08 (s, 3H).

Example 52: Synthesis of Compound (E)-2-(1-cyano-2-(1-(3-cyano-4,5-dimethylfuran-2-yl)-2,5-dimethyl-1H-pyrrol-3-yl)vinyl)-N-(2-(dimethyl-amino)ethyl)-1H-benzo[d]imidazole-6-carboxamide (AB24206)

Compound AB24206 was obtained in the same manner as in Example 49 (yield: 15%), $^1$H NMR (400 MHz, DMSO) δ 9.40 (s, 1H), 8.71 (t, J=5.8 Hz, 1H), 8.21 (s, 1H), 8.13 (s, 1H), 7.78 (d, J=8.5 Hz, 1H), 7.64 (d, J=8.5 Hz, 1H), 6.99 (s, 1H), 3.63 (t, J=2.4 Hz, 2H), 3.30 (t, J=6.0 Hz, 2H), 2.87 (d, J=4.4 Hz, 6H), 2.38 (s, 3H), 2.33 (s, 3H), 2.17 (s, 3H), 2.11 (s, 3H).

Example 53: Synthesis of Compound ethyl (E)-2-(1-cyano-2-(1-(3-cyano-4,5-dimethylfuran-2-yl)-2,5-dimethyl-1H-pyrrol-3-yl)vinyl)-1H-benzo[d]imidazole-6-carboxylate (AB24208)

Compound AB24208 was obtained in the same manner as in Example 49 (yield: 35%), $^1$H NMR (400 MHz, DMSO) δ 13.22 (s, 1H), 8.14 (d, J=17.1 Hz, 2H), 7.81 (d, J=8.5 Hz, 1H), 7.73-7.50 (m, 1H), 6.95 (s, 1H), 4.29 (q, J=7.1 Hz, 2H), 2.33 (s, 3H), 2.28 (s, 3H), 2.12 (s, 3H), 2.07 (s, 3H), 1.31 (t, J=7.1 Hz, 3H).

Example 54: Synthesis of Compound (E)-2-(3-(2-(6-bromo-1H-benzo[d]imidazol-2-yl)-2-cyanovinyl)-2,5-dimethyl-1H-pyrrol-1-yl)-4,5-dimethylfuran-3-carbonitrile (AB24213)

Compound AB24213 was obtained in the same manner as in Example 49 (yield: 52.6%), $^1$H NMR (400 MHz, dmso) δ 13.03 (s, 1H), 8.13 (s, JH), 7.74 (s, 1H), 7.50 (s, 1H), 7.32 (d, J=8.4 Hz, 1H), 6.95 (s, 1H), 2.33 (s, 3H), 2.29 (s, 3H), 2.12 (s, 3H), 2.07 (s, 3H).

Example 55: Synthesis of Compound (E)-2-(3-(2-cyano-2-(6-nitro-1H-benzo[d]imidazol-2-yl)vinyl)-2,5-dimethyl-1H-pyrrol-1-yl)-4,5-dimethylfuran-3-carbonitrile (AB24217)

Compound AB24217 was obtained in the same manner as in Example 49 (yield: 56.8%), H NMR (399 MHz, DMSO-d6) δ 8.42 (s, 1H), 8.22 (s, 1H), 8.10 (d, J=8.9 Hz, 1H), 7.71 (d, J=8.9 Hz, 1H), 6.96 (s, 1H), 2.36 (s, 3H), 2.31 (s, 3H), 2.14 (s, 3H), 2.09 (s, 3H).

Example 56: Synthesis of Compound (E)-2-(3-(2-(6-amino-1H-benzo[d]imidazol-2-yl)-2-cyanovinyl)-2,5-dimethyl-1H-pyrrol-1-yl)-4,5-dimethylfiran-3-carbonitrile (AB24221)

Compound AB24221 was obtained in the same manner as in Example 49 (yield: 7.8%), $^1$H NMR (399 MHz, DMSO-d6) δ 8.16 (s, 1H), 7.49 (d, J=8.4 Hz, 1H), 7.18 (s, 1H), 7.04-6.98 (m, 2H), 2.36 (s, 3H), 2.31 (s, 3H), 2.15 (s, 3H), 2.12 (s, 3H).

Example 57: Synthesis of Compound (E)-2-(3-(2-cyano-2-(6-(dimethylamino)-1H-benzo[d]imidazol-2-yl)vinyl)-2,5-dimethyl-1H-pyrrol-1-yl)-4,5-dimethylfuran-3-carbonitrile (AB24222)

Compound AB24222 was obtained in the same manner as in Example 49 (yield: 39.3%), $^1$H NMR (400 MHz, DMSO-d6) δ 12.44 (s, 1H), 7.94 (s, 1H), 7.41 (d, J=8.9 Hz, 1H), 6.92 (s, 1H), 6.74 (d. J=8.7 Hz, JH), 6.61 (s, 1H), 2.90 (s, 6H), 2.30 (d, J=8.3 Hz, 6H), 2.10 (d, J=18.4 Hz, 6H).

Example 58: Synthesis of Compound (E)-2-(3-(2-cyano-2-(6-(2-methoxyethoxy)-1H-benzo[d]imidazol-2-yl)vinyl)-2,5-dimethyl-1H-pyrrol-1-yl)-4,5-dimethylfuran-3-carbonitrile (AB24230)

Compound AB24230 was obtained in the same manner as in Example 49 (yield: 30%), $^1$H NMR (400 MHz, DMSO-d6) δ 8.04 (s, 0H), 7.43 (s, 0H), 7.03 (s, 0H), 6.93 (s, 1H), 6.82 (d, J=8.6 Hz, 1H), 4.09 (s, 1H), 3.65 (s, 1H), 2.30 (d, J=10.7 Hz, 31H), 2.10 (d, J=19.0 Hz, 3H).

Example 59: Synthesis of Compound (E)-2-(3-(2-cyano-2-(6-(trifluoromethyl)-1H-benzo[d]imidazol-2-yl)vinyl)-2,5-dimethyl-1H-pyrrol-1-yl)-4,5-dimethylfuran-3-carbonitrile (AB24243)

Compound AB24243 was obtained in the same manner as in Example 49 (yield: 80.7%), $^1$H NMR (400 MHz, dmso) a 8.20 (s, 1H), 7.91 (s, 1H), 7.73 (d, J=8.1 Hz, 1H), 7.52 (d, J=8.0 Hz, 1H), 6.96 (s, 1H), 2.32 (d, J=20.5 Hz, 6H), 2.11 (d. J=21.6 Hz, 6H).

Example 60: Synthesis of Compound (E)-2-(3-(2-cyano-2-(6-(trifluoromethoxy)-1H-benzo[d]imidazol-2-yl)vinyl)-2,5-dimethyl-1H-pyrrol-1-yl)-4,5-dimethylfuran-3-carbonitrile (AB24255)

Compound AB24255 was obtained in the same manner as in Example 49 (yield: 57.6%). $^1$H NMR (400 MHz, dmso) a 8.16 (s, 1H), 7.63 (d, J=8.7 Hz, 1H), 7.56 (s, 1H), 7.19 (d, J=8.7 Hz, 1H), 6.95 (s, 1H), 2.34 (s, 3H), 2.29 (s, 3H), 2.13 (s, 3H), 2.08 (s, 3H).

Example 61: Synthesis of Compound ((E)-2-(3-(2-cyano-2-(6-(hydroxymethyl)-1H-benzo[d]imidazol-2-yl)vinyl)-2,5-dimethyl-1H-pyrrol-1-yl)-4,5-dimethylfuran-3-carbonitrile) (AB24225)

(1) Synthesis of Compound 10 (2-(6-(hydroxymethyl)-1H-benzo[d]imidazol-2-yl)acetonitrile)

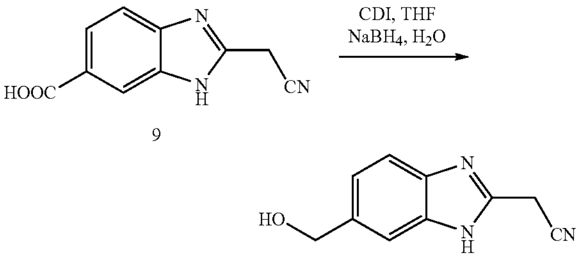

9

10

Compound 9 (2-(cyanomethyl)-1H-benzo[d]imidazole-6-carboxylic acid) (157 mg, 0.78 mmol, 1.0 eq) was dissolved in 6 mL of tetrahydrofuran (THF), carbonyldiimidazole (CDI) (152 mg, 0.94 mmol, 1.2 eq) was slowly added thereto, and the mixture was then mixed gently. Afterwards, a solution of sodium borohydride ($NaBH_4$) (88 mg, 2.34 mmol, 3.0 eq) in 5 mL of water was slowly added, and the mixed solution was stirred and reacted at room temperature for 16 hours. The mixed solution was extracted with ethyl acetate, and the organic layer was dried, filtered and concentrated. The resulting residue was purified by preparative TLC, so as to obtain Compound 10 (2-(6-(hydroxymethyl)-1H-benzo[d]imidazol-2-yl)acetonitrile) (59 mg, yield: 40.4%) as a yellow oily liquid. TLC:dichloromethane/methanol (10:1); $R_f$ (Compound 9)=0.1; $R_f$ (Compound 10)=0.3; $^1$H NMR (400 MHz, $CD_3OD$-d4) δ 7.86 (s, 1H), 7.57 (s, 1H), 7.53 (d, J=8.1 Hz, 1H), 7.28 (d, J=8.1 Hz, 1H), 7.13 (s, 1H), 4.71 (s, 2H), 3.34 (s, 2H).

(2) Synthesis of Compound AB24225 ((E)-2-(3-(2-cyano-2-(6-(hydroxymethyl)-1H-benzo[d]imidazol-2-yl)vinyl)-2,5-dimethyl-1H-pyrrol-1-yl)-4,5-dimethylfuran-3-carbonitrile)

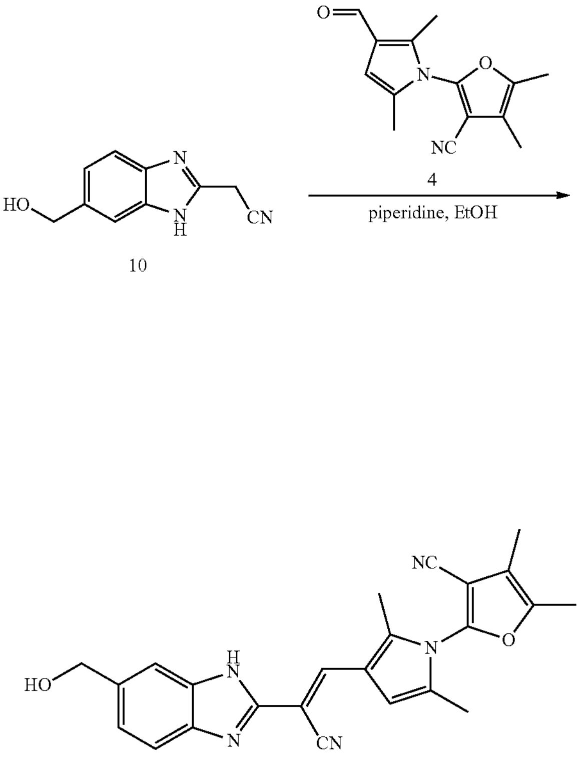

10

AB24225

To a solution of Compound 10 in 1 mL of ethanol, Compound 4 (2-(3-formyl-2,5-dimethyl-1H-pyrrol-1-yl)-4,5-dimethylfuran-3-carbonitrile) (75 mg, 0.31 mmol, 1.0 eq) and piperidine (26 mg, 0.31 mmol, 1.0 eq) were added. The mixture was heated under reflux and stirred for 1 hour. After the completion of the above operation, the mixture was concentrated and purified by preparative high performance liquid chromatography, so as to obtain AB24225 ((E)-2-(3-(2-cyano-2-(6-(hydroxymethyl)-1H-benzo[d]imidazol-2-yl)vinyl)-2,5-dimethyl-1H-pyrrol-1-yl)-4,5-dimethylfuran-3-carbonitrile) (25 mg, yield: 19.7%) as a yellow solid. MS (ESI) m/z: 412 $[M+H]^+$. $^1$H NMR (400 MHz, DMSO-d6) δ 8.16 (s, 1H), 7.55-7.51 (m, 2H), 7.22 (d, J=8.4 Hz, 1H), 6.96 (s, 1H), 4.59 (s, 2H), 2.28 (d, J=11.2 Hz, 6H), 2.07 (d, J=12 Hz, 6H).

Example 62: Synthesis of Compound ((E)-2-(3-(2-cyano-2-(5,7-dichloro-1H-benzo[d]imidazol-2-yl]vinyl)vinyl)-2,5-dimethyl-1H-pyrrol-1-yl)-4,5-dimethylfuran-3-carbonitrile)) (AB24239)

(1) Synthesis of Compound 12 (2-amino-3,5-dichloroaniline)

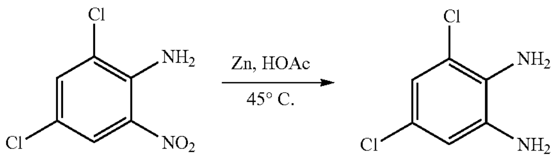

11 12

A mixture of Compound 11 (2,4-dichloro-6-nitroaniline) (2.5 g, 12.1 mmol, 1.0 eq) and zinc (6.3 g, 96.6 mmol, 8.0 eq) was dissolved in methanol/acetic acid (10/1, 30 mL), and the resulting mixture was stirred at 45° C. for 16 hours. After cooling, the solvent was removed. The residue was separated and purified by flash column chromatography (petroleum ether/ethyl acetate=100/1 to 5/1), so as to obtain Compound 12 (2-amino-3,5-dichloroaniline) as a brown solid (1.56 g, yield: 72.9%). MS (ESI) m/z: 177 $[M+H]^+$. TLC:petroleum ether:ethyl acetate=(5:1); $R_f$ (Compound 11)=0.7; $R_f$ (Compound 12)=0.4.

(2) Synthesis of Compound 13-(2-amino-4,6-dichlorophenyl)-2-cyanoacetamide)

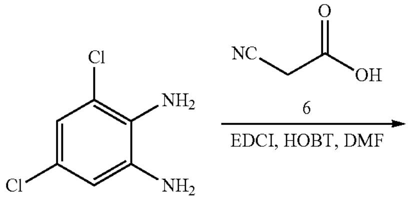

12

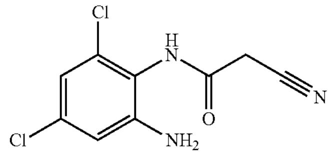
13

To a solution of Compound 12 (2-amino-3,5-dichloroaniline) (1.56 g, 8.8 mmol, 1.0 eq) in 20 mL of dimethylformamide, Compound 6 (cyanoacetic acid) (0.9 g, 10.6 mmol, 1.2 eq), 1-ethyl-(3-dimethylaminopropyl)carbodiimide hydrochloride (2.0 g, 10.6 mmol, 1.2 eq) and 1-hydroxybenzotriazole (1.2 g, 8.8 mmol, 1.0 eq) were added. The mixture was stirred at room temperature overnight. The mixture was diluted with water and then extracted with dichloromethane. The organic layer was washed with brine, dried over sodium sulfate, filtered and concentrated. The residue was purified by flash column chromatography (dichloromethane/methanol=100/1 to 50/1), so as to obtain Compound 13 (N-(2-amino-4,6-dichlorophenyl)-2-cyanoacetamide) as a black solid powder (1.0 g, yield: 46.6%). MS (ESI) m/z: 244 $[M+H]^+$. TLC:DCM/MeOH (10:1); $R_f$ (Compound 12)=0.5; $R_f$ (Compound 13)=0.7.

(3) Synthesis of Compound 14 (2-(5,7-dichloro-1H-benzo[d]imidazol-2-yl)acetonitrile)

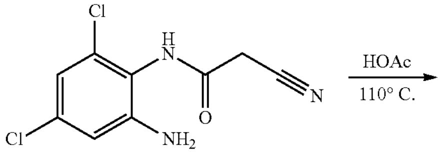

13

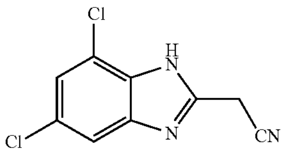
14

Compound 13 (N-(2-amino-4,6-dichlorophenyl)-2-cyanoacetamide) (1.0 g, 4.10 mmol, 1.0 eq) was dissolved in 20 mL of acetic acid, and the mixture was stirred at 110° C. overnight. The mixture was diluted with water and then extracted with dichloromethane. The organic layer was washed with brine, dried over sodium sulfate and concentrated. The residue was purified by flash column chromatography (dichloromethane/methanol=100/1 to 20/1), so as to obtain Compound 14 (2-(5,7-dichloro-1H-benzo[d]imidazol-2-yl)acetonitrile) as a yellow solid powder (520 mg, yield: 56.2%). MS (ESI) m/z: 226$[M+H]^+$. TLC:DCM/MeOH (20:1); $R_f$(Compound 13)=0.6; $R_f$ (Compound 14)=0.7.

(4) Synthesis of Compound AB24239 ((E)-2-(3-(2-cyano-2-(5,7-dichloro-1H-benzo[d]imidazol-2-yl]vinyl)vinyl)-2,5-dimethyl-1H-pyrrol-1-yl)-4,5-dimethylfuran-3-carbonitrile)

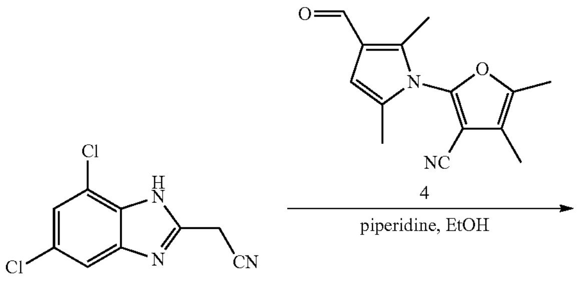

14

-continued

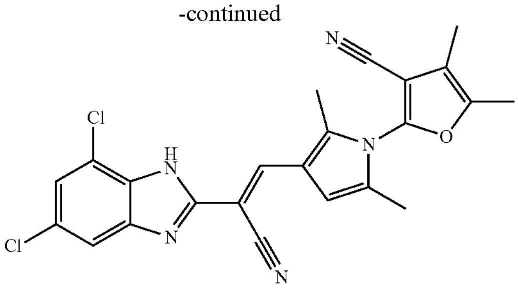

AB24239

Compound 14 (2-(5,7-dichloro-1H-benzo[d]imidazol-2-yl)acetonitrile) (56 mg, 0.25 mmol, 1.0 eq) was dissolved in ethanol (1.0 mL). Compound 4 (2-(3-formyl-2,5-dimethyl-1H-pyrrol-1-yl)-4,5-dimethylfuran-3-carbonitrile) (60 mg, 0.25 mmol, 1.0 eq) and piperidine (21 mg, 0.25 mmol, 1.0 eq) were added thereto. The mixture was heated under reflux and stirred for 1 hour. After the completion of the reaction, the resulting mixture was cooled to room temperature and filtered. The solid was collected and dried so as to obtain AB24239 ((E)-2-(3-(2-cyano-2-(5,7-dichloro-1H-benzo[d]imidazol-2-yl]vinyl)vinyl)-2,5-dimethyl-1H-pyrrol-1-yl)-4,5-dimethylfuran-3-carbonitrile) as a yellow powder (74 mg, yield: 66.7%). MS (ESI) m/z: 450 $[M+H]^+$. $^1H$ NMR (400 MHz, DMSO-d6) δ 13.33 (s, 1H), 8.20 (s, 1H), 7.57 (s, 1H), 7.38 (s, 1H), 6.97 (s, 1H), 2.36 (s, 3H), 2.31 (s, 3H), 2.14 (s, 3H), 2.09 (s, 3H).

Example 63: Synthesis of Compound (E)-2-(3-(2-cyano-2-(5-fluoro-6-methoxy-1H-benzo[d]imidazol-2-yl]vinyl)-2,5-dimethyl-1H-pyrrol-1-yl)-4,5-dimethylfuran-3-carbonitrile (AB24246)

(1) Synthesis of Compound 16 (2-cyano-N-(5-fluoro-4-methoxy-2-nitrophenyl)acetamide)

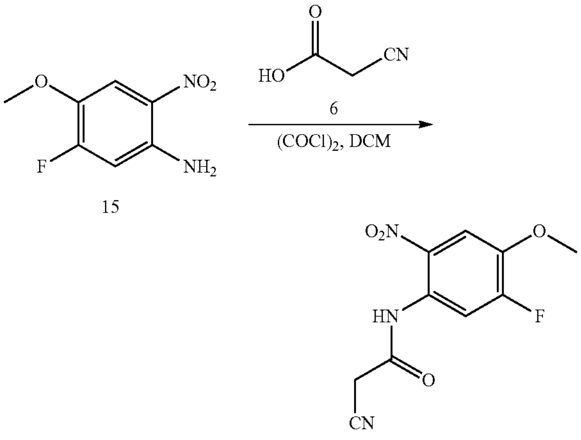

15 6 16

At 0° C. $(COCl)_2$ (1.36 g, 16.12 mmol, 1.2 eq) was added to a solution of Compound 6 (cyanoacetic acid) (1.1 g, 12.9 mmol, 1.2 eq) in 20 mL of dichloromethane (DCM). The mixture was stirred at 0° C. for 30 minutes, and then Compound 15 (5-fluoro-4-methoxy-2-nitroaniline) (2.0 g, 10.75 mmol, 1.0 eq) was added thereto. At room temperature, the mixture was stirred for 2 hours, and then the mixture was diluted with water and extracted with dichloromethane. The organic layer was washed with brine, dried over sodium sulfate, filtered and concentrated. The residue was purified by flash column chromatography (dichloromethane/methanol=200/1 to 30/1), so as to obtain Compound 16 (2-cyano-N-(5-fluoro-4-methoxy-2-nitrophenyl) acetamide) as a yellow solid (1.3 g, yield: 47.7%). MS (ESI) m/z: 254 $[M+H]^+$. TLC:PE/EA (5:1); $R_f$ (Compound 15)=0.6; $R_f$(Compound 16)=0.4.

(2) Synthesis of Compound 17 (2-(5-fluoro-6-methoxy-1H-benzo[d]imidazol-2-yl)

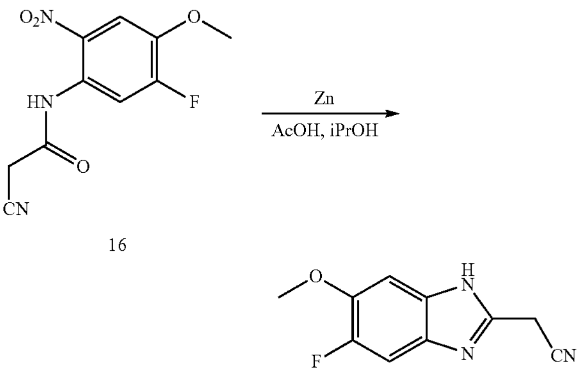

16 17

To a solution of Compound 16 (2-cyano-N-(5-fluoro-4-methoxy-2-nitrophenyl)acetamide) (500 mg, 1.97 mmol, 1.0 eq) in 5 mL of isopropanol (iPrOH), zinc (1.0 g, 15.76 mmol, 8 eq) and acetic acid (5 mL) were added, and the mixture was stirred at 110° C. overnight. The mixed solution was diluted with water and extracted with dichloromethane. The organic layer was washed with brine, dried over sodium sulfate, filtered and concentrated. The residue was purified by flash column chromatography (dichloromethane/methanol=50/1 to 1/1), so as to obtain Compound 17 (2-(5-fluoro-6-methoxy-1H-benzo[d]-imidazol-2-yl)acetonitrile) as a grey solid (100 mg, yield: 24.5%). MS (ESI) m/z: 206$[M+H]^+$. TLC:DCM/MeOH=50/1; $R_f$ (Compound 16)=0.7; $R_f$ (Compound 17)=0.3. $^1H$ NMR (DMSO-d, 400 Hz): δ 12.35 (s, 1H), 7.44-7.31 (m, 1H), 7.01 (s, 1H), 6.80-6.74 (m, 1H), 4.28 (s, 2H), 3.73 (s, 3H).

(3) Synthesis of Compound AB24246 ((E)-2-(3-(2-cyano-2-(5-fluoro-6-methoxy-1H-benzo[d]imidazol-2-yl]vinyl)-2,5-dimethyl-1H-pyrrol-1-yl)-4,5-dimethylfuran-3-carbonitrile)

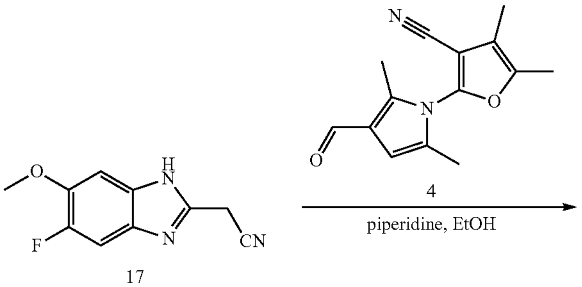

17 4

-continued

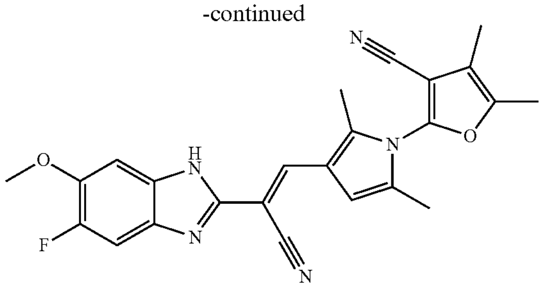

AB24246

To a solution of Compound 17 (2-(5-fluoro-6-methoxy-1H-benzo[d]-imidazol-2-yl)acetonitrile) (50 ng, 0.24 mmol, 1.0 eq) in 1 mL of ethanol, Compound 4 (2-(3-formyl-2,5-dimethyl-1H-pyrrol-1-yl)-4,4-dimethylfuran-3-carbonitrile) (60 mg, 0.24 mmol, 1.0 eq) and piperidine (20 mg, 0.24 mmol, 1.0 eq) were added. The mixture was heated under reflux and stirred for 1 h. After the completion of the above operation, the mixture was cooled to room temperature and filtered. The solid was collected and dried, so as to obtain Compound AB24246 ((E)-2-(3-(2-cyano-2-(5-fluor-6-methoxy-1H-benzo[d]-imidazol-2-yl)vinyl)-2,5-dimethyl-1H-pyrrol-1-yl)-4,5-dimethylfuran-3-carbonitrile) as a yellow solid (85 mg, yield: 81%). MS (ESI) m/z: 412.3 $[M+H]^+$. $^1H$ NMR (399 MHz, DMSO-d6) δ 8.06 (s, 1H), 7.42 (d, J=11.2 Hz, 0H), 7.22 (s, 1H), 6.94 (s, 0H), 3.86 (s, 2H), 2.32 (d, J=10.2 Hz, 3H), 2.11 (d, J=18.9 Hz, 3H).

Example 64: Synthesis of Compound (E)-2-(3-(2-(5-bromo-6-methoxy-1H-benzo[d]imidazol-2-yl]-2-cyanovinyl)-2,5-dimethyl-1H-pyrrol-1-yl)-4,5-dimethylfuran-3-carbonitrile (AB24266)

Compound AB24266 was obtained in the same manner as in Example 63 (yield: 82%), $^1H$ NMR (399 MHz, DMSO-d6) δ 8.08 (s, 1H), 7.76 (s, 1H), 7.18 (s, 1H), 6.94 (s, 1H), 3.86 (s, 3H), 2.31 (d, J=12.0 Hz, 6H), 2.11 (d. J=18.9 Hz, 6H).

Example 65: Synthesis of Compound (E)-2-(3-(2-(1H-benzo[d]imidazol-2-yl)-2-cyanovinyl)-2,5-dimethyl-1H-pyrrol-1-yl)-5-phenylfuran-3-carbonitrile (AB24283)

Compound AB24283 was obtained in the same manner as in Example 63 (yield: 63.5%), $^1H$ NMR (DMSO-d6, 400 Hz): δ 12.91 (s, 1H), 8.16 (s, 1H), 7.80 (d, J=7.6 Hz, 2H), 7.72 (s, 1H), 7.53-7.44 (m, 5H), 7.20 (s, 2H), 7.03 (s, 1H), 2.44 (s, 3H), 2.23 (s, 3H).

Example 66: Synthesis of Compound (E)-2-(3-(2-cyano-2-(5,6-dichloro-1H-benzo[d]imidazol-2-yl)vinyl)-2,5-dimethyl-1H-pyrrol-1-yl)-4,5-dimethylfuran-3-carbonitrile (AB24214)

(1) Synthesis of Compound 19 (N-(2-amino-4,5-dichlorophenyl)-2-cyanoacetamide)

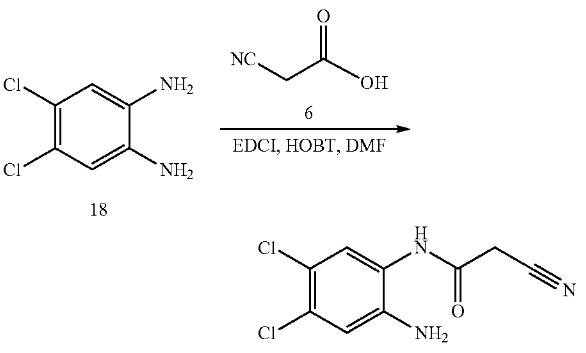

18

19

Compound 18 (4,5-dichloro-1,2-phenylenediamine) (2.0 g, 11.3 mmol, 1.0 eq) was dissolved in dimethylformamide (20 mL). Compound 6 (cyanoacetic acid) (1.2 g, 13.6 mmol, 1.2 eq), 1-(3-dimethylaminopropyl)-3-ethylcarbodiimide hydrochloride (2.61 g, 13.6 mmol, 1.2 eq) and 1-hydroxybenzotriazole (1.53 g, 11.3 mmol, 1.0 eq) were added thereto. The mixture was stirred at room temperature overnight, diluted with water, and then extracted with dichloromethane. The organic layer was washed with brine, dried over sodium sulfate, filtered and concentrated. The residue was purified by flash column chromatography (dichloromethane/methanol=100/1 to 30/1), so as to obtain Compound 19 (N-(2-amino-4,5-dichlorophenyl)-2-cyanoacetamide) as a black solid powder (470 mg, yield: 17.2%). TLC:DCM/MeOH (10:1); $R_f$(Compound 18)=0.4; $R_f$(Compound 19)=0.5.

(2) Synthesis of Compound 20 (2-(5,6-dichloro-1H-benzo[d]imidazol-2-yl)acetonitrile)

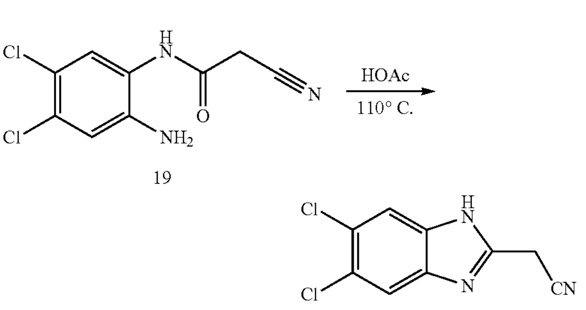

19

20

Compound 19 (N-(2-amino-4,5-dichlorophenyl)-2-cyanoacetamide) (470 mg, 1.9 mmol, 1.0 eq) was dissolved in acetic acid (10 mL), and the mixture was heated to 110° C. and stirred overnight. The mixture was diluted with water and then extracted with dichloromethane. The organic layer was washed with brine, dried over sodium sulfate, filtered and concentrated. The residue was purified by flash column chromatography (petroleum ether/ethyl acetate=100/1 to 20/1), so as to obtain Compound 20 (2-(5,6-dichloro-1H-benzo[d]imidazol-2-yl)acetonitrile) as a black powder (300 mg, yield: 22.4%). TLC:EA; $R_f$ (Compound 19)=0.7; $R_f$ (Compound 20)=0.75.

(3) Synthesis of Compound AB24214 ((E)-2-(3-(2-cyano-2-(5,6-dichloro-1H-benzo[d]imidazol-2-yl) vinyl)-2,5-dimethyl-1H-pyrrol-1-yl)-4,5-dimethyl-furan-3-carbonitrile)

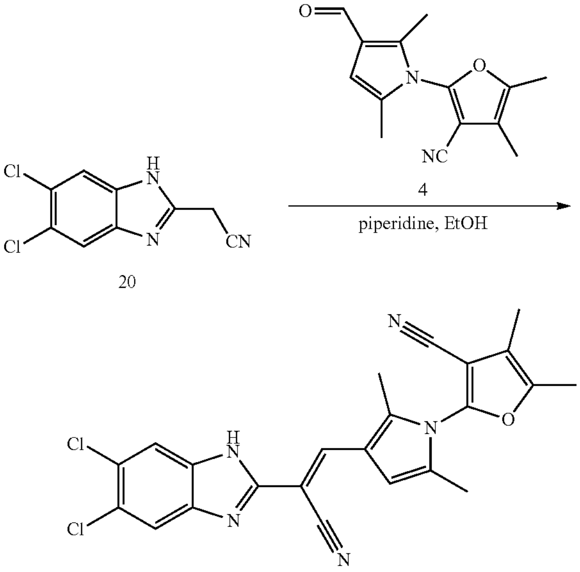

20

AB24214

Compound 20 (2-(5,6-dichloro-1H-benzo[d]imidazol-2-yl)acetonitrile) (56 mg, 0.248 mmol, 1.0 eq) was dissolved in ethanol (1 mL). Compound 4 (2-(3-formyl-2,5-dimethyl-1H-pyrrol-1-yl)-4,5-dimethylfuran-3-carbonitrile) (60 mg, 0.248 mmol, 1.0 eq) and piperidine (21 mg, 0.248 mmol, 1.0 eq) were added thereto. The mixture was heated under reflux and stirred for 2 hours. After the completion of the reaction, the resulting mixture was filtered and dried, so as to obtain Compound AB24214 ((E)-2-(3-(2-cyano-2-(5,6-dichloro-1H-benzo[d]imidazol-2-yl)vinyl)-2,5-dimethyl-1H-pyrrol-1-yl)-4,5-dimethylfuran-3-carbonitrile) as a yellow solid powder (37 mg, yield: 28.6%). MS (ESI) m/z: 450 $[M+H]^+$. $^1H$ NMR (400 MHz, DMSO) δ 8.16 (s, 1H), 7.81 (s, 2H), 6.95 (s, 1H), 2.31 (d, J=15.5 Hz, 6H), 2.10 (d, J=20.0 Hz, 6H).

Example 67: Synthesis of Compound (E)-2-(3-(2-cyano-2-(5,6-dimethoxy-1H-benzo[d]imidazol-2-yl) vinyl)-2,5-dimethyl-H-pyrrol-1-yl)-4,5-dimethyl-furan-3-carbonitrile (AB24229)

Compound AB24229 was obtained in the same manner as in Example 66 (yield: 45.6%), $^1H$ NMR (400 MHz, dmso) δ 12.60 (s, 1H), 7.96 (s, 1H), 7.16 (s, 1H), 6.91 (s, 2H), 3.76 (s, 6H), 2.29 (d, J=5.8 Hz, 6H), 2.09 (d, J=18.5 Hz, 6H).

Example 68: Synthesis of Compound (E)-2-(3-(2-cyano-2-(6,7-dihydro-1H-[1,4]dioxin[2',3': 4,5] benzo[1,2-d]imidazol-2-yl)vinyl)-2,5-dimethyl-1H-pyrrol-1-yl)-4,5-dimethylfuran-3-carbonitrile (AB24287)

Compound AB24287 was obtained in the same manner as in Example 66 (yield: 31.3%), $^1H$ NMR (400 MHz, dmso) δ 8.06 (s, 1H), 6.92 (s, 3H), 4.22 (s, 4H), 2.31 (d, J=12.6 Hz, 6H), 2.10 (d, J=17.2 Hz, 6H).

Example 69: Synthesis of Compound (E)-2-(3-(2-cyano-2-(7-methyl-1H-benzo[d]imidazol-2-yl)vinyl]-2,5-dimethyl-1H-pyrrol-1-yl)-4,5-dimethyl-furan-3-carbonitrile (AB24242)

(1) Synthesis of Compound 22 (N-(2-amino-6-methylphenyl)-2-cyanoacetamide)

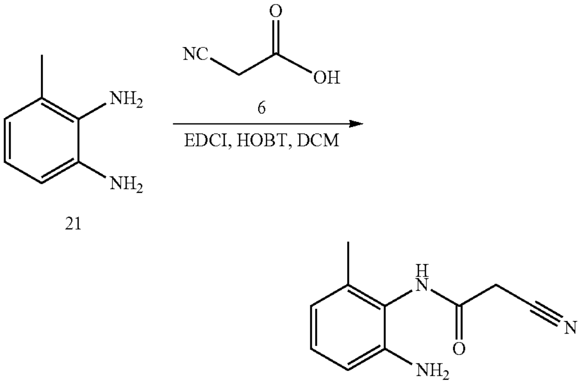

21

22

Compound 21 (2,3-diaminotoluene) (2.0 g, 16.37 mmol, 1.0 eq) was dissolved in dichloromethane (20 mL). Compound 6 (cyanoacetic acid) (2.1 g, 24.56 mmol, 1.5 eq), 1-(3-dimethylaminopropyl)-3-ethylcarbodiimide hydrochloride (4.71 g, 24.56 mmol, 1.5 eq) and 1-hydroxybenzotriazole (3.32 g, 24.56 mmol, 1.5 eq) were added thereto. The mixture was stirred at room temperature overnight, and was then diluted with water and extracted with dichloromethane. The organic layer was washed with brine, sodium sulfate was added to dry the mixture, and the resulting mixture was filtered and concentrated. The residue was purified by flash column chromatography (dichloromethane/methanol=100/1 to 50/1), so as to obtain Compound 22 (N-(2-amino-6-methylphenyl)-2-cyanoacetamide) as a black solid powder (1.48 g, yield: 47.8%). TLC:DCM/MeOH (10:1); $R_f$ (Compound 21)=0.2; $R_f$ (Compound 22)=0.3.

(2) Synthesis of Compound 23 (2-(7-methyl-1H-benzo[d]imidazol-2-yl)acetonitrile)

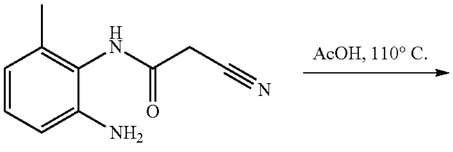

22

-continued

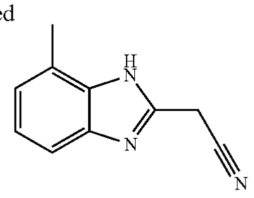

23

Compound 22 (N-(2-amino-6-methylphenyl)-2-cyanoacetamide) (1.478 mg, 7.82 mmol, 1.0 eq) was dissolved in acetic acid (10 mL), and the mixture was heated to 110° C. and then stirred overnight. Afterwards, the resulting mixture was diluted with water and extracted with dichloromethane. The organic layer was washed with brine, sodium sulfate was added to dry the mixture, and the resulting mixture was filtered and concentrated. The residue was purified by flash column chromatography (dichloromethane/methanol=100/1 to 20/1), so as to obtain Compound 23 (2-(7-methyl-1H-benzo[d]imidazol-2-yl)acetonitrile) as a black solid powder (300 mg, yield: 22.4%). TLC:DCM/MeOH (20:1); $R_f$(Compound 22)=0.7; $R_f$ (Compound 23)=0.75. $^1$H NMR (400 MHz $CDCl_3$) δ 7.54 (d, J=7.9 Hz, 1H), 7.40 (t, J=7.6 Hz, 1H), 7.29 (d, J=7.1 Hz, 1H), 4.56 (s, 2H), 2.63 (s, 3H).

(3) Synthesis of Compound AB24242 ((E)-2-(3-(2-cyano-2-(7-methyl-1H-benzo[d]imidazol-2-yl)vinyl]-2,5-dimethyl-1H-pyrrol-1-yl)-4,5-dimethylfuran-3-carbonitrile)

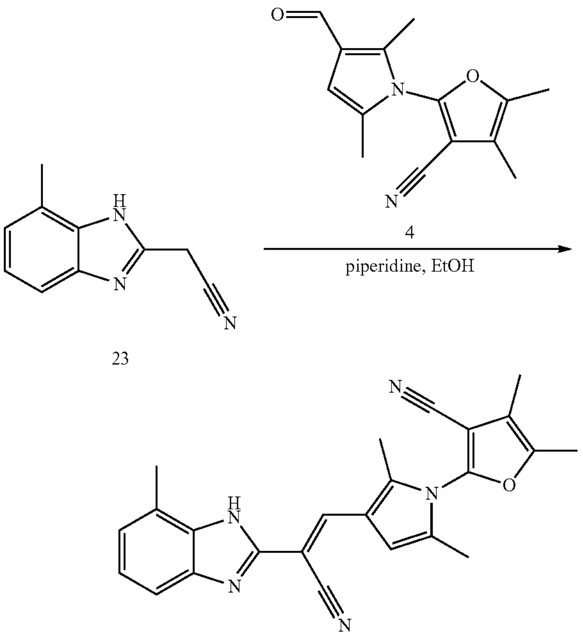

AB24242

Compound 23 (2-(7-methyl-1H-benzo[d]imidazol-2-yl) acetonitrile) (56 mg, 0.327 mmol, 1.0 eq) was dissolved in ethanol (1 mL). Compound 4 (79 mg, 0.327 mmol, 1.0 eq) and piperidine (28 mg, 0.327 mmol, 1.0 eq) were added thereto. The mixture was heated under reflux and stirred for 2 hours. After the completion of the reaction, the resulting mixture was filtered to obtain Compound AB24242 ((E)-2-(3-(2-cyano-2-(7-methyl-1H-benzo[d]imidazol-2-yl)vinyl)-2,5-dimethyl-1H-pyrrol-1-yl)-4,5-dimethylfuran-3-carbonitrile) as a yellow solid powder (37 mg, yield: 28.6%). MS (ESI) m/z: 396 [M+H]$^+$. $^1$H NMR (400 MHz, DMSO) δ 12.66 (d. J=10.8 Hz, 1H), 8.11 (s, 1H), 7.35 (d, J=45.7 Hz, 1H), 7.02 (d, J=43.9 Hz, 3H), 2.47 (s, 4H), 2.32 (d, J=19.9 Hz, 6H), 2.11 (d, J=20.7 Hz, 6H).

Example 70: Synthesis of Compound (E)-2-(3-(2-(7-chloro-1H-benzo[d]imidazol-2-yl)-2-cyanovinyl)-2,5-dimethyl-1H-pyrol-1-yl)-4,5-dimethylfuran-3-carbonitrile (AB24218)

Compound AB24218 was obtained in the same manner as in Example 69 (yield: 61%), $^1$H NMR (400 MHz, DMSO-d6) δ 13.16 (s, 1H), 8.27-8.12 (m, 1H), 7.57-7.43 (m, 1H), 7.19-7.17 (m, 2H), 6.95 (s, 1H), 2.45 (s, 3H), 2.32 (s, 3H), 2.11 (s, 3H), 2.06 (s, 3H).

Example 71: Synthesis of Compound (E)-2-(3-(2-cyano-2-(6-isopropoxy-1H-benzo[d]imidazol-2-yl) vinyl)-2,5-dimethyl-1H-pyrrol-1-yl)-4,5-dimethylfuran-3-carbonitrile (AB24297)

(1) Synthesis of Compound 25 (5-isopropoxy-2-nitroaniline)

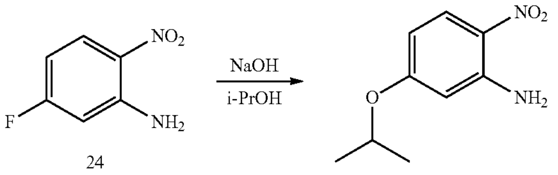

25

Compound 24 (5-fluoro-2-nitroaniline) (3.0 g, 19.23 mmol, 1.0 eq) was dissolved in isopropanol (i-PrOH) (30 mL), and sodium hydroxide (1.1 g, 27.5 mmol, 1.5 eq) was added thereto. The mixture was stirred at 90° C. for 4 hours. After cooling, the mixture was poured into ice water. The residue was purified by using flash column chromatography (FCC) (petroleum ether:ethyl acetate=5:1), and a yellow solid, i.e. Compound 25 (5-isopropoxy-2-nitroaniline) (2.3 g, yield: 63%) was obtained. MS (ESI) m/z: 197[M+H]$^+$. TLC:PE/EA (5/1); $R_f$(Compound 24)=0.5; $R_f$ (Compound 25)=0.2.

(2) Synthesis of Compound 26 (4-isopropoxybenzene-1,2-diamine)

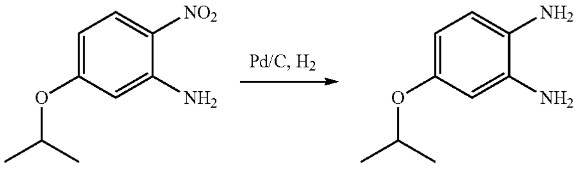

25 26

Compound 25 (5-isopropoxy-2-nitroaniline) (1.0 g, 5.1 mmol, 1.0 eq) was dissolved in methanol (10 mL), and palladium on carbon (200 mg, 0.2 wt %) was added thereto.

The mixture was stirred at room temperature for 16 hours under hydrogen atmosphere. The solid was filtered off, and the filtrate was concentrated to obtain a brown solid, i.e. Compound 26 (4-isopropoxybenzene-1,2-diamine) (800 mg, yield: 94.4%). MS (ESI) m/z: 167[M+H]$^+$. TLC:DCM/MeOH (20:1); $R_f$ (Compound 25)=0.7; $R_f$ (Compound 26)=0.2.

(3) Synthesis of Compound 28 (2-(6-isopropoxy-H-benzo[d]imidazol-2-yl)acetonitrile)

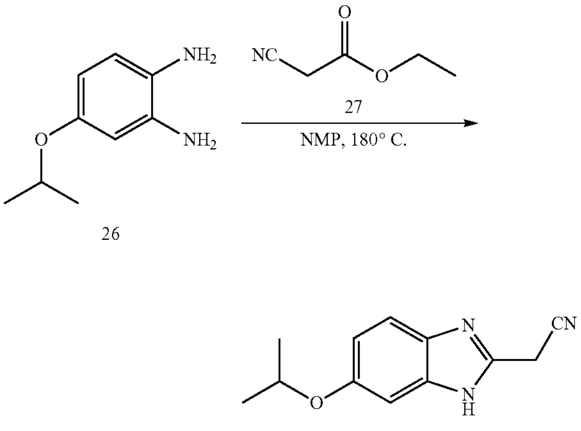

26

27

28

Compound 26 (4-isopropoxybenzene-1,2-diamine) (500 mg, 3.01 mmol, 1.0 eq) and Compound 27 (ethyl cyanoacetate) (850 mg, 7.53 mmol, 2.5 eq) were added into N-methylpyrrolidone (NMP) (2 mL), and the mixture was stirred at 180° C. for 4 hours. After cooling, the mixture was diluted with water and extracted with a mixed solution (dichloromethane:methanol=10:1). The organic phase was dried, filtered and concentrated. The residue was purified by using preparative high performance liquid chromatograph, and a yellow solid. i.e. Compound 28 (2-(6-isopropoxy-1H-benzo[d]imidazol-2-yl)acetonitrile) (310 mg, yield: 47.9%) was obtained. MS (ESI) m/z: 216.0 [M+H]$^+$.

(4) Synthesis of Compound AB24297 ((E)-2-(3-(2-cyano-2-(6-isopropoxy-1H-benzo[d]imidazol-2-yl)vinyl)-2,5-dimethyl-1H-pyrrol-1-yl)-4,5-dimethylfuran-3-carbonitrile)

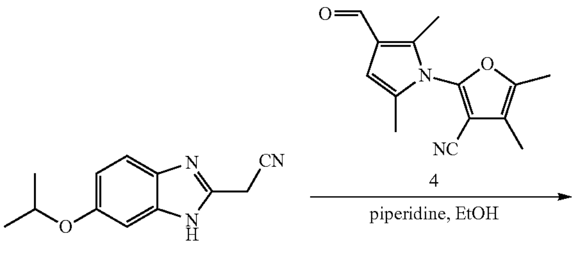

4

28

-continued

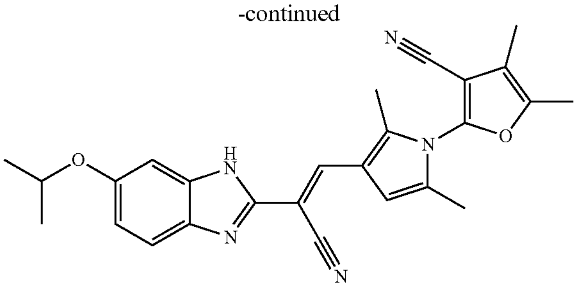

AB24297

Compound 28 (2-(6-isopropoxy-1H-benzo[d]imidazol-2-yl)acetonitrile) (70 mg, 0.32 mmol, 1.0 eq) was dissolved in ethanol (1 mL). Compound 4 (2-(3-formyl-2,5-dimethyl-1H-pyrrol-1-yl)-4,5-dimethylfuran-3-carbonitrile) (79 mg, 0.32 mmol, 1.0 eq) and piperidine (55 mg, 0.64 mmol, 2.0 eq) were added thereto. The mixture was heated under reflux and stirred for 1 hour. The mixture was cooled to room temperature and filtered. The solid was collected and dried to obtain a yellow solid, i.e. AB24297 (32 mg, yield: 22.8%). MS (ESI) m/z: 440.0 [M+H]$^+$. $^1$H NMR (400 MHz, DMSO-d6) δ 12.69 (s, 1H), 8.05 (s, 1H), 7.42 (s, 1H), 7.01 (s, 1H), 6.94 (s, 1H), 6.79 (d, J=8 Hz, 1H), 4.60-4.58 (m, 1H), 2.31 (d, J=8 Hz, 6H), 6.79 (d, J=20 Hz, 6H), 1.25 (d, J=4 Hz, 6H).

Example 72: Synthesis of Compound (E)-2-(3-(2-cyano-2-(1-methyl-1H-benzo[d]imidazol-2-yl]vinyl)-2,5-dimethyl-1H-pyrrol-1-yl)-4,5-dimethylfuran-3-carbonitrile (AB24231)

(1) Synthesis of Compound 30 (2-(1-methyl-1H-benzo[d]imidazol-2-yl)acetonitrile)

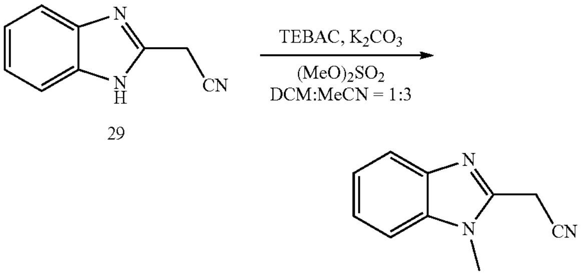

29

30

Benzyltriethylammonium chloride (TEBAC) (18 mg, 0.08 mmol, 0.08 eq) was dissolved in acetonitrile (3 mL). Potassium carbonate (138 mg, 1 mmol, 1 eq) and a solution of Compound 29 (2-cyanomethylbenzimidazole) (157 ng, 1 mmol, 1 eq) in 1 ml of dichloromethane were added thereto. The mixture was stirred at room temperature for half an hour, and dimethyl sulfate (139 mg, 1.1 mmol, 1.1 eq) was added thereto. The mixture was stirred at room temperature for 16 hours. After the resulting mixture was concentrated, the residue was quenched with water and then extracted with dichloromethane. The organic layer was dried, filtered and concentrated. The residue was purified by preparative thin layer chromatography (dichloromethane/methanol=20/1), so as to obtain Compound 30 (2-(1-methyl-1H-benzo[d]imidazol-2-yl)acetonitrile) as a yellow oil (76 mg, yield:

44.4%). MS (ESI) m/z: 172 $[M+H]^+$. TLC:dichloromethane/methanol (20/1); $R_f$ (Compound 29)=0.5; $R_f$ (Compound 30)=0.2; $^1H$ NMR (400 MHz, $CDCl_3$) δ 7.76 (d, J=8 Hz, 1H), 7.36-7.31 (m, 3H), 4.08 (s, 2H), 3.86 (s, 3H).

(2) Synthesis of Compound AB24231 ((E)-2-(3-(2-cyano-2-(1-methyl-1H-benzo[d]imidazol-2-yl]vinyl)-2,5-dimethyl-1H-pyrrol-1-yl)-4,5-dimethylfuran-3-carbonitrile)

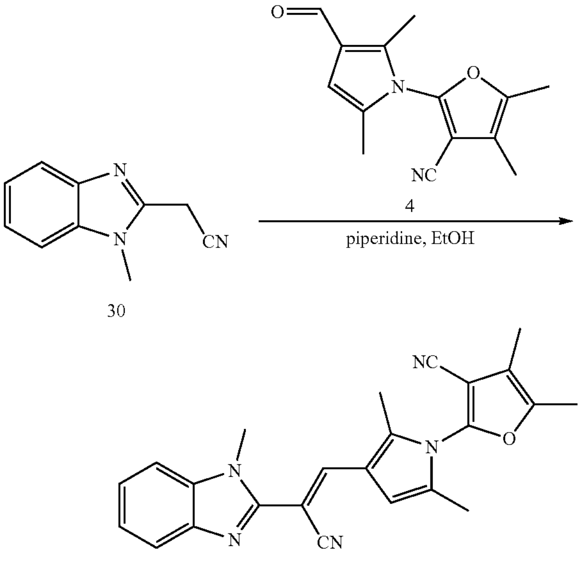

30

AB24231

To a solution of Compound 30 (2-(1-methyl-1H-benzo[d]imidazol-2-yl)acetonitrile) (75 mg, 0.436 mmol, 1.0 eq) in 2 ml of ethanol, Compound 4 (2-(3-formyl-2,5-dimethyl-1H-pyrrol-1-yl)-4,5-dimethylfuran-3-carbonitrile) (105 mg, 0.436 mmol, 1.0 eq) and piperidine (37 mg, 0.436 mmol, 1.0 eq) were added, and the mixture was heated under reflux and stirred for 1 hour. After the completion of the reaction, the mixture was cooled to room temperature and filtered. The solid was collected and dried, so as to obtain Compound AB24231 ((E)-2-(3-(2-cyano-2-(1-methyl-1H-benzo[d]imidazol-2-yl]vinyl)-2,5-dimethyl-1H-pyrrol-1-yl)-4,5-dimethylfuran-3-carbonitrile) as a yellow solid (102 ng, yield: 67.7%). MS (ESI) m/z: 396 $[M+H]^+$. $^1H$ NMR (400 MHz, DMSO-d6) δ 7.89 (s, 1H), 7.62-7.45 (m, 2H), 7.27-7.18 (m, 2H), 6.94 (s, 1H), 3.90 (s, 3H), 2.25 (d. J=8 Hz, 6H), 2.10 (s, 3H), 2.05 (s, 3H).

Example 73: Synthesis of Compound (E)-2-(3-(2-cyano-2-(1-(methoxymethyl)-1H-benzo[d]imidazol-2-yl)vinyl)-2,5-dimethyl-1H-pyrrol-1-yl)-4,5-dimethylfuran-3-carbonitrile (AB24263)

(1) Synthesis of Compound 31 (2-(1-(methoxymethyl)-1H-benzo[d]imidazol-2-yl)acetonitrile)

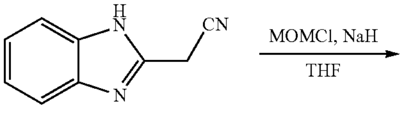

29

-continued

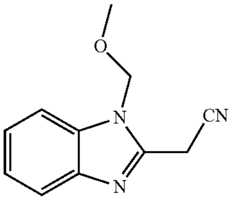

31

Compound 29 (2-cyanomethylbenzimidazole) (1.0 g, 6.36 mmol, 1.0 eq) was dissolved in 16 ml of tetrahydrofuran. NaH (267 mg, 6.68 mmol, 1.05 eq, 60% in mineral oil) was added thereto at 0° C. The mixture was stirred at 0° C. for 15 minutes, and then chloromethyl methyl ether (665 mg, 8.27 mmol, 1.3 eq) was added thereto. The mixture was stirred at room temperature for 2 hours. The reaction mixture was quenched with sodium bicarbonate, and the resulting mixture was extracted with ethyl acetate. The organic layer was dried, filtered and concentrated. The residue was purified by preparative high-pressure liquid chromatographic column, so as to obtain Compound 31 (2-(1-(methoxymethyl)-1H-benzo[d]imidazol-2-yl)acetonitrile) as a yellow oily liquid (230 mg, yield: 17.9%). MS (ESI) m/z: 202 $[M+H]^+$. TLC:petroleum ether/ethyl acetate (2/1); $R_f$ (Compound 29)=0.5; $R_f$ (Compound 31)=0.3. $^1H$ NMR (400 MHz, $CDCl_3$) δ 7.64 (d, J=9.2 Hz, 2H), 7.29-7.20 (m, 2H), 5.56 (s, 2H), 4.50 (s, 2H), 3.18 (s, 3H).

(2) Synthesis of Compound AB24263 ((E)-2-(3-(2-cyano-2-(1-(methoxymethyl)-1H-benzo[d]imidazol-2-yl)vinyl)-2,5-dimethyl-1H-pyrrol-1-yl)-4,5-dimethylfuran-3-carbonitrile)

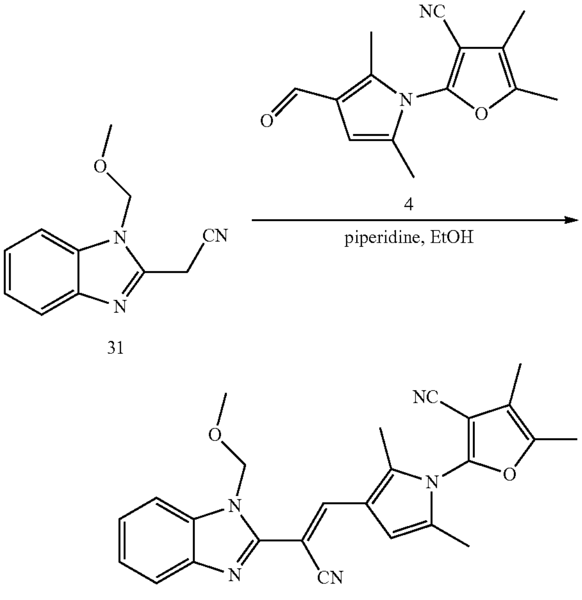

31

AB24263

Compound 31 (2-(1-(methoxymethyl)-1H-benzo[d]imidazol-2-yl)acetonitrile) (50 mg, 0.249 mmol, 1.0 eq) was dissolved in 1.5 ml of ethanol. Compound 4 (2-(3-formyl-2,5-dimethyl-1H-pyrrol-1-yl)-4,5-dimethylfuran-3-carbonitrile) (60 mg, 0.249 mmol, 1.0 eq) and piperidine (21 mg, 0.249 mmol, 1.0 eq) were added thereto. The mixture was heated under reflux and stirred for 1 hour. After the completion of the reaction, the mixture was cooled to room temperature and filtered. The solid was collected and dried, so as to obtain AB24263 ((E)-2-(3-(2-cyano-2-(1-(methoxymethyl)-1H-benzo[d]imidazol-2-yl)vinyl)-2,5-dimethyl-1H-pyrrol-1-yl)-4,5-dimethylfuran-3-carbonitrile) as a yellow solid (22 mg, yield: 20.9%). MS (ESI) m/z: 426 $[M+H]^+$. 1H NMR (400 MHz, DMSO-d6) δ 8.05 (s, 1H), 7.67-7.58 (m, 2H), 7.27-7.20 (m, 2H), 6.98 (s, 1H), 5.66 (s, 2H), 3.38 (s, 3H), 2.29 (s, 3H), 2.24 (s, 3H), 2.14 (s, 3H), 2.08 (s, 3H).

Example 74: Synthesis of Compound AB24350 (2-(3-(7-methoxy-9H-carbazol-2-yl)-2,5-dimethyl-1H-pyrrol-1-yl)-5-methylthiophene-3-carbonitrile)

(1) Preparation of Compound 3 (2-methoxy-7-(4,4,5,5-tetramethyl-1,3,2-dioxaboran-2-yl)-9H-carbazole)

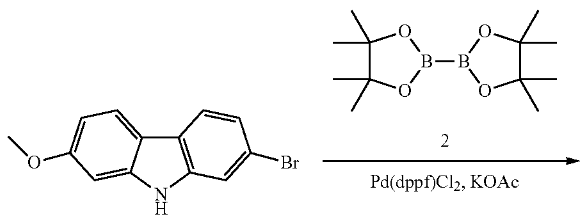

2

1

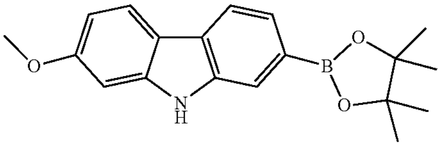

3

Compound 1 (2-bromo-7-methoxycarbazole) (300 mg, 1.08 mmol, 1 eq) was dissolved in 1,4-dioxane (2 mL). Compound 2 (bis(pinacolato)diboron) (331 mg, 1.30 mmol, 1.2 eq), potassium acetate (213 mg, 2.17 mmol, 2.0 eq) and 1,1'-bis(diphenylphosphino)ferrocene (24 mg, 0.032 mmol, 0.03 eq) were added thereto. The mixture was heated to 90° C. and reacted for 16 hours under the protection of nitrogen gas. After the completion of the reaction, the mixture was purified by flash column chromatography (petroleum ether/ethyl acetate=50/1 to 25/1 to 10/1), so as to obtain Compound 3 (2-methoxy-7-(4,4,5,5-tetramethyl-1,3,2-dioxaboran-2-yl)-9H-carbazole) as a yellow solid (314 mg, yield: 89%). MS (ESI) m/z: 324 $[M+H^+]$. TLC:petroleum ether/ethyl acetate (5/1); $R_f$ (Compound 1)=0.4; $R_f$ (Compound 2)=0.3; $^1$H NMR (400 MHz, $CDCl_3$) δ 7.98-7.93 (m, 3H), 7.85 (s, 1H), 7.65 (d, J=7.2 Hz, 1H), 6.91 (s, 1H), 6.84 (d, J=8.4 Hz, 1H), 3.89 (s, 3H), 1.38 (s, 12H).

(2) Synthesis of Compound 5 (2-(3-bromo-2,5-dimethyl-1H-pyrrol-1-yl)-5-methylthiophene-3-carbonitrile)

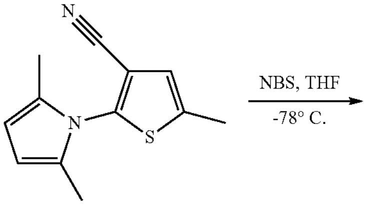

4

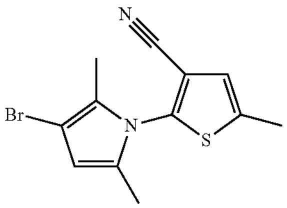

5

The crude Compound 4 (2-(2,5-dimethyl-1H-pyrrol-1-yl)-5-methylthiophene-3-carbonitrile) (300 mg, 1.38 mmol, 1.0 eq) was dissolved in tetrahydrofuran (10 mL), and N-bromosuccinimide (269 mg, 1.51 mmol, 1.09 eq) was added thereto at −78° C. The mixture was stirred for 0.5 hour at −78° C. The mixture was diluted with water and then extracted with ethyl acetate. The organic layer was dried, filtered and concentrated. The residue was purified by flash column chromatography (petroleum ether/ethyl acetate=10/1), so as to obtain Compound 5 (2-(3-bromo-2,5-dimethyl-1H-pyrrol-1-yl)-5-methylthiophene-3-carbonitrile) as a yellow solid (216 mg, yield: 53%). MS (ESI) m/z: 295 $[M+H^+]$. TLC:petroleum ether/ethyl acetate (10/1); $R_f$ (Compound 4)=0.6; $R_f$ (Compound 5)=0.5.

(3) Preparation of Compound AB24350 (2-(3-(7-methoxy-9H-carbazol-2-yl)-2,5-dimethyl-1H-pyrrol-1-yl)-5-methylthiophene-3-carbonitrile)

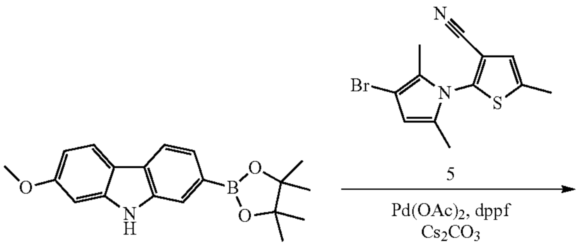

5

3

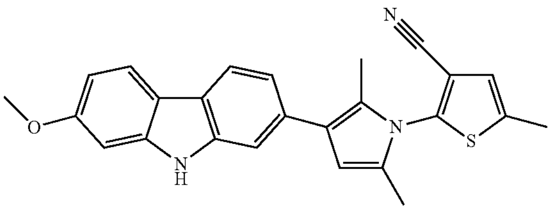

AB24350

Compound 3 ((2-methoxy-7-(4,4,5,5-tetramethyl-1,3,2-dioxaboran-2-yl)-9H-carbazole)) (164 mg, 0.508 mmol, 1.5 eq) was dissolved in a mixture of 1,4-dioxane and water (1.5 mL/0.3 mL). Compound 5 (2-(3-bromo-2,5-dimethyl-1H-pyrrol-1-yl)-5-methylthiophene-3-carbonitrile) (100 mg, 0.339 mmol, 1.0 eq), cesium carbonate (221 mg, 0.678 mmol, 2.0 eq), palladium acetate (4 mg, 0.0169 mmol, 0.05 eq) and 1,1'-bis(diphenylphosphino)ferrocene (19 mg, 0.0339 mmol, 0.3 eq) were added thereto. The mixture was placed in a sealed tube, and was stirred and reacted for 3 hours at −78° C. After the completion of the reaction, the mixture was concentrated and purified by flash column chromatography (petroleum ether/ethyl acetate=20/1 to 10/1), so as to obtain Compound AB24350 (2-(3-(7-methoxy-9H-carbazol-2-yl)-2,5-dimethyl-1H-pyrrol-1-yl)-5-methylthiophene-3-carbonitrile) as an off-white solid (27 mg, yield: 19.3%). MS (ESI) m/z: 412 [M+H$^+$]. $^1$H NMR (400 MHz, DMSO-d$_6$) δ 11.05 (s, 1H), 7.95-7.90 (m, 2H), 7.38 (s, 1H), 7.28 (s, 1H), 7.15 (d, J=7.6 Hz, 1H), 6.93 (s, 1H), 6.73 (d, J=8 Hz, 1H), 6.28 (s, 1H), 3.81 (S, 3H), 2.51 (s, 3H), 2.21 (s, 3H), 2.09 (s, 3H).

Example 75: Synthesis of Compound AB24374 (2-(3-(7-methoxy-3-methyl-9H-carbazol-2-yl)-2,5-dimethyl-1H-pyrrol-1-yl)-5-methylthiophene-3-carbonitrile)

(1) Synthesis of Compound 7 (4-bromo-5-methyl-2-nitrobenzenediazonium tetrafluoroborate)

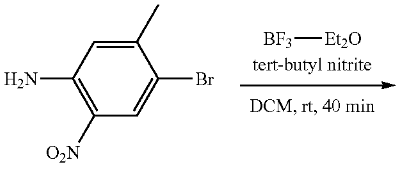

6

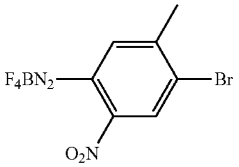

7

Compound 6 (4-bromo-5-methyl-2-nitroaniline) (1 g, 4.33 mmol, 1 eq) was dissolved in dichloromethane (100 mL). At 0° C., boron trifluoride-diethyl ether complex (737 mg, 5.19 mmol, 1.2 eq) was added, and then tert-butyl nitrite (669 mg, 6.49 mmol, 1.5 eq) was added. The reactants were stirred at room temperature for 40 minutes. After the completion of the reaction, the mixture was filtered, and the solid was subjected to vacuum drying so as to obtain Compound 7 (4-bromo-5-methyl-2-nitrobenzenediazonium tetrafluoroborate) as a white solid (1.03 g, yield: 72.1%). MS (ESI) m/z: 330.0 [M−H$^+$]. TLC:petroleum ether/ethyl acetate (10/1); R$_f$ (Compound 6)=0.2; R$_f$ (Compound 7)=0.7.

(2) Preparation of Compound 9 (4-bromo-4'-methoxy-5-methyl-2-nitro-1,1'-biphenyl)

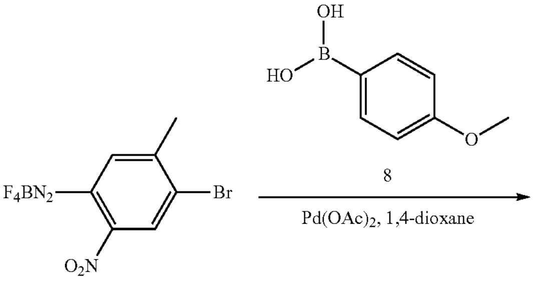

8

7

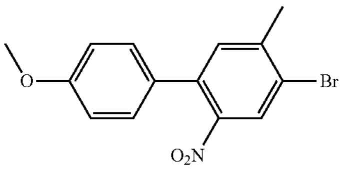

9

Compound 7 (4-bromo-5-methyl-2-nitrobenzenediazonium tetrafluoroborate) (1.03 g, 3.16 mmol, 1.1 eq) and Compound 8 ((4-methoxyphenyl)boronic acid) (436 mg, 2.87 mmol, 1.0 eq) were dissolved in 1,4-dioxane (100 mL), and palladium acetate (19 mg, 0.08 mmol, 0.03 eq) was added thereto. The mixture was stirred and reacted at room temperature for two hours under the protection of nitrogen gas. After the completion of the reaction, the mixture was purified by flash column chromatography (petroleum ether/ethyl acetate=101), so as to obtain Compound 9 (4-bromo-4'-methoxy-5-methyl-2-nitro-1,1'-biphenyl) as a yellow solid (611 mg, yield: 60.2%). MS (ESI) m/z: 322.1 [M+H$^+$]. TLC:petroleum ether/ethyl acetate (10/1); R$_f$ (Compound 7)=0.7; R$_f$ (Compound 9)=0.6.

(3) Preparation of Compound 10 (2-bromo-7-methoxy-3-methyl-9H-carbazole)

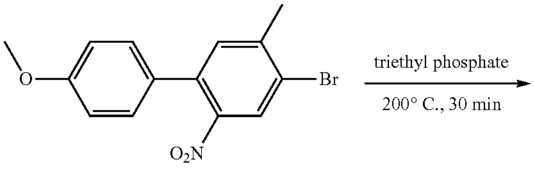

9

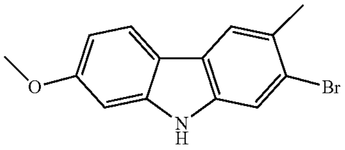

10

Compound 9 (4-bromo-4'-methoxy-5-methyl-2-nitro-1,1'-biphenyl) (300 mg, 0.93 mmol, 1 eq) was added to triethyl phosphate (3 mL). The reactants were heated to 200° C. and stirred for 30 minutes. After the completion of the reaction, the mixture was cooled to room temperature and filtered. The resulting solid was subjected to vacuum drying so as to obtain Compound 10 (2-bromo-7-methoxy-3-methyl-9H-carbazole) as a white solid (120 mg, yield: 60.2%). MS (ESI) m/z: 290.1 [M+H$^+$]. TLC:petroleum ether/ethyl acetate (10/1); $R_f$(Compound 9)=0.6; $R_f$ (Compound 10)=0.4.

(4) Preparation of Compound 11 (7-methoxy-3-methyl-2-(4,4,5,5-tetramethyl-1,3,2-dioxaboran-2-yl)-9H-carbazole)

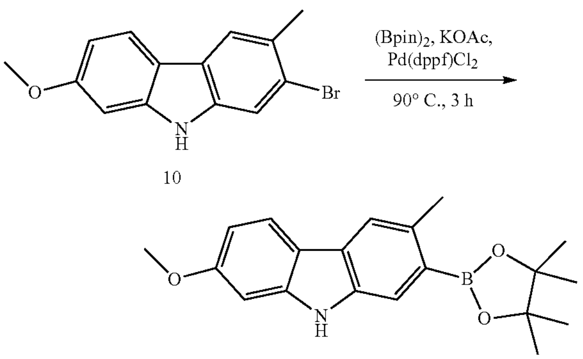

10

11

Compound 10 (2-bromo-7-methoxy-3-methyl-9H-carbazole) (120 mg, 0.40 mmol, 1 eq) and (Bpin)$_2$ (123 mg, 0.49 mmol, 1.2 eq) were dissolved in 1,4-dioxane (10 mL). Potassium acetate (79 mg, 0.81 mmol, 2 eq) and [1,1'-bis (diphenylphosphino)ferrocene]dichloride palladium (34 mg, 0.04 mmol, 0.1 eq) were added thereto. The mixture was heated to 90° C. and stirred for two hours under the protection of nitrogen gas. After the completion of the reaction, the mixture was purified by flash column chromatography (dichloromethane/methanol=100/1), so as to obtain Compound 11 (7-methoxy-3-methyl-2-(4,4,5,5-tetramethyl-1,3,2-dioxaboran-2-yl)-9H-carbazole) as a white solid (130 mg, yield: 94.2%). MS (ESI) m/z: 338.1 [M+H$^+$]. TLC:petroleum ether/ethyl acetate (5/1); $R_f$ (Compound 10)=0.3; $R_f$ (Compound 11)=0.2.

(5) Preparation Method of Compound AB24374 (2-(3-(7-methoxy-3-methyl-9H-carbazol-2-yl)-2,5-dimethyl-1H-pyrrol-1-yl)-5-methylthiophene-3-carbonitrile)

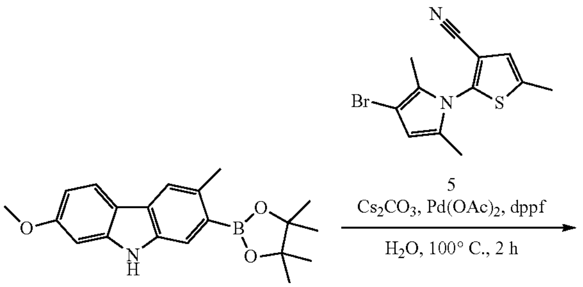

5

11

-continued

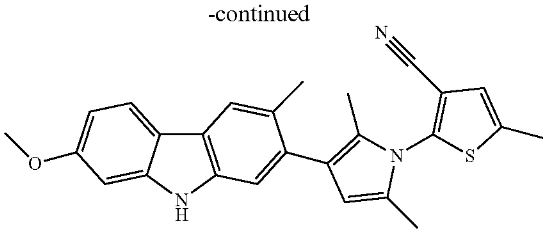

AB24374

Compound 11 ((7-methoxy-3-methyl-2-(4,4,5,5-tetramethyl-1,3,2-dioxaboran-2-yl)-9H-carbazole)) (100 mg, 0.30 mmol, 1.5 eq) and Compound 5 (2-(3-bromo-2,5-dimethyl-1H-pyrrol-1-yl)-5-methylthiophene-3-carbonitrile) (60 mg, 0.20 mmol, 1.0 eq) were dissolved in a mixture of 1,4-dioxane and water (3 mL/0.6 mL). Afterwards, cesium carbonate (130 mg, 0.40 mmol, 2 eq), palladium acetate (24 mg, 0.10 mmol, 0.5 eq) and 1,1'-bis diphenylphosphinoferrocene (110 mg, 0.20 mmol, 0.1 eq) were added thereto. Under the protection of nitrogen gas, the reactants were heated to 100° C. and were stirred and reacted for two hours. After the completion of the reaction, the mixture was diluted with water (20 mL) and then extracted three times with dichloromethane (20 mL×3). The organic layers were dried, filtered and concentrated. The residue was purified by preparative thin layer chromatography (petroleum ether/ethyl acetate=5:1), so as to obtain Compound AB24374 (2-(3-(7-methoxy-3-methyl-9H-carbazol-2-yl)-2,5-dimethyl-1H-pyrrol-1-yl)-5-methylthiophene-3-carbonitrile) as a white solid (6 mg, yield: 6.9%). MS (ESI) m/z: 426.15 [M+H$^+$]. $^1$H NMR (400 MHz, DMSO-d$_6$) δ 10.90 (s, 1H), 7.88 (d, J=4 Hz, 1H), 7.82 (s, 1H), 7.27 (s, 1H), 7.15 (s, 1H), 6.91 (s, 1H), 6.71 (s, 1H), 6.06 (s, 1H), 3.81 (s, 3H), 2.30 (s, 3H), 2.11 (s, 3H), 1.93 (s, 3H), 1.21 (s, 3H).

Example 76: Synthesis of Compound AB24375 (2-(3-(6-methoxy-9H-carbazol-2-yl)-2,5-dimethyl-1H-pyrrol-1-yl)-5-methylthiophene-3-carbonitrile)

Compound AB24375 was obtained in the same manner as in Example 74 (yield: 8.5%). $^1$H NMR (400 MHz, CDCl$_3$) δ 8.01 (d, J=4 Hz, 1H), 7.92 (s, 1H), 7.53 (s, 1H), 7.33 (s, 1H), 7.31 (s, 1H), 7.04 (s, 1H), 6.91 (s, 1H), 6.24 (s, 1H), 3.93 (s, 3H), 2.54 (s, 3H), 2.29 (s, 3H), 2.18 (s, 3H).

Example 77: Synthesis of Compound AB24385 (2-(3-(2-methoxybenzo[4,5]imidazo[1,2-a]pyridin-7-yl)-2,5-dimethyl-1H-pyrrol-1-yl)-5-methylthiophene-3-carbonitrile)

(1) Synthesis of Compound 14 (7-bromo-2-methoxybenzo[4,5]imidazo[1,2-a]pyridine)

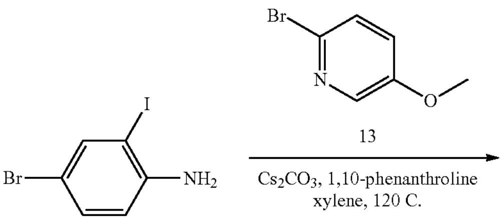

13

12

-continued

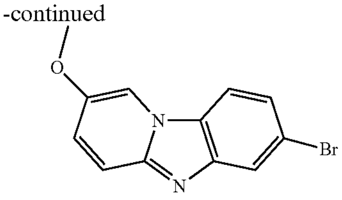

14

Compound 12 (4-bromo-2-iodobenzylamine) (5 g, 16.78 mmol, 1 eq) and Compound 13 (2-bromo-5-methoxypyridine) (4.7 g, 25.17 mmol, 1.5 eq) were dissolved in xylene (50 mL). Cuprous iodide (639 mg, 3.35 mmol, 0.2 eq), cesium carbonate (16.4 g, 50.34 nmol, 2 eq) and 1,10-phenanthroline (1.2 g, 6.71 mmol, 0.4 eq) were added thereto. The mixture was heated to 120° C. and stirred for 16 hours. After the completion of the reaction, the mixture was purified by flash column chromatography (dichloromethane/methanol=300/1 to 250/1), so as to obtain a black oily Compound 14 (7-bromo-2-methoxybenzo[4,5]imidazo[1,2-a]pyridine) (390 mg, yield: 8.3%). MS (ESI) m/z: 277.1 [M+H$^+$]. TLC:dichloromethane/methanol (20/1); $R_f$(Compound 12)=0.8; $R_f$ (Compound 14)=0.3.

(2) Synthesis of Compound 16 (2-methoxy-7-(4,4,5,5-tetramethyl-1,3,2-dioxaboran-2-yl)benzo[4,5]imidazo[1,2-a]pyridine)

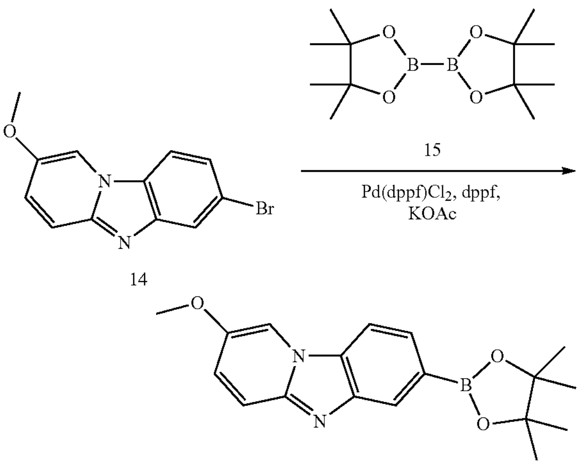

15

14

16

Compound 14 (7-bromo-2-methoxybenzo[4,5]imidazo[1,2-a]pyridine) (330 mg, 1.19 mmol, 1 eq) and Compound 15 (bis(pinacolato)diboron) (906 mg, 3.57 mmol, 3 eq) were dissolved in 1,4-dioxane (10 mL). Potassium carbonate (350 mg, 3.57 mmol, 3 eq), [1,1'-bis(diphenylphosphino)ferrocene]palladium dichloride (44 mg, 0.059 mmol, 0.05 eq) and 1,1'-bis(diphenylphosphino)ferrocene (66 mg, 0.119 mmol, 0.1 eq) were added thereto. The reactants were heated to 100° C. and stirred for 16 hours. After the completion of the reaction, the mixture was purified by flash column chromatography (dichloromethane/methanol=100/1), so as to obtain a black oily Compound 16 (2-methoxy-7-(4,4,5,5-tetramethyl-1,3,2-dioxaboran-2-yl)benzo[4,5]imidazo[1,2-a]pyridine) (210 mg of crude product). MS (ESI) m/z:

415.10[M+H$^+$]. TLC:dichloromethane/methanol (30/1); $R_f$ (Compound 14)=0.4; $R_f$(Compound 16)=0.4.

(3) Preparation of Compound AB24385 (2-(3-(2-methoxybenzo[4,5]imidazo[1,2-a]pyridin-7-yl)-2,5-dimethyl-1H-pyrrol-1-yl)-5-methylthiophene-3-carbonitrile)

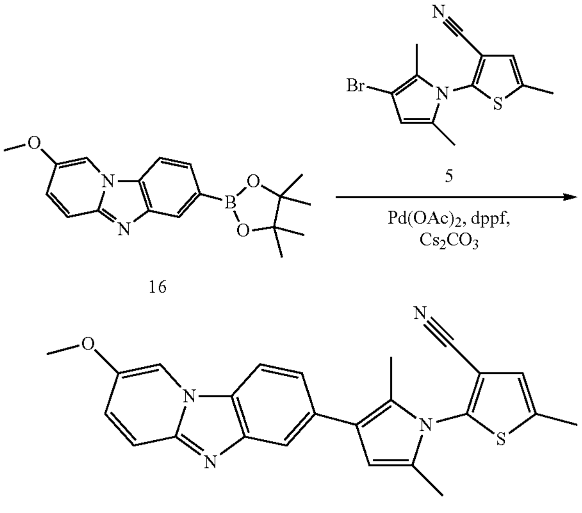

5

16

AB24385

To a mixture of Compound 16 (2-methoxy-7-(4,4,5,5-tetramethyl-1,3,2-dioxaboran-2-yl)benzo[4,5]imidazo[1,2-a]pyridine) (210 mg, 0.648 mmol, 1 eq) and Compound 5 (2-(3-bromo-2,5-dimethyl-1H-pyrrol-1-yl)-5-methylthiophene-3-carbonitrile) (247 mg, 0.842 mmol, 1.3 eq) in 1,4-dioxane/water (5 mL/0.5 mL), cesium carbonate (422 mg, 1.29 mmol, 2 eq), palladium acetate (8 ug, 0.032 mmol, 0.05 eq) and 1,2-bis(diphenylphosphino)ethane (36 mg, 0.064 mmol, 0.1 eq) were added. The mixture was heated to 100° C. and stirred for 16 hours. After the completion of the reaction, the mixture was diluted with water (20 mL) and extracted three times with dichloromethane (20 mL×3). The organic layers were dried, filtered and concentrated. The residue was purified by preparative high-pressure liquid chromatography, so as to obtain AB24385 (2-(3-(2-methoxybenzo[4,5]imidazo[1,2-a]pyridin-7-yl)-2,5-dimethyl-1H-pyrrol-1-yl)-5-methylthiophene-3-carbonitrile) as a yellow solid (9 mg, yield: 3.3%). MS (ESI) m/z: 413.1 [M+H]$^+$. $^1$H NMR (400 MHz, $CD_3OD$-$d_4$): δ 8.48 (s, 1H), 8.17 (d, J=6.8 Hz, 1H), 7.73 (s, 1H), 7.58 (d, J=8.4 Hz, 1H), 7.46 (d, J=8.4 Hz, 1H), 7.41 (d, J=8.0 Hz, 1H), 7.09 (s, 1H), 6.25 (s, 1H), 3.95 (s, 3H), 2.56 (s, 3H), 2.25 (s, 3H), 2.16 (s, 3H).

Example 78: Synthesis of Compound AB24379 (2-(3-(3-methoxybenzo[4,5]imidazo[1,2-a]pyridin-7-yl)-2,5-dimethyl-1H-pyrrol-1-yl)-5-methylthiophene-3-carbonitrile)

Compound AB24379 was obtained in the same manner as in Example 77 (yield: 2.0%), $^1$H NMR (400 MHz, $CD_3OD$-d4): δ8.70 (s, 1H), 8.48 (s, 1H), 7.64 (s, 1H), 7.35 (s, 1H), 7.09 (s, 1H), 6.93 (s, 1H), 6.74 (s, 1H), 6.24 (s, 1H), 3.97 (s, 3H), 2.56 (s, 3H), 2.25 (s, 3H), 2.16 (s, 3H).

Example 79: Synthesis of Compound AB29506 ((S,E)-3-(2,5-dimethyl-1-(1-phenylethyl)-1H-pyrrol-3-yl)-2-(6-methoxy-3H-imidazo[4,5-c]pyridin-2-yl) acrylonitile)

(1) Preparation Method of Compound 3 ((R)-2,5-dimethyl-1-(I-phenylethyl)-1H-pyrrole)

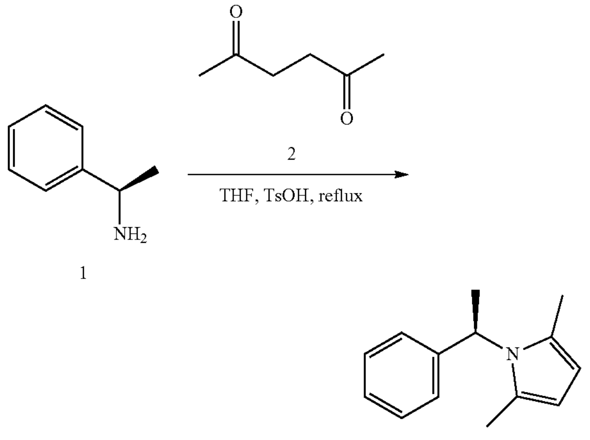

1 2 3

Compound 1 (R (+)-α-methylbenzylamine) (1 g, 8.25 mmol, 1.0 eq) was dissolved in tetrahydrofuran (30 mL). Compound 2 (2,5-hexanedione) (1.4 g, 12.37 mmol, 1.5 eq), 3 A molecular sieve (2 g) and p-toluenesulfonic acid (567 mg, 3.3 mmol, 0.4 eq) were added thereto. The mixture was stirred at 80° C. for 16 hours. The solid was filtered and concentrated. The residue was purified by flash column chromatography (petroleum ether/ethyl acetate=30/1), so as to obtain Compound 3 ((R)-2,5-dimethyl-1-(1-phenylethyl)-1H-pyrrole) as a yellow solid (320 mg, yield: 19.4%). MS (ESI) m/z: 200 $[M+H]^+$. TLC:petroleum ether/ethyl acetate (5:1); $R_f$ (Compound 1)=0.1; $R_f$ (Compound 3)=0.6.

(2) Preparation Method of Compound 4 ((R)-2,5-dimethyl-1-(1-phenylethyl)-1H-pyrrole-3-carbaldehyde)

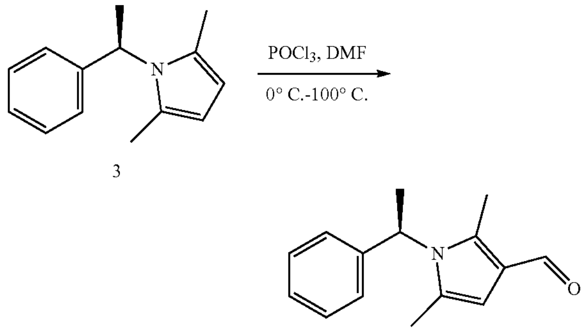

3 4

Under the protection of nitrogen gas, phosphorus oxychloride (115 mg, 0.75 mmol, 1.5 eq) was added dropwise to dimethylformamide (5 mL) at 0° C. The mixture was stirred at 0° C. for 30 minutes and then warmed to room temperature. Afterwards, a solution of Compound 3 ((R)-2,5-dimethyl-1-(1-phenylethyl)-1H-pyrrole) (100 mg, 0.50 mmol, 1.0 eq) in dimethylformamide (2 mL) was added to the above-mentioned mixed solution. In the presence of nitrogen gas, the mixture was heated to 100° C. and then stirred for 2 hours. After the reaction mixture was cooled, the mixture was poured into ice water, and then the pH of the resulting mixture was adjusted to 10 with 30% aqueous sodium hydroxide solution. The mixture was extracted with ethyl acetate and then washed with saturated aqueous sodium chloride solution. The organic layers were combined, dried over anhydrous sodium sulfate, filtered and concentrated. The residue was purified by flash column chromatography (petroleum ether/ethyl acetate=30/1), so as to obtain Compound 4 ((R)-2,5-dimethyl-1-(I-phenylethyl)-1H-pyrrole-3-carbaldehyde) as a yellow solid (110 mg, yield: 97.3%). MS (ESI) m/z: 228 $[M+H]^+$. TLC:petroleum ether/ethyl acetate (5:1); $R_f$ (Compound 3)=0.6; $R_f$ (Compound 4)=0.4.

(3) Preparation Method of Compound AB29506 ((S,E)-3-(2,5-dimethyl-1-(1-phenylethyl)-1H-pyrrol-3-yl)-2-(6-methoxy-3H-imidazo[4,5-c]pyridin-2-yl) acrylonitrile)

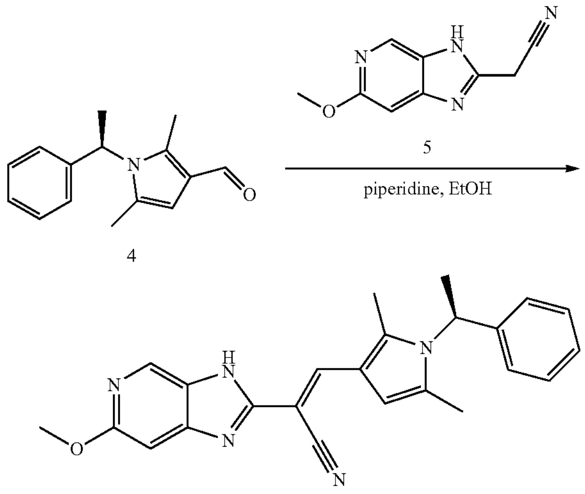

5 4 AB29506

Compound 4 ((R)-2,5-dimethyl-1-(1-phenylethyl)-1H-pyrrole-3-carbaldehyde) (60 mg, 0.26 mmol, 1 eq) was dissolved in ethanol (2 mL). Compound 5 (2-(6-methoxy-3H-imidazo[4,5-c]pyridin-2-yl)acetonitrile) (49 mg, 0.26 mmol, 1 eq) and piperidine (22 mg, 0.26 mmol, 1 eq) were added thereto. The mixture was heated under reflux and stirred for 2 hours. After the reaction mixture was cooled, the solid was filtered and concentrated, so as to obtain Compound AB29506 ((S,E)-3-(2,5-dimethyl-1-(1-phenylethyl)-1H-pyrrol-3-yl)-2-(6-methoxy-3H-imidazo[4,5-c]pyridin-2-yl)acrylonitrile) as a yellow solid (32 mg, yield: 31%). MS (ESI) m/z: 398 $[M+H^+]$. $^1H$ NMR (400 MHz, DMSO-$d_6$) δ 8.53 (s, 1H), 8.15 (s, 1H), 7.41-7.37 (m, 2H), 7.31-7.29 (m, 1H), 7.11 (d, J=8 Hz, 2H), 6.92 (s, 1H), 6.84 (s, 1H), 5.77-5.71 (m, 1H), 3.92 (s, 3H), 2.35 (s, 3H), 2.06 (s, 3H), 1.84 (d, J=8 Hz, 1H).

Example 80: Synthesis of Compound AB29507 ((E)-3-(2,5-dimethyl-1-(pyridin-2-ylmethyl)-1H-pyrrol-3-yl)-2-(6-methoxy-3H-imidazo[4,5-c]pyridin-2-yl)acrylonitrile)

AB29507 was synthesized in the same manner as in Example 79 (yield: 42.2%). $^{1}H$ NMR (400 MHz, DMSO-$d_6$) δ 12.82 (s, 1H), 8.51 (d, J=5.2 Hz, 1H), 8.44 (s, 1H), 8.08 (s, 1H), 7.53-7.51 (m, 1H), 7.26-7.24 (m, 1H), 6.98 (d, J=7.2 Hz, 1H), 6.82 (s, 1H), 6.73 (s, 1H), 5.25 (s, 2H), 3.84 (s, 3H), 2.39 (s, 3H), 2.16 (s, 3H).

Example 81: Synthesis of Compound AB29508 ((E)-3-(2,5-dimethyl-1-(pyrazin-2-ylmethyl)-1H-pyrrol-3-yl)-2-(6-methoxy-3H-imidazo[4,5-c]pyridin-2-yl)acrylonitrile)

AB29508 was synthesized in the same manner as in Example 79 (yield: 37.3%). $^{1}H$ NMR (400 MHz, DMSO-$d_6$) δ 12.83 (s, 1H), 8.59 (d, J=1.2 Hz, 2H), 8.58 (d, J=2.4 Hz, 1H), 8.44 (s, 1H), 8.07 (s, 1H), 6.81 (s, 1H), 6.74 (s, 1H), 5.36 (s, 2H), 3.85 (s, 3H), 2.41 (s, 3H), 2.18 (s, 3H).

Example 82: Synthesis of Compound AB29512 ((E)-3-(2,5-dimethyl-1-(pyridin-4-ylmethyl)-1H-pyrrol-3-yl)-2-(6-methoxy-3H-imidazo[4,5-c]pyridin-2-yl)acrylonitrile)

AB29512 was synthesized in the same manner as in Example 79 (yield: 41.2%). $^{1}H$ NMR (400 MHz, DMSO-$d_6$) δ 12.84 (s, 1H), 8.52-8.50 (m, 2H), 8.44 (s, 1H), 8.10 (s, 1H), 6.92 (d, J=8 Hz, 2H), 6.88 (s, 1H), 6.74 (s, 1H), 5.26 (s, 2H), 3.84 (s, 3H), 2.33 (s, 3H), 2.12 (s, 3H).

Example 83: Synthesis of Compound AB24397 ((E)-3-(1-(furan-2-ylmethyl)-2,5-dimethyl-1H-pyrrol-3-yl)-2-(6-methoxy-3H-imidazo[4,5-c]pyridin-2-yl)acrylonitrile)

(1) Synthetic Method of Compound 3 (1-(furan-2-ylmethyl)-2,5-dimethyl-1H-pyrrole)

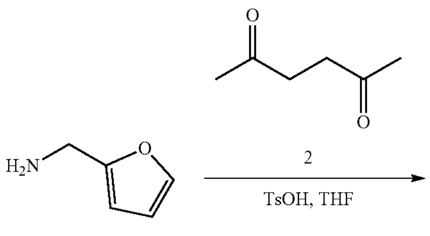

2

1

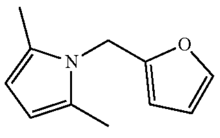

3

Compound 1 (2-furanmethylamine) (3 g, 30.89 mmol, 1.0 eq) was dissolved in tetrahydrofuran (50 mL). Compound 2 (2,5-hexanedione) (5.3 g, 46.33 nmol, 1.5 eq), 3 A molecular sieve (3 g) and p-toluenesulfonic acid (2.1 g, 12.35 nmol, 0.4 eq) were added thereto. The reactants were heated under reflux and stirred overnight. The solid was filtered and then concentrated. The residue was purified by flash column chromatography FCC (petroleum ether/ethyl acetate=1/1), so as to obtain Compound 3 (1-(furan-2-ylmethyl)-2,5-dimethyl-1H-pyrrole) as a white solid (4.7 g, yield: 87%). MS (ESI) m/z: 176 $[M+H]^+$. TLC:petroleum ether/ethyl acetate (10:1); $R_f$(Compound 1)=0.1; $R_f$(Compound 3)=0.6.

(2) Preparation Method of Compound 4 (1-(furan-2-ylmethyl)-2,5-dimethyl-1H-pyrrole-3-carbaldehyde)

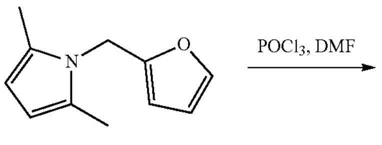

3

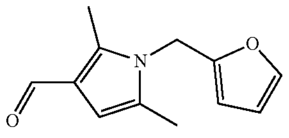

4

Under the protection of nitrogen gas, phosphorus oxychloride (1.3 g, 8.55 mmol, 1.5 eq) was added dropwise to dimethylformamide (10 mL) at 0° C. The mixture was stirred and reacted at 0° C. for 30 minutes and then warmed to room temperature. Compound 3 (1-(furan-2-ylmethyl)-2,5-dimethyl-1H-pyrrole) (1 g, 5.7 mmol, 1.0 eq) was dissolved in dimethylformamide (3 mL). Under the protection of nitrogen gas, the reactants were heated to 100° C. and then stirred for 1 hour. After the reaction mixture was cooled, the mixture was poured into ice water, and the pH of the resulting mixture was adjusted to 10 with 30% NaOH aqueous solution. The mixture was extracted with ethyl acetate and then washed with brine. The organic layer was dried over anhydrous sodium sulfate, filtered and concentrated. The residue was purified by flash column chromatography (petroleum ether/ethyl acetate=30/1), so as to obtain Compound 4 (1-(furan-2-ylmethyl)-2,5-dimethyl-1H-pyrrole-3-carbaldehyde) as a white solid (630 mg, yield: 54.3%). MS (ESI) m/z: 204 $[M+H]^+$. TLC:petroleum ether/ethyl acetate (5:1); $R_f$ (Compound 3)=0.7; $R_f$ (Compound 4)=0.5.

(3) Synthetic Method of Compound AB24397 ((E)-3-(1-(furan-2-ylmethyl)-2,5-dimethyl-1H-pyrol-3-yl)-2-(6-methoxy-3H-imidazo[4,5-c]pyridin-2-yl) acrylonitrile)

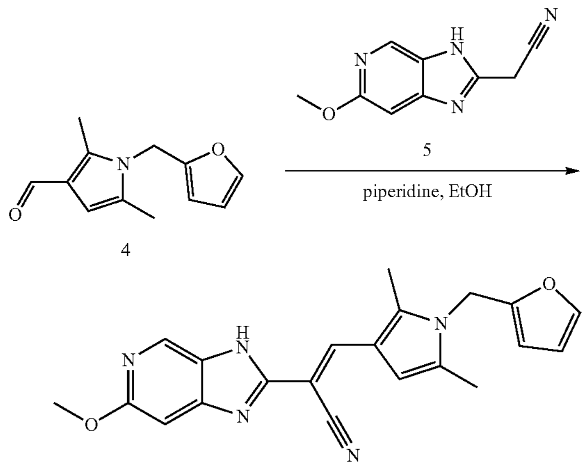

5
4
AB24397

Compound 4 (1-(furan-2-ylmethyl)-2,5-dimethyl-1H-pyrrole-3-carbaldehyde) (100 mg, 0.429 mmol, 1.0 eq) was dissolved in ethanol (2 mL). Compound 5 (2-(6-methoxy-3H-imidazo[4,5-c]pyridin-2-yl)acetonitrile) (92 mg, 0.492 mmol, 1 eq) and piperidine (42 mg, 0.492 mmol, 1 eq) were added thereto. The mixture was heated under reflux and stirred for 2 hours. After the reaction mixture was cooled, the solid was filtered and concentrated, so as to obtain Compound AB24397 ((E)-3-(1-(furan-2-ylmethyl)-2,5-dimethyl-1H-pyrrol-3-yl)-2-(6-methoxy-3H-imidazo[4,5-c]pyridin-2-yl)acrylonitrile) as a yellow solid (94 mg, yield, 51.1%). MS (ESI) m/z: 374 [M+H$^+$]. $^1$H NMR (400 MHz, DMSO-d$_6$) δ 12.81 (s, 1H), 8.42 (s, 1H), 8.07 (s, 1H), 7.59 (s, 1H), 6.76 (s, 2H), 6.40 (s, 2H), 5.14 (s, 2H), 3.84 (s, 3H), 2.49 (s, 3H) 2.27 (s, 3H).

Example 84: Synthesis of Compound AB24398 ((E)-3-(1-benzyl-2,5-dimethyl-1H-pyrrol-3-yl)-2-(6-methoxy-3H-imidazo[4,5-c]pyridin-2-yl)acrylonitrile)

AB24398 was synthesized in the same manner as in Example 83 (yield: 48.5%). $^1$H NMR (400 MHz, DMSO-d$_6$) δ 8.42 (s, 1H), 8.11 (s, 1H), 7.33-7.25 (m, 3H), 6.94 (d, J=4 Hz, 2H), 6.85 (s, 1H), 6.76 (s, 1H), 5.19 (s, 2H), 3.84 (s, 3H), 2.35 (s, 3H) 2.13 (s, 3H).

Example 85: Synthesis of Compound AB24399 ((E)-3-(2,5-dimethyl-1-(thiophen-2-ylmethyl)-1H-pyrrol-3-yl)-2-(6-methoxy-3H-imidazo[4,5-c]pyridin-2-yl)acrylonitrile)

AB24399 was synthesized in the same manner as in Example 83 (yield: 56.3%). $^1$H NMR (400 MHz, DMSO-d$_6$) δ 12.82 (s, 1H), 8.43 (s, 1H), 8.09 (s, 1H), 7.45 (s, 1H), 6.99-6.95 (m, 2H), 6.81 (s, 1H), 6.77 (s, 1H), 5.35 (s, 2H), 3.85 (s, 3H), 2.46 (s, 3H) 2.25 (s, 3H).

Example 86: Synthesis of Compound AB24264 ((E)-2-(3-(2-(1-(1-H-benzo[d]imidazol-2-yl]-2-cyanovinyl])-2,5-dimethyl-1H-pyrrol-1-yl)-4,5-dimethylthiophene-3-carbonitrile)

(1) Synthesis of Compound 3 (2-(2,5-dimethyl-1H-pyrrol-1-yl)-4,5-dimethylthiophene-3-carbonitrile)

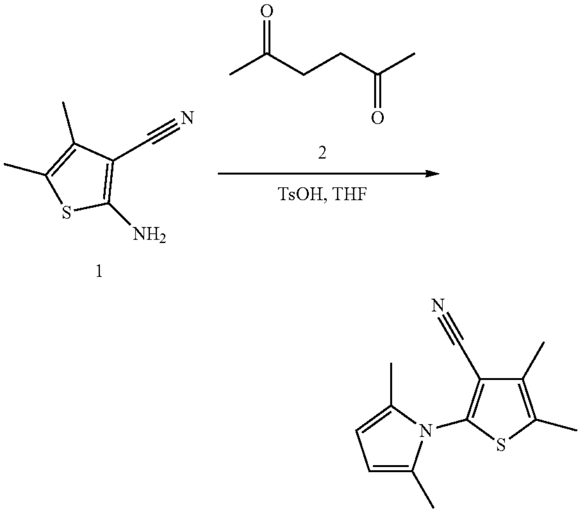

2
1
3

Compound 1 (2-amino-3-cyano-4,5-dimethylthiophene) (1.0 g, 6.57 mmol, 1.0 eq) was dissolved in tetrahydrofuran (30 mL). Compound 2 (2,5-hexanedione) (1.2 g, 10.51 mmol, 1.6 eq), 3 A molecular sieve (2 g) and p-toluenesulfonic acid hydrate (450 mg, 2.63 mmol, 0.4 eq) were added thereto. The reactants were heated under reflux and stirred overnight. The solid was filtered off, and the filtrate was concentrated. The residue was purified by flash column chromatography (petroleum ether/ethyl acetate=100/1), so as to obtain Compound 3 (2-(2,5-dimethyl-1H-pyrol-1-yl)-4,5-dimethylthiophene-3-carbonitrile) as a yellow solid (650 mg, yield: 42.9%). MS (ESI) m/z: 231 [M+H]$^+$. TLC: petroleum ether/ethyl acetate (10:1); $R_f$ (Compound 1)=0.2; $R_f$ (Compound 3)=0.7.

(2) Synthesis of Compound 4 (2-(3-formyl-2,5-dimethyl-1H-pyrrol-1-yl)-4,5-dimethylfuran-3-carbonitrile)

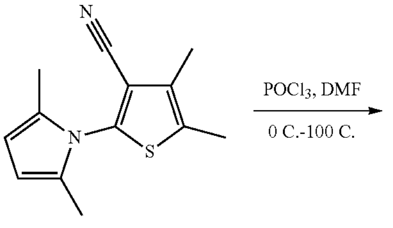

3

-continued

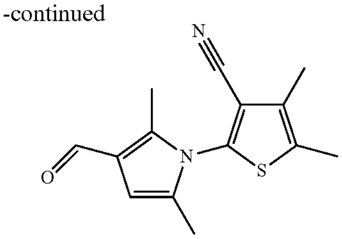

4

Under the protection of nitrogen gas, phosphorus oxychloride (432 mg, 2.82 mmol, 1.0 eq) was added dropwise to dimethylformamide (5 mL) at 0° C. The mixture was stirred at 0° C. for 30 minutes and was then warmed to room temperature. A solution of Compound 3 (2-(2,5-dimethyl-1H-pyrrol-1-yl)-4,5-dimethylthiophene-3-carbonitrile) (650 mg, 2.82 mmol, 1.0 eq) in 2 ml of dimethylformamide was added to the above-mentioned reaction system. The mixture was heated to 100° C., and was stirred for 2 hours under the protection of nitrogen gas. After the reaction mixture was cooled, the reaction mixture was poured into ice water, and then the pH of the resulting mixture was adjusted to 10 with 30% NaOH solution. The reaction solution was extracted with ethyl acetate and washed with brine. Afterwards, the organic layer was dried over anhydrous sodium sulfate, filtered and concentrated. The residue was purified by flash column chromatography (petroleum ether/ethyl acetate=100/1), so as to obtain Compound 4 (2-(3-formyl-2,5-dimethyl-1H-pyrrol-1-yl)-4,5-dimethylfuran-3-carbonitrile) as a yellow solid (390 mg, yield: 52.5%). MS (ESI) m/z: 259 $[M+H]^+$. TLC:petroleum ether/ethyl acetate (20:1); R(Compound 3)=0.7; $R_f$ (Compound 4)=0.5.

(3) Preparation of Compound AB24264 ((E)-2-(3-(2-(1-(1-H-benzo[d]imidazol-2-yl]-2-cyanovinyl])-2,5-dimethyl-1H-pyrrol-1-yl)-4,5-dimethylthiophene-3-carbonitrile

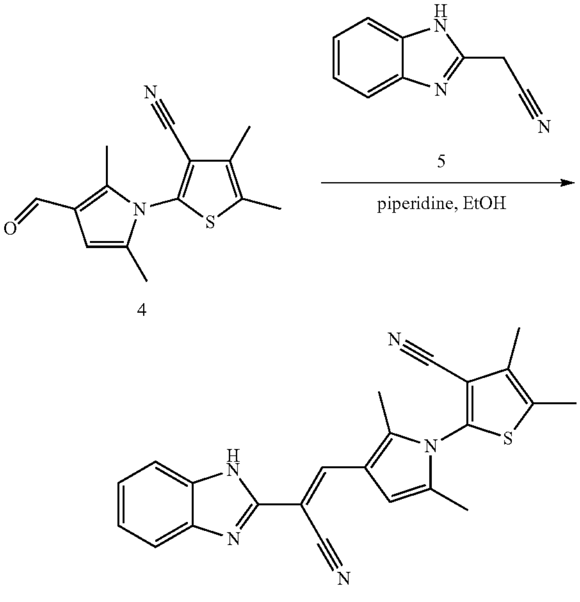

5

4

AB24264

Compound 4 (2-(3-formyl-2,5-dimethyl-1H-pyrrol-1-yl)-4,5-dimethylfuran-3-carbonitrile) (160 mg, 0.62 mmol, 1.0 eq) was dissolved in ethanol (3 mL). Compound 5 (2-cyanomethylbenzimidazole) (98 mg, 0.62 mmol, 1.0 eq) and piperidine (53 mg, 0.62 mmol, 1.0 eq) were added thereto. The mixture was heated under reflux and stirred for 1 hour. After the completion of the reaction, the mixture was cooled to room temperature and filtered. The solid was collected and dried, so as to obtain Compound AB24264 ((E)-2-(3-(2-(1-(1-H-benzo[d]imidazol-2-yl]-2-cyanovinyl])-2,5-dimethyl-1H-pyrrol-1-yl)-4,5-dimethylthiophene-3-carbonitrile) as a yellow solid (120 mg, yield: 48.8%). MS (ESI) m/z: 398 $[M+H]^+$. HNMR $^1H$ NMR (400 MHz, $CDCl_3$) δ 8.12 (s, 1H), 7.53 (s, 2H), 7.18 (d, J=3.1 Hz, 2H), 6.96 (s, 1H), 2.41 (s, 3H), 2.30 (s, 3H), 2.23 (s, 3H), 2.09 (s, 3H).

Example 87: Synthesis of Compound AB24354 ((E)-5-(3-(2-cyano-2-(5-methoxy-1H-benzo[d]imidazol-2-yl)vinyl)-2,5-dimethyl-1H-pyrrol-1-yl)-2-methyloxazole-4-carbonitrile)

(1) Synthesis of Compound 3 (5-(2,5-dimethyl-1H-pyrrol-1-yl)-2-methyloxazole-4-carbonitrile)

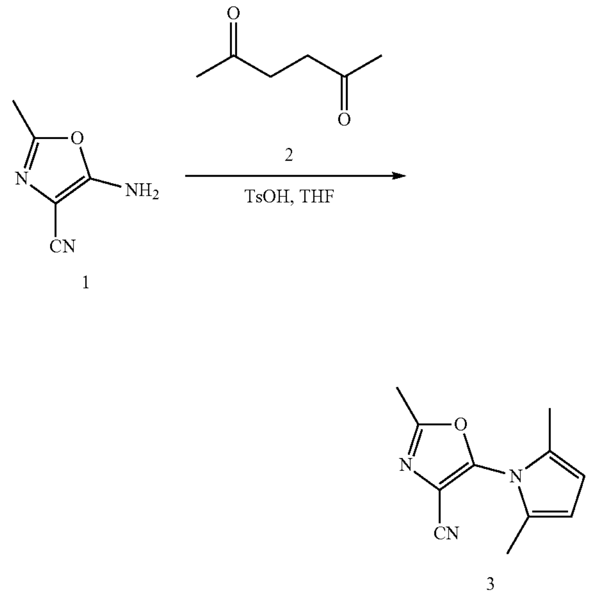

2

1

3

Compound 1 (5-amino-2-methyloxazole-4-carbonitrile) (2 g, 16.26 mmol, 1.0 eq) was dissolved in tetrahydrofuran (20 mL). Afterwards, Compound 2 (2,5-hexanedione) (2.78 g, 24.39 mmol, 1.5 eq), 3 A molecular sieve 3 A MS (2.0 g) and p-toluenesulfonic acid hydrate (300 mg, 3.252 mmol, 0.2 eq) were added thereto. The mixture was heated under reflux and stirred overnight. The solid was collected, filtered and concentrated. The residue was purified by flash column chromatography (petroleum ether/ethyl acetate=20/1), so as to obtain Compound 3 (5-(2,5-dimethyl-1H-pyrrol-1-yl)-2-methyloxazole-4-carbonitrile) as a white solid (2.3 g, yield: 70.3%). MS (ESI) m/z: 202 $[M+H]^+$. TLC:petroleum ether/ethyl acetate (10:1); $R_f$ (Compound 1)=0.2; $R_f$ (Compound 3)=0.7.

(2) Synthesis of Compound 4 (5-(3-formyl-2,5-dimethyl-1H-pyrrol-1-yl)-2-methyloxazole-4-carbonitrile)

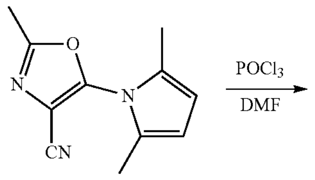

3

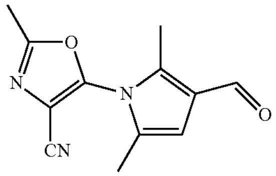

4

Under the protection of nitrogen gas, phosphorous oxychloride (453 mg, 2.98 mmol, 1.2 eq) was added dropwise to dimethylformamide (30 mL) at zero degrees Celsius. The mixture was stirred at zero degrees Celsius for 30 minutes and then warmed to room temperature. A solution of Compound 3 (5-(2,5-dimethyl-1H-pyrrol-1-yl)-2-methyloxazole-4-carbonitrile) (500 mg, 2.48 mmol, 1.0 eq) in 5 mL of dimethylformamide was added to the above-mentioned reaction system. Under the protection of nitrogen gas, the above-mentioned mixture was heated to 100 degrees Celsius and stirred for two hours. After the reaction mixture was cooled, the mixture was poured into ice water, and the pH of the resulting mixture was adjusted to 10 with 30% sodium hydroxide solution. The mixture was extracted with ethyl acetate and washed with brine. The organic layer was dried over anhydrous sodium sulfate, filtered and concentrated. The residue was purified by flash column chromatography (petroleum ether/ethyl acetate=100/1), so as to obtain Compound 4 (5-(3-formyl-2,5-dimethyl-1H-pyrol-1-yl)-2-methyloxazole-4-carbonitrile) as a yellow solid (300 mg, yield: 52%). MS (ESI) m/z: 230 [M+H]$^+$. TLC:petroleum ether/ethyl acetate (5:1); $R_f$ (Compound 3)=0.7; $R_f$ (Compound 4)=0.3.

(3) Synthesis of Compound AB24354 ((E)-5-(3-(2-cyano-2-(5-methoxy-1H-benzo[d]imidazol-2-yl)vinyl)-2,5-dimethyl-1H-pyrrol-1-yl)-2-methyloxazole-4-carbonitrile)

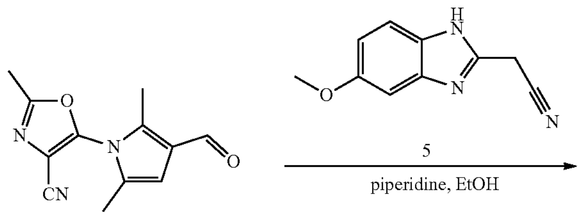

4

-continued

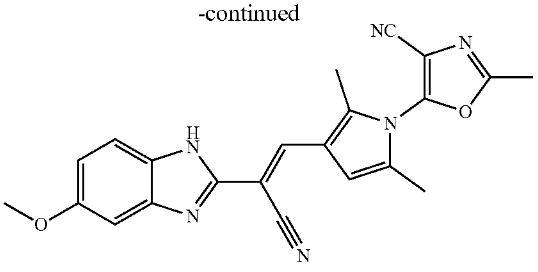

AB24354

Compound 4 (5-(3-formyl-2,5-dimethyl-1H-pyrol-1-yl)-2-methyloxazole-4-carbonitrile) (52 mg, 0.228 mmol, 1 eq) was dissolved in 1 mL of ethanol. Compound 5 (2-(5-methoxy-1H-benzo[d]imidazol-2-yl)acetonitrile) (43 mg, 0.228 mmol, 1 eq) and two drops of piperidine were added thereto. The mixture was heated under reflux and stirred for 2 hours. After the completion of the reaction, the mixture was cooled to room temperature and filtered. The solid was collected and dried, so as to obtain Compound AB24354 ((E)-5-(3-(2-cyano-2-(5-methoxy-1H-benzo[d]imidazol-2-yl)vinyl)-2,5-dimethyl-1H-pyrrol-1-yl)-2-methyloxazole-4-carbonitrile) as a yellow solid (30 mg, yield: 33.2%). MS (ESI) m/z: 399 [M+H$^+$]. $^1$H NMR (400 MHz, DMSO-$d_6$) δ 12.76 (s, 1H), 8.50 (s, 1H), 7.45 (s, 1H), 6.98 (s, 2H), 6.82 (d, J=8.8 Hz, 1H), 3.77 (s, 3H), 2.54 (s, 3H), 2.39 (s, 3H), 2.20 (s, 3H).

Example 88: Synthesis of Compound AB24359 ((E)-5-(3-(2-cyano-2-(6-methoxy-3H-imidazo[4,5-c]pyridyl-2-yl)vinyl)-2,5-dimethyl-1H-pyrrol-1-yl)-2-methyloxazole-4-carbonitrile)

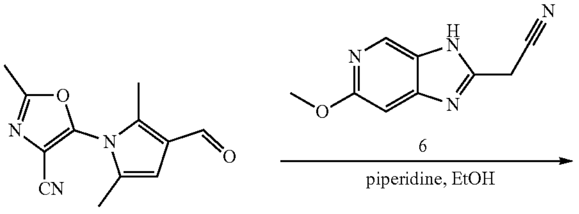

4

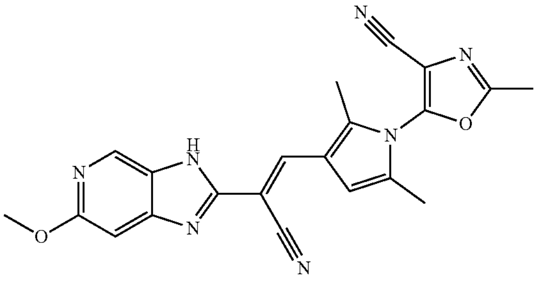

AB24359

Compound 4 was prepared according to Example 87 as mentioned above. Afterwards, Compound 4 (5-(3-formyl-2,5-dimethyl-1H-pyrrol-1-yl)-2-methyloxazole-4-carbonitrile) (80 mg, 0.349 mmol, 1 eq) was dissolved in ethanol (1 mL). Compound 6 (2-(6-methoxy-3H-imidazo[4,5-c]pyridin-2-yl)acetonitrile) (66 mg, 0.349 mmol, 1 eq) and two drops of piperidine were added thereto. The mixture was heated under reflux and stirred for 2 h. After the completion of the reaction, the resulting mixture was cooled to room temperature and filtered. The solid was collected and dried, so as to obtain Compound AB24359 ((E)-5-(3-(2-cyano-2-(6-methoxy-3H-imidazo[4,5-c]pyridyl-2-yl)vinyl)-2,5-dimethyl-1H-pyrrol-1-yl)-2-methyloxazole-4-carbonitrile) as a yellow solid (30 mg, yield: 21.6%). MS (ESI) m/z: 400 $[M+H^+]$. $^1H$ NMR (400 MHz, DMSO-$d_6$) δ 12.97 (s, 1H), 8.50 (s, 1H), 8.13 (s, 1H), 6.99 (s, 1H), 6.81 (s, 1H), 3.85 (s, 3H), 2.54 (s, 3H), 2.41 (s, 3H), 2.20 (s, 3H).

Example 89: Synthesis of Compound AB24358 ((E)-2-(3-chloro-4-(2-cyano-2-(6-methoxy-3H-imidazo[4,5-c]pyridin-2-yl)vinyl)-2,5-dimethyl-1H-pyrrol-1-yl)-5-methylthiophene-3-carbonitrile)

(1) Synthesis of Compound 2 (2-(3-chloro-4-formyl-2,5-dimethyl-1H-pyrrol-1-yl)-5-methylthiophene-3-carbonitrile)

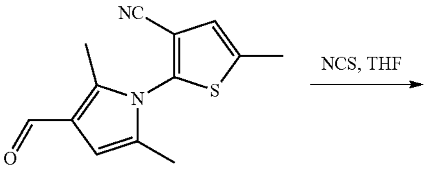

1

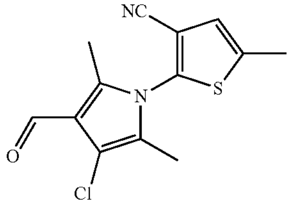
2

At −78° C., NCS (192 mg, 1.44 mmol, 1.1 eq) was added to a solution of Compound 1 (2-(3-formyl-2,5-dimethyl-1H-pyrrol-1-yl)-5-methylthiophene-3-carbonitrile) (320 mg, 1.31 mmol, 1.0 eq) in tetrahydrofuran (8 mL). The mixture was stirred at room temperature for 8 h. After the completion of the reaction, the resulting mixture was concentrated. The residue was purified by preparative high-pressure liquid chromatography, so as to obtain Compound 2 (2-(3-chloro-4-formyl-2,5-dimethyl-1H-pyrrol-1-yl)-5-methylthiophene-3-carbonitrile) as a white solid (27 mg, yield: 7.4%). MS (ESI) m/z: 279.10 $[M+H^+]$. TLC:petroleum ether/ethyl acetate (3/1); $R_f$(Compound 1)=0.5; $R_f$(Compound 2)=0.55.

(2) Synthesis of Compound AB24358 ((E)-2-(3-chloro-4-(2-cyano-2-(6-methoxy-3H-imidazo[4,5-c]pyridin-2-yl)vinyl)-2,5-dimethyl-1H-pyrrol-1-yl)-5-methylthiophene-3-carbonitrile)

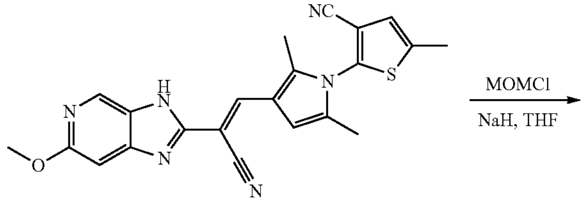

3

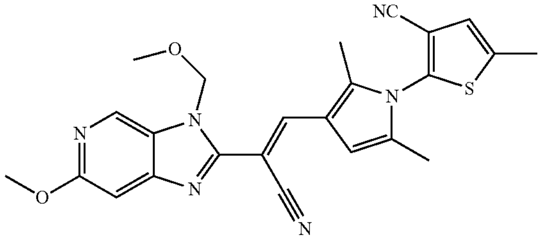
AB24369

To a solution of Compound 2 (2-(3-chloro-4-formyl-2,5-dimethyl-1H-pyrrol-1-yl)-5-methylthiophene-3-carbonitrile) (27 mg, 0.10 mmol, 1.0 eq) in ethanol (1.0 mL), Compound 3 (2-(6-methoxy-3H-imidazo[4,5-c]pyridin-2-yl)acetonitrile) (18.2 mg, 0.1 mmol, 1.0 eq) and piperidine (8.5 mg, 0.1 mmol, 1 eq) were added. The mixture was heated under reflux and stirred for 1 h. After the completion of the reaction, the mixture was concentrated and then purified by preparative high-pressure liquid chromatography, so as to obtain Compound AB24358 ((E)-2-(3-chloro-4-(2-cyano-2-(6-methoxy-3H-imidazo[4,5-c]pyridin-2-yl)vinyl)-2,5-dimethyl-1H-pyrrol-1-yl)-5-methylthiophene-3-carbonitrile) as a yellow solid (12 mg, yield: 26.8%). MS (ESI) m/z: 449.00 $[M+H^+]$. $^1H$ NMR (400 MHz, $CD_3OD$-d4): δ 8.67 (s, 1H), 8.32 (s, 1H), 7.25 (s, 1H), 7.16 (s, 1H), 4.12 (s, 3H), 2.58 (s, 3H), 2.30 (s, 3H), 2.06 (s, 3H).

Example 90: Synthesis of Compound AB24370 ((E)-ethyl-3-(2-cyano-2-(6-methoxy-3H-imidazo[4,5-c]pyridin-2-yl)vinyl)-2,5,5'-trimethyl-1'H-[1,2'-bipyrrole]-3'-carboxylate)

(1) Synthesis of Compound 3 (ethyl 2,5,5'-trimethyl-1'H-[1,2'-bipyrrole]-3'-carboxylate)

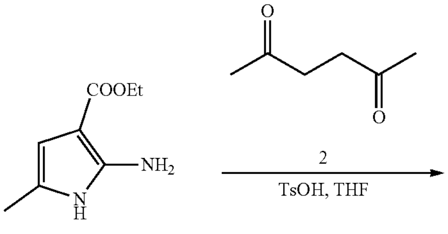

1

-continued

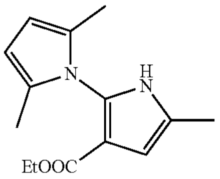

3

Compound 1 (ethyl 2-amino-5-methyl-1H-pyrrole-3-carboxylate) (0.8 g, 4.761 mmol, 1.0 eq) was dissolved in tetrahydrofuran (10 mL). Compound 2 (2,5-hexanedione) (0.815 g, 7.142 mmol, 1.5 eq), 3 A molecular sieve (50 g) and p-toluenesulfonic acid hydrate (1.4 g, 7.44 mmol, 0.4 eq) were added thereto. The mixture was heated under reflux and stirred overnight. The solid was filtered and concentrated. The residue was purified by flash column chromatography (petroleum ether/ethyl acetate=5/1), so as to obtain Compound 3 (ethyl 2,5,5'-trimethyl-1'H-[1,2'-bipyrrole]-3'-carboxylate) as a white solid (0.94 g, yield: 80.2%). MS (ESI) m/z: 247 $[M+H]^+$. TLC:petroleum ether/ethyl acetate (5:1); $R_f$ (Compound 1)=0.1; $R_f$(Compound 3)=0.6.

(2) Synthesis of Compound 4 (ethyl 3-formyl-2,5,5'-trimethyl-1'H-[1,2'-bipyrrole]-3'-carboxylate)

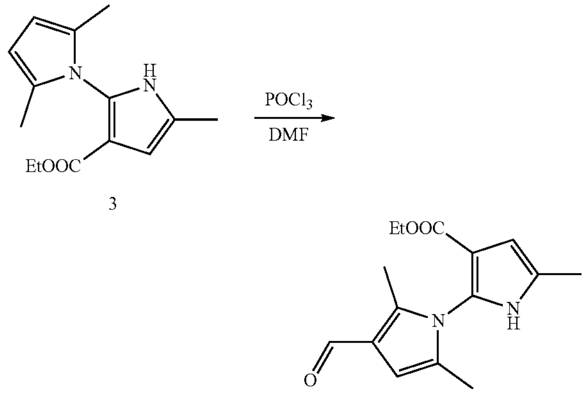

3

4

Phosphorus oxychloride (202 mg, 1.33 mmol, 1.5 eq) was added dropwise to dimethylformamide (30 mL) at 0° C. in the presence of nitrogen gas. The mixture was stirred at 0° C. for 30 minutes and then warmed to room temperature. Afterwards, a solution of Compound 3 (ethyl 2,5,5'-trimethyl-1'H-[1,2'-bipyrrole]-3'-carboxylate) (200 mg, 0.88 mmol, 1.0 eq) in dimethylformamide (4 mL) was added to the above-mentioned reaction system. In the presence of nitrogen gas, the mixture was heated to 80° C. and stirred for 1 h. After the reactants were cooled, the mixture was poured into ice water, and then the pH of the resulting mixture was adjusted to 10 with 30% NaOH aqueous solution. The mixture was extracted with ethyl acetate and then washed with saturated sodium chloride solution. The organic layer was dried over anhydrous sodium sulfate, filtered and then concentrated. The residue was purified by flash column chromatography (petroleum ether/ethyl acetate=2/1), so as to obtain Compound 4 (ethyl 3-formyl-2,5,5'-trimethyl-1'H-[1,2'-bipyrrole]-3'-carboxylate) as a white solid (150 mg, yield: 67%). MS (ESI) m/z: 275 $[M+H]^+$. TLC:petroleum ether/ethyl acetate (2:1); $R_f$ (Compound 3)=0.5; $R_f$ (Compound 4)=0.3.

(3) Synthesis of AB24370 ((E)-ethyl-3-(2-cyano-2-(6-methoxy-3H-imidazo[4,5-c]pyridin-2-yl)vinyl)-2,5,5'-trimethyl-1'H-[1,2'-bipyrrole]-3'-carboxylate)

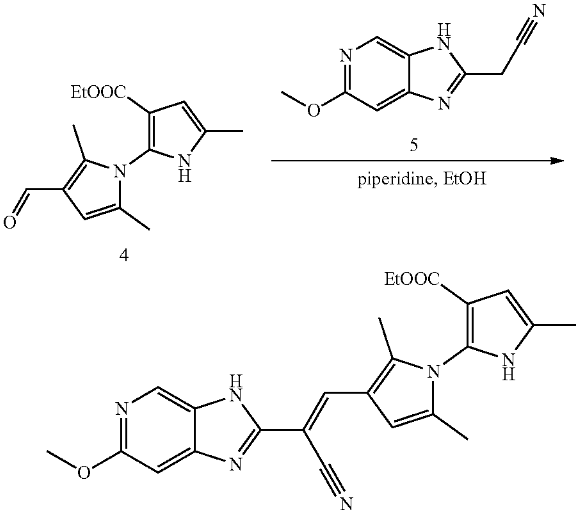

4

5

AB24370

To a solution of Compound 4 (ethyl 3-formyl-2,5,5'-trimethyl-1'H-[1,2'-bipyrrole]-3'-carboxylate) (68 mg, 0.268 mmol, 1.0 eq) in EtOH (1.5 mL), Compound 5 (2-(6-methoxy-3H-imidazo[4,5-c]pyridin-2-yl)acetonitrile) (50 mg, 0.268 mmol, 1 eq) and piperidine (45 mg, 0.536 mmol, 2 eq) were added. The mixture was heated to reflux and stirred for 1 h. After the completion of the reaction, the mixture was concentrated and purified by preparative HPLC, so as to obtain AB24370 ((E)-ethyl-3-(2-cyano-2-(6-methoxy-3H-imidazo[4,5-c]pyridin-2-yl)vinyl)-2,5,5'-trimethyl-1'H-[1,2'-bipyrrole]-3'-carboxylate) as a yellow solid (20 mg, yield: 18.1%). MS (ESI) m/z: 445 $[M+H^+]$. $^1H$ NMR (400 MHz, DMSO-$d_6$) δ 12.91 (s, 1H), 11.95 (s, 1H), 8.48 (s, 1H), 8.16 (s, 1H), 6.89 (s, 1H), 6.80 (s, 1H), 6.27 (s, 1H), 4.01 (s, 2H), 3.88 (s, 3H), 2.20 (s, 611) 1.98 (s, 3H), 1.05 (s, 3H).

Example 91: Synthesis of Compound AB24366 ((E)-3-(2,5-dimethyl-1-(4-methylthiazol-2-yl)-1H-pyrrol-3-yl)-2-(6-methoxy-3H-imidazo[4,5-c]pyridin-2-yl)acrylonitrile)

Compound AB24366 was obtained in the same manner as in Example 90 (yield: 22.7%). $^1H$ NMR (400 MHz, DMSO-$d_6$s) δ 12.98 (s, 1H), 8.50 (s, 1H), 8.12 (s, 1H), 7.54 (s, 1H), 6.92 (s, 1H), 6.77 (s, 1H), 3.86 (s, 31), 2.41 (s, 3H), 2.35 (s, 3H), 2.14 (s, 3H).

Example 92: Synthesis of Compound AB24367 ((E)-3-(2,5-dimethyl-1-(5-methyl-1,3,4-thiadiazol-2-yl)-1H-pyrrol-3-yl)-2-(6-methoxy-3H-imidazo[4,5-c]pyridin-2-yl) acrylonitrile)

Compound AB24367 was obtained in the same manner as in Example 90 (yield: 48%). $^1H$ NMR (400 MHz, DMSO- $d_6$s) δ 12.99 (s, 1H), 8.49 (s, 1H), 8.16 (s, 1H), 6.97 (s, 1H), 6.80 (s, 1H), 3.85 (s, 3H), 2.81 (s, 3H), 2.37 (s, 3H), 2.16 (s, 3H).

Example 93: Synthesis of Compound AB24368 ((E)-3-(2,5-dimethyl-1-(5-methyl-1,3,4-oxadiazol-2-yl)-1H-pyrrol-3-yl)-2-(6-methoxy-3H)-imidazo[4,5-c]pyridin-2-yl)acrylonitrile)

Compound AB24368 was obtained in the same manner as in Example 90 (yield: 29.5%). $^1$H NMR (400 MHz, DMSO-$d_6$) δ 8.55 (s, 1H), 8.16 (s, 1H), 6.97 (s, 1H), 6.87 (s, 1H), 3.88 (s, 3H), 2.56 (s, 3H), 2.47 (s, 3H), 2.29 (s, 3H).

Example 94: Synthesis of Compound AB24376 ((E)-3-(1-(4,5-dimethyloxazol-2-yl)-2,5-dimethyl-1H-pyrrol-3-yl)-2-(6-methoxy-3H-imidazo[4,5-c]pyridin-2-yl)acrylonitrile)

Compound AB24376 was obtained in the same manner as in Example 90 (yield: 24.2%). $^1$H NMR (400 MHz, DMSO-$d_6$) δ 13.00 (s, 1H), 8.49 (s, 1H), 8.12 (s, 1H), 6.90 (s, 1H), 6.79 (s, 1H), 3.85 (s, 3H), 2.43 (s, 3H), 2.30 (s, 3H), 2.21 (s, 3H), 2.09 (s, 3H).

Example 95: Synthesis of Compound AB24361 ((E)-2-(3-(2-cyano-2-(6-methoxy-3H-imidazo[4,5-c]pyridin-2-yl)vinyl)-2,5-dimethyl-1H-pyrrol-1-yl)-5-methoxythiophene-3-carbonitrile)

(1) Preparation Method of Compound 2(2-amino-5-chlorothiophene-3-carbonitrile)

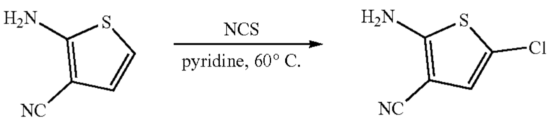

1 2

Compound 1 (2-aminothiophene-3-carbonitrile) (2.00 g, 16.1 mmol, 1 eq) was suspended in a pyridine solution (100 mL), and NCS (2.57 g, 19.3 mmol, 1.2 eq) was added thereto. In the presence of nitrogen gas, the mixture was heated to 60° C. and stirred for 4 h. After the completion of the reaction, the mixture was concentrated and then purified by flash column chromatography (petroleum ether/ethyl acetate=5/1), so as to obtain Compound 2 (2-amino-5-chlorothiophene-3-carbonitrile) as a white solid (1.2 g, yield: 47.0%). MS (ESI) m/z: 159 [M+H$^+$]. TLC:petroleum ether/ethyl acetate (5:1); $R_f$ (Compound 1)=0.4; $R_f$ (Compound 2)=0.42.

(2) Synthesis of Compound 4 (5-chloro-2-(2,5-dimethyl-1H-pyrrol-1-yl)thiophene-3-carbonitrile)

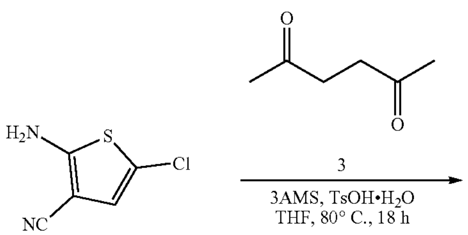

2

-continued

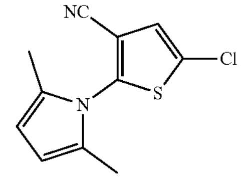

4

The crude Compound 2 (2-amino-5-chlorothiophene-3-carbonitrile) (1 g, 6.33 mmol, 1.0 eq) was dissolved in tetrahydrofuran (100 mL). Compound 3 (2,5-hexanedione) (1.08 g, 9.49 mmol, 1.5 eq), 3 A molecular sieve (3 g) and p-toluenesulfonic acid hydrate (240 mg, 1.27 mmol, 0.2 eq) were added thereto. The mixture was heated to 80° C., stirred for 24 h, filtered and concentrated, so as to obtain a solid, which was then purified by flash column chromatography (petroleum ether/ethyl acetate=3/1) to obtain Compound 4 (5-chloro-2-(2,5-dimethyl-1H-pyrrol-1-yl)thiophene-3-carbonitrile) as a white solid (400 mg, yield: 26.7%). MS (ESI) m/z: 237 [M+H$^+$]. TLC:petroleum ether/ethyl acetate (5:1); $R_f$ (Compound 2)=0.55; R (Compound 4)=0.7.

(3) Synthesis of Compound 5 (2-(2,5-dimethyl-1H-pyrrol-1-yl)-5-methoxythiophene-3-carbonitrile)

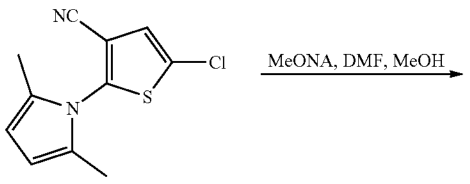

4

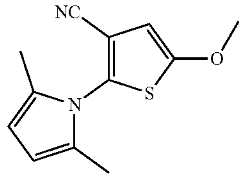

5

The crude Compound 4 (5-chloro-2-(2,5-dimethyl-1H-pyrrol-1-yl)thiophene-3-carbonitrile) (290 mg, 1.23 mmol, 1.0 eq) was dissolved in dimethylformamide (10 mL). Afterwards, a solution of MeONa (132 mg, 2.45 mmol, 2.0 eq) in methanol (2 mL) was added to the above-mentioned crude compound. The reactants were heated to 90° C. and stirred for 2 h. After the completion of the reaction, the resulting mixture was concentrated and then purified by flash column chromatography (petroleum ether/ethyl acetate=10/1), so as to obtain a colorless oily Compound 5 (2-(2,5-dimethyl-1H-pyrrol-1-yl)-5-methoxythiophene-3-carbonitrile). MS (ESI) m/z: 233 [M+H]$^+$. TLC:petroleum ether/ethyl acetate (10:1); $R_f$(Compound 4)=0.6; $R_f$ (Compound 5)=0.4.

(4) Synthesis of Compound 6 (2-(3-formyl-2,5-dimethyl-1H-pyrrol-1-yl)-5-methoxythiophene-3-carbonitrile)

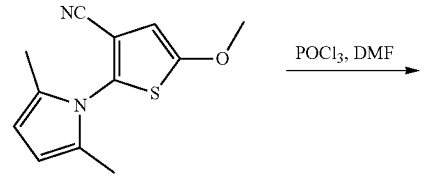

5

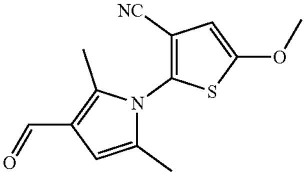

6

In the presence of nitrogen gas, phosphorus oxychloride (105 mg, 0.68 mmol, 2.0 eq) was added dropwise to dimethylformamide (4 mL) at 0° C. and then warmed to room temperature. Compound 5 (2-(2,5-dimethyl-1H-pyrrol-1-yl)-5-methoxythiophene-3-carbonitrile) was dissolved in dimethylformamide (2 mL). In the presence of nitrogen gas, the reactants were heated to 90° C. and stirred for 1 h. After the reaction mixture was cooled, the mixture was poured into ice water, and then the pH of the resulting mixture was adjusted to 9 with 30% NaOH aqueous solution. The mixture was extracted with ethyl acetate and then washed with saturated sodium chloride solution. The organic layer was dried over anhydrous sodium sulfate, filtered and concentrated. The residue was purified by flash column chromatography (petroleum ether/ethyl acetate=3/1), so as to obtain a colorless oily Compound 6 (2-(3-formyl-2,5-dimethyl-1H-pyrrol-1-yl)-5-methoxythiophene-3-carbonitrile). MS (ESI) m/z: 261 $[M+H]^+$. TLC:petroleum ether/ethyl acetate (3:1); $R_f$ (Compound 5)=0.8; $R_f$ (Compound 6)=0.3.

(5) Synthesis of Compound AB24361 ((E)-2-(3-(2-cyano-2-(6-methoxy-3H-imidazo[4,5-c]pyridin-2-yl)vinyl)-2,5-dimethyl-1H-pyrrol-1-yl)-5-methoxythiophene-3-carbonitrile)

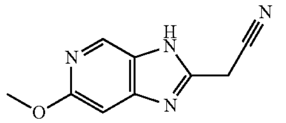

7

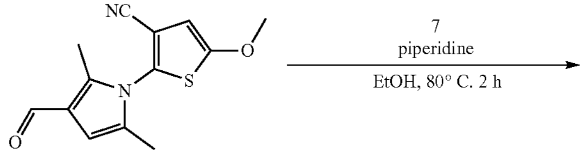

6

-continued

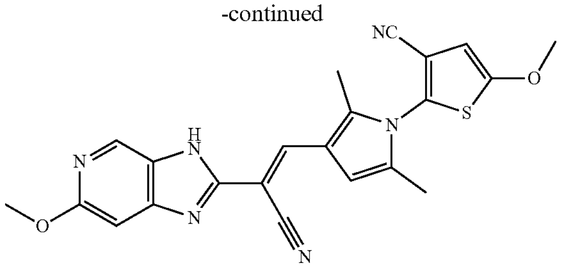

AB24361

Compound 6 (2-(3-formyl-2,5-dimethyl-1H-pyrrol-1-yl)-5-methoxythiophene-3-carbonitrile) (30 mg) was dissolved in ethanol (1 mL). Compound 7 (2-(6-methoxy-3H-imidazo[4,5-c]pyridin-2-yl)acetonitrile) (22 mg, 0.11 mmol, 1 eq) and one drop of piperidine were added thereto. The reactants were heated under reflux and stirred for 2 h. After the completion of the reaction, the resulting mixture was concentrated and then purified by preparative high-pressure liquid chromatography, so as to obtain Compound AB24361 ((E)-2-(3-(2-cyano-2-(6-methoxy-3H-imidazo[4,5-c]pyridin-2-yl)vinyl)-2,5-dimethyl-1H-pyrrol-1-yl)-5-methoxythiophene-3-carbonitrile) as a yellow solid (30 mg). MS (ESI) m/z: 431.25 $[M+H^+]$. $^1H$ NMR (400 MHz, DMSO-$d_6$): δ 8.52 (s, 1H), 8.16 (s, 1H), 6.96 (s, 1H), 6.88 (s, 1H), 6.85 (s, 1H), 3.97 (s, 3H), 3.88 (s, 3H), 2.32 (s, 3H), 2.11 (s, 3H).

Example 96: Synthesis of Compound AB24363 ((E)-2-(3-(2-cyano-2-(6-methoxy-3H-imidazo[4,5-c]pyridin-2-yl)vinyl)-2,5-dimethyl-1H-pyrrol-1-yl)-5-(trifluoromethyl)thiophene-3-carbonitrile)

(1) Synthesis of Compound 3 (2-(3-formyl-2,5-dimethyl-1H-pyrrol-1-yl)-5-(trifluoromethyl)thiophene-3-carbonitrile)

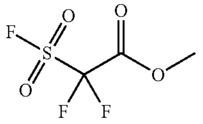

2

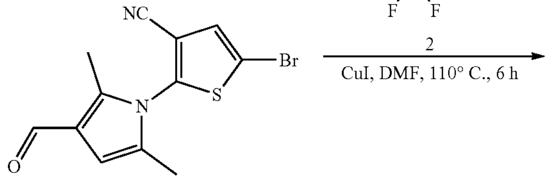

1

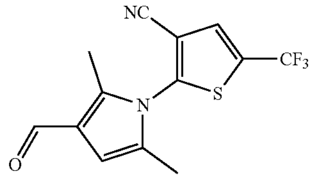

3

Compound 1 (5-bromo-2-(3-formyl-2,5-dimethyl-1H-pyrrol-1-yl)thiophene-3-carbonitrile) (20 mg, 0.06 mmol, 1 eq) and Compound 2 (methyl fluorosulfonyldifluoroacetate) (124 mg, 0.60 mmol, 10 eq) were dissolved in dimethylformamide (2 mL), and cuprous iodide CuI (34 mg, 0.18 mmol, 3.0 eq) was added thereto. In the presence of nitrogen gas, the mixture was heated to 100° C. and stirred for 1 h. After the reaction mixture was cooled, the mixture was poured into ice water, extracted with ethyl acetate, and washed with saturated aqueous sodium chloride solution. The organic layer was dried over anhydrous sodium sulfate, filtered and then concentrated. The residue was purified by flash column chromatography (petroleum ether/ethyl acetate=3/1), so as to obtain a colorless oily Compound 3 (2-(3-formyl-2,5-dimethyl-1H-pyrrol-1-yl)-5-(trifluoromethyl)thiophene-3-carbonitrile) (9 mg, yield: 46.7%). MS (ESI) m/z: 299 [M+H$^+$]. TLC:petroleum ether/ethyl acetate (3:1); $R_f$ (Compound 1)=0.4; $R_f$(Compound 3)=0.6.

(2) Synthesis of Compound AB24363 ((E)-2-(3-(2-cyano-2-(6-methoxy-3H-imidazo[4,5-c]pyridin-2-yl)vinyl)-2,5-dimethyl-1H-pyrrol-1-yl)-5-(trifluoromethyl)thiophene-3-carbonitrile)

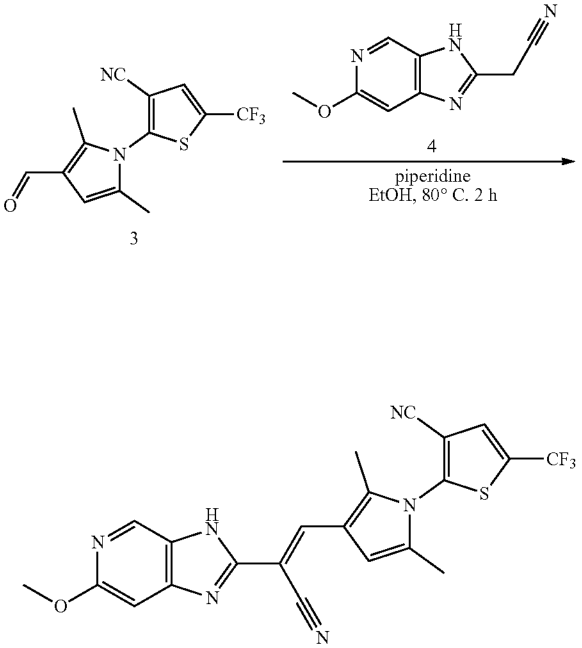

4

3

AB24363

Compound 3 (2-(3-formyl-2,5-dimethyl-1H-pyrrol-1-yl)-5-(trifluoromethyl)thiophene-3-carbonitrile) (9 mg, 0.03 mmol, 1 eq) was dissolved in ethanol (1 mL). Compound 4 (2-(6-methoxy-3H-imidazo[4,5-c]pyridin-2-yl)acetonitrile) (5 mg, 0.03 mmol, 1 eq) and one drop of piperidine were added thereto. The mixture was heated under reflux and stirred for 2 h. After the completion of the reaction, the mixture was cooled to room temperature and then filtered. The solid was collected and dried, so as to obtain Compound AB24363 ((E)-2-(3-(2-cyano-2-(6-methoxy-3H-imidazo[4,5-c]pyridin-2-yl)vinyl)-2,5-dimethyl-1H-pyrrol-1-yl)-5-(trifluoromethyl)thiophene-3-carbonitrile) as a yellow solid (3 mg, yield: 21.2%). MS (ESI) m/z: 469.30 [M+H$^+$]. $^1$H NMR (400 MHz, DMSO-$d_6$): δ 8.46 (d, J 12 Hz, 2H), 8.16 (s, 1H), 7.01 (s, 1H), 6.79 (s, 1H), 3.85 (s, 3H), 2.35 (s, 3H), 2.14 (s, 3H).

Example 97: Synthesis of Compound AB24369 ((E)-2-(3-(2-cyano-2-(6-methoxy-3-(methoxymethyl)-3H-imidazo[4,5-c]pyridin-2-yl)vinyl)-2,5-dimethyl-1H-pyrrol-1-yl)-5-methylthiophene-3-carbonitrile)

(1) Synthesis of Compound 3 ((E)-2-(3-(2-cyano-2-(6-methoxy-3H-imidazo[4,5-c]pyridin-2-yl)vinyl)-2,5-dimethyl-1H-pyrrol-1-yl)-5-methylthiophene-3-carbonitrile)

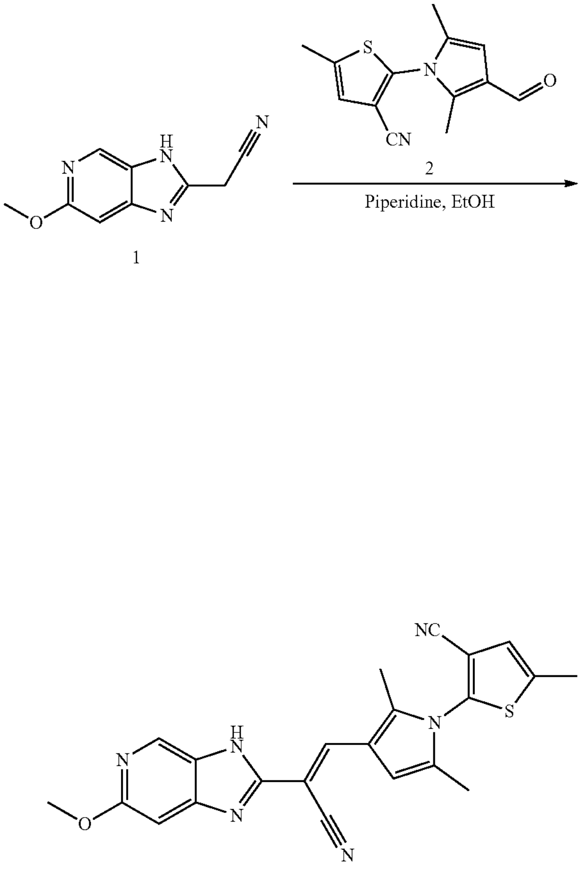

2

1

3

Compound 1 (2-(6-methoxy-3H-imidazo[4,5-c]pyridin-2-yl)acetonitrile) (200 mg, 1.069 mmol, 1 eq) was dissolved in ethanol (4 mL). Compound 2 (2-(3-formyl-2,5-dimethyl-1H-pyrrol-1-yl)-5-methylthiophene-3-carbonitrile) (260 mg, 1.069 mmol, 1 eq) and five drops of piperidine were added thereto. The mixture was heated under reflux and stirred for 2 h. After the completion of the reaction, the mixture was cooled to room temperature and then filtered. The solid was collected and dried, so as to obtain Compound 3 ((E)-2-(3-(2-cyano-2-(6-methoxy-3H-imidazo[4,5-c]pyridin-2-yl)vinyl)-2,5-dimethyl-1H-pyrrol-1-yl)-5-methylthiophene-3-carbonitrile) as a yellow solid (380 mg, yield: 86%). MS (ESI) m/z: 415.10 [M+H$^+$]. $^1$H NMR (400 MHz, DMSO-$d_6$) δ 8.53 (s, 1H), 8.16 (s, 1H), 7.31 (s, 1H), 6.96 (s, 1H), 6.89 (s, 1H), 3.89 (s, 3H), 2.51 (s, 3H), 2.30 (s, 3H), 2.08 (s, 3H).

(2) Synthesis of Compound AB24369 ((E)-2-(3-(2-cyano-2-(6-methoxy-3-(methoxymethyl)-3H-imidazo[4,5-c]pyridin-2-yl)vinyl)-2,5-dimethyl-1H-pyrrol-1-yl)-5-methylthiophene-3-carbonitrile)

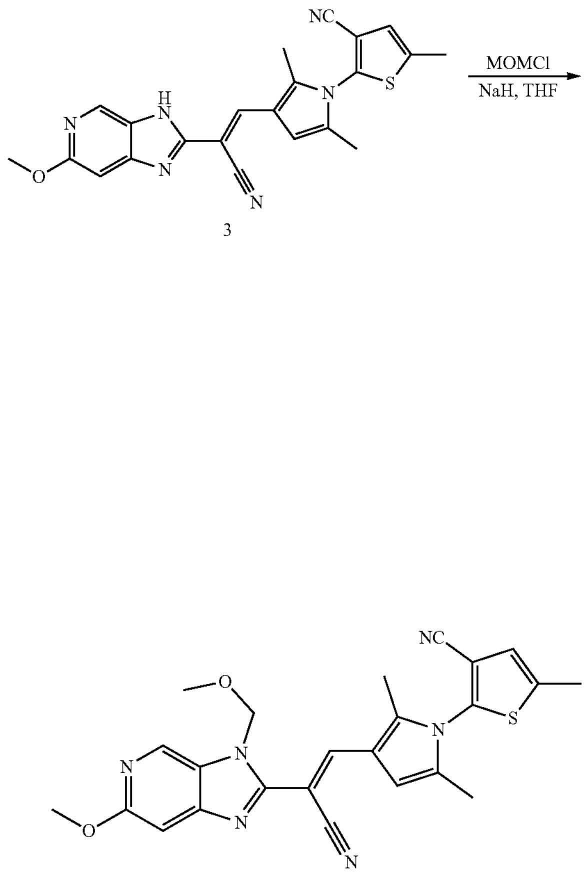

3

AB24369

Compound 3 ((E)-2-(3-(2-cyano-2-(6-methoxy-3H-imidazo[4,5-c]pyridin-2-yl)vinyl)-2,5-dimethyl-1H-pyrrol-1-yl)-5-methylthiophene-3-carbonitrile) (200 mg, 0.484 mmol, 1 eq) was dissolved in dimethylformamide (5 mL). At 0° C., sodium hydride NaH (43 mg, 0.532 mmol, 1.1 eq) was added, chloromethyl methyl ether MOMCl (23.2 mg 0.581 mmol 1.2 eq) was then added, and the resulting mixture was stirred for 30 minutes. After the completion of the reaction, the resulting mixture was concentrated and then purified by preparative high-pressure liquid chromatography, so as to obtain Compound AB24369 ((E)-2-(3-(2-cyano-2-(6-methoxy-3-(methoxymethyl)-3H-imidazo[4,5-c]pyridin-2-yl)vinyl)-2,5-dimethyl-1H-pyrrol-1-yl)-5-methylthiophene-3-carbonitrile) as a yellow solid (150 mg, 51%). MS (ESI) m/z: 459.10 $[M+H]^+$. $^1H$ NMR (400 MHz, DMSO-$d_6$) δ 8.70 (s, 1H), 8.17 (s, 1H), 7.33 (s, 1H), 7.18 (s, 1H), 7.00 (s, 1H), 5.69 (s, JH), 5.60 (s, 1H), 3.90 (s, 3H), 3.37 (s, 3H), 2.52 (s, 3H), 2.22 (s, 3H), 2.09 (s, 3H).

Example 98: Synthesis of Compound AB24395 ((E)-2-(4-(2-cyano-2-(6-methoxy-3H-imidazo[4,5-c]pyridin-2-yl)vinyl)-2,5-dimethyl-1H-imidazol-1-yl)-5-methylthiophene-3-carbonitrile)

(1) Preparation Method of Compound 3 (ethyl 1-(3-cyano-5-methylthiophen-2-yl)-2,5-dimethyl-1H-imidazole-4-carboxylate)

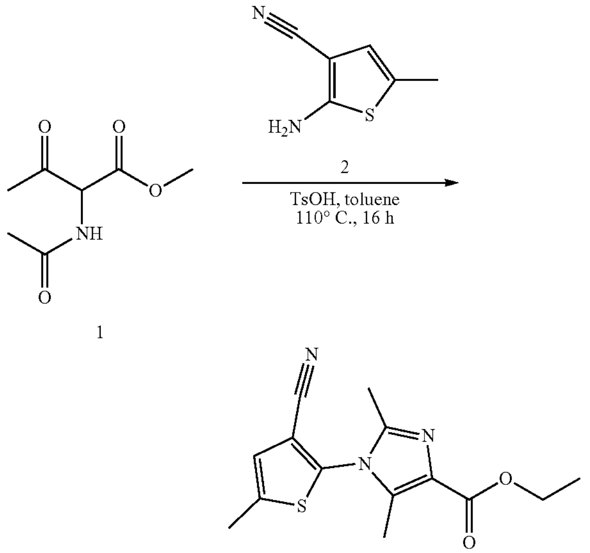

1

3

Compound 1 (methyl 2-acetamido-3-oxobutyrate) (6.4 g, 46.2 mmol, 1.25 eq) was dissolved in a mixed solution of toluene/dimethylformamide (5/1, 80 mL). Compound 2 (2-amino-5-methylthiophene-3-carbonitrile) (6.4 g, 37.0 mmol, 1.0 eq) and p-toluenesulfonic acid hydrate (1.2 g, 7.4 mmol, 0.2 eq) were added thereto. The mixture was heated under reflux and stirred for 16 h. The solid was filtered, concentrated and then purified by flash column chromatography (dichloromethane/methanol=10/1), so as to obtain Compound 3 (ethyl 1-(3-cyano-5-methylthiophen-2-yl)-2,5-dimethyl-1H-imidazole-4-carboxylate) as a white solid (1.76 g, yield: 16.4%). MS (ESI) m/z: 290 $[M+H]^+$. TLC: dichloromethane/methanol=(10/1); $R_f$ (Compound 2)=0.7; $R_f$ (Compound 3)=0.3.

(2) Preparation Method of Compound 4 (2-(4-(hydroxymethyl)-2,5-dimethyl-1H-imidazol-1-yl)-5-methylthiophene-3-carbonitrile)

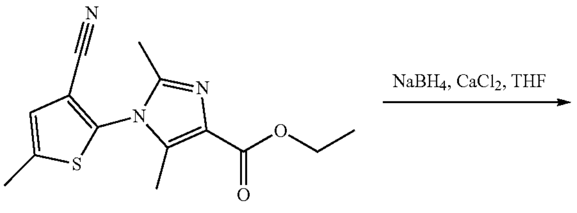

3

-continued

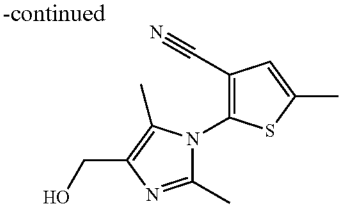

4

Compound 3 (ethyl 1-(3-cyano-5-methylthiophen-2-yl)-2,5-dimethyl-1H-imidazole-4-carboxylate) (1.23 g, 4.47 mmol, 1.0 eq) was dissolved in tetrahydrofuran (15 mL). Sodium borohydride $NaBH_4$ (338 mg, 8.94 mmol, 2.0 eq) and calcium chloride (1.5 g, 13.4 mmol, 3.0 eq) were added thereto. The mixture was stirred at room temperature overnight. The solid was filtered, concentrated and then purified by flash column chromatography (dichloromethane/methanol=10/1), so as to obtain Compound 4 (2-(4-(hydroxymethyl)-2,5-dimethyl-1H-imidazol-1-yl)-5-methylthiophene-3-carbonitrile) as a white solid (1.1 g, yield: 100%). MS (ESI) m/z: 248 $[M+H]^+$. TLC:dichloromethane/methanol=(10/1); $R_f$ (Compound 3)=0.5; $R_f$ (Compound 4)=0.2.

(3) Preparation Method of Compound 5 (2-(4-formyl-2,5-dimethyl-1H-imidazol-1-yl)-5-methylthiophene-3-carbonitrile)

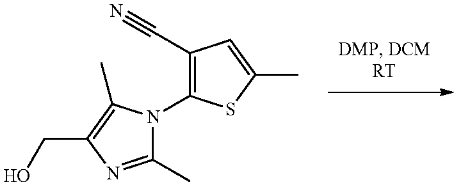

4

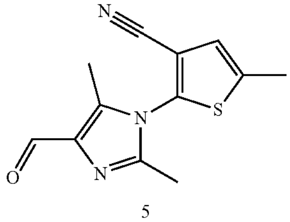

5

Compound 4 (2-(4-(hydroxymethyl)-2,5-dimethyl-1H-imidazol-1-yl)-5-methylthiophene-3-carbonitrile) (400 mg, 1.62 mmol, 1.0 eq) was dissolved in dichloromethane (10 mL), and Dess-Martin periodinane DMP (1.37 g, 3.24 mmol, 2.0 eq) was added thereto. The reactants were stirred at room temperature for 6 h. After the completion of the reaction, the solid was filtered and concentrated. The residue was purified by flash column chromatography (dichloromethane/methanol=10/1), so as to obtain Compound 5 (2-(4-formyl-2,5-dimethyl-1H-imidazol-1-yl)-5-methylthiophene-3-carbonitrile) as a white solid (90 mg, yield 22.8%). MS (ESI) m/z: 246 $[M+H^+]$. TLC:dichloromethane/methanol=(10/1); $R_f$ (Compound 4)=0.3; $R_f$ (Compound 5)=0.6.

(4) Synthesis of Compound AB24395 ((E)-2-(4-(2-cyano-2-(6-methoxy-3H-imidazo[4,5-c]pyridin-2-yl)vinyl)-2,5-dimethyl-1H-imidazol-1-yl)-5-methylthiophene-3-carbonitrile)

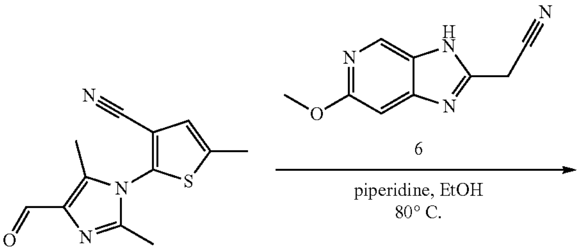

5

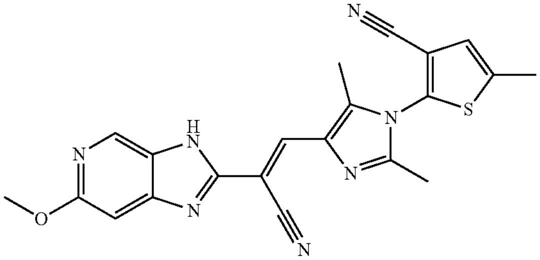

AB24395

Compound 5 (2-(4-formyl-2,5-dimethyl-1H-imidazol-1-yl)-5-methylthiophene-3-carbonitrile) (50 mg, 0.204 nmol, 1.0 eq) was dissolved in ethanol (1 mL). Compound 6 (2-(6-methoxy-3H-imidazo[4,5-c]pyridin-2-yl)acetonitrile) (36 mg, 0.204 mmol, 1.0 eq) and two drops of piperidine were added thereto. The reactants were heated to 80° C. and stirred for 2 h. After the completion of the reaction, the resulting mixture was cooled to room temperature and then filtered. The solid was collected and dried, so as to obtain Compound AB24395 ((E)-2-(4-(2-cyano-2-(6-methoxy-3H-imidazo[4,5-c]pyridin-2-yl)vinyl)-2,5-dimethyl-1H-imidazol-1-yl)-5-methylthiophene-3-carbonitrile) as a yellow solid (34 mg, yield: 40.2%). MS (ESI) m/z: 416.25 $[M+H^+]$. $^1H$ NMR (400 MHz, DMSO-d4) δ 8.60 (s, 1H), 7.75 (s, 1H), 7.38 (s, 1H), 7.16 (s, 1H), 3.86 (s, 3H), 3.44 (s, 3H), 2.54 (s, 3H), 2.33 (s, 3H).

Example 99: Synthesis of Compound AB29504 ((E)-N-((2-(3-(2-cyano-2-(6-methoxy-3H-imidazo[4,5-c]pyridin-2-yl)vinyl)-2,5-dimethyl-1H-pyrrol-1-yl)-5-methylthiophen-3-yl)methyl)acetamide)

(1) Synthesis of Compound 3 ((2,5-dimethyl-1H-pyrrol-1-yl)-5-methylthiophene-3-carboxamide)

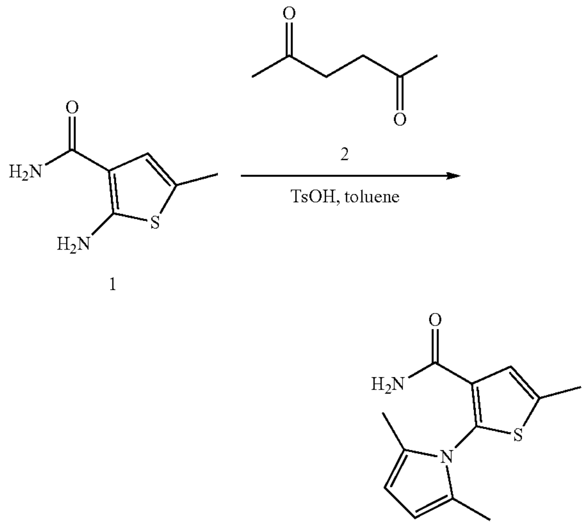

1 2 3

To a solution of Compound 1 (2-amino-5-methylthiophene-3-carboxamide) (5 g, 32 mmol, 1.0 eq) in toluene (100 mL), Compound 2 (2,5-hexanedione) (5.1 g, 44.8 mmol, 1.4 eq), 3 A molecular sieve (10 g) and p-toluenesulfonic acid ((2.2 g, 12.8 mmol, 0.4 eq) were added. The mixture was heated under reflux and stirred overnight. The precipitate was filtered, and the filtrate was concentrated. The residue was purified by high-pressure liquid chromatography (petroleum ether/ethyl acetate=50/1 to 10/1), so as to obtain Compound 3 (2-(2,5-dimethyl-1H-pyrrol-1-yl)-5-methylthiophene-3-carboxamide) as a grey solid (1.9 g, yield: 25.3%). MS (ESI) m/z: 235 $[M+H]^+$. TLC:petroleum ether/ethyl acetate (1:1); $R_E$(Compound 1)=0.2; $R_f$ (Compound 3)=0.5.

(2) Synthesis of Compound 4 ((2-(2,5-dimethyl-1H-pyrrol-1-yl)-5-methylthiophene-3-yl)methylamine)

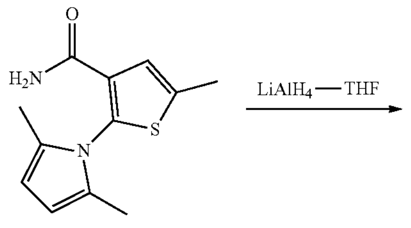

3

-continued

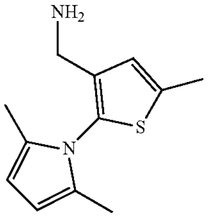
4

At 0° C., to a solution of lithium aluminum hydride (776 mg, 20.49 mmol, 3.0 eq) in anhydrous tetrahydrofuran (10 mL), a solution of Compound 3 (2-(2,5-dimethyl-1H-pyrrol-1-yl)-5-methylthiophene-3-carboxamide) (1.6 g, 6.83 mmol, 1.0 eq) in anhydrous tetrahydrofuran (10 mL) was added. The mixture was stirred at room temperature for 3 h. The mixture was quenched with saturated NHCl solution, and was filtered to remove the solid. The filtrate was extracted with ethyl acetate and washed with concentrated brine. The resulting mixture was dried and filtered, and the organic layer was concentrated. The residue was purified by high-pressure liquid chromatography (dichloromethane/methanol=50/1 to 20/1), so as to obtain a yellow oily Compound 4 ((2-(2,5-dimethyl-1H-pyrol-1-yl)-5-methylthiophen-3-yl)methylamine) (1.1 g, yield: 73.3%). MS (ESI) m/z: 221$[M+H]^+$. TLC:dichloromethane/methanol (10:1); $R_f$(Compound 3)=0.8; $R_f$(Compound 4)=0.3.

(3) Synthesis of Compound 6 (N-((2-(2,5-dimethyl-1H-pyrrol-1-yl)-5-methylthiophen-3-yl)methyl)acetamide)

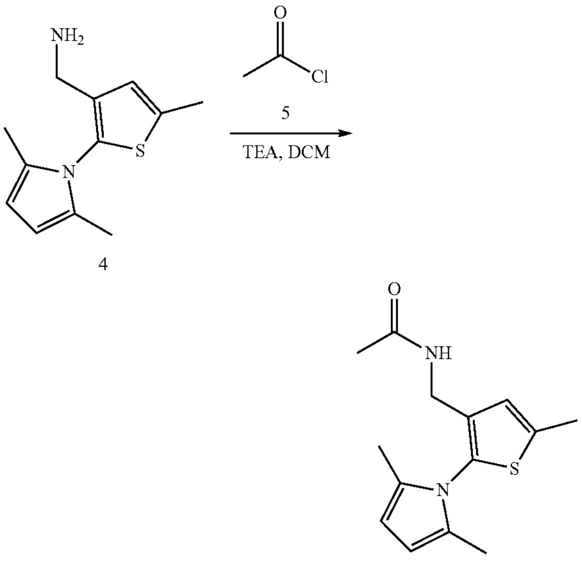

4 6

To a solution of Compound 4 ((2-(2,5-dimethyl-1H-pyrrol-1-yl)-5-methylthiophen-3-yl)methylamine) (1.1 g, 4.99 mmol, 1.0 eq) in dichloromethane (20 mL), triethylamine (1.0 g, 9.98 mmol, 2.0 eq) and Compound 5 (392 mg, 4.99 mmol, 1.0 eq) were added. The mixture was stirred at room temperature for 4 h. The mixture was diluted with dichloromethane and washed with water. The resulting mixture was dried and filtered, and the organic layer was concentrated. The residue was purified by high-pressure liquid chromatography (petroleum ether/ethyl acetate=20/1 to 5/1), so as to obtain Compound 6 ((2-(2,5-dimethyl-1H-pyrrol-1-yl)-5-methylthiophen-3-yl)methylamine) as a yellow solid (1.2 g, yield: 92.3%). MS (ESI) m/z: 263 $[M+H]^+$. TLC: dichloromethane/methanol (10:1); $R_f$ (Compound 4)=0.3; $R_f$ (Compound 6)=0.6.

(4) Synthesis of Compound 7 (N-((2-(3-formyl-2,5-dimethyl-1H-pyrrol-1-yl)-5-methylthiophen-3-yl) methyl)acetamide)

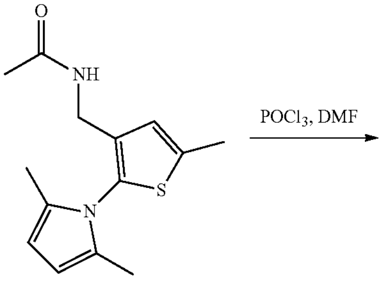

6

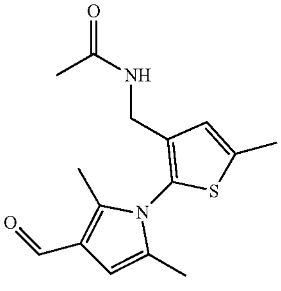

7

Under the protection of $N_2$, phosphorus oxychloride (175 mg, 1.14 mmol, 1.5 eq) was added dropwise to dimethylformamide (10 mL) at 0° C. The mixture was stirred at 0° C. for 30 min and then warmed to room temperature. A solution of Compound 6 (N-((2-(2,5-dimethyl-1H-pyrrol-1-yl)-5-methylthiophen-3-yl)methyl)acetamide) (200 mg, 0.76 mmol, 1.0 eq) in dimethylformamide (3 mL) was added thereto. Under the protection of $N_2$, the mixture was heated to 80° C. and stirred for 2 h. After being cooled, the mixture was poured into ice water which was basified to a pH of 10 with 30% NaOH aqueous solution in advance. The mixture was extracted with ethyl acetate and washed with concentrated brine. The organic layer was dried over $Na_2SO_4$ and filtered, and the filtrate was concentrated. The residue was purified by high-pressure liquid chromatography (petroleum ether/ethyl acetate=2/1), so as to obtain Compound 7 (N-((2-(3-formyl-2,5-dimethyl-1H-pyrrol-1-yl)-5-methylthiophen-3-yl)methyl)acetamide) as a yellow solid (132 mg, yield: 60%). MS (ESI) m/z: 291 $[M+H]^+$. TLC:petroleum ether/ethyl acetate (2:1); $R_f$ (Compound 6)=0.5; $R_f$ (Compound 0.3.

(5) Synthesis of AB29504 ((E)-N-((2-(3-(2-cyano-2-(6-methoxy-3H-imidazo[4,5-c]pyridin-2-yl)vinyl)-2,5-dimethyl-1H-pyrrol-1-yl)-5-methylthiophen-3-yl)methyl)acetamide)

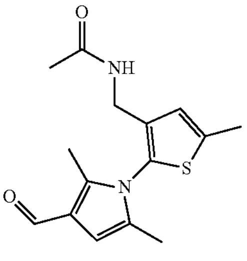

7

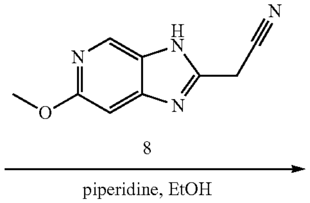

8

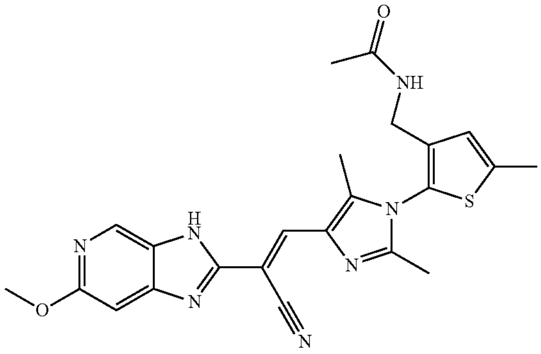

AB29504

To a solution of Compound 7 (N-((2-(3-formyl-2,5-dimethyl-1H-pyrrol-1-yl)-5-methylthiophen-3-yl)methyl)acetamide) (75 mg, 0.26 mmol, 1.0 eq) in ethanol (2 mL), Compound 8 (2-(2-(6-methoxy-3H-imidazo[4,5-c]pyridin-2-yl)acetonitrile) (49 mg, 0.26 mmol, 1 eq) and piperidine (22 mg, 0.26 mmol, 1 eq) were added. The mixture was heated under reflux for 2 h. After being cooled, the mixture was filtered, and the residue was collected and concentrated so as to obtain AB29504 ((E)-N-((2-(3-(2-cyano-2-(6-methoxy-3H-imidazo[4,5-c]pyridin-2-yl)vinyl)-2,5-dimethyl-1H-pyrrol-1-yl)-5-methylthiophen-3-yl)methyl)acetamide) as a yellow solid (40 mg, yield: 33.4%). MS (ESI) m/z: 461 $[M+H^+]$. $^1H$ NMR (400 MHz, DMSO-$d_6$) δ 12.90 (s, 1H), 8.45 (s, 1H), 8.25-8.22 (m, 1H), 8.11 (s, 1H), 6.89 (s, 1H), 6.78 (s, 2H), 3.84 (s, 3H), 3.80-3.78 (m, 2H), 2.43 (s, 3H), 2.23 (s, 3H), 2.02 (s, 3H), 1.75 (s, 3H).

Example 100: Synthesis of Compound AB29511 ((E)-2-(6-methoxy-3H-imidazo[4,5-c]pyridin-2-yl)-3-(1-methyl-2-phenyl-1H-imidazol-5-yl)acrylonitrile)

(1) Synthesis of Compound 2 (methyl 2-bromo-1-methyl-1H-imidazole-5-carboxylate)

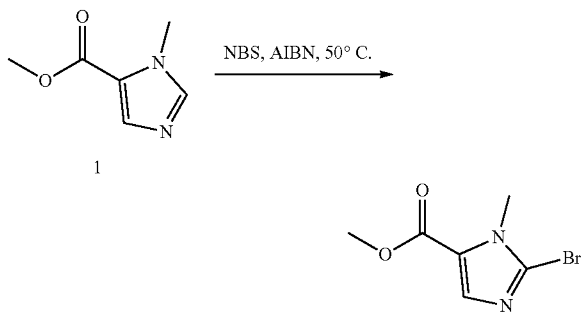

1
2

Compound 1 (methyl 1-methyl-imidazole-5-carboxylate) (5 g, 35.6 mmol, 1.0 eq) was dissolved in tetrachloromethane $CCl_4$ (100 mL). N-bromosuccinimide NBS (4.6 g, 39.16 mmol, 1.1 eq) and azobisisobutyronitrile AIBN (292 mg, 1.78 mmol, 0.05 eq) were added thereto. The mixture was stirred for 3 h at 50° C., and then the solid was filtered and concentrated. The residue was purified by flash column chromatography (petroleum ether/ethyl acetate=50/1), so as to obtain Compound 2 (methyl 2-bromo-1-methyl-1H-imidazole-5-carboxylate) as a yellow solid (2.3 g, yield: 29.4%). MS (ESI) m/z: 219 $[M+H]^+$. TLC:petroleum ether/ethyl acetate (10:1); $R_f$ (Compound 1)=0.2; $R_f$ (Compound 3)=0.7.

(2) Preparation Method of Compound 4 (methyl 1-methyl-2-phenyl-1H-imidazole-5-carboxylate)

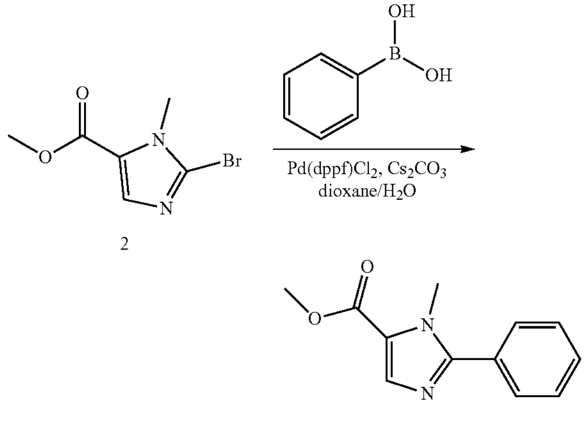

2
4

Compound 2 (methyl 2-bromo-1-methyl-1H-imidazole-5-carboxylate) (450 mg, 2.05 mmol, 1.0 eq) and Compound 3 (phenylboronic acid) (375 mg, 3.07 mmol, 1.5 eq) were dissolved in a mixed solution of 1,4-dioxane and water (15 mL/1.5 mL). Cesium carbonate (2.0 g, 6.15 mmol, 3 eq) and [1,1'-bis(diphenylphosphino)ferrocene]palladium dichloride Pd (dppf)$Cl_2$ (75 mg, 0.102 mmol, 0.05 eq) were added thereto. The mixture was stirred for 5 h at 100° C. After the completion of the reaction and the concentration of the resulting mixture, the residue was purified by flash column chromatography (petroleum ether/ethyl acetate=20/1 to 15/1), so as to obtain Compound 4 (methyl 1-methyl-2-phenyl-1H-imidazole-5-carboxylate) as a yellow solid (339 mg, yield: 76.5%). MS (ESI) m/z: 217 $[M+H]^+$. TLC: petroleum ether/ethyl acetate (5:1); $R_f$ (Compound 2)=0.7; $R_f$ (Compound 4)=0.3.

(3) Preparation Method of Compound 5 ((1-methyl-2-phenyl-1H-imidazol-5-yl)methanol)

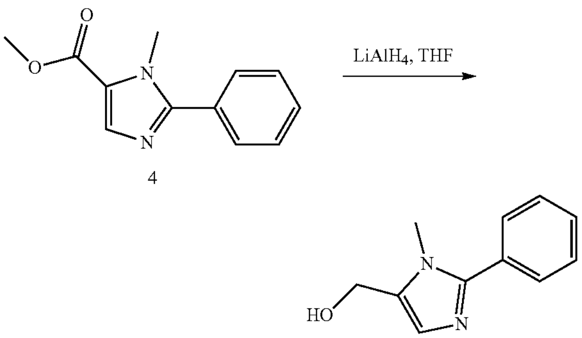

4
5

At 0° C., lithium aluminum hydride LiAlH (105 mg, 2.77 mmol, 1.8 eq) was dissolved in tetrahydrofuran (5 mL), and a solution of Compound 4 (methyl 1-methyl-2-phenyl-1H-imidazole-5-carboxylate) (339 mg, 1.56 mmol, 1.0 eq) in tetrahydrofuran (8 mL) was added thereto. The mixture was stirred at room temperature for 2 h, and then the mixture was quenched with saturated ammonium chloride solution (30 mL). Afterwards, the solid was filtered and then the resulting mixture was extracted with ethyl acetate. The organic layer was dried, filtered and concentrated, so as to obtain Compound 5 ((1-methyl-2-phenyl-1H-imidazol-5-yl)methanol) as a yellow solid (254 mg, yield: 86.1%). MS (ESI) m/z: 189 $[M+H]^+$. TLC:dichloromethane/methanol (20:1); $R_f$ (Compound 4)=0.7; $R_f$ (Compound 5)=0.3.

(4) Preparation Method of Compound 6 (1-methyl-2-phenyl-1H-imidazole-5-carbaldehyde)

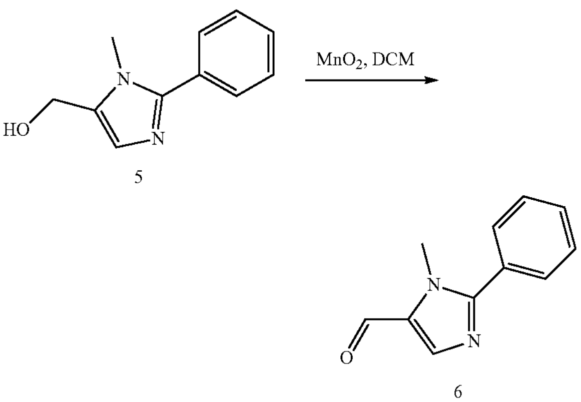

5
6

Compound 5 ((1-methyl-2-phenyl-1H-imidazol-5-yl) methanol) (100 mg, 0.53 mmol, 1.0 eq) was dissolved in dichloromethane (5 mL), and manganese dioxide (462 mg, 5.31 mmol, 10 eq) was added. After the mixture was stirred at room temperature for 3 h, the solid was filtered off and the resulting mixture was concentrated so as to obtain Compound 6 (1-methyl-2-phenyl-1H-imidazole-5-carbaldehyde) as a yellow solid (100 mg, yield: 100%). MS (ESI) m/z: 187 $[M+H]^+$. TLC:petroleum ether/ethyl acetate (1:1); $R_f$(Compound 5)=0.1; $R_f$(Compound 6)=0.5.

(5) Synthesis of Compound AB29511 ((E)-2-(6-methoxy-3H-imidazo[4,5-c]pyridin-2-yl)-3-(1-methyl-2-phenyl-1H-imidazol-5-yl)acrylonitrile)

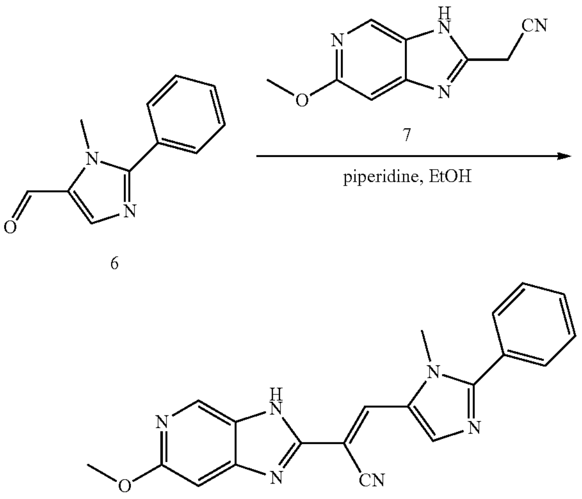

7

6

AB29511

Compound 6 (1-methyl-2-phenyl-1H-imidazole-5-carbaldehyde) (50 mg, 0.27 mmol, 1.0 eq) was dissolved in ethanol (1 mL). Compound 7 (2-(6-methoxy-3H-imidazo[4,5-c] pyridin-2-yl)acetonitrile) (50 mg, 0.27 mmol, 1.0 eq) and piperidine (23 mg, 0.27 mmol, 1.0 eq) were added thereto. The mixture was heated to 80° C. and stirred for 2 h. After the reaction was completed and the reaction mixture was cooled, the solid was filtered and concentrated, so as to obtain Compound AB29511 ((E)-2-(6-methoxy-3H-imidazo [4,5-c]pyridin-2-yl)-3-(1-methyl-2-phenyl-1H-imidazol-5-yl)acrylonitrile) as a yellow solid (63.8 mg, yield: 66.8%). MS (ESI) m/z: 357.05 $[M+H]^+$. HNMR (400 MHz, DMSO-d6) δ 13.13 (s, 1H), 8.54 (s, 1H), 8.23 (s, 1H), 8.18 (s, 1H), 7.73 (d, J=4 Hz, 2H), 7.55-7.53 (m, 3H), 6.83 (s, 3H), 3.86 (s, 3H), 3.83 (s, 3H).

Pharmacological Activity Test and Analysis of Results

Preparation of Recombinant DHX33

Regarding the isolation and purification of proteins, please refer to Wang X, Ge W, and Zhang Y. Recombinant DHX33 Protein Possesses Dual DNA/RNA Helicase Activity. *Biochemistry.* 2019:58 (4):250-8. RNA helicase gene (mouse DHX33 gene) was cloned into a pET32M-3C vector (between BamH I/Not I restriction sites). Afterward, the plasmid was transformed into BL-21pLysS (DE3) *E. coli.* 0.5 mM isopropyl 1-thio-βp-D-galactopyranoside (IPTG) was added, and the expression of the recombinant protein was induced at 16° C. for 16 hours. Cells were allowed to precipitate and were resuspended in a cell lysis buffer [50 mM Tris-HCl (pH7.2), 150 mM NaCl, 1% Triton X-100, and 50 mM imidazole supplemented with a protease inhibitor]. Thereafter, cells were subjected to ultrasonic treatment and centrifuged at a rotation speed of 13000 rpm for 25 minutes. The supernatant was incubated with the nickel-nitrilotriacetic acid beads equilibrated in Tris buffer, followed by sufficient washing. Thereafter, the purified protein was eluted with a solution of 300 mM imidazole in Tris buffer, and was then subjected to dialysis against an imidazole-free Tris buffer at 4° C. overnight.

FIG. 1 showed the analysis of the results obtained after the recombinant DHX33 protein prepared by the above-mentioned method was separated by SDS-PAGE and then stained with Coomassie brilliant blue. The arrow in the figure indicated the target recombinant DHX33 protein (containing a thioredoxin tag), and the molecular weight of the target band was 90 kDa.

Analysis of the Helicase Activity of DHX33

The components involved in the reaction for testing the helicase activity were added to a 96-well opaque white plate. The method was outlined as follows. The 96-well plate was coated with neutravidin at a final concentration of 10 μg/mL (100 μL/well) overnight at 4° C. Afterwards, the neutravidin-coated plate was blocked with 100 μL of 0.1% (w/v) BSA (dissolved in normal PBS) at 22° C. for 2 hours. After washing, a DNA duplex (2.5 ng) that was resulted from the annealing of two single-stranded DNA oligonucleotides (the sequence of one single strand was biotin-labeled 5'-GCTGACCCTGCTCCCAATCGTAATCTATAG-3'; and the sequence of the other single strand was DIG-labeled 5'-CGATTGGGAGCAGGGTCAGC-3') [the annealing reaction was carried out in PBS (pH 7.0) containing 1M NaCl] was added, and the resulting mixture was incubated at 22° C. for 4 hours. After the addition of 90 μL of the reaction mixture, the helicase reaction was initiated [0.25 pig of purified full-length DHX33 protein, dissolved in 25 mM 4-MOPS (pH 7.0), 5 mM ATP 2 mM DTT, 3 mM $MnCl_2$ and 100 μg/mL BSA]. The reaction was conducted at 37° C. for 60 minutes. After being washed, each well was incubated with a blocking solution [10% (w/v) BSA in 0.1 M maleic acid and 0.15 M NaCl (pH 7.5)] for 30 minutes, and was then incubated with 20 μL of antibody solution (anti-DIG-AP, Roche, in blocking buffer) for 30 minutes. After being washed with 100 μL of detection buffer [0.1 M Tris-HCl and 0.1 M NaCl (pH 9.5)], each well was added with 1 μL of chemiluminescent substrate (CSPD-0.25 mM), and the plate was incubated at 17° C. for 5 minutes. Afterwards, the plate was patted dry and incubated at 37° C. for 30 minutes. The remaining DIG-AP marker control in each well was counted for 10 minutes by a luminescence multi-well plate reader (Enspire, PerkinElmer). Higher reading indicated weaker helicase activity.

Positive control and negative controls were set for this acticity assay. Among them, one negative control group, which differed from the experimental group only in that the former was not added with ATP (other conditions were the same as the experimental group), was used for the comparison with the experimental group; another negative control group, which differed from the experimental group only in that the former was not added with DHX33 protein (other conditions were the same as the experimental group), was used for the comparison with the experimental group. The positive control group was set for the comparison with the wild-type DHX33 protein (standard substance). The results obtained from the comparison with DHX33 protein (standard substance) indicated that DHX33 protein prepared by the above-mentioned method had helicase activity.

Regarding the specific analytical method of helicase activity, please refer to Wang X, Ge W, and Zhang Y. Recombinant DHX33 Protein Possesses Dual DNA/RNA Helicase Activity. *Biochemistry.* 2019:58 (4):250-8.

Quantitative Real-Time PCR

Primers were designed by online "Realtime PCR Tool" of IDT (http://sg.idtdna.com/site), purchased from BGI (Shenzhen) Corporation. Total RNA was extracted by using High Pure RNA Isolation Kit (Roche), and was then transcribed into cDNA by using PrimeScript Mix Kit (Takara). Real-time PCR was conducted by using ABI One step plus cycler, and was managed by using the corresponding software. In order to analyze mRNA level, SYBR green Supermix (Bio-Rad) was used, and after the data were normalized to GAPDH value, $^{\Delta\Delta}$CT value was used to calculate and quantify the transcript. The melting curve was used for the confirmation of the amplification of a single product. Regarding the sequence of the primers, please refer to Yuan B, Wang X, Fan C, You J, Liu Y, Weber J D, Zhong H, and Zhang Y. DHX33 Transcriptionally Controls Genes Involved in the Cell Cycle. *Molecular and cellular biology* 2016; 36 (23):2903-17.

Regulation of Known Downstream Genes of DHX33 by Compounds

U251 cells were treated with AB24254 (having a concentration of 30 nM, 40 nM and 50 nM, respectively) or an equal volume of dimethyl sulfoxide for 16 hours. Total RNA was extracted and was then subjected to reverse transcription to obtain cDNA. Thereafter, real-time quantitative PCR was conducted to analyze the transcript levels of the target genes (including CCNE2, E2F1 and MCM3) in each sample, and GAPDH was used as the internal reference.

Figure 2:
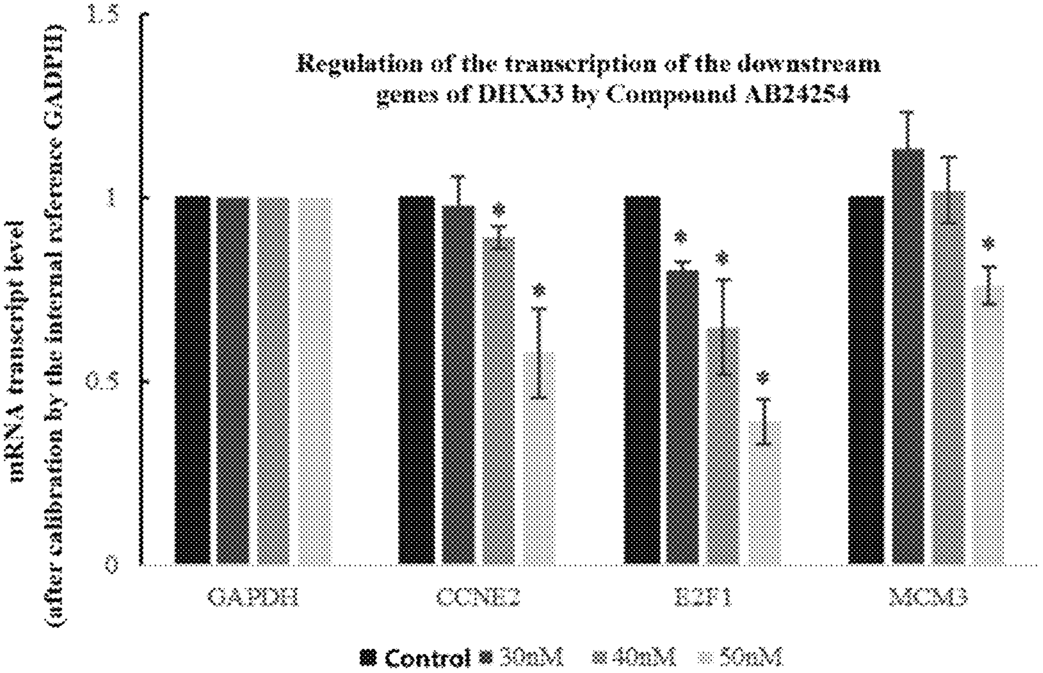
FIG. 2 shows the transcriptional regulation of the downstream genes (regulated by DHX33) by a compound of the present disclosure.

FIG. 2 illustrated the regulation of known downstream genes of DHX33 by Compound AB24254 of the present disclosure, wherein the selected genes. i.e., CCNE2, MCM3 and E2F, were all identified as downstream genes regulated by DHX33 in published articles (Yuan B, Wang X, Fan C, You J. Liu Y, Weber J D, Zhong H, and Zhang Y. DHX33 Transcriptionally Controls Genes Involved in the Cell Cycle. Molecular and cellular biology. 2016; 36 (23):2903-17). In a case where DHX33 was genetically knocked out or suppressed, these downstream genes were significantly down-regulated. As could be seen from FIG. 2, the compounds of the present disclosure had significant inhibitory effects on the transcription of these downstream genes (*, P<0.05, n=3, the data were collected from three independent experiments) and showed dose-dependent effects.

Inhibition of the Helicase Activity of DHX33 by Compounds

Compounds having a series of concentration (the concentrations were set at 1 nM, 5 nM, 10 nM, 20 nM, 50 nM, 100 nM, 250 nM, 500 nM, and 1000 nM) were used to conduct the helicase activity assay of DHX33 protein in vitro. The half-maximal inhibitory concentrations of the compounds of the present disclosure on the helicase activity of DHX33 protein were as shown in Table 1. As could be seen from Table 1, the compounds of the present disclosure had significant inhibitory effects on the helicase activity of DHX33 protein.

TABLE 1

Assay of the inhibitory effects of the compounds on the helicase activity of DHX33 protein

| Compound | Structure | $IC_{50}$ |
|---|---|---|
| Compound as control | 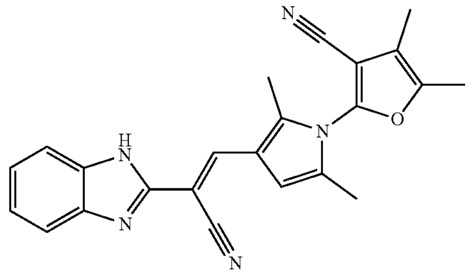 | * |
| AB24386 | 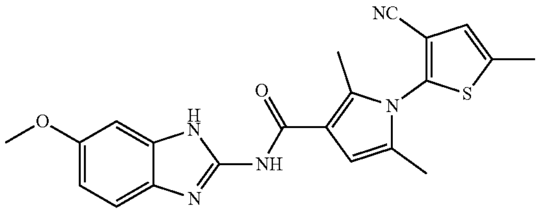 | **** |
| AB24387 | 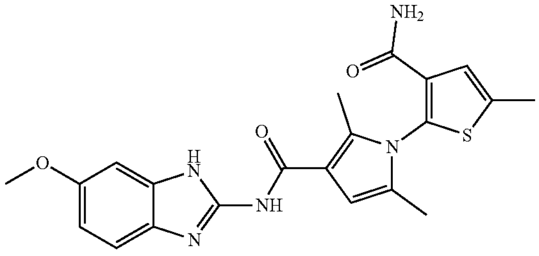 | *** |

TABLE 1-continued
| Assay of the inhibitory effects of the compounds on the helicase activity of DHX33 protein | | |
|---|---|---|
| Compound | Structure | $IC_{50}$ |
| AB29501 | 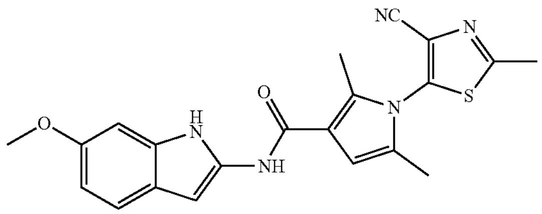 | **** |
| AB24202 | 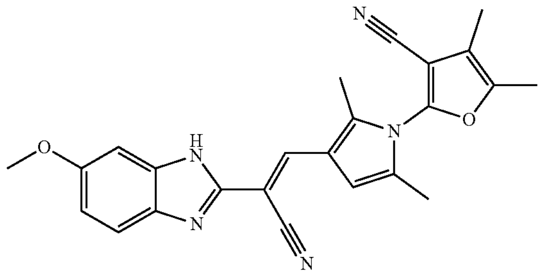 | *** |
| AB24205 | 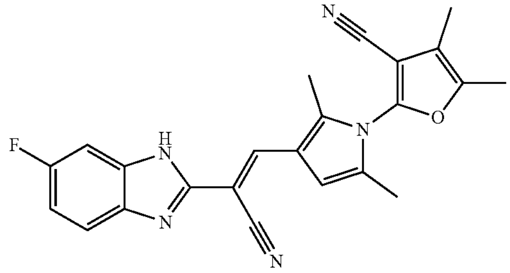 [SMILES: Cc1oc(-n2c(C)cc(/C=C(\C#N)c3nc4ccc(F)cc4[nH]3)c2C)c(C#N)c1C] | ** |
| AB24243 | 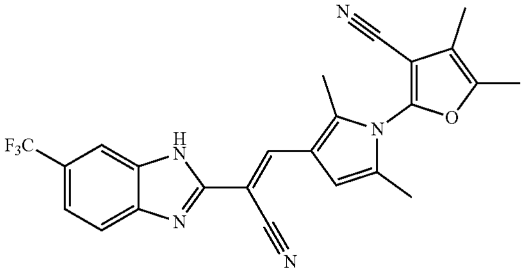 [SMILES: Cc1oc(-n2c(C)cc(/C=C(\C#N)c3nc4ccc(C(F)(F)F)cc4[nH]3)c2C)c(C#N)c1C] | ** |
| AB24283 | 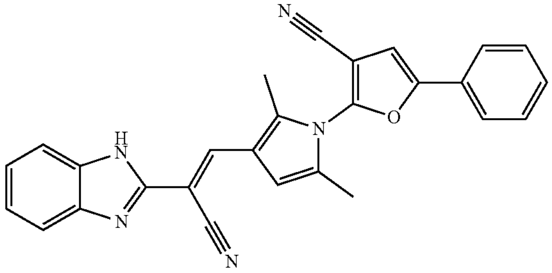 [SMILES: Cc1cc(/C=C(\C#N)c2nc3ccccc3[nH]2)c(C)n1-c1oc(-c2ccccc2)cc1C#N] | ** |

TABLE 1-continued
| Assay of the inhibitory effects of the compounds on the helicase activity of DHX33 protein | | |
|---|---|---|
| Compound | Structure | $IC_{50}$ |
| AB24264 | 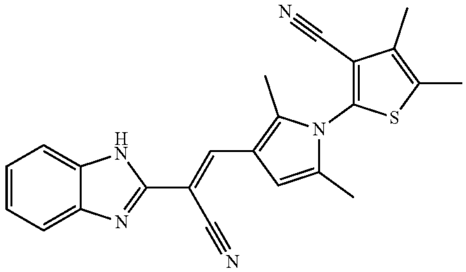 | ** |
| AB24270 | 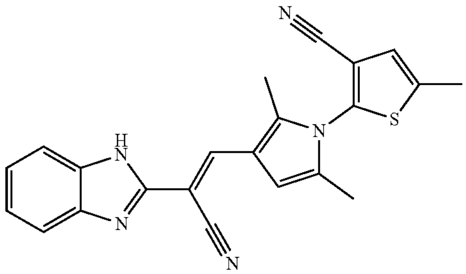 [SMILES: Cc1cc(C#N)c(-n2c(C)cc(/C=C(\C#N)c3nc4ccccc4[nH]3)c2C)s1] | *** |
| AB24259 | 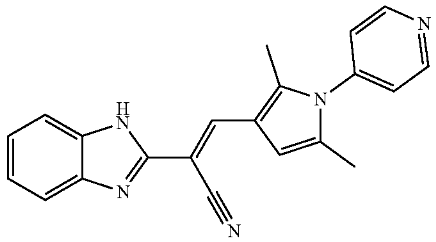 [SMILES: Cc1cc(/C=C(\C#N)c2nc3ccccc3[nH]2)c(C)n1-c1ccncc1] | ** |
| AB24322 | 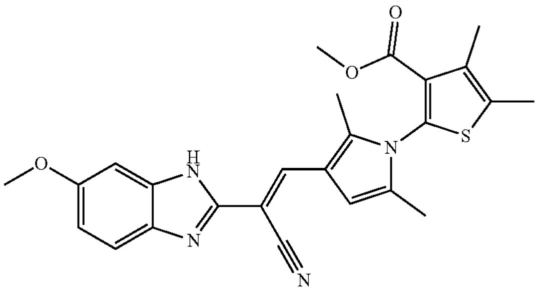 | ** |
| AB24249 | 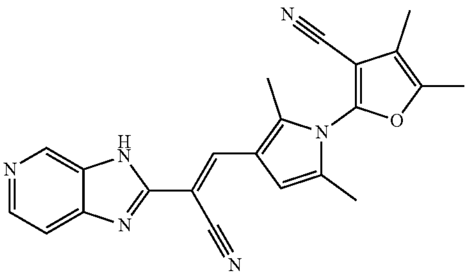 [SMILES: Cc1oc(-n2c(C)cc(/C=C(\C#N)c3nc4ccncc4[nH]3)c2C)c(C#N)c1C] | ** |

TABLE 1-continued
| Assay of the inhibitory effects of the compounds on the helicase activity of DHX33 protein | | |
|---|---|---|
| Compound | Structure | $IC_{50}$ |
| AB24254 | 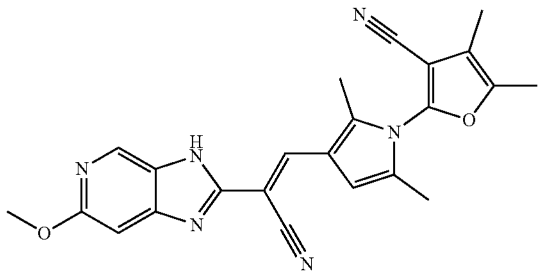 | **** |
| AB24335 | 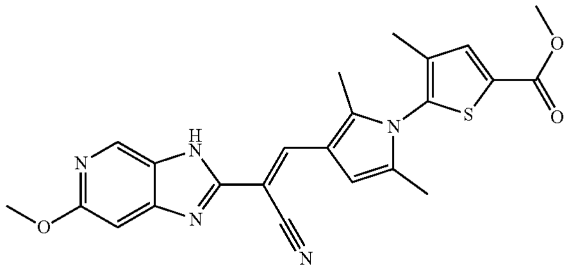 [SMILES: COC(=O)c1cc(C)c(-n2c(C)cc(/C=C(\C#N)c3nc4cc(OC)ncc4[nH]3)c2C)s1] | *** |
| AB24336 | 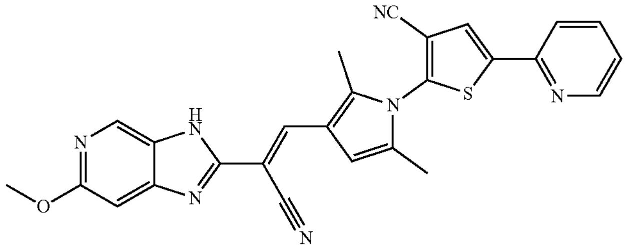 [SMILES: COc1cc2nc(/C(C#N)=C/c3cc(C)n(-c4sc(-c5ccccn5)cc4C#N)c3C)[nH]c2cn1] | ** |
| AB24350 | 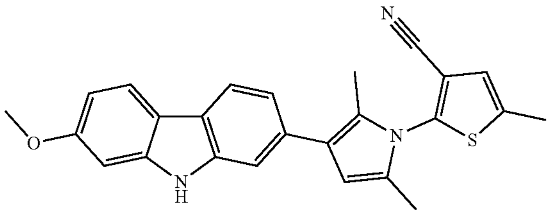 | ** |
| AB24379 | 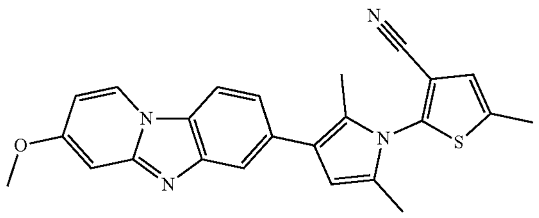 | *** |
| AB24399 | 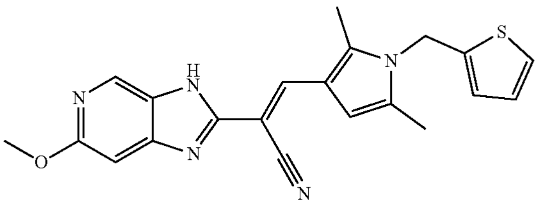 | **** |

TABLE 1-continued
| Assay of the inhibitory effects of the compounds on the helicase activity of DHX33 protein | | |
|---|---|---|
| Compound | Structure | $IC_{50}$ |
| AB29506 | 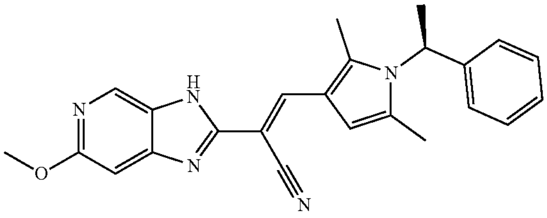 [SMILES: COc1cc2nc(/C(C#N)=C/c3cc(C)n([C@@H](C)c4ccccc4)c3C)[nH]c2cn1] | **** |
| AB24351 | 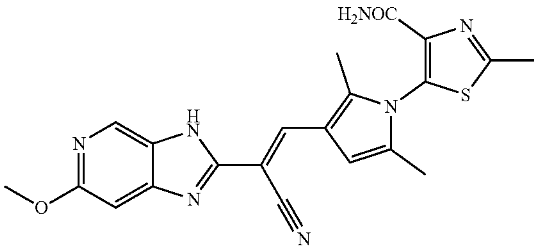 | *** |
| AB24314 | 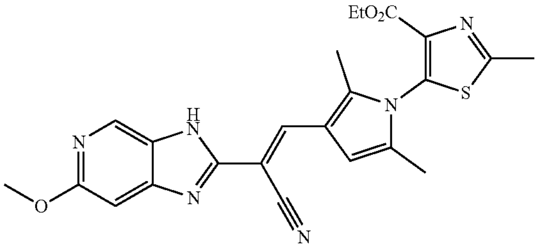 | *** |
| AB24288 | 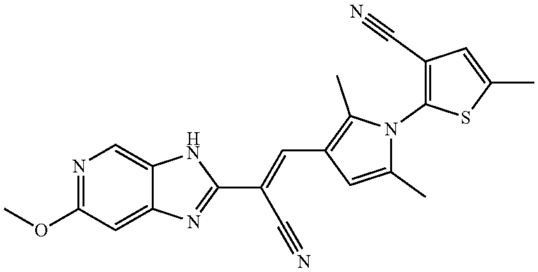 | **** |
| AB29511 | 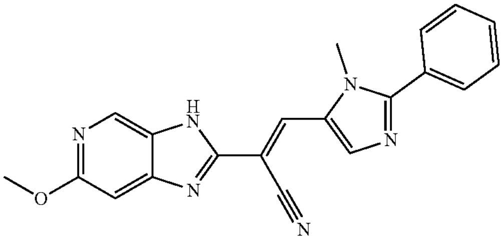 [SMILES: COc1cc2nc(/C(C#N)=C/c3cnc(-c4ccccc4)n3C)[nH]c2cn1] | * |

TABLE 1-continued

| Assay of the inhibitory effects of the compounds on the helicase activity of DHX33 protein | | |
|---|---|---|
| Compound | Structure | $IC_{50}$ |
| AB24321 | 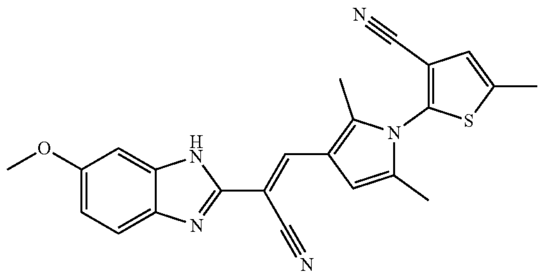 | **** |

* denoted that the half-maximal inhibitory concentration was 400 nM or more and less than 1000 nM;
** denoted that the half-maximal inhibitory concentration was 100 nM or more and less than 400 nM;
*** denoted that the half-maximal inhibitory concentration was 20 nM or more and less than 100 nM; and
**** denoted that the half-maximal inhibitory concentration was less than 20 nM.

Cell Culture and Sources

U251-MG cells were purchased from the cell bank of the Chinese Academy of Sciences. Cells were cultured in MEM medium containing 10% fetal bovine serum (FBS), 2 mM L-glutamine, streptomycin and penicillin. The growth conditions were set as follows: a humidified cell incubator (37° C., 5% $CO_2$). Cells were passaged every 3 days and were discarded after 10 passages.

Determination of Half-Maximal Cell-Inhibitory Concentrations ($IC_{50}$)

U251-MG cells (a DHX33-overexpressing cancer cell strain) were seeded on a 96-well plate at $1\times10^4$ cells/100 μL/well. After the cells were completely attached, the compounds were added to the cell culture medium at a concentration of 5 nM, 10 nM, 25 nM, 50 nM, 100 nM, 250 nM, 500 nM, 1000 nM, 2000 nM, 5000 nM, 10 μM or 20 μM, and the resulting mixture was uniformly mixed with a multichannel pipette. After the cells were incubated with the compound for 48 hours, CCK-8 reagent (Yeasen Biotechnology (Shanghai) Co., Ltd.) was added to the medium in the 96-well plate in accordance with the standard procedure. After being incubated for 2 hours, the plate was read with a microplate reader (OD=450 nm). The experiment was repeated three times, the inhibition curve of the compound at different concentrations was plotted, and the half-maximal inhibitory concentration ($IC_{50}$) of the compound was calculated.

TABLE 2

| Determination of the half-maximal inhibitory concentrations of compounds on U251-MG cells | | |
|---|---|---|
| Compound No. | Structure of compound | $IC_{50}$ |
| Compound as control | 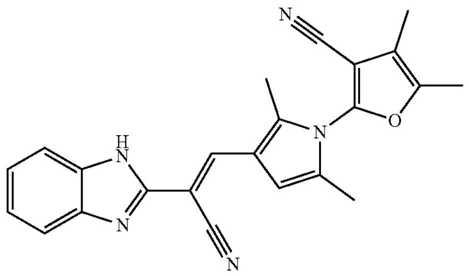 [SMILES: Cc1oc(-n2c(C)cc(/C=C(\C#N)c3nc4ccccc4[nH]3)c2C)c(C#N)c1C] | * |
| AB24249 | 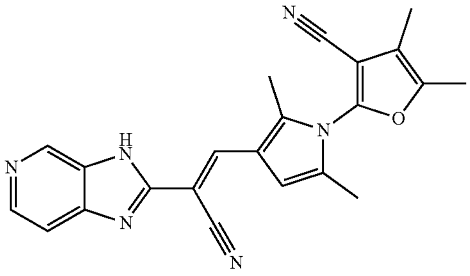 [SMILES: Cc1oc(-n2c(C)cc(/C=C(\C#N)c3nc4ccncc4[nH]3)c2C)c(C#N)c1C] | * |

TABLE 2-continued
| Determination of the half-maximal inhibitory concentrations of compounds on U251-MG cells | | |
|---|---|---|
| Compound No. | Structure of compound | $IC_{50}$ |
| AB24254 | 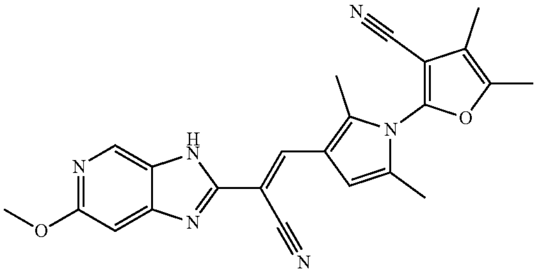 | **** |
| AB24281 | 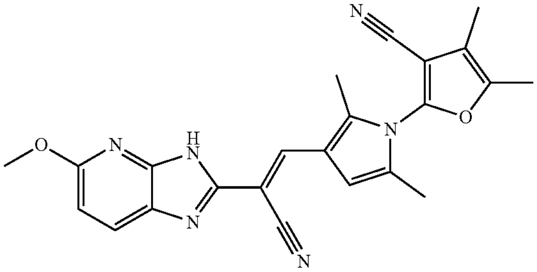 | ** |
| AB24288 | 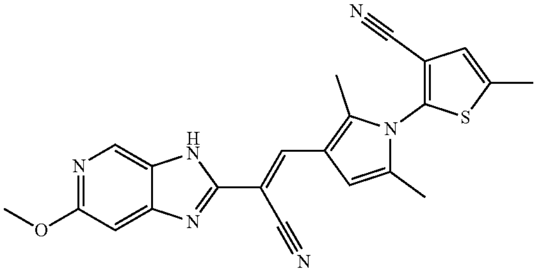 | **** |
| AB24289 | 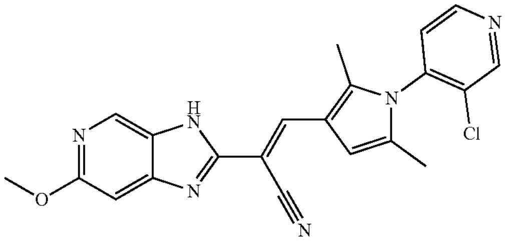 [SMILES: COc1cc2nc(/C(C#N)=C/c3cc(C)n(-c4ccncc4Cl)c3C)[nH]c2cn1] | ** |
| AB24295 | 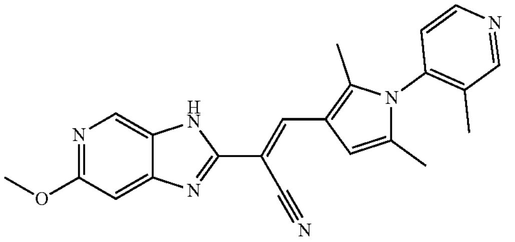 [SMILES: COc1cc2nc(/C(C#N)=C/c3cc(C)n(-c4ccncc4C)c3C)[nH]c2cn1] | ** |

TABLE 2-continued
| Determination of the half-maximal inhibitory concentrations of compounds on U251-MG cells | | |
|---|---|---|
| Compound No. | Structure of compound | $IC_{50}$ |
| AB24300 | 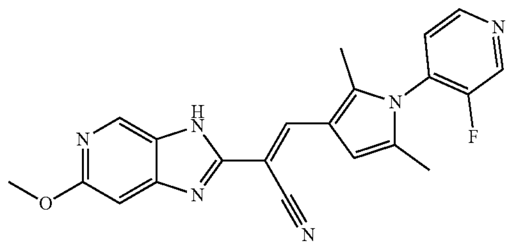 | ** |
| AB24301 | 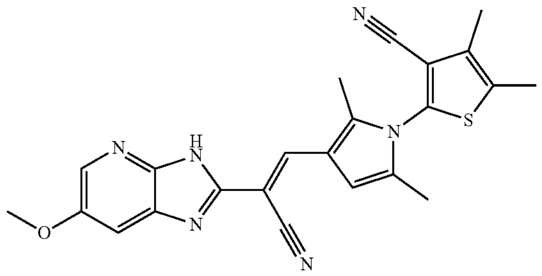 | *** |
| AB24302 | 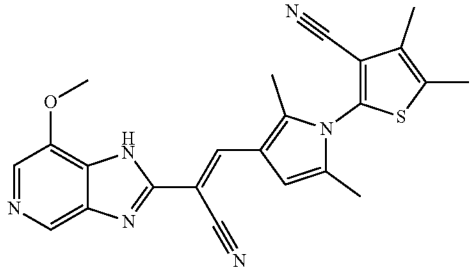 [SMILES: COc1cncc2nc(/C(C#N)=C/c3cc(C)n(-c4sc(C)c(C)c4C#N)c3C)[nH]c12] | ** |
| AB24308 | 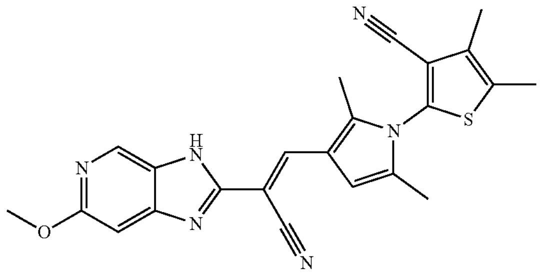 | **** |
| AB24309 | 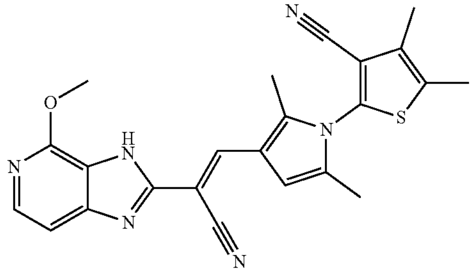 [SMILES: COc1nccc2nc(/C(C#N)=C/c3cc(C)n(-c4sc(C)c(C)c4C#N)c3C)[nH]c12] | ** |

TABLE 2-continued
| Determination of the half-maximal inhibitory concentrations of compounds on U251-MG cells | | |
|---|---|---|
| Compound No. | Structure of compound | $IC_{50}$ |
| AB24310 | 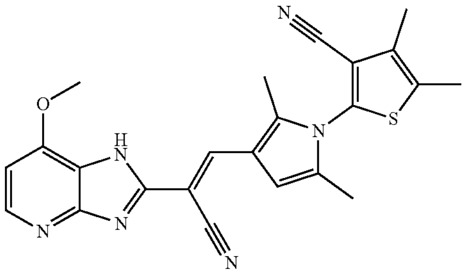 [SMILES: COc1ccnc2nc(/C(C#N)=C/c3cc(C)n(-c4sc(C)c(C)c4C#N)c3C)[nH]c12] | * |
| AB24311 | 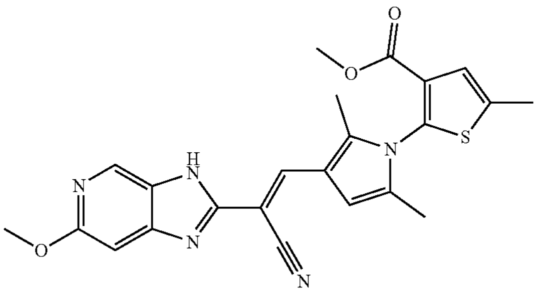 | **** |
| AB24313 | 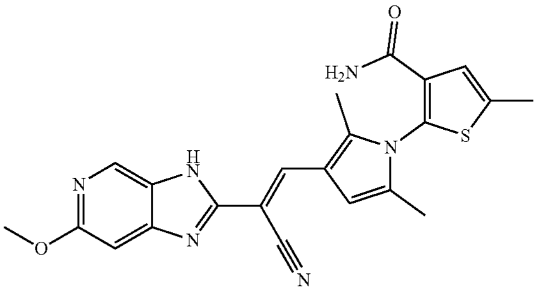 | *** |
| AB24314 | 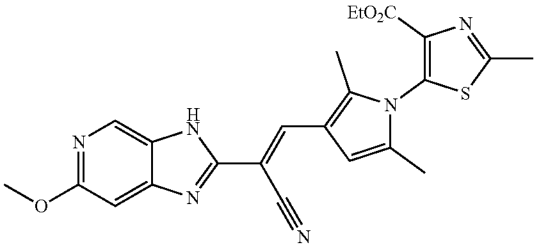 | *** |
| AB24316 | 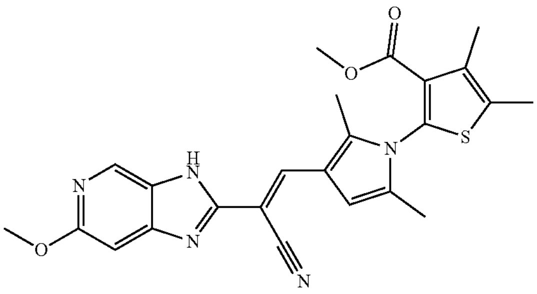 | *** |

TABLE 2-continued
Determination of the half-maximal inhibitory concentrations of compounds on U251-MG cells
| Compound No. | Structure of compound | $IC_{50}$ |
|---|---|---|
| AB24317 | 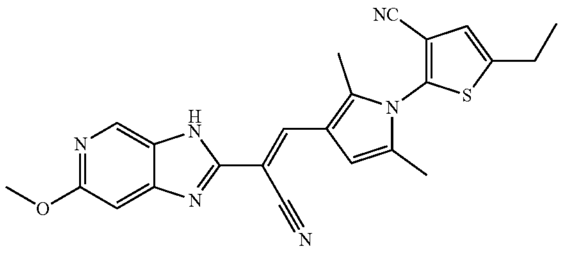 [SMILES: CCc1cc(C#N)c(-n2c(C)cc(/C=C(\C#N)c3nc4cc(OC)ncc4[nH]3)c2C)s1] | **** |
| AR24318 | 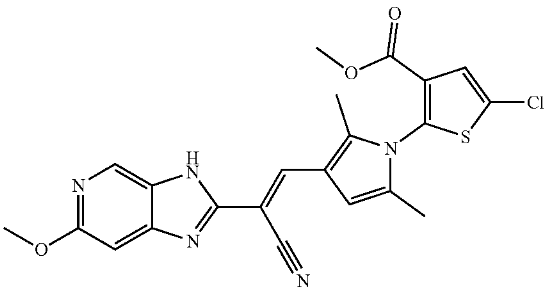 [SMILES: COC(=O)c1cc(Cl)sc1-n1c(C)cc(/C=C(\C#N)c2nc3cc(OC)ncc3[nH]2)c1C] | *** |
| AB24319 | 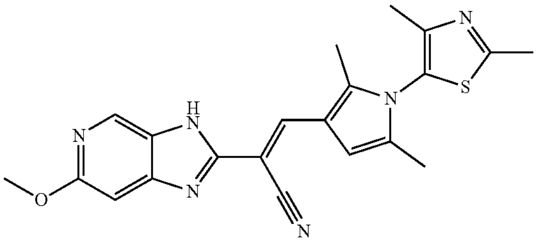 | *** |
| AB24320 | 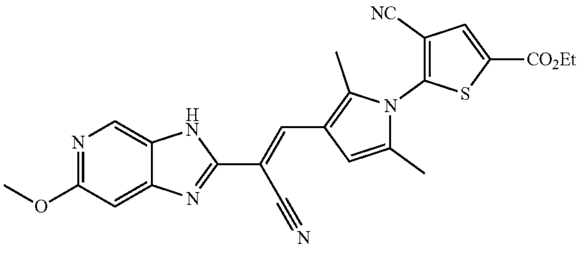 [SMILES: CCOC(=O)c1cc(C#N)c(-n2c(C)cc(/C=C(\C#N)c3nc4cc(OC)ncc4[nH]3)c2C)s1] | ** |
| AB24323 | 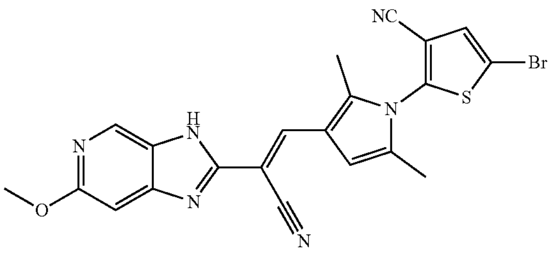 [SMILES: COc1cc2nc(/C(C#N)=C/c3cc(C)n(-c4sc(Br)cc4C#N)c3C)[nH]c2cn1] | **** |

TABLE 2-continued
| Compound No. | Structure of compound | $IC_{50}$ |
|---|---|---|
| AB24324 | 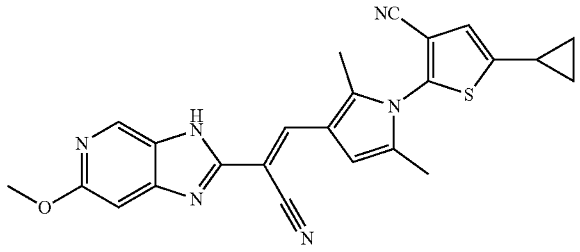 [SMILES: COc1cc2nc(/C(C#N)=C/c3cc(C)n(-c4sc(C5CC5)cc4C#N)c3C)[nH]c2cn1] | **** |
| AB24325 | 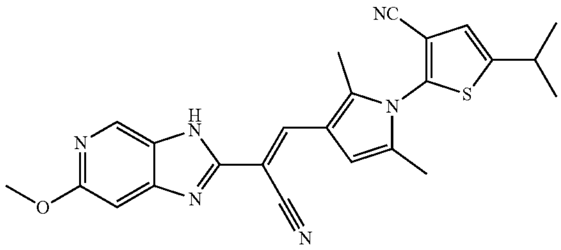 [SMILES: COc1cc2nc(/C(C#N)=C/c3cc(C)n(-c4sc(C(C)C)cc4C#N)c3C)[nH]c2cn1] | *** |
| AB24326 | 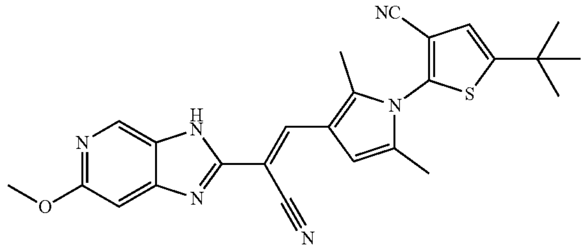 [SMILES: COc1cc2nc(/C(C#N)=C/c3cc(C)n(-c4sc(C(C)(C)C)cc4C#N)c3C)[nH]c2cn1] | *** |
| AB24328 | 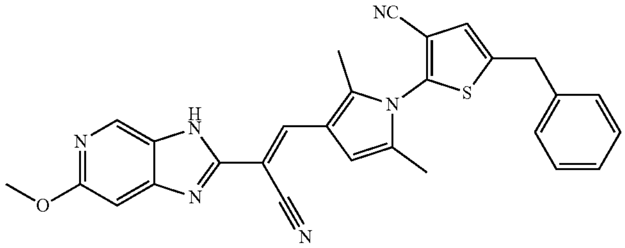 [SMILES: COc1cc2nc(/C(C#N)=C/c3cc(C)n(-c4sc(Cc5ccccc5)cc4C#N)c3C)[nH]c2cn1] | *** |
| AB24333 | 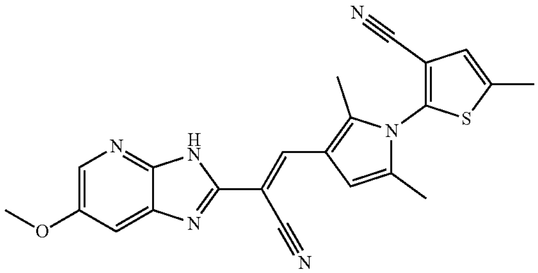 | **** |
Determination of the half-maximal inhibitory concentrations of compounds on U251-MG cells TABLE 2-continued
| Determination of the half-maximal inhibitory concentrations of compounds on U251-MG cells | | |
|---|---|---|
| Compound No. | Structure of compound | $IC_{50}$ |
| AB24334 | 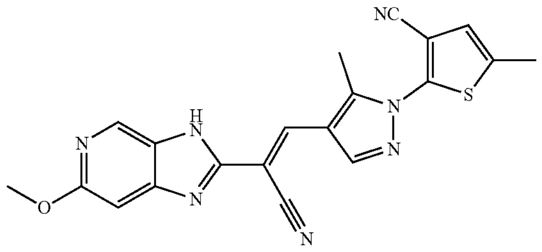 | *** |
| AB24335 | 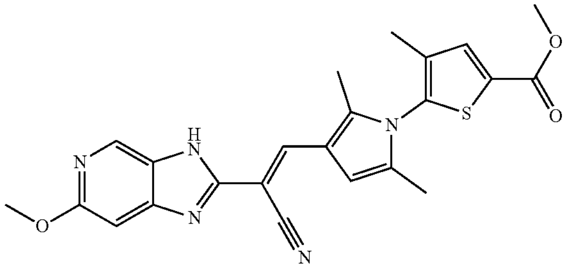 [SMILES: COC(=O)c1cc(C)c(-n2c(C)cc(/C=C(\C#N)c3nc4cc(OC)ncc4[nH]3)c2C)s1] | ** |
| AB24336 | 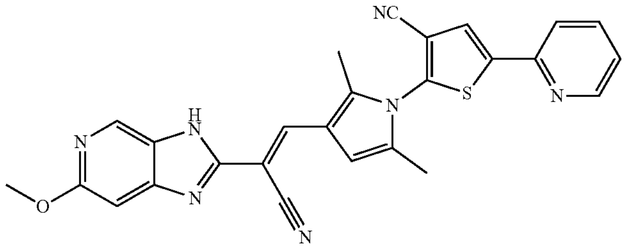 [SMILES: COc1cc2nc(/C(C#N)=C/c3cc(C)n(-c4sc(-c5ccccn5)cc4C#N)c3C)[nH]c2cn1] | ** |
| AB24337 | 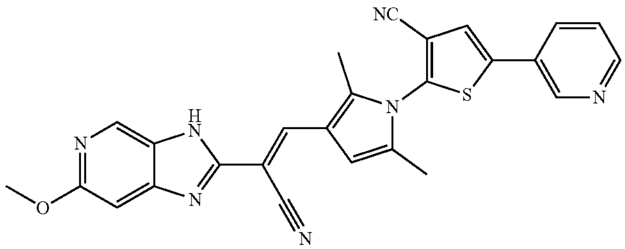 [SMILES: COc1cc2nc(/C(C#N)=C/c3cc(C)n(-c4sc(-c5cccnc5)cc4C#N)c3C)[nH]c2cn1] | ** |
| AB24338 | 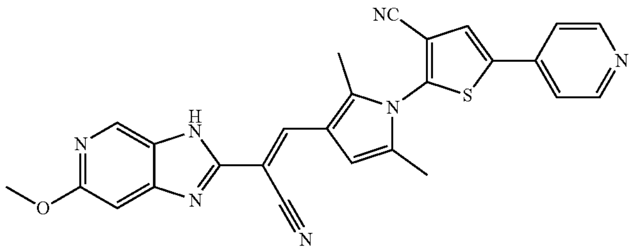 [SMILES: COc1cc2nc(/C(C#N)=C/c3cc(C)n(-c4sc(-c5ccncc5)cc4C#N)c3C)[nH]c2cn1] | ** |

TABLE 2-continued
Determination of the half-maximal inhibitory concentrations of compounds on U251-MG cells
| Compound No. | Structure of compound | $IC_{50}$ |
| --- | --- | --- |
| AB24341 | 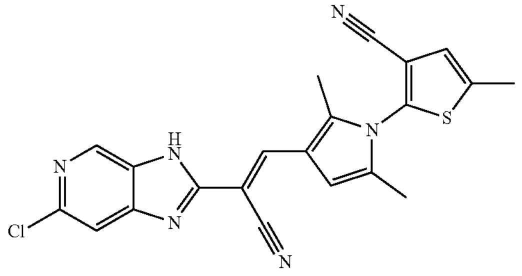 [SMILES: Cc1cc(C#N)c(-n2c(C)cc(/C=C(\C#N)c3nc4cc(Cl)ncc4[nH]3)c2C)s1] | **** |
| AB24342 | 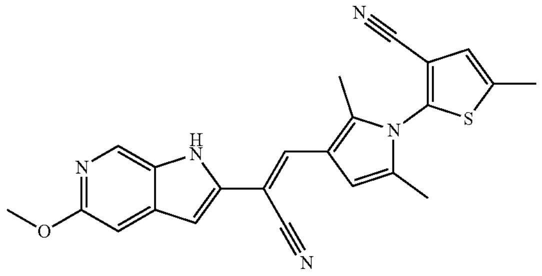 | *** |
| AB24345 | 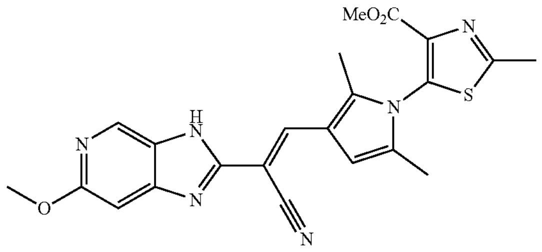 | *** |
| AB24347 | 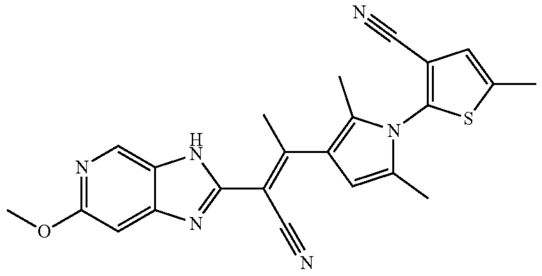 | *** |
| AB24348 | 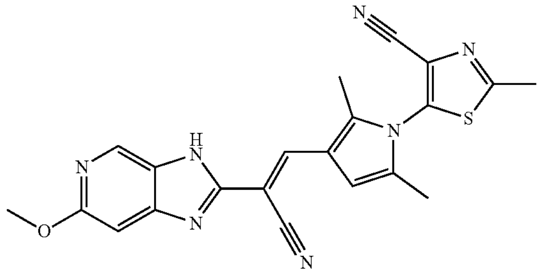 | **** |

TABLE 2-continued
Determination of the half-maximal inhibitory concentrations of compounds on U251-MG cells
| Compound No. | Structure of compound | $IC_{50}$ |
| --- | --- | --- |
| AB24349 | 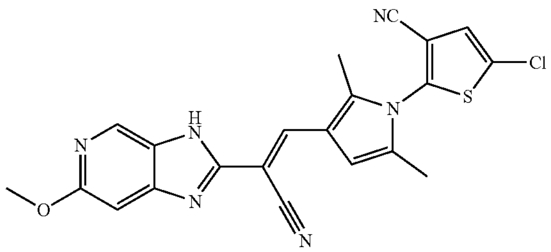 [SMILES: COc1cc2nc(/C(C#N)=C/c3cc(C)n(-c4sc(Cl)cc4C#N)c3C)[nH]c2cn1] | **** |
| AB24351 | 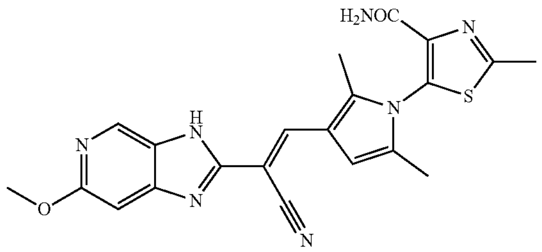 | *** |
| AB24352 | 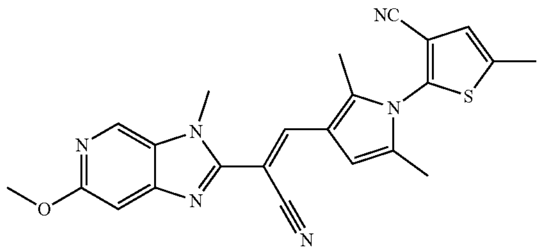 | *** |
| AB24355 | 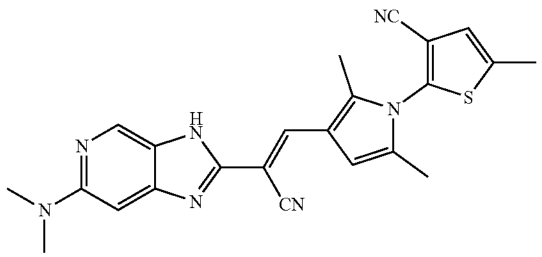 | **** |
| AB24386 | 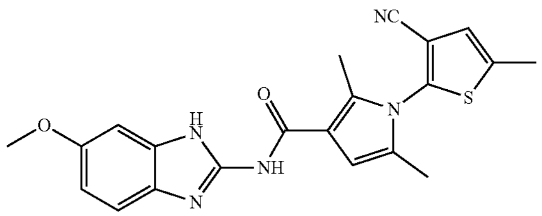 | **** |
| AB24387 | 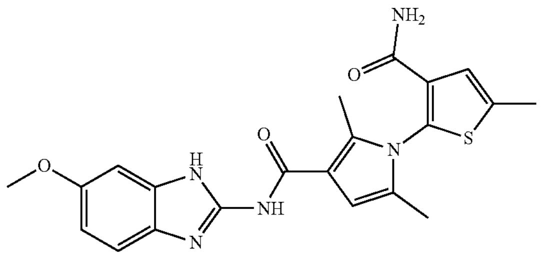 | *** |

TABLE 2-continued
| Determination of the half-maximal inhibitory concentrations of compounds on U251-MG cells | | |
|---|---|---|
| Compound No. | Structure of compound | $IC_{50}$ |
| AB29501 | 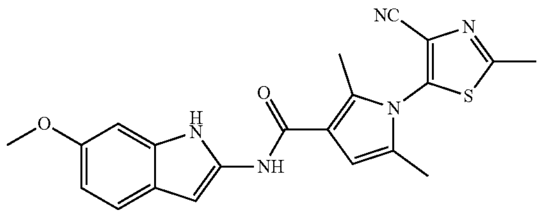 | **** |
| AB29502 | 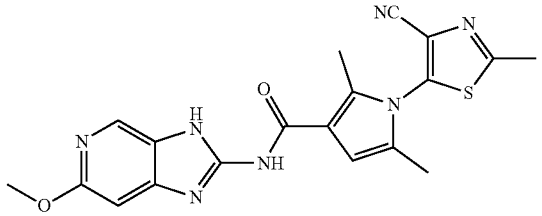 | *** |
| AB29505 | 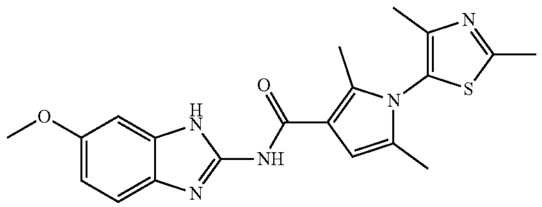 | *** |
| AB29509 | 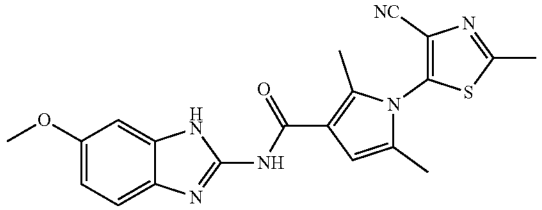 | *** |
| AB29510 | 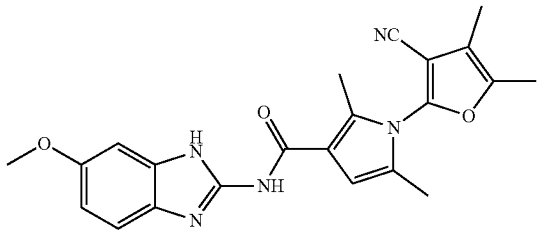 | *** |
| AB29513 | 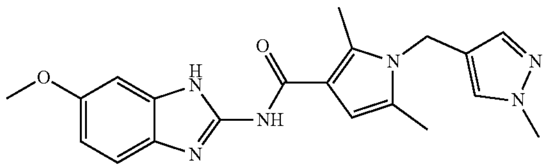 | * |
| AB24397 | 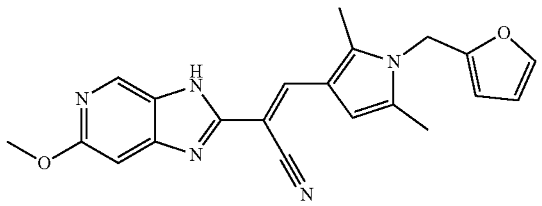 [SMILES: COc1cc2nc(/C(C#N)=C/c3cc(C)n(Cc4ccco4)c3C)[nH]c2cn1] | **** |

TABLE 2-continued
Determination of the half-maximal inhibitory concentrations of compounds on U251-MG cells
| Compound No. | Structure of compound | $IC_{50}$ |
| --- | --- | --- |
| AB24398 | 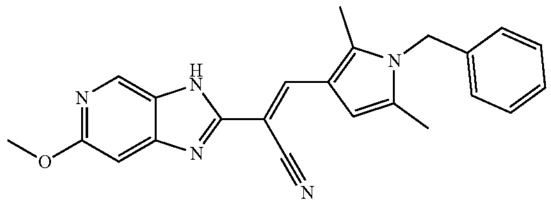 | **** |
| AB24399 | 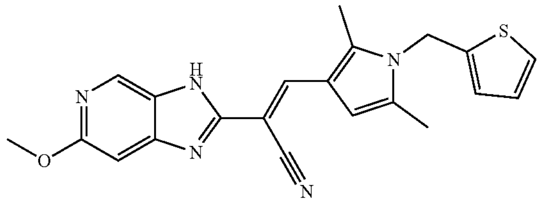 [SMILES: COc1cc2nc(/C(C#N)=C/c3cc(C)n(Cc4cccs4)c3C)[nH]c2cn1] | **** |
| AB29506 | 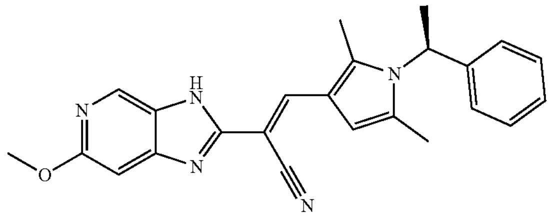 [SMILES: COc1cc2nc(/C(C#N)=C/c3cc(C)n([C@@H](C)c4ccccc4)c3C)[nH]c2cn1] | **** |
| AB29507 | 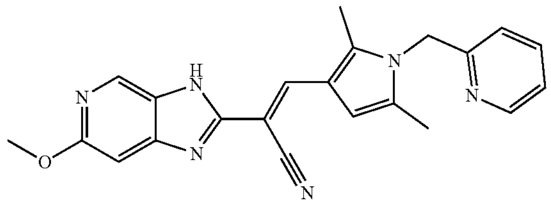 [SMILES: COc1cc2nc(/C(C#N)=C/c3cc(C)n(Cc4ccccn4)c3C)[nH]c2cn1] | **** |
| AB29508 | 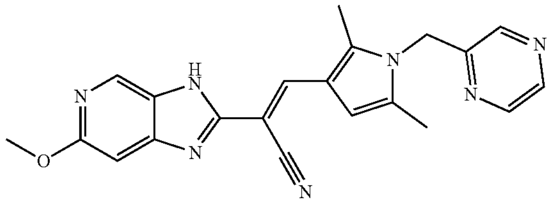 [SMILES: COc1cc2nc(/C(C#N)=C/c3cc(C)n(Cc4cnccn4)c3C)[nH]c2cn1] | **** |
| AB29512 | 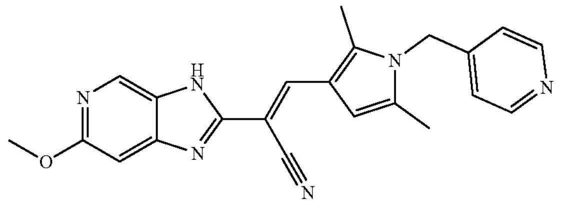 [SMILES: COc1cc2nc(/C(C#N)=C/c3cc(C)n(Cc4ccncc4)c3C)[nH]c2cn1] | **** |
| AB24385 | 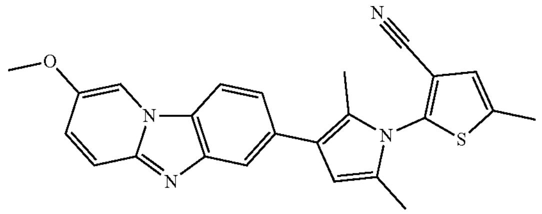 | ** |

TABLE 2-continued
| Determination of the half-maximal inhibitory concentrations of compounds on U251-MG cells | | |
|---|---|---|
| Compound No. | Structure of compound | $IC_{50}$ |
| AB24374 | 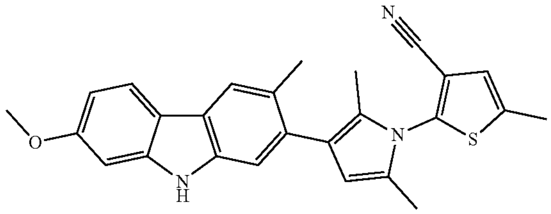 | * |
| AB24375 | 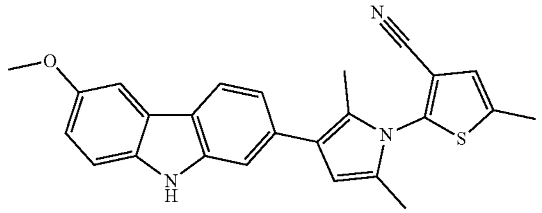 | * |
| AB24379 | 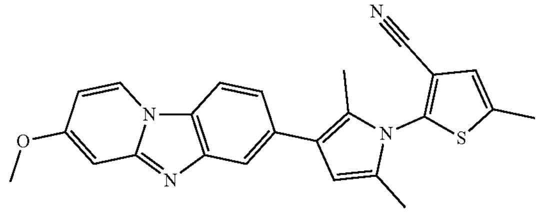 | ** |
| AB29511 | 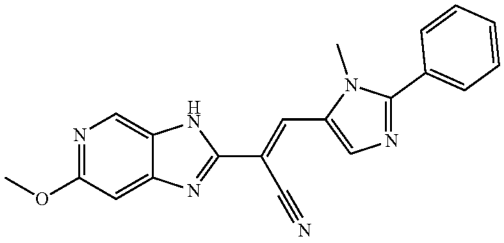 [SMILES: COc1cc2nc(/C(C#N)=C/c3cnc(-c4ccccc4)n3C)[nH]c2cn1] | * |
| AB24237 | 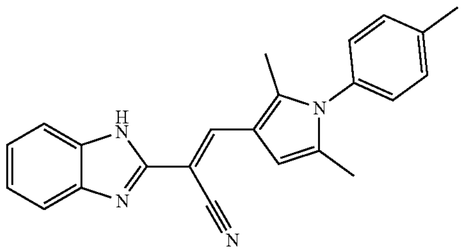 [SMILES: Cc1ccc(-n2c(C)cc(/C=C(\C#N)c3nc4ccccc4[nH]3)c2C)cc1] | * |
| AB24321 | 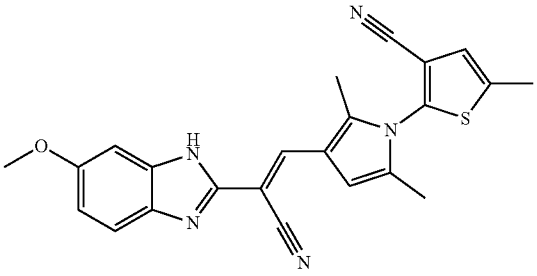 | *** |

TABLE 2-continued
| Determination of the half-maximal inhibitory concentrations of compounds on U251-MG cells | | |
|---|---|---|
| Compound No. | Structure of compound | $IC_{50}$ |
| AB24223 | 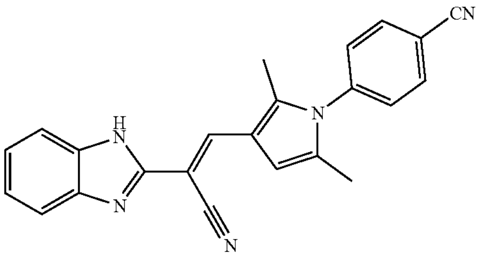 [SMILES: Cc1cc(/C=C(\C#N)c2nc3ccccc3[nH]2)c(C)n1-c1ccc(C#N)cc1] | * |
| AB24267 | 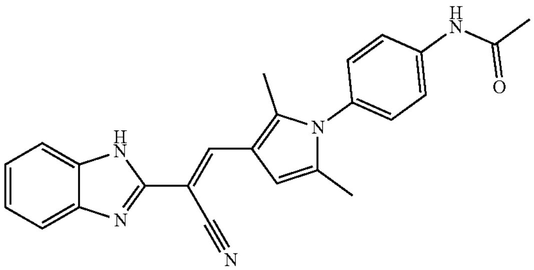 [SMILES: CC(=O)Nc1ccc(-n2c(C)cc(/C=C(\C#N)c3nc4ccccc4[nH]3)c2C)cc1] | * |
| AB24227 | 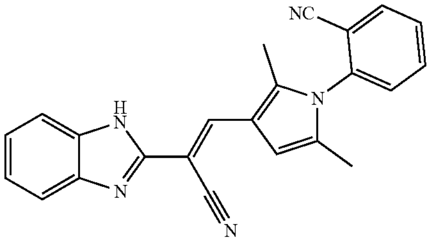 [SMILES: Cc1cc(/C=C(\C#N)c2nc3ccccc3[nH]2)c(C)n1-c1ccccc1C#N] | * |
| AB24233 | 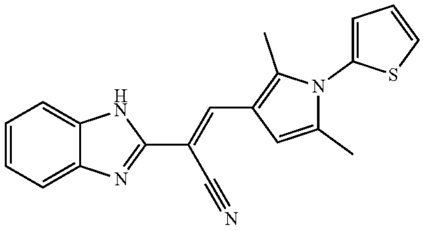 [SMILES: Cc1cc(/C=C(\C#N)c2nc3ccccc3[nH]2)c(C)n1-c1cccs1] | * |
| AB24258 | 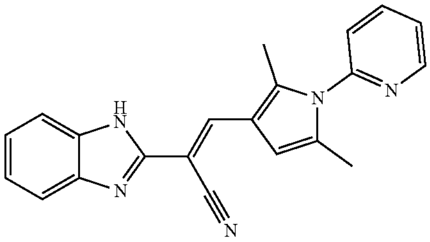 [SMILES: Cc1cc(/C=C(\C#N)c2nc3ccccc3[nH]2)c(C)n1-c1ccccn1] | * |
| AB24259 | 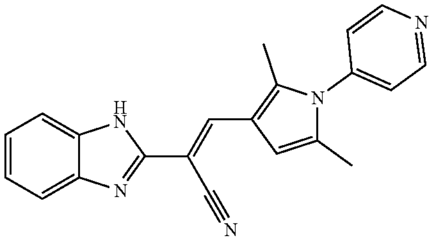 [SMILES: Cc1cc(/C=C(\C#N)c2nc3ccccc3[nH]2)c(C)n1-c1ccncc1] | ** |

TABLE 2-continued
| Determination of the half-maximal inhibitory concentrations of compounds on U251-MG cells | | |
|---|---|---|
| Compound No. | Structure of compound | $IC_{50}$ |
| AB24264 | 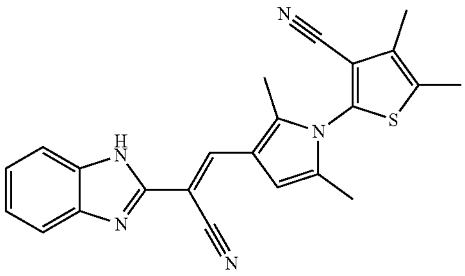 | ** |
| AB24270 | 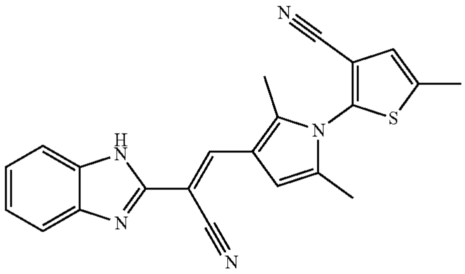 [SMILES: Cc1cc(C#N)c(-n2c(C)cc(/C=C(\C#N)c3nc4ccccc4[nH]3)c2C)s1] | *** |
| AB24273 | 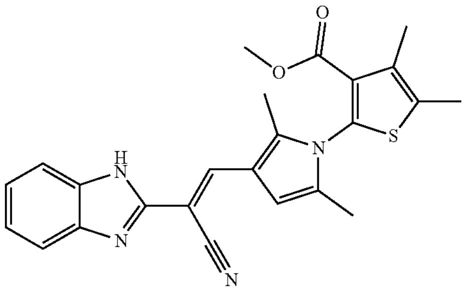 [SMILES: COC(=O)c1c(-n2c(C)cc(/C=C(\C#N)c3nc4ccccc4[nH]3)c2C)sc(C)c1C] | *** |
| AB24274 | 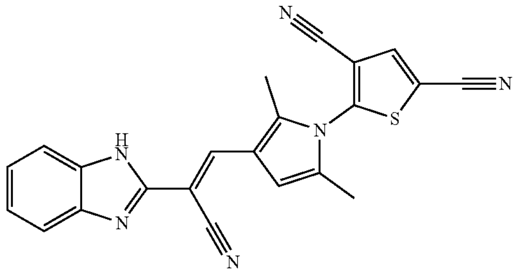 [SMILES: Cc1cc(/C=C(\C#N)c2nc3ccccc3[nH]2)c(C)n1-c1sc(C#N)cc1C#N] | * |
| AB24276 | 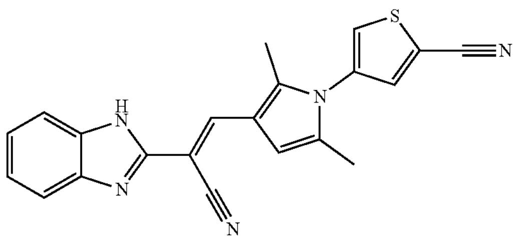 [SMILES: Cc1cc(/C=C(\C#N)c2nc3ccccc3[nH]2)c(C)n1-c1csc(C#N)c1] | * |

TABLE 2-continued
| Determination of the half-maximal inhibitory concentrations of compounds on U251-MG cells | | |
|---|---|---|
| Compound No. | Structure of compound | $IC_{50}$ |
| AB24277 | 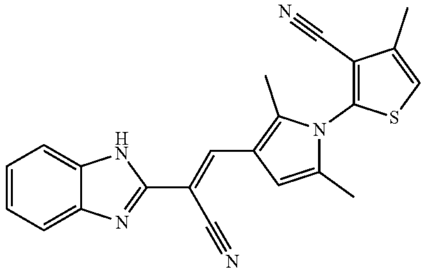 [SMILES: Cc1csc(-n2c(C)cc(/C=C(\C#N)c3nc4ccccc4[nH]3)c2C)c1C#N] | * |
| AB24322 | 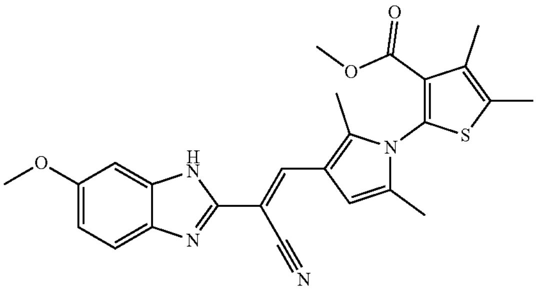 | ** |
| AB24284 | 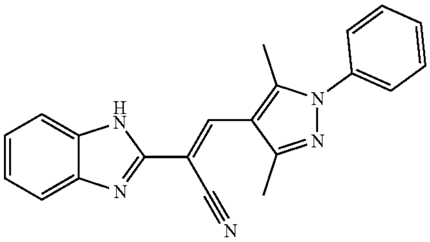 [SMILES: Cc1nn(-c2ccccc2)c(C)c1/C=C(\C#N)c1nc2ccccc2[nH]1] | * |
| AB24285 | 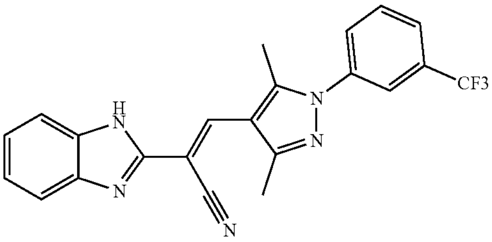 [SMILES: Cc1nn(-c2cccc(C(F)(F)F)c2)c(C)c1/C=C(\C#N)c1nc2ccccc2[nH]1] | * |
| AB24307 | 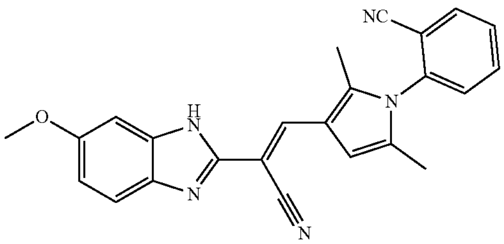 [SMILES: COc1ccc2nc(/C(C#N)=C/c3cc(C)n(-c4ccccc4C#N)c3C)[nH]c2c1] | * |

TABLE 2-continued
Determination of the half-maximal inhibitory concentrations of compounds on U251-MG cells
| Compound No. | Structure of compound | $IC_{50}$ |
|---|---|---|
| AB24290 | 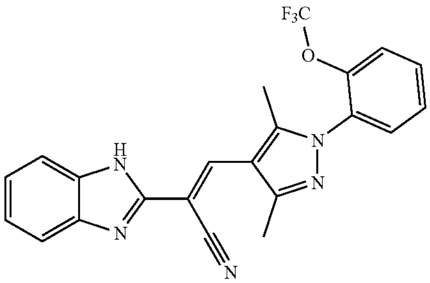 [SMILES: Cc1nn(-c2ccccc2OC(F)(F)F)c(C)c1/C=C(\C#N)c1nc2ccccc2[nH]1] | * |
| AB24243 | 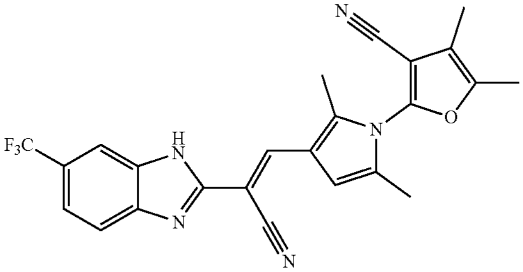 [SMILES: Cc1oc(-n2c(C)cc(/C=C(\C#N)c3nc4ccc(C(F)(F)F)cc4[nH]3)c2C)c(C#N)c1C] | ** |
| AB24201 | 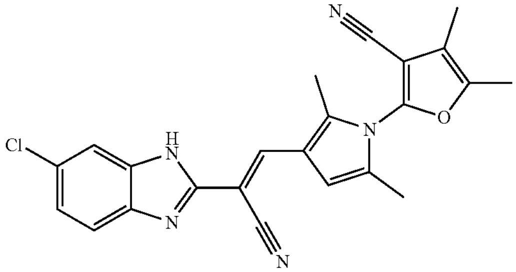 [SMILES: Cc1oc(-n2c(C)cc(/C=C(\C#N)c3nc4ccc(Cl)cc4[nH]3)c2C)c(C#N)c1C] | ** |
| AB24202 | 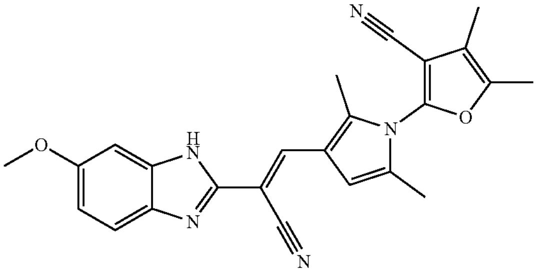 | *** |
| AB24203 | 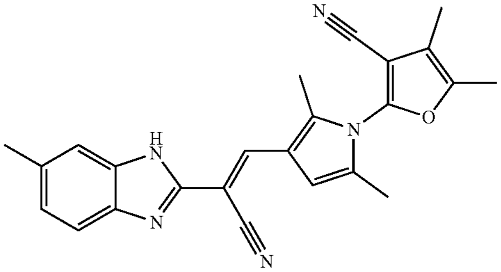 | ** |

TABLE 2-continued
| Determination of the half-maximal inhibitory concentrations of compounds on U251-MG cells | | |
|---|---|---|
| Compound No. | Structure of compound | $IC_{50}$ |
| AB24205 | 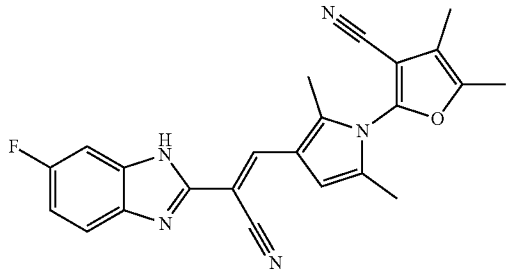 [SMILES: Cc1oc(-n2c(C)cc(/C=C(\C#N)c3nc4ccc(F)cc4[nH]3)c2C)c(C#N)c1C] | ** |
| AB24206 | 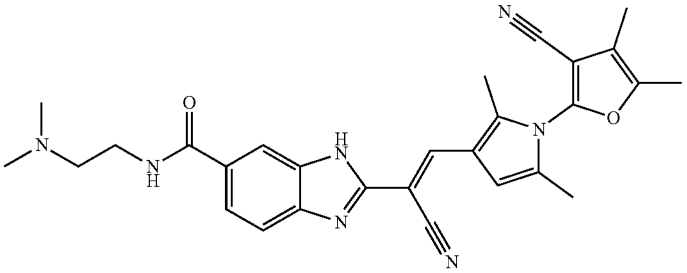 | ** |
| AB24208 | 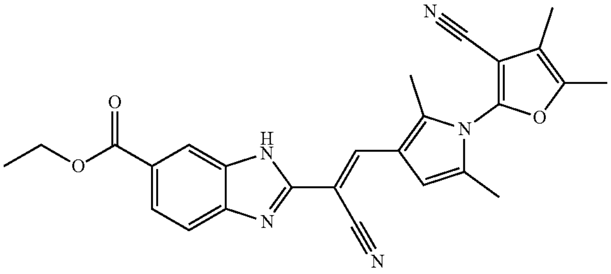 [SMILES: CCOC(=O)c1ccc2nc(/C(C#N)=C/c3cc(C)n(-c4oc(C)c(C)c4C#N)c3C)[nH]c2c1] | * |
| AB24213 | 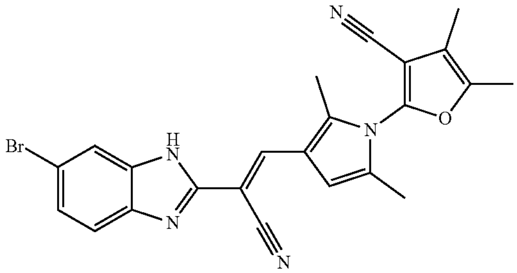 | ** |
| AB24214 | 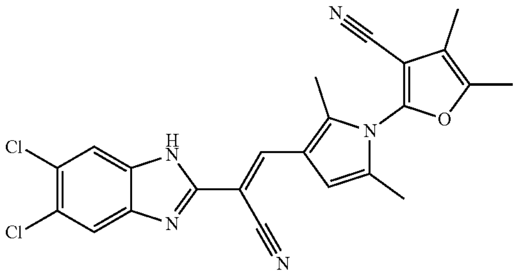 [SMILES: Cc1oc(-n2c(C)cc(/C=C(\C#N)c3nc4cc(Cl)c(Cl)cc4[nH]3)c2C)c(C#N)c1C] | * |

TABLE 2-continued
| Determination of the half-maximal inhibitory concentrations of compounds on U251-MG cells | | |
|---|---|---|
| Compound No. | Structure of compound | $IC_{50}$ |
| AB24217 | 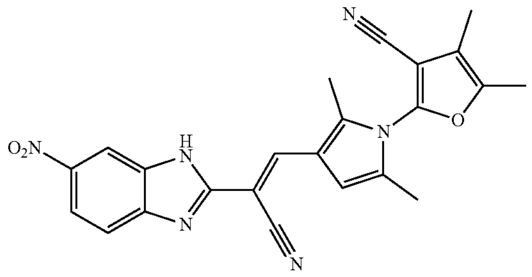 | * |
| AB24221 | 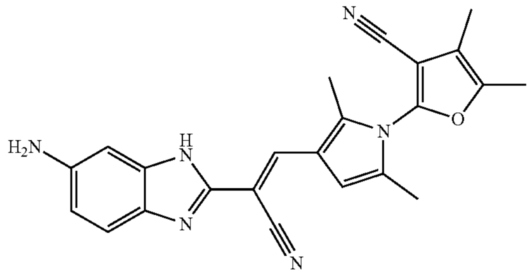 [SMILES: Cc1oc(-n2c(C)cc(/C=C(\C#N)c3nc4ccc([N+](=O)[O-])cc4[nH]3)c2C)c(C#N)c1C] | * |
| AB24287 | 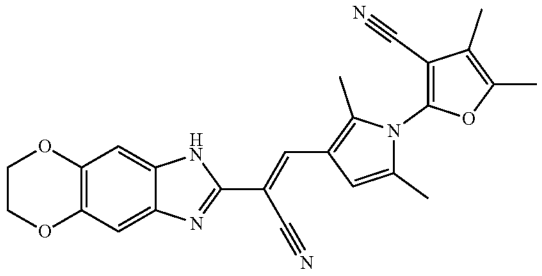 [SMILES: Cc1oc(-n2c(C)cc(/C=C(\C#N)c3nc4cc5c(cc4[nH]3)OCCO5)c2C)c(C#N)c1C] | ** |
| AB24225 | 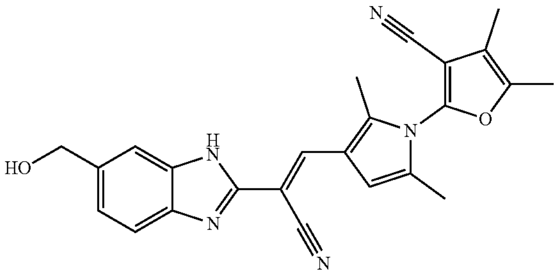 [SMILES: Cc1oc(-n2c(C)cc(/C=C(\C#N)c3nc4ccc(CO)cc4[nH]3)c2C)c(C#N)c1C] | ** |
| AB24283 | 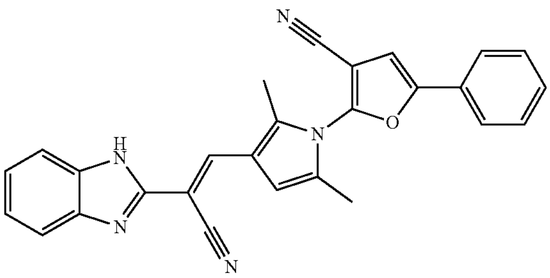 [SMILES: Cc1cc(/C=C(\C#N)c2nc3ccccc3[nH]2)c(C)n1-c1oc(-c2ccccc2)cc1C#N] | ** |

TABLE 2-continued

Determination of the half-maximal inhibitory concentrations of compounds on U251-MG cells

| Compound No. | Structure of compound | $IC_{50}$ |
| --- | --- | --- |
| AB24229 | 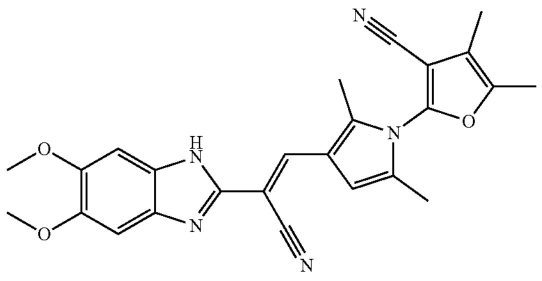 | ** |
| AB24266 | 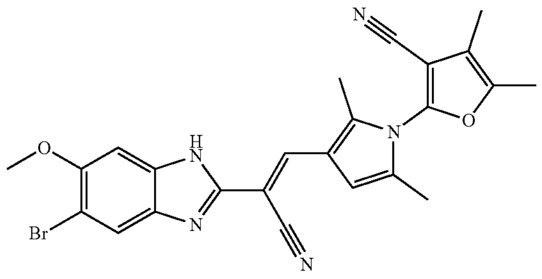 | ** |
| AB24246 | 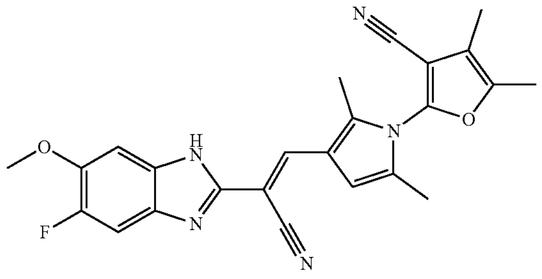 | ** |
| AB24239 | 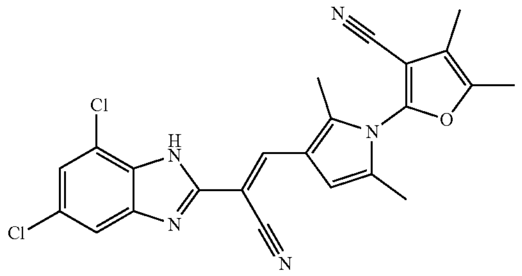 [SMILES: Cc1oc(-n2c(C)cc(/C=C(\C#N)c3nc4cc(Cl)cc(Cl)c4[nH]3)c2C)c(C#N)c1C] | ** |

* denoted that the half-maximal inhibitory concentration was 5 μM or more and less than 20 μM;

** denoted that the half-maximal inhibitory concentration was 1 μM or more and less than 5 μM;

*** denoted that the half-maximal inhibitory concentration was 100 nM or more and less than 1000 nM;

**** denoted that the half-maximal inhibitory concentration was less than 100 nM.

As could be seen from Table 2, the compounds of the present disclosure had significant inhibitory effects on U251-MG cells (a DHX33-overexpressing cancer cell strain).

What is claimed is:

1. A compound having the structure of formula III or a pharmaceutically acceptable form thereof:

III

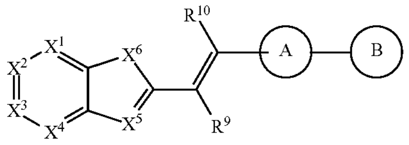

wherein $X^1$ is N or $CR^1$, $X^2$ is N or $CR^2$, $X^3$ is N or $CR^3$, $X^4$ is N or $CR^4$, provided that one of $X^1$, $X^2$, $X^3$ and $X^4$ is N;

$R^1$, $R^2$, $R^3$ and $R^4$ are each independently hydrogen, halogen, amino, nitro, hydroxyl, $C_{1-4}$ alkyl, $C_{1-4}$ haloalkyl, $C_{1-4}$ alkoxy, $C_{1-4}$ haloalkoxy, —NH($C_{1-4}$ alkyl), or —N($C_{1-4}$ alkyl)$_2$;

$X^5$ is N, $X^6$ is $NR^6$;

$R^6$ is hydrogen, or $C_{1-4}$ alkyl;

$R^{10}$ is hydrogen, or $C_{1-4}$ alkyl;

$R^9$ is cyano;

ring A is a pyrrole ring;

ring A is optionally substituted with one or more $R^{11}$;

each $R^{11}$ is independently halogen, $C_{1-4}$ alkyl, or $C_{1-4}$ haloalkyl;

ring B is a furan ring, a thiophene ring, or a thiazole ring;

ring B is optionally substituted with one or more $R^{12}$;

each $R^{12}$ is independently halogen, cyano, amino, nitro, hydroxyl, $C_{1-4}$ alkyl, $C_{1-4}$ haloalkyl, $C_{1-4}$ alkoxy, $C_{1-4}$ haloalkoxy, $C_{3-6}$ cycloalkyl, —C(═O)—O—($C_{1-4}$ alkyl), phenyl, benzyl, pyridyl, or —C(═O)—$NH_2$, said phenyl, benzyl and pyridyl are optionally substituted with one or more substituents selected from hydrogen, halogen, cyano, amino, hydroxyl, $C_{1-4}$ alkyl and $C_{1-4}$ alkoxy; and said pharmaceutically acceptable form is a pharmaceutically acceptable salt.

2. The compound or the pharmaceutically acceptable form thereof according to claim 1, wherein $R^1$, $R^2$, $R^3$ and $R^4$ are each independently hydrogen, fluorine, chlorine, bromine, amino, nitro, methyl, ethyl, isopropyl, trifluoromethyl, methoxy, ethoxy, isopropoxy, trifluoromethoxy, —NH($CH_3$), —NH($CH_2CH_3$), —N($CH_3$)$_2$, or —N($CH_2CH_3$)$_2$, $R^6$ is hydrogen, methyl, ethyl, or isopropyl, $R^{10}$ is hydrogen, methyl, ethyl, or isopropyl, $R^9$ is cyano, ring A is

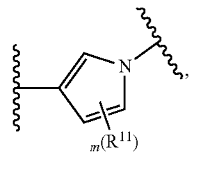

each $R^{11}$ is independently fluorine, chlorine, bromine, methyl, ethyl, isopropyl, or trifluoromethyl, ring B is

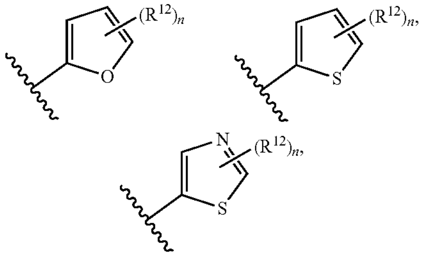

each $R^{12}$ is independently fluorine, chlorine, bromine, cyano, amino, nitro, methyl, ethyl, isopropyl, tert-butyl, cyclopropyl, cyclopentyl, cyclohexyl, trifluoromethyl, methoxy, ethoxy, isopropoxy, trifluoromethoxy, —C(═O)—$OCH_3$, —C(═O)—$OCH_2CH_3$, phenyl, benzyl, pyridyl, or —C(═O)—$NH_2$.

3. The compound or the pharmaceutically acceptable form thereof according to claim 1, being a compound of any one of formula IIIa-1, formula IIIa-4, formula IIIa-6, and formula IIIa-7 or a pharmaceutically acceptable form thereof:

IIIa-1

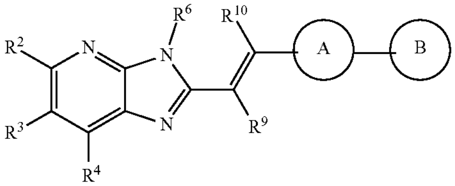

IIIa-4

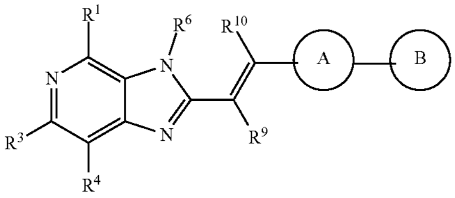

IIIa-6

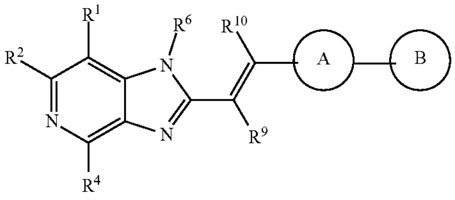

IIIa-7

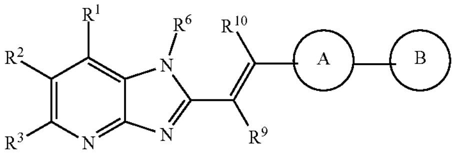

wherein ring A, ring B, $R^1$, $R^2$, $R^3$, $R^4$, $R^6$, $R^9$ and $R^{10}$ are as defined in claim 1.

4. The compound or the pharmaceutically acceptable form thereof according to claim 1, wherein the compound is selected from the group consisting of the following compounds:

-continued
AB24281
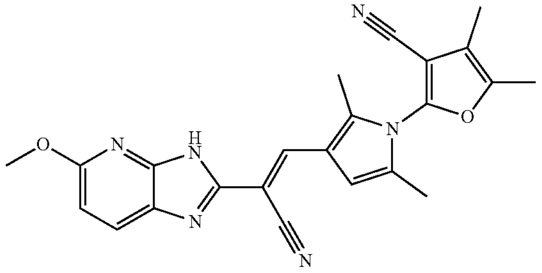
AB24254
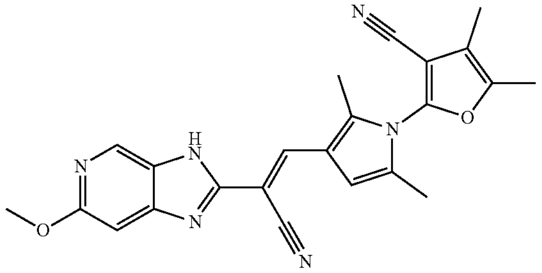
AB24288
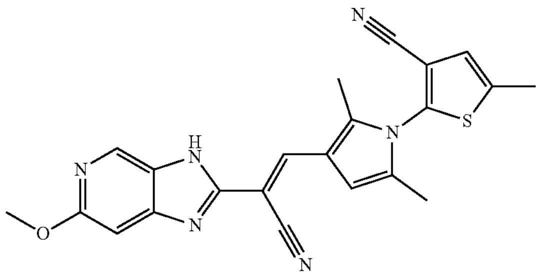
AB24301
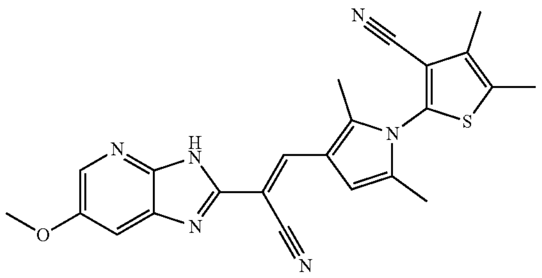
AB24302
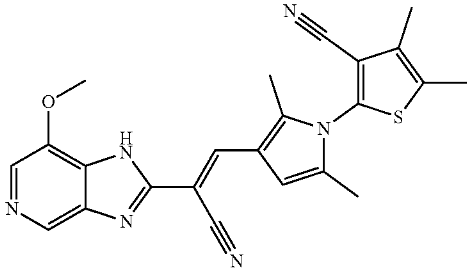
AB24308
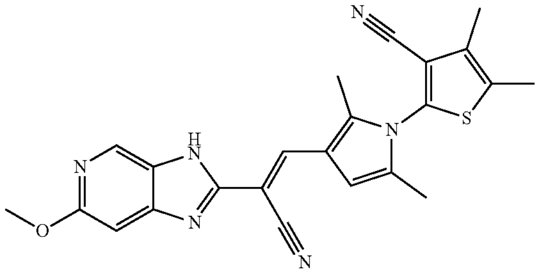
AB24310
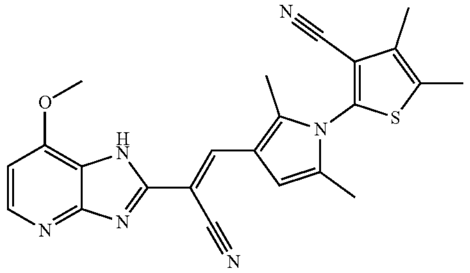
AB24311
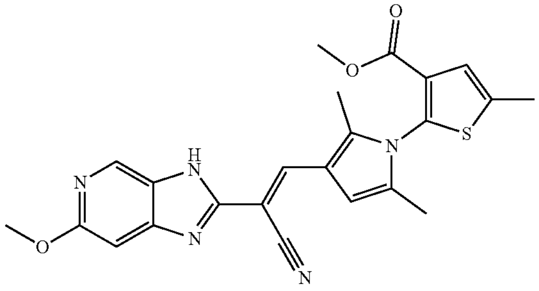
AB24313
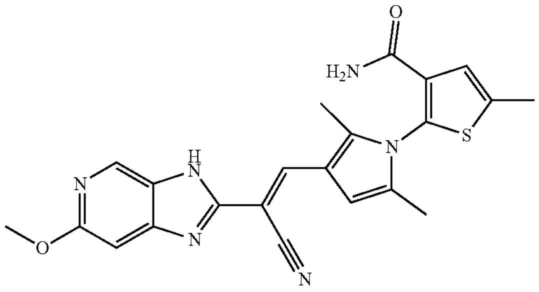
AB24314
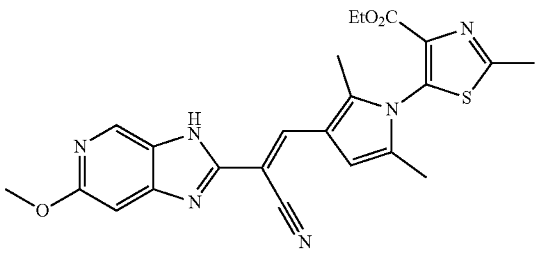

-continued
AB24351
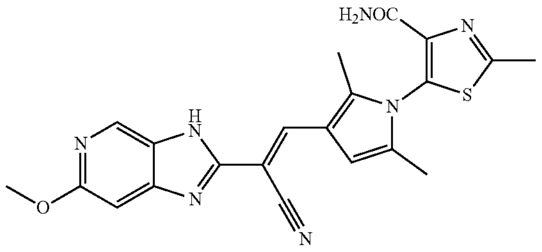
AB24325
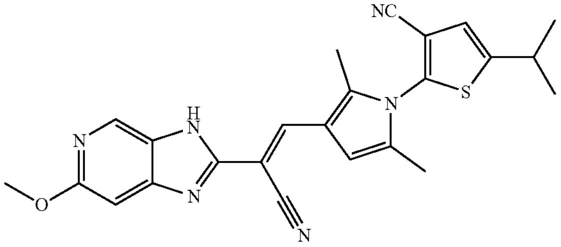
AB24333
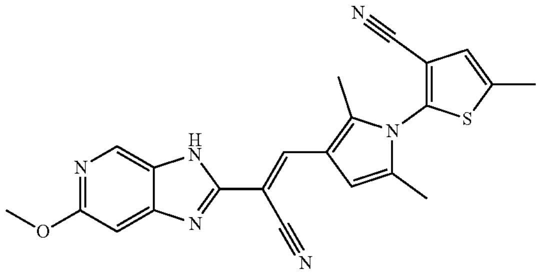
AB24348
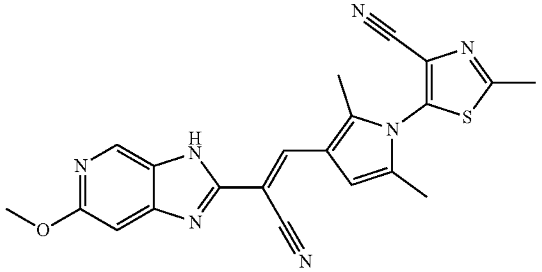
AB24317
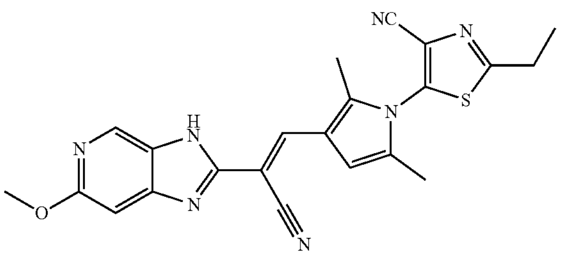
-continued
AB24318
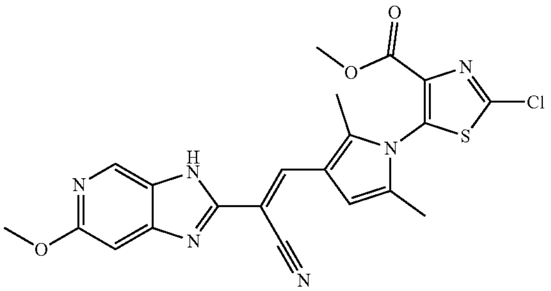
AB24323
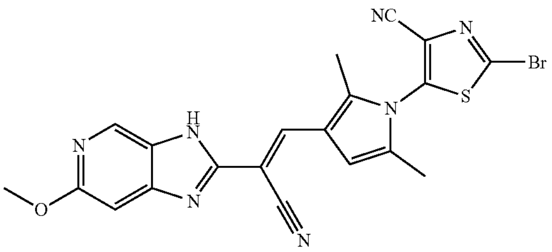
AB24324
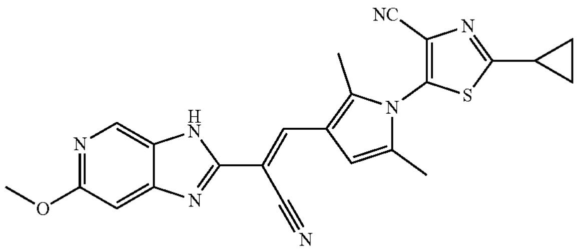
AB24328
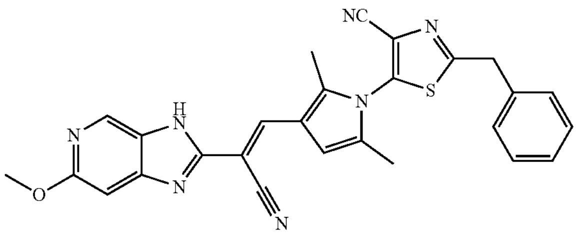
AB24336
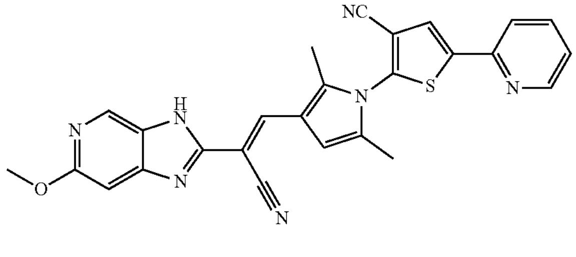

-continued
AB24341
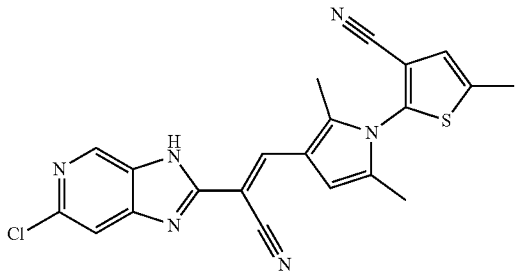
AB24347
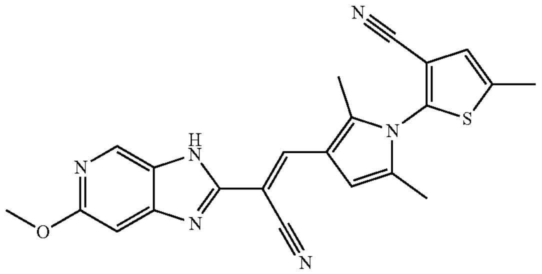
AB24352
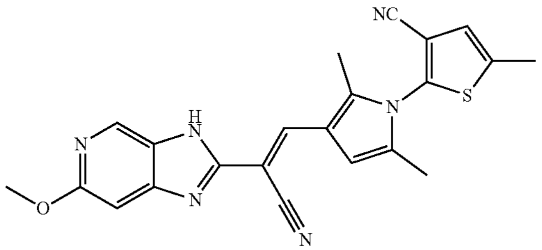
AB24355
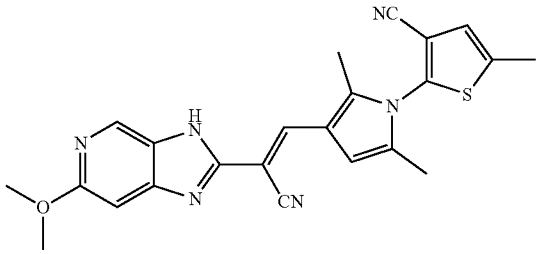
AB24249
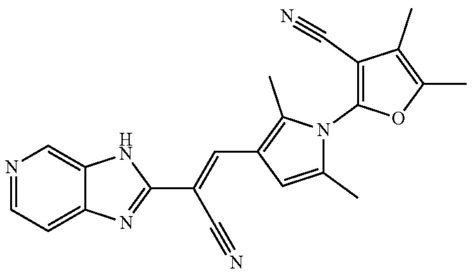
-continued
AB24335
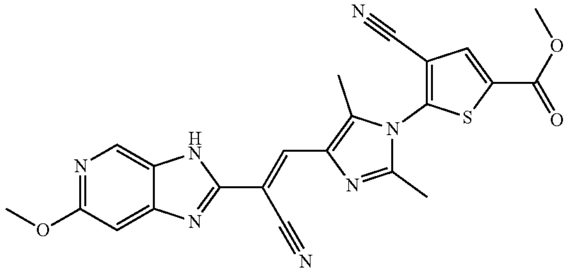
AB24351
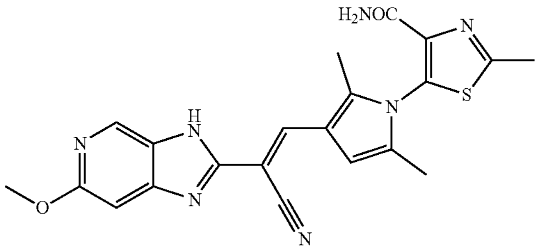
AB24309
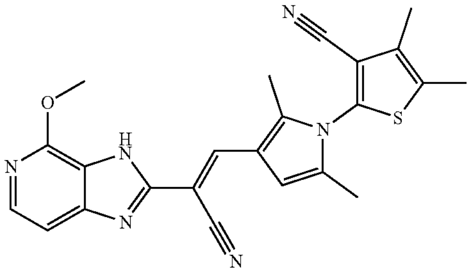
AB24316
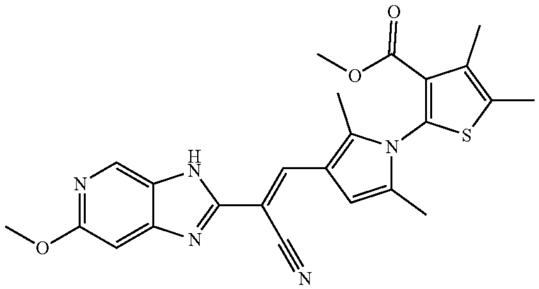
AB24319
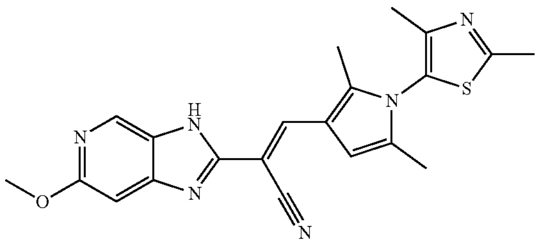

-continued

AB24320

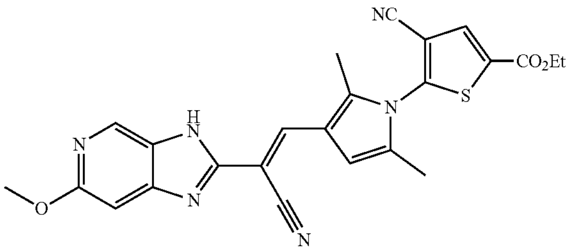

AB24326

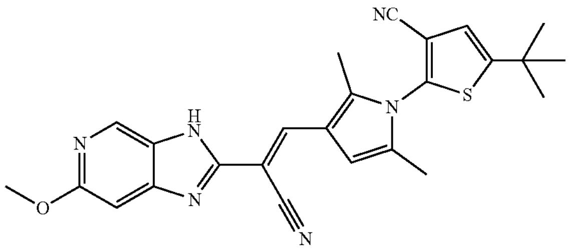

AB24349

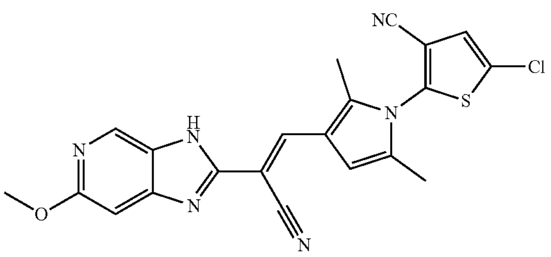

AB24337

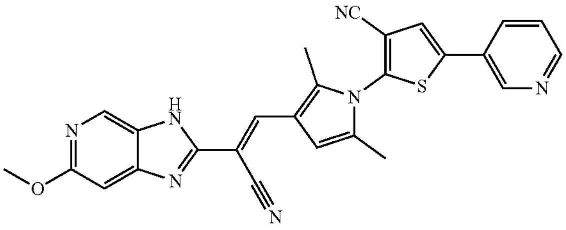

-continued

AB24338

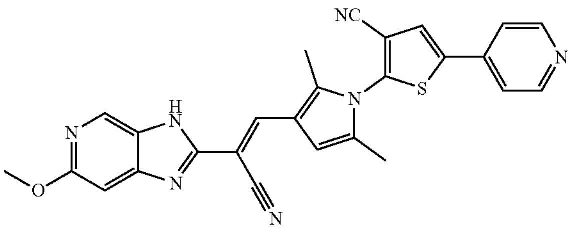

AB24345

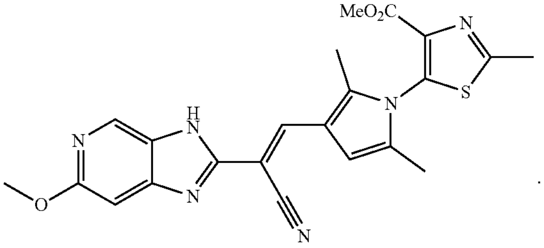

5. A pharmaceutical composition, comprising the compound or the pharmaceutically acceptable form thereof according to claim 1 and one or more pharmaceutically acceptable carriers.

6. A method for preventing and/or treating a disease or a disorder at least partially mediated by DHX33, comprising administering an effective amount of the compound or the pharmaceutically acceptable form thereof according to claim 1 to an individual in need thereof, wherein the disease is selected from cancer, viral infection and inflammation that are mediated by DHX33.

7. A pharmaceutical composition, comprising the compound or the pharmaceutically acceptable form thereof according to claim 4 and one or more pharmaceutically acceptable carriers.

8. A method for preventing and/or treating a disease or a disorder at least partially mediated by DHX33, comprising administering an effective amount of the compound or the pharmaceutically acceptable form thereof according to claim 4 to an individual in need thereof, wherein the disease is selected from cancer, viral infection and inflammation that are mediated by DHX33.

* * * * *